US010903430B2

(12) United States Patent
Jatsch et al.

(10) Patent No.: US 10,903,430 B2
(45) Date of Patent: Jan. 26, 2021

(54) MATERIALS FOR ELECTRONIC DEVICES

(71) Applicant: Merck Patent GmbH, Darmstadt (DE)

(72) Inventors: Anja Jatsch, Frankfurt am Main (DE); Amir Hossain Parham, Frankfurt am Main (DE); Thomas Eberle, Landau (DE); Tobias Grossmann, Darmstadt (DE); Jonas Valentin Kroeber, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 303 days.

(21) Appl. No.: 15/327,790

(22) PCT Filed: Jun. 30, 2015

(86) PCT No.: PCT/EP2015/001315
§ 371 (c)(1),
(2) Date: Jan. 20, 2017

(87) PCT Pub. No.: WO2016/012075
PCT Pub. Date: Jan. 28, 2016

(65) Prior Publication Data
US 2017/0222157 A1    Aug. 3, 2017

(30) Foreign Application Priority Data

Jul. 21, 2014  (EP) .................................. 14002528

(51) Int. Cl.
| | |
|---|---|
| *H01L 51/00* | (2006.01) |
| *C07D 401/14* | (2006.01) |
| *C07D 405/14* | (2006.01) |
| *C07D 403/04* | (2006.01) |
| *C07D 403/10* | (2006.01) |
| *C07D 403/14* | (2006.01) |
| *C07D 235/18* | (2006.01) |
| *C07D 405/10* | (2006.01) |
| *C07D 401/10* | (2006.01) |
| *C09K 11/02* | (2006.01) |
| *H01L 51/50* | (2006.01) |

(52) U.S. Cl.
CPC ........ *H01L 51/0067* (2013.01); *C07D 235/18* (2013.01); *C07D 401/10* (2013.01); *C07D 401/14* (2013.01); *C07D 403/04* (2013.01); *C07D 403/10* (2013.01); *C07D 403/14* (2013.01); *C07D 405/10* (2013.01); *C07D 405/14* (2013.01); *C09K 11/025* (2013.01); *H01L 51/0052* (2013.01); *H01L 51/0056* (2013.01); *H01L 51/0058* (2013.01); *H01L 51/0072* (2013.01); *H01L 51/0073* (2013.01); *H01L 51/0002* (2013.01); *H01L 51/0003* (2013.01); *H01L 51/5012* (2013.01); *H01L 51/5016* (2013.01); *H01L 51/5072* (2013.01); *H01L 51/5092* (2013.01); *H01L 2251/5384* (2013.01); *Y02E 10/549* (2013.01)

(58) Field of Classification Search
CPC ............. H01L 51/0067; H01L 51/0073; H01L 51/0056; H01L 51/0072; H01L 51/0058; H01L 51/0052; H01L 2251/5384; H01L 51/0002; H01L 51/0003; H01L 51/5092; H01L 51/5016; H01L 51/5012; H01L 51/5072; C09K 11/025; C07D 403/14; C07D 405/10; C07D 403/04; C07D 401/10; C07D 405/14; C07D 401/14; C07D 403/10; C07D 235/18; C07D 409/14; Y02E 10/549
USPC .......................... 252/500, 501.1, 583, 301.16
See application file for complete search history.

(56) References Cited

U.S. PATENT DOCUMENTS

| | | | | |
|---|---|---|---|---|
| 8,629,430 | B2 * | 1/2014 | Kawamura | C07D 307/79 257/103 |
| 9,847,499 | B2 * | 12/2017 | Stoessel | C07F 15/0086 |
| 10,644,246 | B2 * | 5/2020 | Parham | C07D 491/20 |
| 2011/0121274 | A1 | 5/2011 | Parham et al. | |
| 2012/0248973 | A1 * | 10/2012 | Ito | C07D 251/24 313/504 |
| 2013/0126791 | A1 | 5/2013 | Heun et al. | |
| 2013/0200356 | A1 | 8/2013 | Jung et al. | |
| 2014/0183422 | A1 * | 7/2014 | Stoessel | C07F 15/0086 252/519.2 |
| 2018/0130962 | A1 * | 5/2018 | Ji | C07F 15/0033 |
| 2019/0288206 | A1 * | 9/2019 | Parham | C07D 209/86 |

FOREIGN PATENT DOCUMENTS

| | | |
|---|---|---|
| DE | 102008036982 A1 | 2/2010 |
| DE | 102010033080 A1 | 2/2012 |
| KR | 1020100075079 A | 7/2010 |
| KR | 1020130115160 A | 10/2013 |
| KR | 1020140014956 A | 2/2014 |
| KR | 1020140014959 A | 2/2014 |
| TW | 201100522 A | 1/2011 |
| WO | 2010126270 A1 | 11/2010 |

OTHER PUBLICATIONS

Office Action dated Dec. 14, 2018 in Japanese Patent Application No. 2017-503578.
Search Report dated Jun. 17, 2019 in corresponding Taiwanese Patent App. No. 2015012313.

* cited by examiner

Primary Examiner — Douglas J McGinty
(74) Attorney, Agent, or Firm — Faegre Drinker Biddle & Reath LLP

(57) ABSTRACT

The present invention relates to compounds, compositions and formulations comprising same and to opto-electronic devices comprising the compounds and compositions according to the invention.

20 Claims, No Drawings

MATERIALS FOR ELECTRONIC DEVICES

RELATED APPLICATIONS

This application is a national stage entry, filed pursuant to 35 U.S.C. § 371, of PCT/EP2015/001315, filed Jun. 30, 2015, which claims the benefit of European Patent Application No. 14002528.9, filed Jul. 21, 2014, which is incorporated herein by reference in its entirety.

The present invention relates to compounds, compositions, formulations and electronic devices comprising the compounds or compositions.

The structure of organic electroluminescent devices (for example OLEDs—organic light-emitting diodes or OLECs—organic light-emitting electrochemical cells) in which organic semiconductors are employed as organic functional materials is described, for example, in U.S. Pat. Nos. 4,539,507, 5,151,629, EP 0676461 and WO 98/27136. The emitting materials employed here, besides fluorescent emitters, are increasingly organometallic complexes which exhibit phosphorescence (M. A. Baldo et al., Appl. Phys. Lett. 1999, 75, 4-6). For quantum-mechanical reasons, an up to four-fold increase in energy and power efficiency is possible using organometallic compounds as phosphorescence emitters. In general, there is still a need for improvement, in particular with respect to efficiency, operating voltage and lifetime, both in the case of OLEDs which exhibit singlet emission and also in the case of OLEDs which exhibit triplet emission.

The properties of organic electroluminescent devices are not determined only by the emitters employed. The other materials used, such as host and matrix materials, hole-blocking materials, electron-transport materials, hole-transport materials and electron- or exciton-blocking materials, in particular, are also of particular importance here. Improvements to these materials may result in significant improvements of electroluminescent devices.

Compounds containing both triazine and benzimidazole groups as electron-transport materials are known from the prior art. WO 2010/126270 discloses compounds of this type. Both groups are bonded to a fluorene skeleton, where the two aromatic rings of the fluorene are in further aromatically condensed form.

KR 101257695 also discloses fluorenes containing a triazine group and a benzimidazole group. However, the triazine group is only substituted in two of the three carbon-containing positions.

WO 2013/100464 discloses spirobifluorenes which contain both a benzimidazole group and also a triazine group. However, the triazines are unsubstituted. In addition, a benzothiophene group has been condensed onto the spirobifluorene.

However, there is still a need for improvement, in particular with respect to the efficiency, operating voltage and lifetime of organic electronic devices, in the case of the use of these materials, as in the case of other materials.

The object of the present invention is therefore the provision of compounds which are suitable for use in an organic electronic device, in particular in an organic electroluminescent device, and which result in good device properties on use in this device, and the provision of the corresponding electronic device.

Surprisingly, it has been found that certain compounds described in greater detail below achieve these objects and overcome the disadvantage from the prior art. The use of the compounds results in very good properties of organic electronic devices, in particular of organic electroluminescent devices, in particular with respect to the lifetime, the efficiency and the operating voltage. The present invention therefore relates to electronic devices, in particular organic electroluminescent devices, which comprise compounds of this type, and to the corresponding preferred embodiments.

The present invention relates to a chemical compound which contains a skeleton of the formula (GK-1) or alternatively a skeleton of the formula (GK-2) and at least one or more groups of the formula (G-2) and at least one or more groups of the formula (G-3),

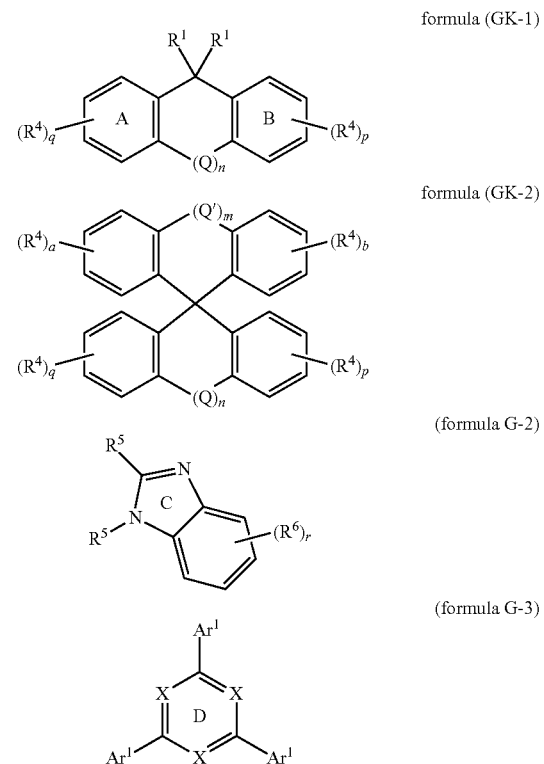

formula (GK-1)

formula (GK-2)

(formula G-2)

(formula G-3)

where it is preferred if the compound according to the invention contains only one group of the formula (GK-1) or alternatively only one group of the formula (GK-2);
and where the skeleton of the formula (GK-1) and the groups of the formulae (G-2) and (G-3) are covalently linked to one another or alternatively the skeleton of the formula (GK-2) and the groups of the formulae (G-2) and (G-3) are covalently linked to one another;
and where the following definitions apply to the symbols and indices used:
$R^1$ is on each occurrence, identically or differently, H, D, F, Cl, Br, I, CHO, $N(Ar^1)_2$, $C(\!=\!O)Ar^1$, $P(\!=\!O)(Ar^1)_2$, $S(\!=\!O)Ar^1$, $S(\!=\!O)_2Ar^1$, $CR^2\!=\!CR^2Ar^1$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more, preferably non-adjacent $CH_2$ groups may be replaced by $R^2C\!=\!CR^2$, $C\!\equiv\!C$, $Si(R^2)_2$, $Ge(R^2)_2$, $Sn(R^2)_2$, $C\!=\!O$, $C\!=\!S$, $C\!=\!Se$, $C\!=\!NR^2$, $P(\!=\!O)(R^2)$, SO, $SO_2$, $NR^2$, O, S or $CONR^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which may be substituted by one or more radicals R$^2$, or a combination of these systems; two or more adjacent substituents R$^1$ here may form a mono- or polycyclic, aliphatic or aromatic ring system with one another;

R$^2$ is, identically or differently on each occurrence, H, D, F, Cl, Br, I, N(R$^3$)$_2$, CN, NO$_2$, Si(R$^3$)$_3$, B(OR$^3$)$_2$, C(=O)R$^3$, P(=O)(R$^3$)$_2$, S(=O)R$^3$, S(=O)$_2$R$^3$, OSO$_2$R$^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals R$^3$, where one or more non-adjacent CH$_2$ groups may be replaced by R$^3$C=CR$^3$, C≡C, Si(R$^3$)$_2$, Ge(R$^3$)$_2$, Sn(R$^3$)$_2$, C=O, C=S, C=Se, C=NR$^3$, P(=O)(R$^3$), SO, SO$_2$, NR$^3$, O, S or CONR$^3$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^3$, or an aryloxy, arylalkoxy or heteroaryloxy group having 5 to 60 aromatic ring atoms, which may be substituted by one or more radicals R$^3$, or a diarylamino group, diheteroarylamino group or arylheteroarylamino group having 10 to 40 aromatic ring atoms, which may be substituted by one or more radicals R$^3$, or a combination of two or more of these groups; two or more adjacent radicals R$^2$ here may form a mono- or polycyclic, aliphatic or aromatic ring system with one another; where it is preferred if two or more adjacent substituents R$^2$ do not form a mono- or polycyclic, aliphatic or aromatic ring system with one another;

R$^3$ is, identically or differently on each occurrence, H, D, F or an aliphatic, aromatic and/or heteroaromatic hydrocarbon radical having 1 to 20 C atoms, in which, in addition, one or more H atoms may be replaced by F; two or more substituents R$^3$ here may also form a mono- or polycyclic, aliphatic or aromatic ring system with one another; where it is preferred if two or more adjacent substituents R$^3$ do not form a mono- or polycyclic, aliphatic or aromatic ring system with one another;

R$^5$ is on each occurrence, identically or differently, F, Cl, Br, I, CHO, N(Ar$^1$)$_2$, C(=O)Ar$^1$, P(=O)(Ar$^1$)$_2$, S(=O)Ar$^1$, S(=O)$_2$Ar$^1$, CR$^2$=CR$^2$Ar$^1$, CN, NO$_2$, Si(R$^2$)$_3$, B(OR$^2$)$_2$, B(R$^2$)$_2$, B(N(R$^2$)$_2$)$_2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^2$, where one or more, preferably non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or hetero-aryloxy group having 5 to 60 aromatic ring atoms, which may be substituted by one or more radicals R$^2$, or a combination of these systems; where two or more adjacent substituents R$^5$ cannot form a mono- or polycyclic, aliphatic or aromatic ring system with one another;

R$^4$ and R$^6$ are on each occurrence, identically or differently. H, D, F, Cl, Br, I, CHO, N(Ar$^1$)$_2$, C(=O)Ar$^1$, P(=O)(Ar$^1$)$_2$, S(=O)Ar$^1$, S(=O)$_2$Ar$^1$, CR$^2$=CR$^2$Ar$^1$, CN, NO$_2$, Si(R$^2$)$_3$, B(OR$^2$)$_2$, B(R$^2$)$_2$, B(N(R$^2$)$_2$)$_2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^2$, where one or more, preferably non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which may be substituted by one or more radicals R$^2$, or a combination of these systems; where two or more adjacent substituents R$^4$ cannot form a mono- or polycyclic, aliphatic or aromatic ring system with one another; where two or more adjacent substituents R$^6$ may form a mono- or polycyclic, aliphatic or aromatic ring system with one another, where it is preferred if two or more adjacent substituents R$^6$ cannot form a mono- or polycyclic, aliphatic or aromatic ring system with one another;

Q, Q' are, identically to or differently from one another, C=O, C=S, S, C(R$^2$)$_2$, NR$^2$ or O, preferably C(R$^2$)$_2$, NR$^2$ or O, very preferably C(R$^2$)$_2$ or NR$^2$ and particularly preferably C(R$^2$)$_2$;

n is 0 or 1, where n=0 is preferred and n=0 means that the two aromatic rings A and B are not linked to one another via the group Q, but instead by a single bond;

m is 0 or 1, where m=0 is preferred and m=0 means that the two aromatic rings are not linked to one another via the group Q', but instead by a single bond;

p is 0, 1, 2, 3 or 4, preferably 0, 1 or 2, very preferably 0 or 1 and particularly preferably equal to 0;

q is 0, 1, 2, 3 or 4, preferably 0, 1 or 2, very preferably 0 or 1 and particularly preferably equal to 0;

p+q is always less than or equal to 7, p+q is preferably equal to 0, 1, 2 or 3, p+q is very preferably equal to 0, 1 or 2, p+q is particularly preferably equal to 0 or 1 and p+q is very particularly preferably equal to 0;

a is 0, 1, 2, 3 or 4, preferably 0, 1 or 2, very preferably 0 or 1 and particularly preferably equal to 0;

b is 0, 1, 2, 3 or 4, preferably 0, 1 or 2, very preferably 0 or 1 and particularly preferably equal to 0;

a+b is always less than or equal to 7, a+b is preferably equal to 0, 1, 2 or 3, a+b is very preferably equal to 0, 1 or 2, a+b is particularly preferably equal to 0 or 1 and a+b is very particularly preferably equal to 0;

r is 0, 1, 2, 3 or 4, preferably 0, 1 or 2, very preferably 0 or 1 and r is particularly preferably equal to 0;

X is, identically or differently on each occurrence, N or CR$^1$, where at least one X is equal to N, preferably at least two of the X are equal to N and very preferably all three X are equal to N;

Ar$^1$ is on each occurrence, identically or differently, an aromatic or heteroaromatic ring system having 5 to 30 aromatic ring atoms, which may be substituted by one or more radicals R$^2$; two of the radicals Ar$^1$ here may also be linked to one another by a single bond or a bridge selected from B(R$^2$), C(R$^2$)$_2$, Si(R$^2$)$_2$, C=O, C=NR$^2$, C=C(R$^2$)$_2$, O, S, S=O, SO$_2$, N(R$^2$), P(R$^2$) and P(=O)R$^2$; it is preferred if two radicals Ar$^1$ are not linked to one another.

It is preferred if the compound containing the skeleton of the formula (GK-1) and the two groups of the formulae (G-2) and (G-3) contains no further spirobifluorene groups and no further fluorene groups.

It is furthermore preferred if the compound containing the skeleton of the formula (GK-2) and the two groups of the formulae (G-2) and (G-3) contains no further spirobifluorene groups and no further fluorene groups.

In a preferred embodiment, both the groups of the formula (G-2) and also those of the formula (G-3) are only bonded to aromatic or heteroaromatic rings of the skeleton (GK-1) or (GK-2).

It is preferred if the compound according to the invention containing either the skeleton of the formula (GK-1) or alternatively the skeleton of the formula (GK-2) and in each case at least one or more groups of the formula (G-2) and in each case at least one or more groups of the formula (G-3) has a molecular weight of at most 3000 g/mol or less, preferably of at most 2000 g/mol or less, very preferably of at most 1500 g/mol or less and very particularly preferably at most 1000 g/mol or less.

It is furthermore preferred for the purposes of the present invention if none of the two or more adjacent radicals R$^1$ to R$^6$ can form a mono- or polycyclic, aliphatic or aromatic ring system with one another.

The fact that two or more adjacent radicals may form a mono- or polycyclic, aliphatic or aromatic ring system with one another means that the two or more adjacent radicals become part of a ring or ring system. If it is required that two or more adjacent radicals cannot form a mono- or polycyclic, aliphatic or aromatic ring system with one another, as, for example, in the case of the radical R$^4$, the two or more radicals R$^4$ cannot be part of a ring or ring system. The following cases illustrate this diagrammatically with reference to the definition of the formula (GK-1) and the radicals R$^4$, R$^2$ and R$^3$. According to the above definition, ring closure is not permitted for two or more radicals R$^4$ (case 1). However, R$^4$ may, as indicated above, be further substituted by R$^2$, where two or more adjacent radicals R$^2$ may form a mono- or polycyclic, aliphatic or aromatic ring system with one another. This means that although the two or more radicals R$^2$ may form a ring or ring system (case 2), they cannot do so in such a way that the various radicals R$^4$ become part of a ring or ring system (case 3). According to the definition of the radical R$^2$, this may be substituted by the radical R$^3$, where two or more adjacent radicals R$^3$ may form a mono- or polycyclic, aliphatic or aromatic ring system with one another. However, this is only permissible in such a way that two or more of the radicals R$^4$ do not become part of a ring (case 4).

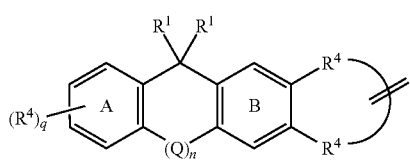

case 1

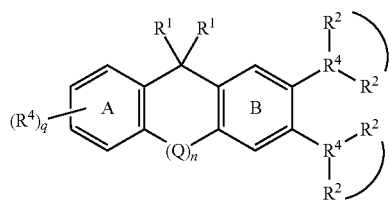

case 2

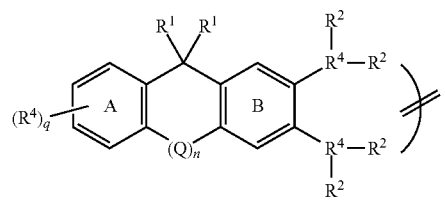

case 3

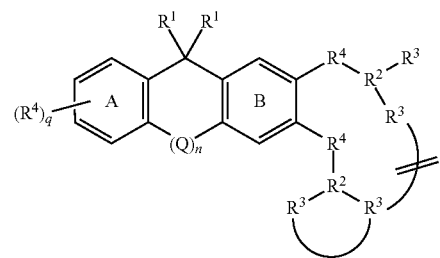

case 4

It is very preferred if the skeleton has the general formula (GK-3),

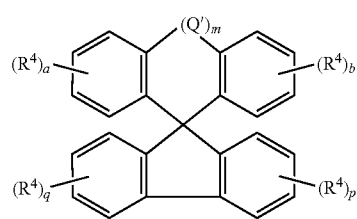

formula (GK-3)

It is very particularly preferred if the skeleton has the general formula (GK-4),

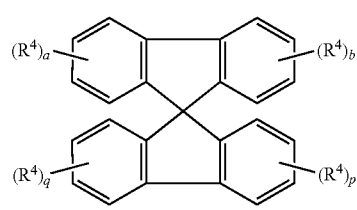

formula (GK-4)

Finally, it is especially preferred if the skeleton has the general formula (GK-5),

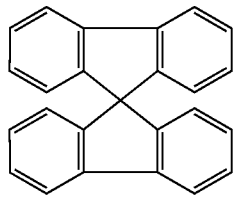

formula (GK-5)

It is furthermore very preferred if the skeleton has the general formula (GK-6),

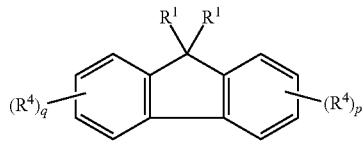

formula (GK-6)

It is furthermore very particularly preferred if the skeleton has the general formula (GK-7),

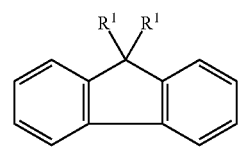

formula (GK-7)

In a preferred embodiment, the present invention relates to a compound of the general formula (1),

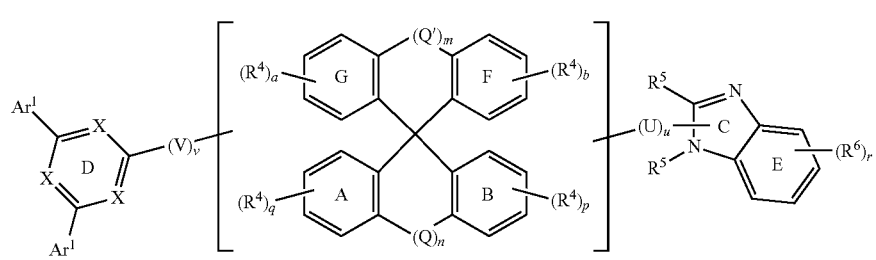

formula (1)

where the indices and symbols are defined as indicated above and where furthermore:
V is a divalent group;
U is a divalent group;
v is 0 or 1, where v=0 means that the ring D is connected directly to the remainder of the compound via a single covalent bond;
u is 0 or 1, where u=0 means that the ring C is connected directly to the remainder of the compound via a single covalent bond.

According to formula (1), the ring D may, for example, be bonded to the ring A via V, whereas the ring C can be bonded to any desired other site via U.

It is preferred if the ring D is covalently bonded to one of the rings A, B, C, E, F or G indicated via V and if the ring C is covalently bonded to one of the rings A, B, D, F or G indicated via U, where at least one of the two rings C and D is covalently bonded to one of the rings A, B, F or G via the divalent group U or V.

The substituent containing the ring C is bonded here in accordance with one of the two formulae depicted below and thus in each case replaces one of the radicals $R^5$ on the ring C.

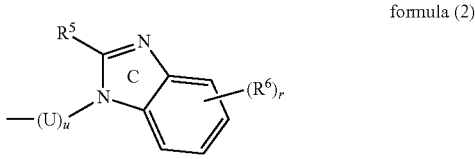

formula (2)

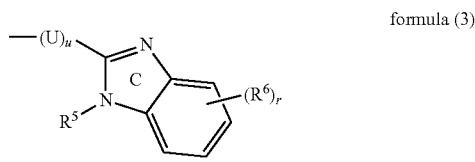

formula (3)

It is preferred if V and U represent, identically or differently on each occurrence, an aromatic or heteroaromatic ring system which contains 5 to 60 ring atoms. It is very preferred if U and V are a phenylene, biphenylene or terphenylene group, very particularly preferably a phenylene or biphenylene group and especially preferably a phenylene group.

It is preferred if the ring D is bonded directly to the ring A via the bridge V, where q can then be at most 3. If the ring C is likewise bonded directly to A via the bridge U, q is at most 2. It furthermore goes without saying that p can be at most 3 if the ring C is bonded directly to the ring B via the bridge U. Entirely analogously, the maximum values of the parameters a and b depend on the substitution of the rings G and F by the groups of the formulae (G-2) and (G-3).

The notation for the compound of the formula (1) accordingly also means that, for example, the group containing the ring D is bonded firstly to ring A of the skeleton and the group containing the ring C may be bonded to the group containing the ring D.

Preference is furthermore given to a compound of the general formula (4),

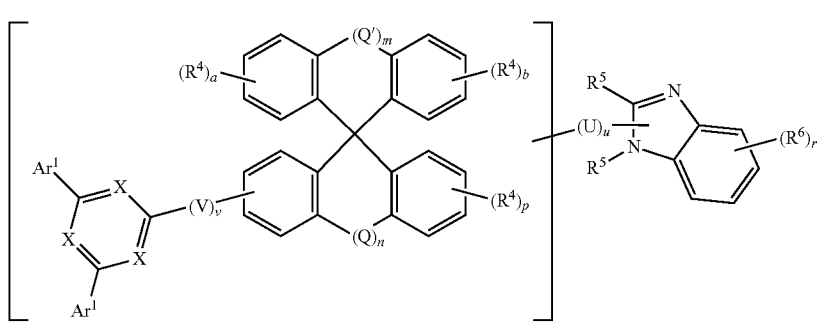

where the above definitions apply to the symbols and indices used and their preferred embodiments also represent preferred embodiments of the compound of the formula (4).

Preference is furthermore given to a compound of the general formula (5),

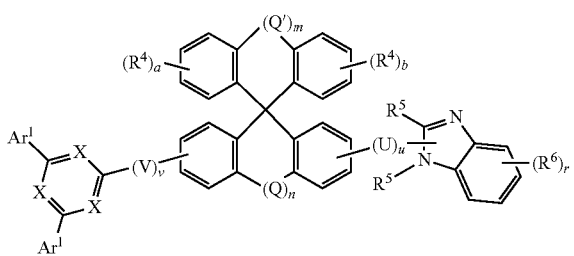

where the above definitions apply to the symbols and indices used and their preferred embodiments also represent preferred embodiments of the compound of the formula (5).

Preference is furthermore given to a compound of the general formula (6),

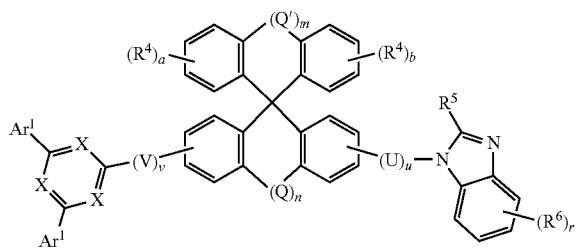

where the above definitions apply to the symbols and indices used and their preferred embodiments also represent preferred embodiments of the compound of the formula (6).

Preference is furthermore given to a compound of the general formula (7),

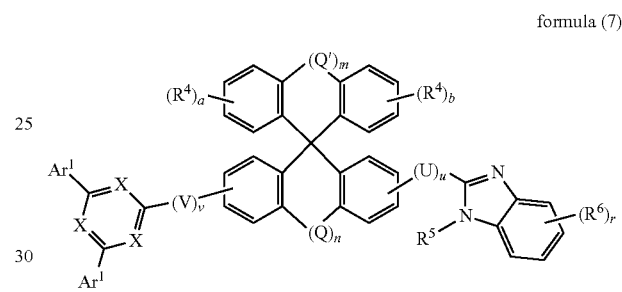

where the above definitions apply to the symbols and indices used and their preferred embodiments also represent preferred embodiments of the compound of the formula (7).

Great preference is given to a compound of the following general formulae (8) to (10), where the above definitions apply to the symbols and indices used and their preferred embodiments also represent preferred embodiments of the compound of the formulae (8) to (10),

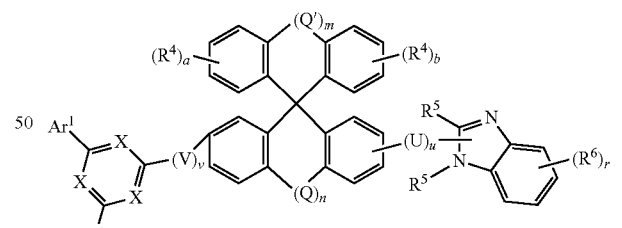

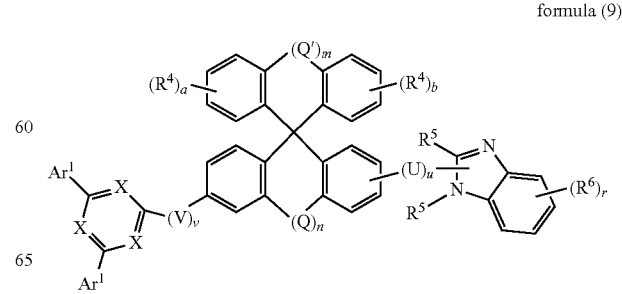

-continued formula (10)

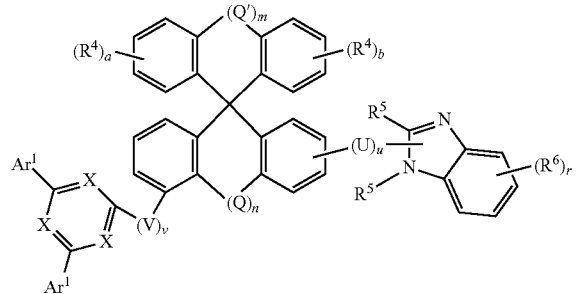

where, of the compounds of the general formulae (8) to (10), those of the formulae (8) and (10) are particularly preferred.

Particular preference is given to a compound of the following general formula (11), where the above definitions apply to the symbols and indices used and their preferred embodiments also represent preferred embodiments of the compound of the formula (11).

formula (11)

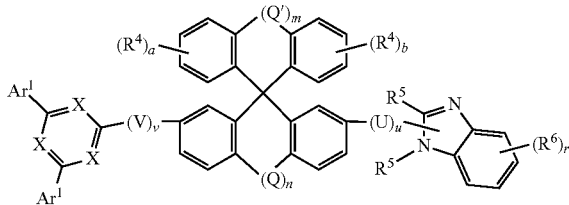

Very particular preference is given to a compound of the following general formulae (12) and (13), where the above definitions apply to the symbols and indices used and their preferred embodiments also represent preferred embodiments of the compound of the formulae (12) and (13).

formula (12)

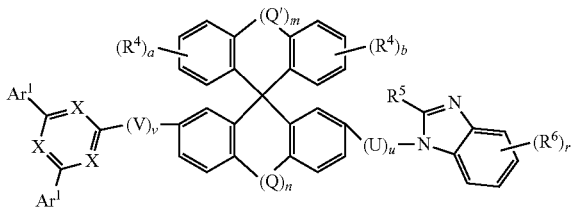

formula (13)

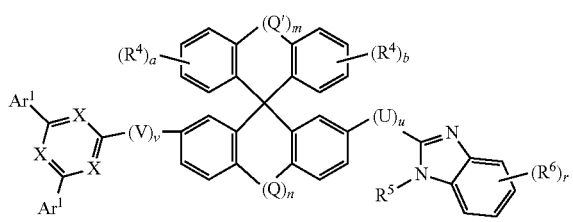

In a further, preferred embodiment, the compound has the general formula (14), formula (14)

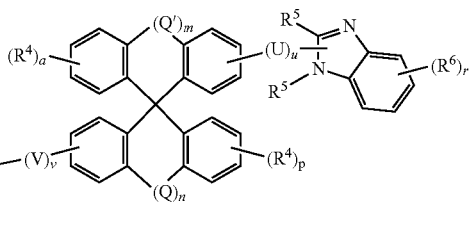

where the above definitions apply to the symbols and indices used and their preferred embodiments also represent preferred embodiments of the compound of the formula (14).

Preference is furthermore given to a compound of the general formula (15), formula (15)

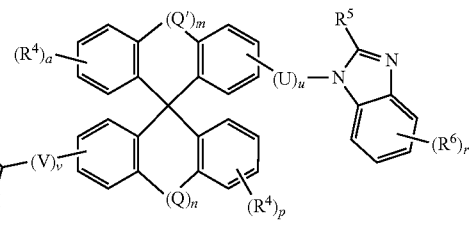

where the above definitions apply to the symbols and indices used and their preferred embodiments also represent preferred embodiments of the compound of the formula (15).

Preference is furthermore given to a compound of the general formula (16), formula (16)

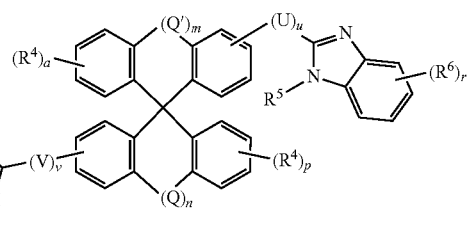

where the above definitions apply to the symbols and indices used and their preferred embodiments also represent preferred embodiments of the compound of the formula (16).

Great preference is given to a compound of the following general formulae (17) to (19), where the above definitions apply to the symbols and indices used and their preferred embodiments also represent preferred embodiments of the compound of the formulae (17) to (19), formula (17)

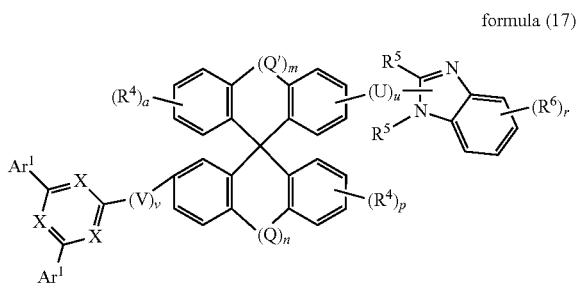

formula (18)

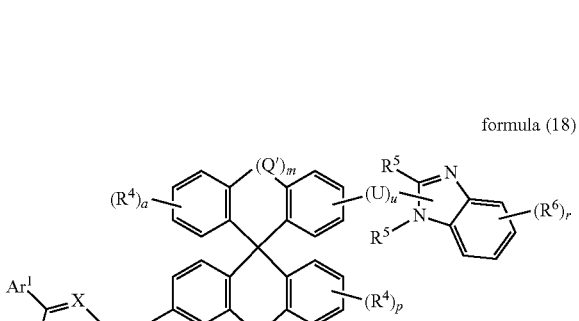

formula (19)

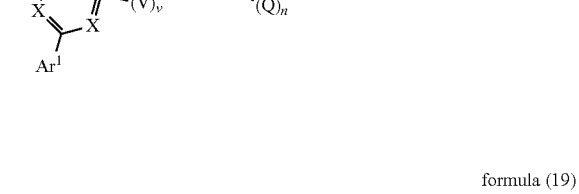

where, of the compounds of the general formulae (17) to (19), those of the formulae (17) and (19) are particularly preferred.

Particular preference is given to a compound of the following general formula (20), where the above definitions apply to the symbols and indices used and their preferred embodiments also represent preferred embodiments of the compound of the formula (20).

formula (20)

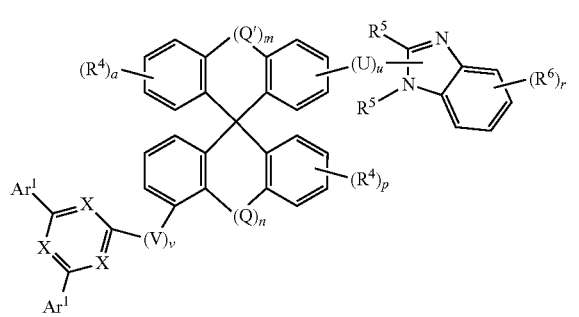

Very particular preference is given to a compound of the following general formulae (21) and (22), where the above definitions apply to the symbols and indices used and their preferred embodiments also represent preferred embodiments of the compound of the formulae (21) and (22).

formula (21)

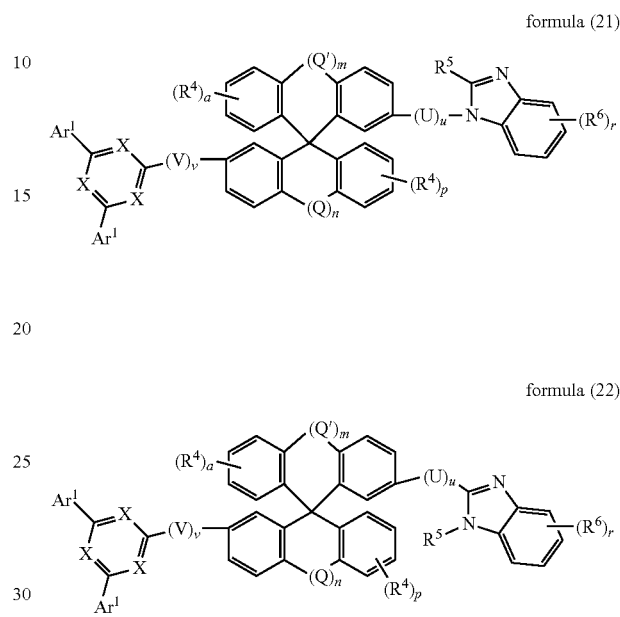

formula (22)

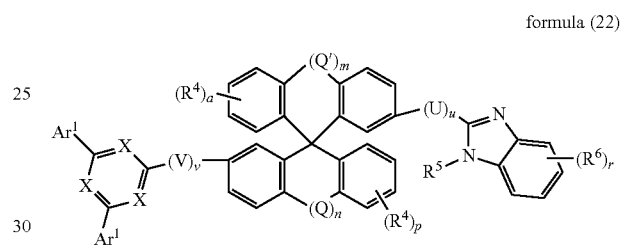

In a further, preferred embodiment, the compound has the general formula (23), formula (23)

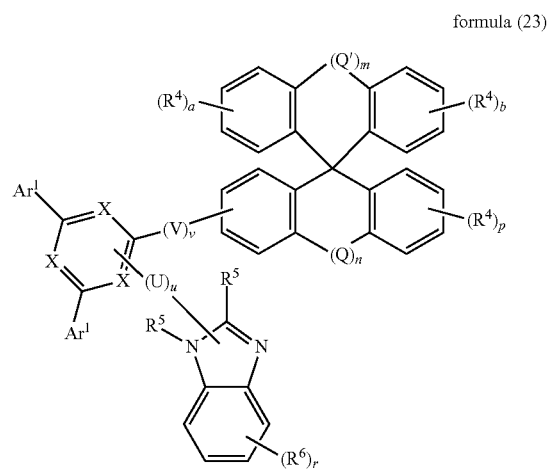

where the above definitions apply to the symbols and indices used and their preferred embodiments also represent preferred embodiments of the compound of the formula (23).

Preference is furthermore given to a compound of the general formula (23a), formula (23a)

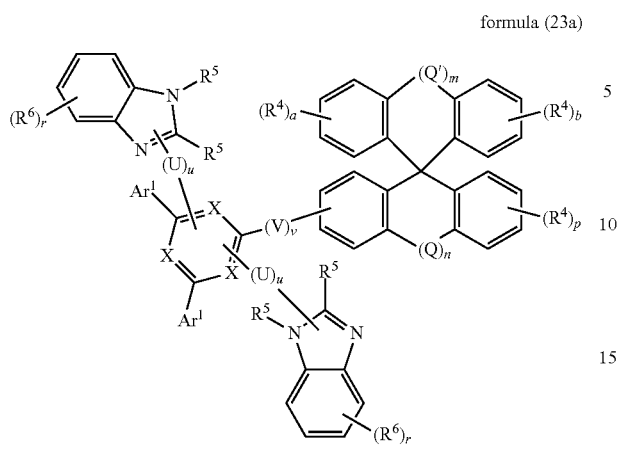

where the above definitions apply to the symbols and indices used and their preferred embodiments also represent preferred embodiments of the compound of the formula (23a).

Great preference is given here to a compound of the general formula (24), where the above definitions apply to the symbols and indices used and their preferred embodiments also represent preferred embodiments of the compound of the formula (24).

formula (24)

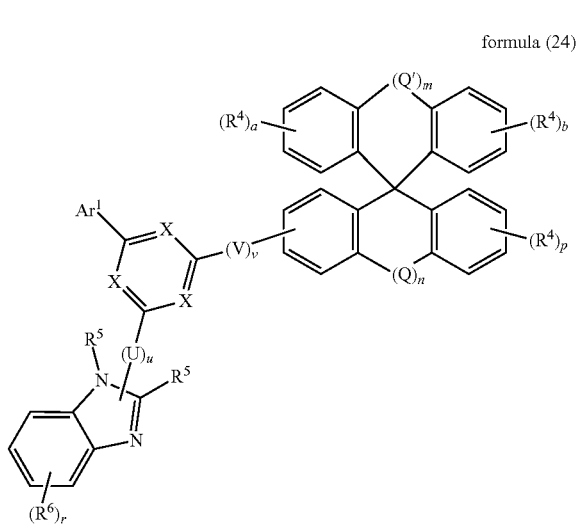

Great preference is furthermore given here to a compound of the general formula (24a), where the above definitions apply to the symbols and indices used and their preferred embodiments also represent preferred embodiments of the compound of the formula (24a).

formula (24a)

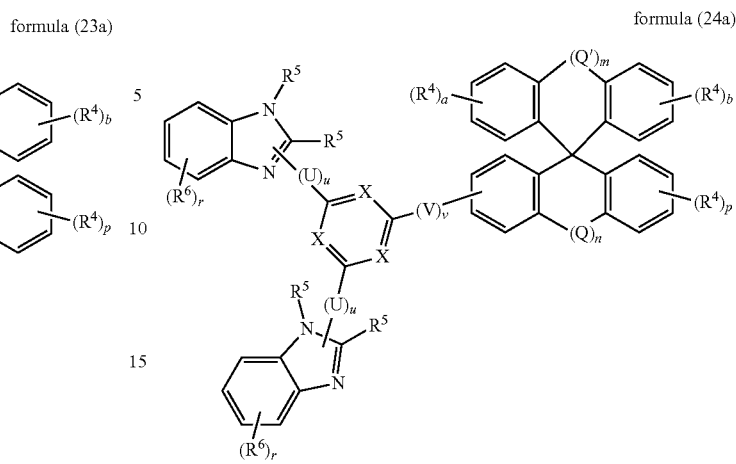

Particular preference is given here to a compound of the general formulae (25) and (26), where the above definitions apply to the symbols and indices used and their preferred embodiments also represent preferred embodiments of the compound of the formulae (25) and (26).

formula (25)

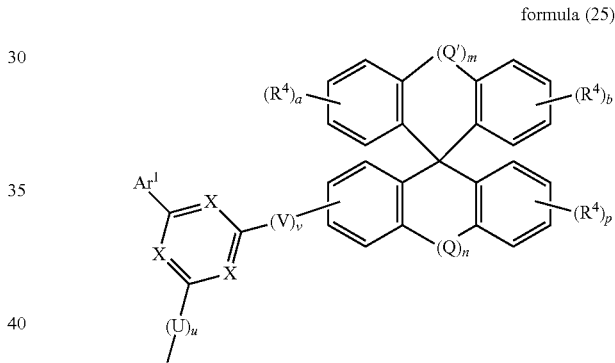

formula (26)

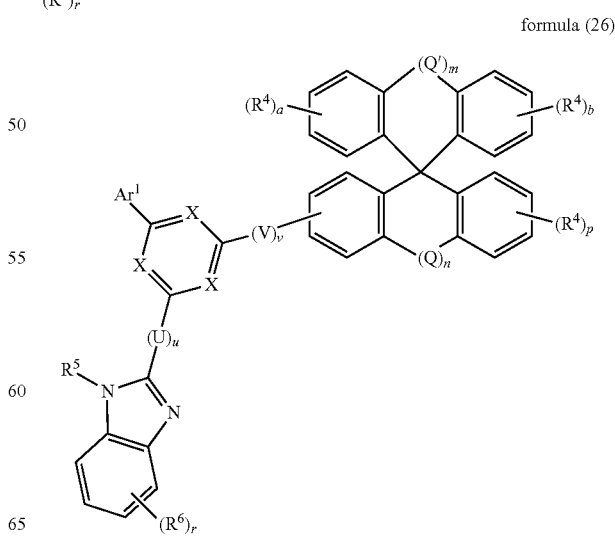

Very particular preference is given here to a compound of the general formulae (27) to (29), where the above definitions apply to the symbols and indices used and their preferred embodiments also represent preferred embodiments of the compound of the formulae (27) to (29).

formula (27)
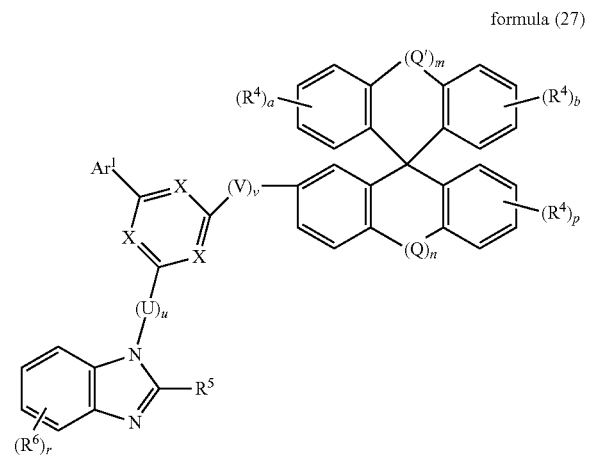

formula (28)
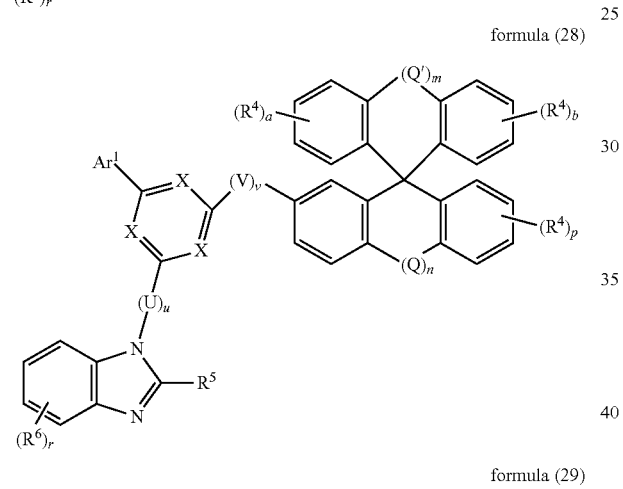

formula (29)
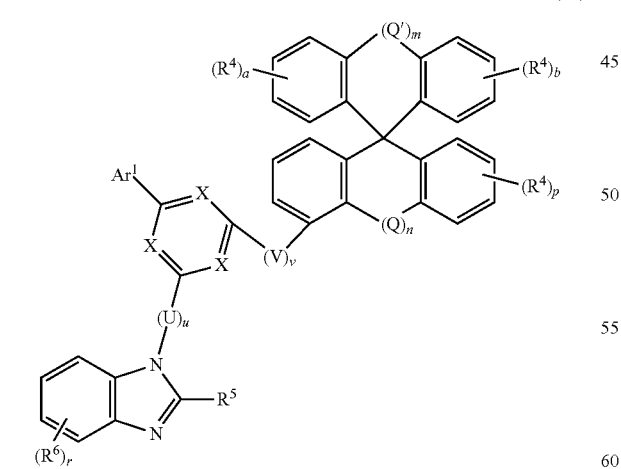

Very particular preference is furthermore given here to a compound of the general formulae (30) to (32), where the above definitions apply to the symbols and indices used and their preferred embodiments also represent preferred embodiments of the compound of the formulae (30) to (32).

formula (30)
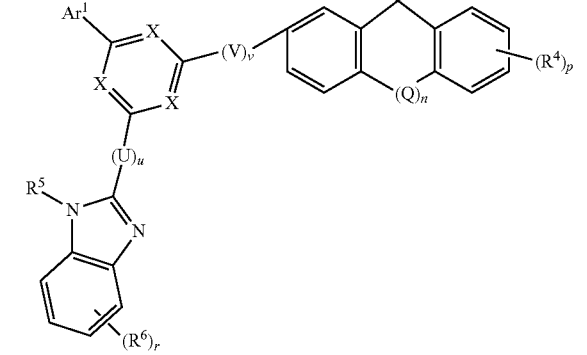

formula (31)
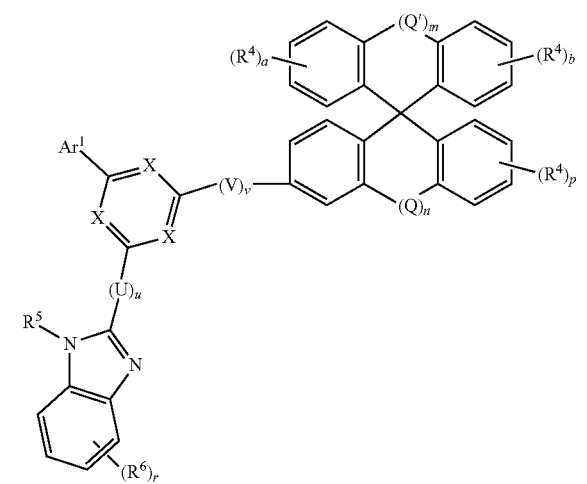

formula (32)
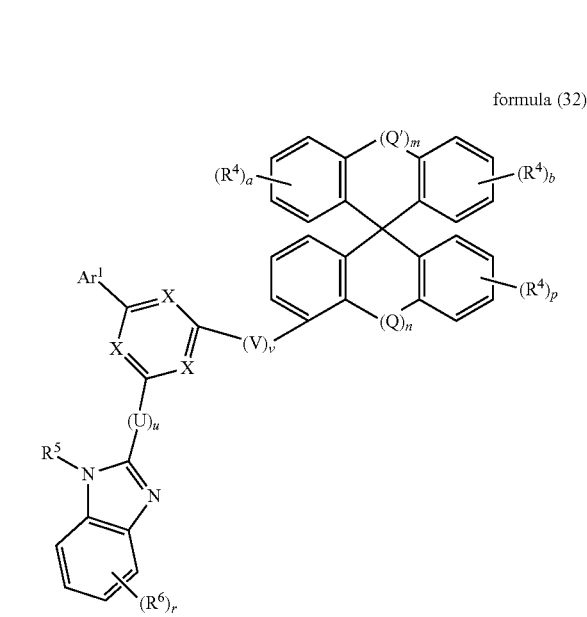

In a further, preferred embodiment, the present invention relates to a compound of the general formula (33),

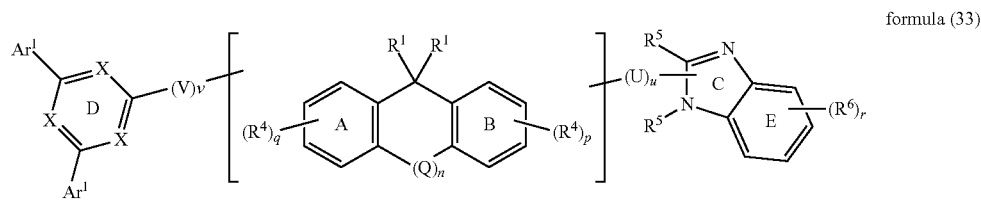

formula (33)

where the indices and symbols and their preferred embodiments are defined as indicated above.

According to formula (1), the ring D may, for example, be bonded to the ring A via V, whereas the ring C can be bonded to any desired other site via U.

It is preferred if the ring D is covalently bonded to one of the rings A, B, C or E indicated via V and if the ring C is covalently bonded to one of the rings A, B or D indicated via U, where at least one of the two rings C and D is covalently bonded to one of the rings A or B via the divalent group U or V respectively.

Preference is furthermore given to a compound of the general formula (34),

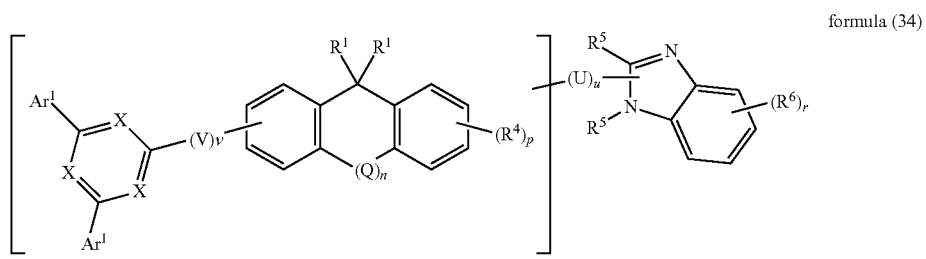

formula (34)

where the above definitions apply to the symbols and indices used and their preferred embodiments also represent preferred embodiments of the compound of the formula (34).

Preference is furthermore given to a compound of the general formula (35), formula (35)

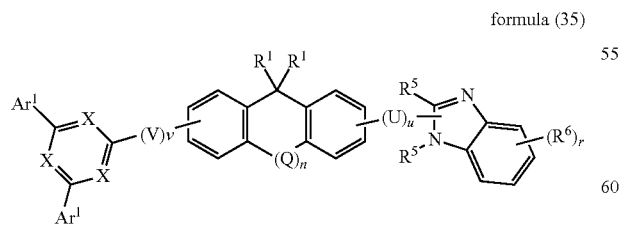

where the above definitions apply to the symbols and indices used and their preferred embodiments also represent preferred embodiments of the compound of the formula (35).

Preference is furthermore given to a compound of the general formula (36),

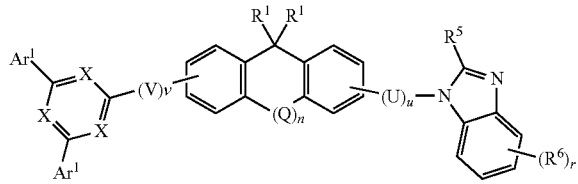

formula (36)

where the above definitions apply to the symbols and indices used and their preferred embodiments also represent preferred embodiments of the compound of the formula (36).

Preference is furthermore given to a compound of the general formula (37),

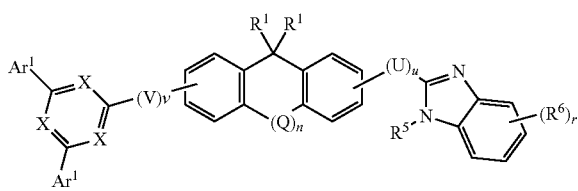

formula (37)

where the above definitions apply to the symbols and indices used and their preferred embodiments also represent preferred embodiments of the compound of the formula (37).

Great preference is given to a compound of the following general formulae (38) to (40), where the above definitions apply to the symbols and indices used and their preferred embodiments also represent preferred embodiments of the compound of the formulae (38) to (40),

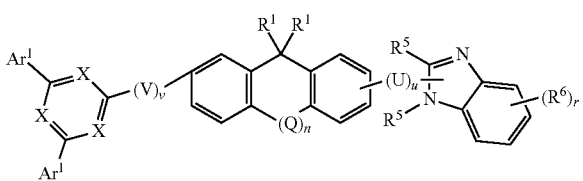

formula (38)

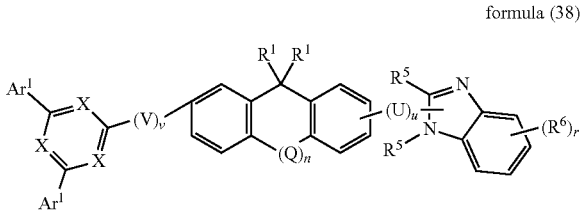

formula (39)

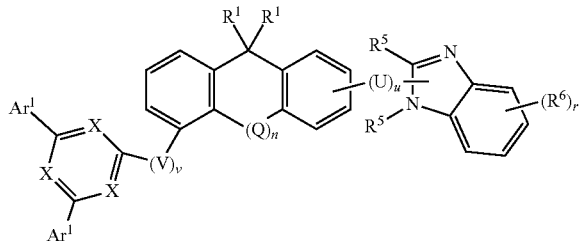

formula (40)

where, of the compounds of the general formulae (38) to (40), those of the formulae (38) and (40) are particularly preferred.

Particular preference is given to a compound of the following general formula (41), where the above definitions apply to the symbols and indices used and their preferred embodiments also represent preferred embodiments of the compound of the formula (41).

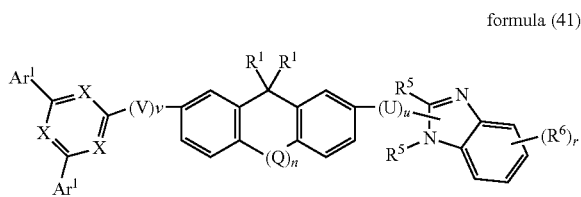

formula (41)

Very particular preference is given to a compound of the following general formulae (42) and (43), where the above definitions apply to the symbols and indices used and their preferred embodiments also represent preferred embodiments of the compound of the formulae (42) and (43).

formula (42)

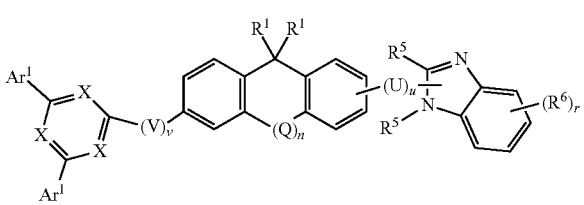

formula (43)

In a further, preferred embodiment, the compound has the general formula (44),

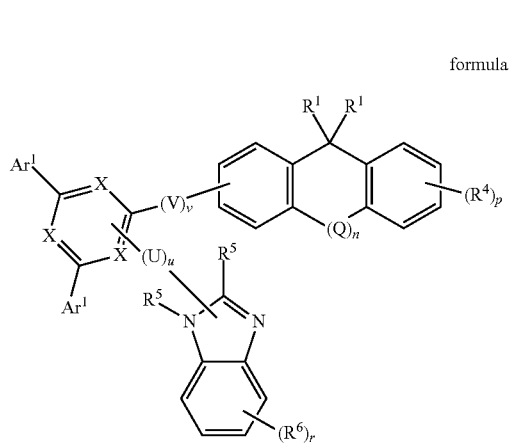

formula (44)

where the above definitions apply to the symbols and indices used and their preferred embodiments also represent preferred embodiments of the compound of the formula (44).

Preference is furthermore given to a compound of the general formula (44a),

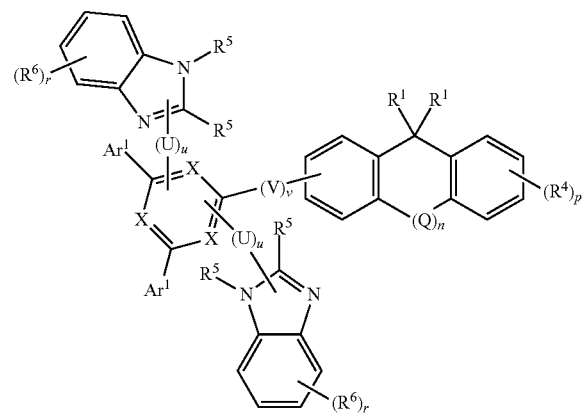

formula (44a)

where the above definitions apply to the symbols and indices used and their preferred embodiments also represent preferred embodiments of the compound of the formula (44a).

Great preference is given here to a compound of the general formula (45), where the above definitions apply to the symbols and indices used and their preferred embodiments also represent preferred embodiments of the compound of the formula (45).

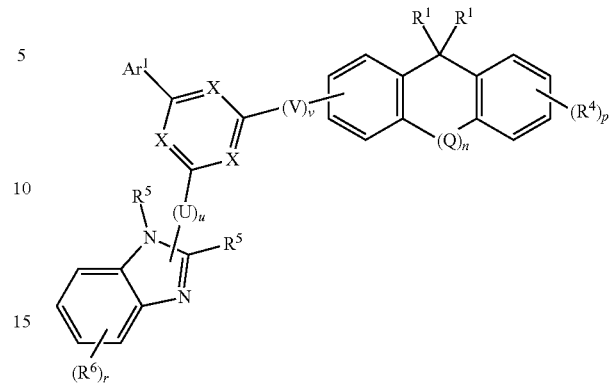

formula (45)

Great preference is furthermore given here to a compound of the general formula (45a), where the above definitions apply to the symbols and indices used and their preferred embodiments also represent preferred embodiments of the compound of the formula (45a).

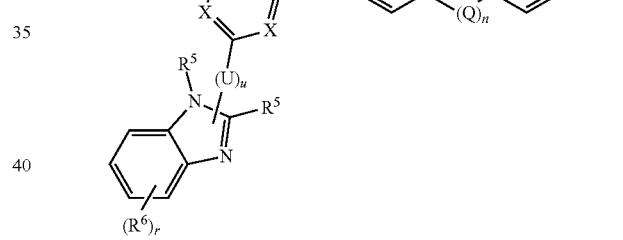

formula (45a)

Particular preference is given here to a compound of the general formulae (46) and (47), where the above definitions apply to the symbols and indices used and their preferred embodiments also represent preferred embodiments of the compound of the formulae (46) and (47).

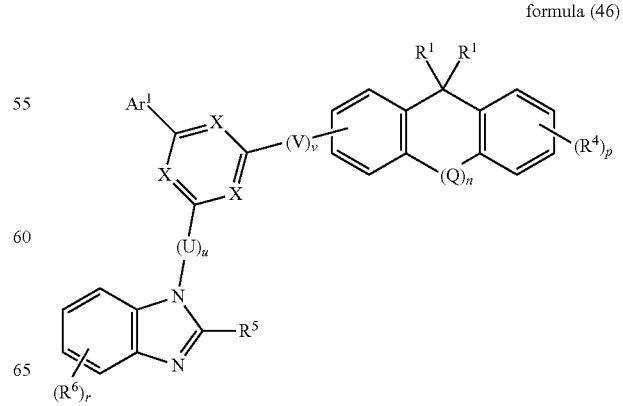

formula (46)

formula (47)

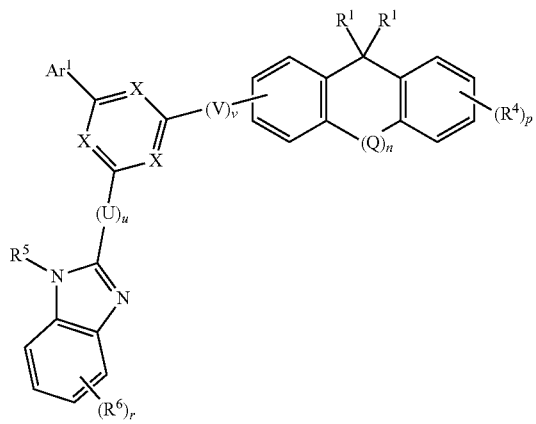

formula (50)

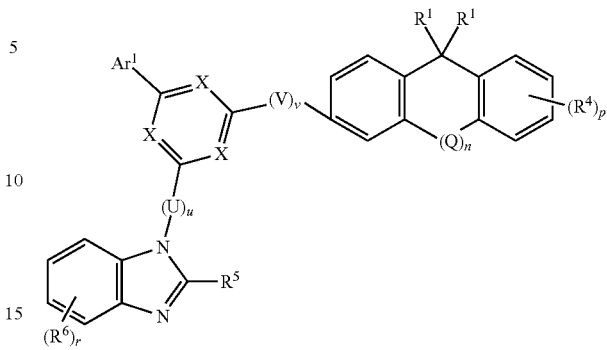

Very particular preference is given here to a compound of the general formulae (48) to (51), where the above definitions apply to the symbols and indices used and their preferred embodiments also represent preferred embodiments of the compound of the formulae (48) to (51).

formula (51)

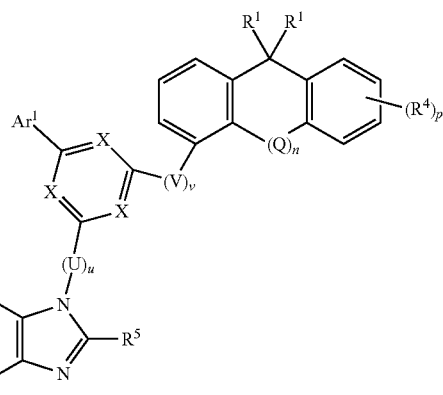

formula (48)

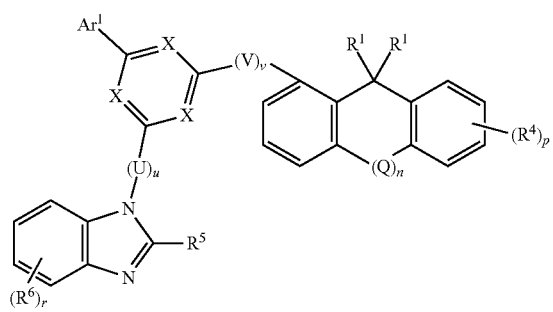

Very particular preference is furthermore given here to a compound of the general formulae (52) to (55), where the above definitions apply to the symbols and indices used and their preferred embodiments also represent preferred embodiments of the compound of the formulae (52) to (55).

formula (49)

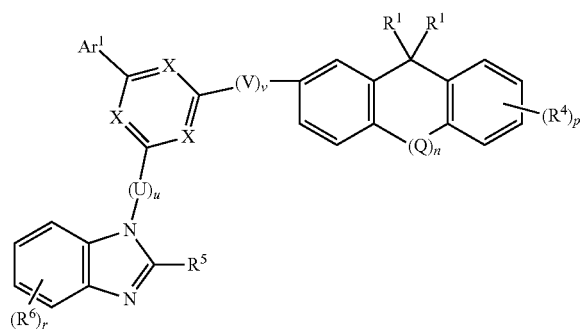

formula (52)

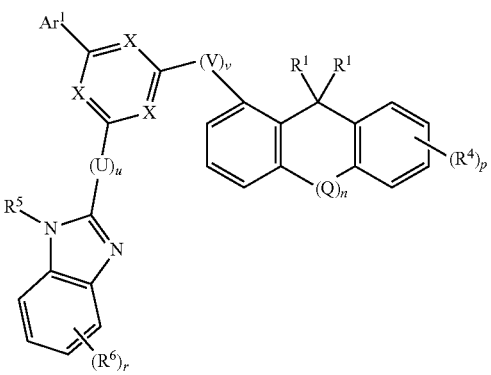

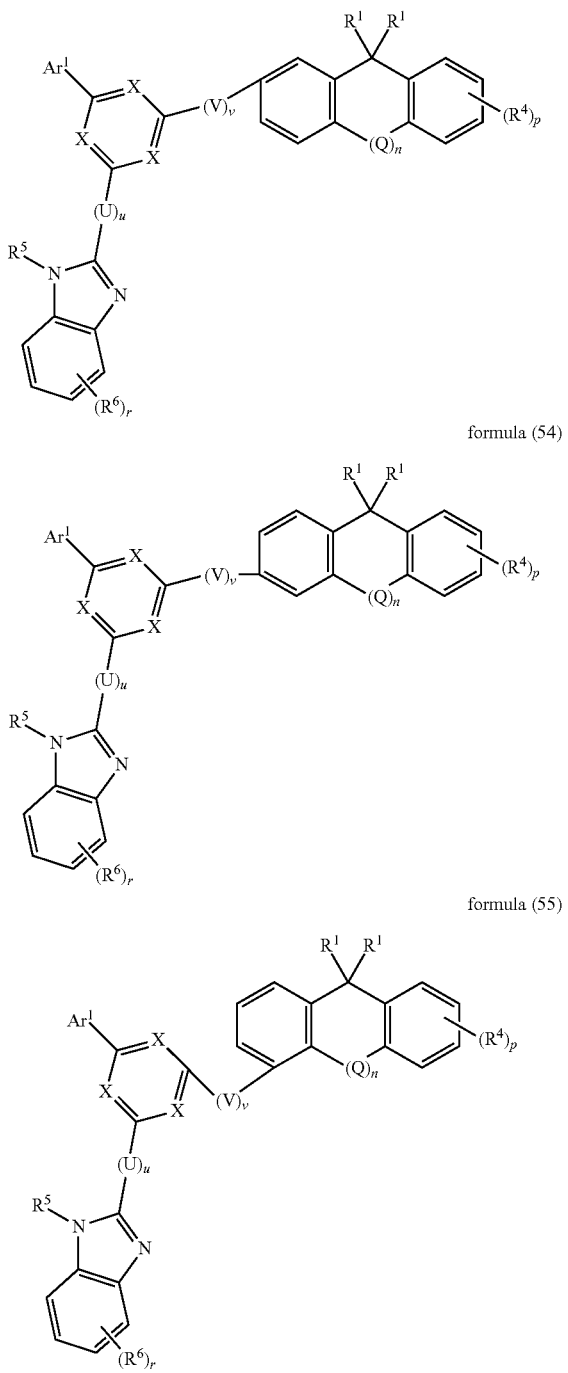

formula (53)

formula (54)

formula (55)

It is especially preferred if either n or m in the compounds of the above-mentioned formulae is equal to 0, and it is even more preferred if both n and m are equal to 0.

It is most preferred for the purposes of the present invention if a, b, q and p are equal to 0 and u and v, independently of one another, are either 0 or 1, where, if v is equal to 1, the group V is a phenylene group and, if u is equal to 1, the group U is a phenylene group.

It is furthermore preferred if the radical $R^1$ is on each occurrence, identically or differently, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems.

It is very preferred if the radical $R^1$ is on each occurrence, identically or differently, a straight-chain alkyl group having 1 to 40 C atoms or a branched or cyclic alkyl group having 3 to 40 C atoms, each of which may be substituted by one or more radicals $R^2$, or an aromatic or heteroaromatic ring system having 5 to 60 aromatic ring atoms, which may in each case be substituted by one or more radicals $R^2$.

It is particularly preferred if the radical $R^1$ is on each occurrence, identically or differently, a straight-chain alkyl group having 1 to 40 C atoms, which may in each case be substituted by one or more radicals $R^2$, or an aromatic or heteroaromatic ring system having 5 to 60 aromatic ring atoms, which may in each case be substituted by one or more radicals $R^2$.

It is very particularly preferred if the radical $R^1$ is on each occurrence, identically or differently, a straight-chain alkyl group having 1 to 40 C atoms, where it is especially preferred if the radical $R^1$ is on each occurrence, identically or differently, a straight-chain alkyl group having 1 to 15 C atoms.

It is furthermore preferred if $R^5$ is on each occurrence, identically or differently, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems; where two or more adjacent substituents $R^5$ cannot form a mono- or polycyclic, aliphatic or aromatic ring system with one another.

It is very preferred if $R^5$ is on each occurrence, identically or differently, a straight-chain alkyl group having 1 to 40 C atoms or a branched or cyclic alkyl group having 3 to 40 C atoms, each of which may be substituted by one or more radicals $R^2$, or an aromatic or heteroaromatic ring system having 5 to 60 aromatic ring atoms, which may in each case be substituted by one or more radicals $R^2$, where two or more adjacent substituents $R^5$ cannot form a mono- or polycyclic, aliphatic or aromatic ring system with one another.

It is particularly preferred if $R^5$ is on each occurrence, identically or differently, a straight-chain alkyl group having 1 to 40 C atoms, which may in each case be substituted by one or more radicals $R^2$, or an aromatic or heteroaromatic ring system having 5 to 60 aromatic ring atoms, which may in each case be substituted by one or more radicals $R^2$, where two or more adjacent substituents $R^5$ cannot form a mono- or polycyclic, aliphatic or aromatic ring system with one another.

It is very particularly preferred if $R^5$ is on each occurrence, identically or differently, a straight-chain alkyl group having 1 to 40 C atoms or an aromatic ring system having 5 to 60 aromatic ring atoms, each of which may be substituted by one or more radicals $R^2$, where two or more adjacent substituents $R^5$ cannot form a mono- or polycyclic, aliphatic or aromatic ring system with one another. Very particularly preferred aromatic ring systems here are selected from the group consisting of the phenyl, biphenyl and terphenyl groups.

It is furthermore preferred if $Ar^1$ is on each occurrence, identically or differently, an aromatic or heteroaromatic ring system having 5 to 30 aromatic ring atoms, which may be substituted by one or more radicals $R^2$; two radicals $Ar^1$ here may also be linked to one another by a single bond or a bridge selected from $C(R^2)_2$, O and S; it is preferred if two radicals $Ar^1$ are not linked to one another.

Very preferred groups for $Ar^1$ are selected from the group consisting of the phenyl, biphenyl, terphenyl, quaterphenyl, dibenzofuranyl, dibenzothiophenyl, fluorenyl, benzimidazolyl, carbazolyl, indenocarbazolyl and indolocarbazolyl groups, where the groups may be substituted by one or more, identical or different radicals $R^2$, where the said phenyl groups are most preferred.

The formulation that two or more radicals may form a ring with one another is, for the purposes of the present application, intended to be taken to mean, inter alia, that the two radicals are linked to one another by a chemical bond. This is illustrated by the following scheme:

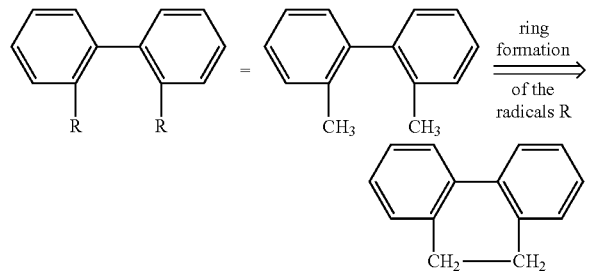

Furthermore, however, the above-mentioned formulation is also intended to be taken to mean that, in the case where one of the two radicals represents hydrogen, the second radical is bonded at the position to which the hydrogen atom was bonded, with formation of a ring. This is intended to be illustrated by the following scheme:

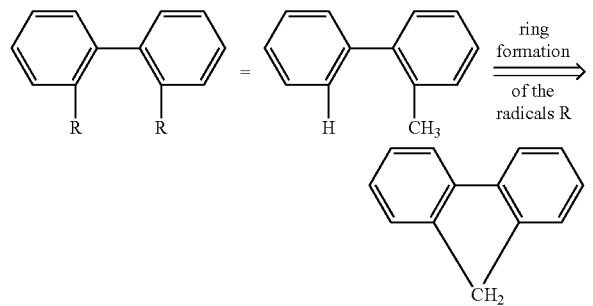

An aryl group in the sense of this invention contains at least 6 C atoms; a heteroaryl group in the sense of this invention contains at least 2 C atoms and at least 1 heteroatom, with the proviso that the sum of C atoms and heteroatoms is at least 5. The heteroatoms are preferably selected from N, O and S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, pyrene, quinoline, isoquinoline, etc.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethyihexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, npropoxy, i-propoxy, n-butoxy, i-butoxy, s-butoxy, t-butoxy, n-pentoxy, spentoxy, 2-methylbutoxy, n-hexoxy, cyclohexyloxy, n-heptoxy, cycloheptyloxy, n-octyloxy, cyclooctyloxy, 2-ethyihexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenyithio, cycloheptenylthio, octenylthio, cyclooctenylthio, ethynylthio, propynylthio, butynylthio, pentynylthio, hexynylthio, heptynylthio or octynylthio.

The compounds according to the invention can be prepared in accordance with Schemes 1 and 2. The corresponding monoboronic acids are commercially available and can be converted into the corresponding target molecules by Suzuki coupling.

Scheme 1

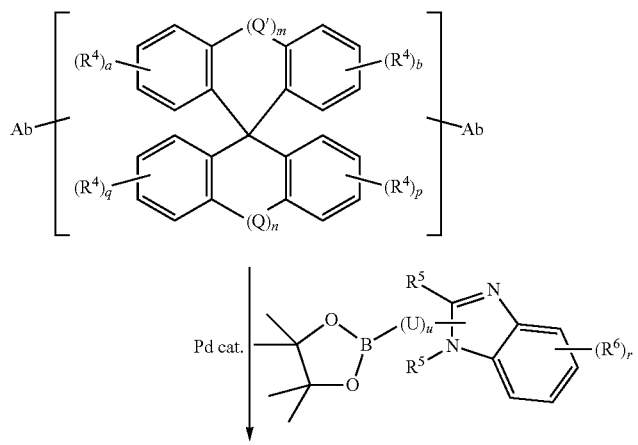

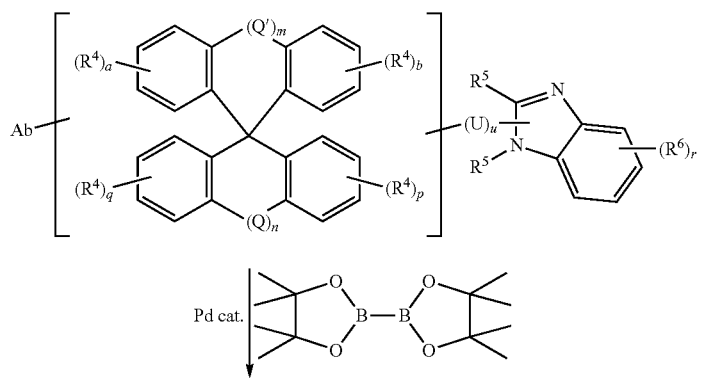

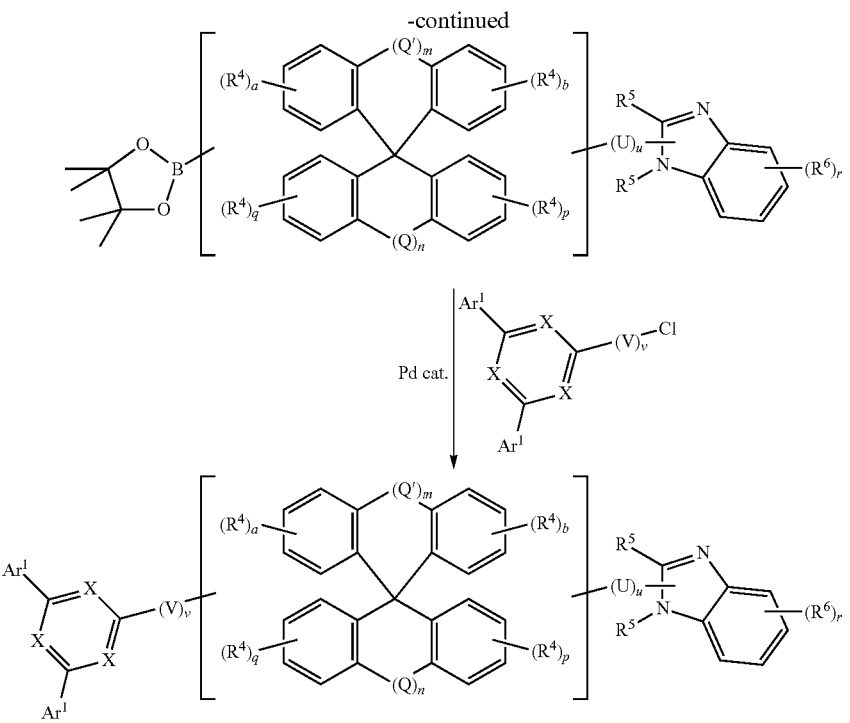

where Ab stands for a leaving group, which is preferably selected from Cl, Br, I and triflate; this is very preferably equal to Br. Besides boron pinacol esters, other esters or boronic acid itself can also be employed here. These are highly familiar to the person skilled in the art.

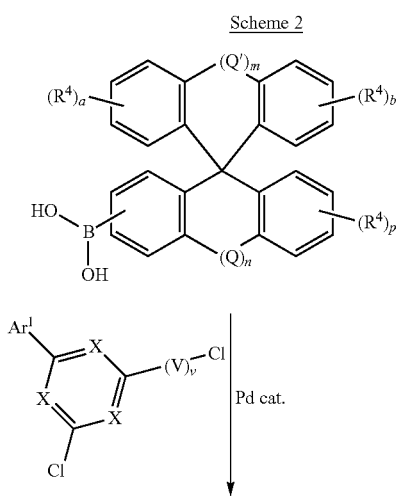

Scheme 2

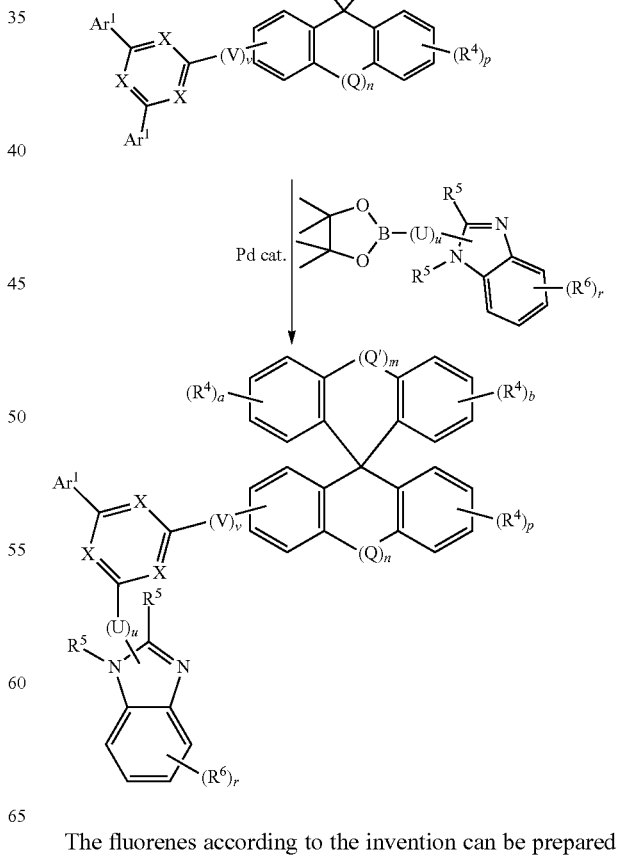

The fluorenes according to the invention can be prepared entirely analogously by Suzuki coupling. Other boron compounds can also be employed here. These are highly familiar to the person skilled in the art.

The general process shown for the synthesis of the compounds according to the invention is illustrative. The person skilled in the art will be able to develop alternative synthetic routes within the bounds of his general expert knowledge.

The following overview contains an illustrative depiction of compounds according to the invention which can be prepared by one of the processes described herein.

formula (E-1)

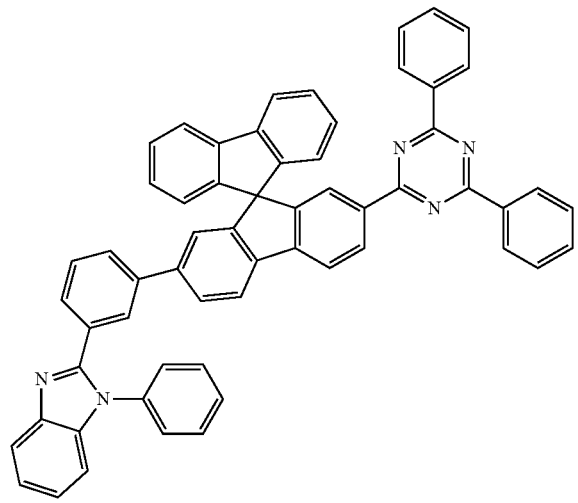

formula (E-2)

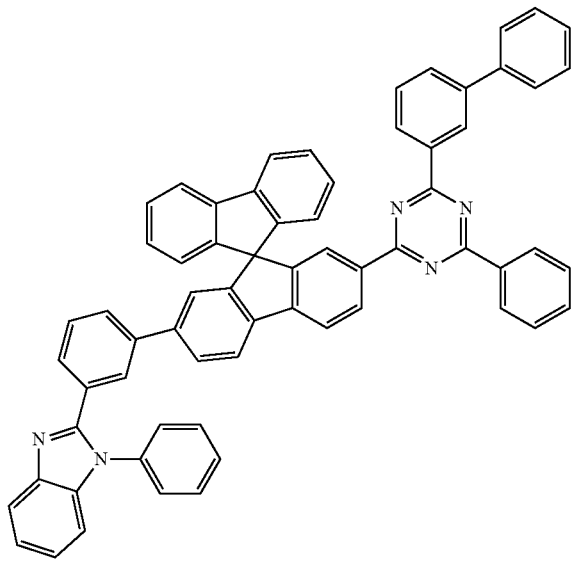

formula (E-3)

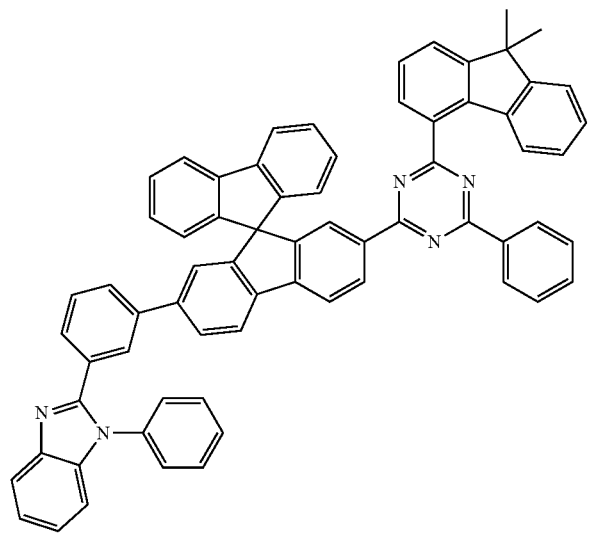

formula (E-4)

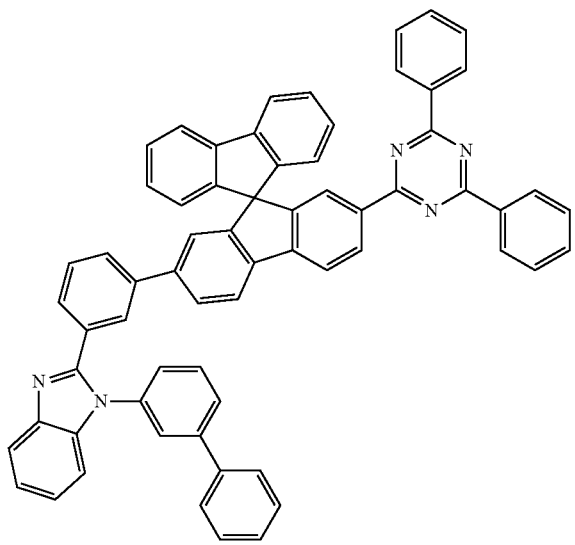

-continued
formula (E-5)
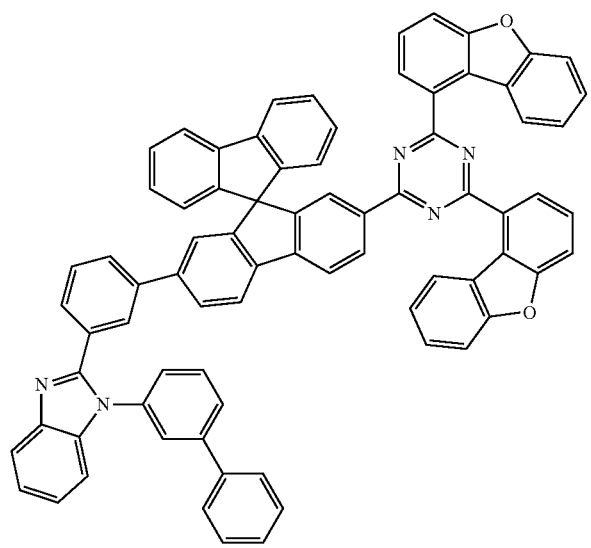
formula (E-6)
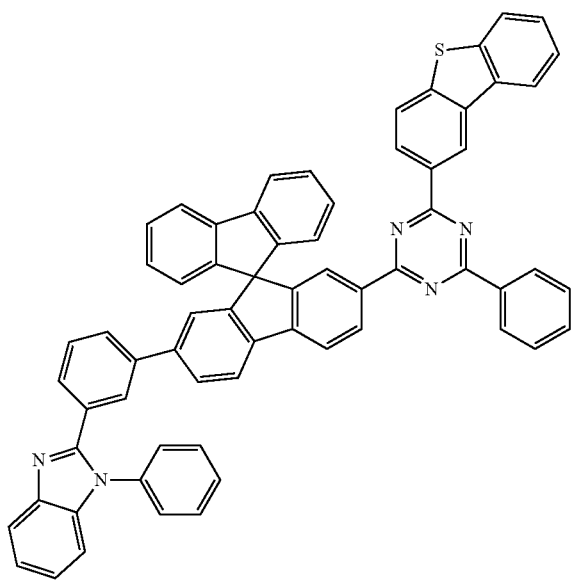
formula (E-7)
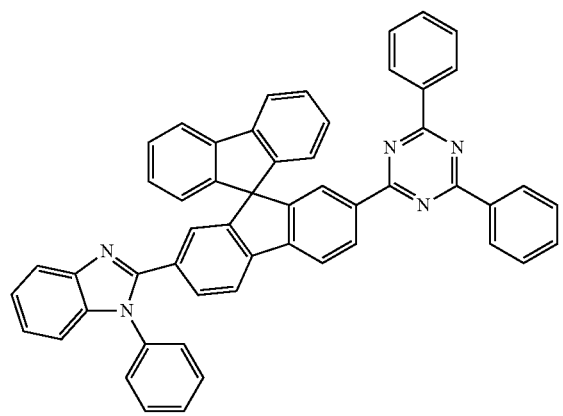
formula (E-8)
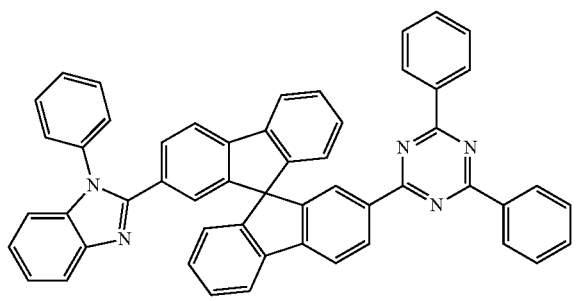
formula (E-9)
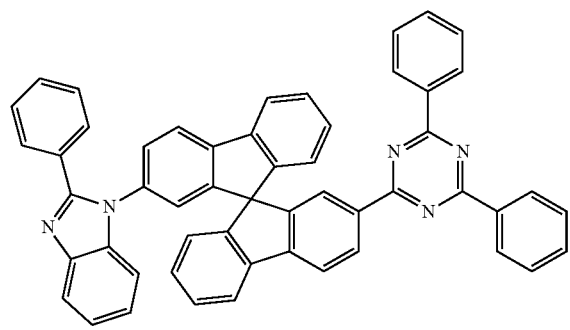
formula (E-10)
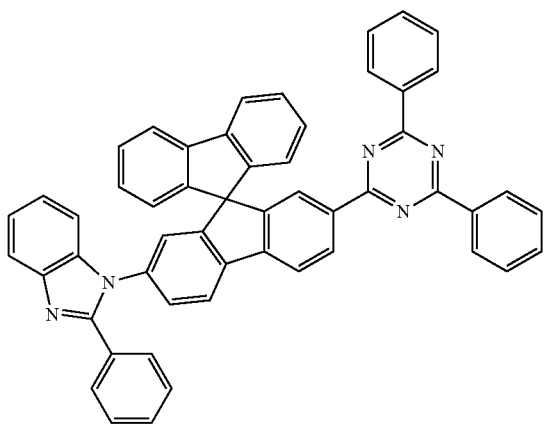

-continued
formula (E-11)
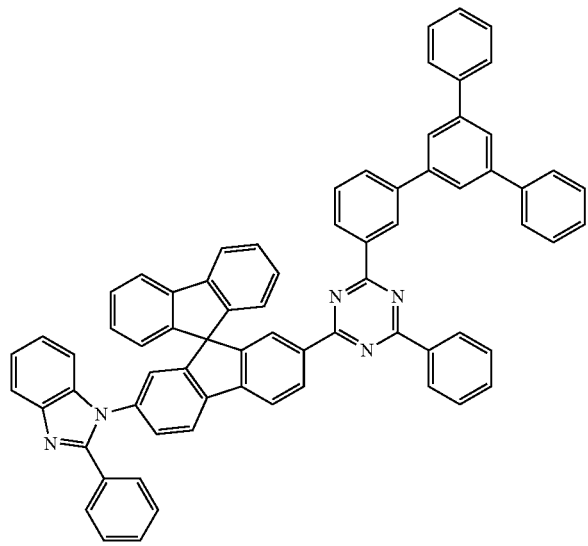
formula (E-12)
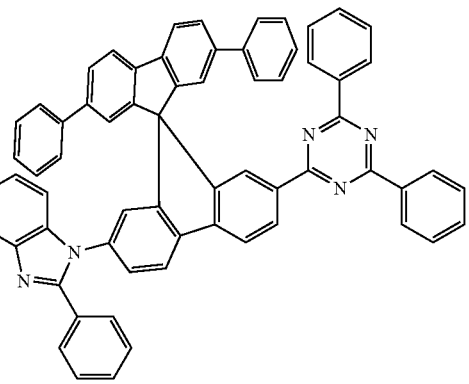
formula (E-13)
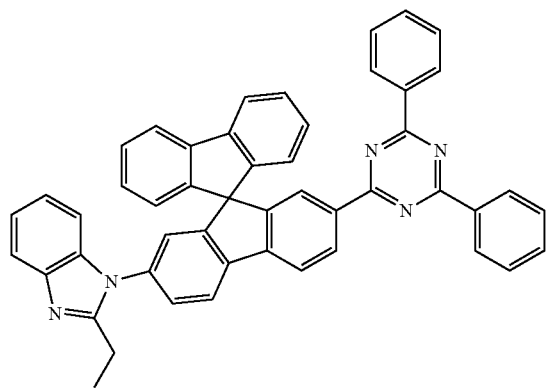
formula (E-14)
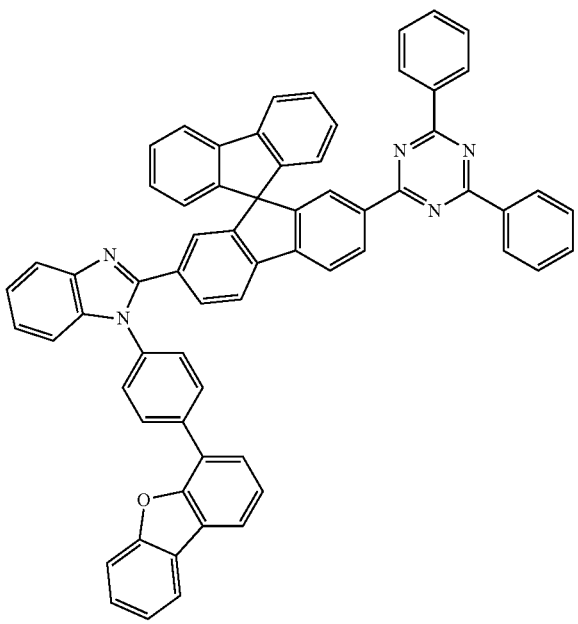

formula (E-15)
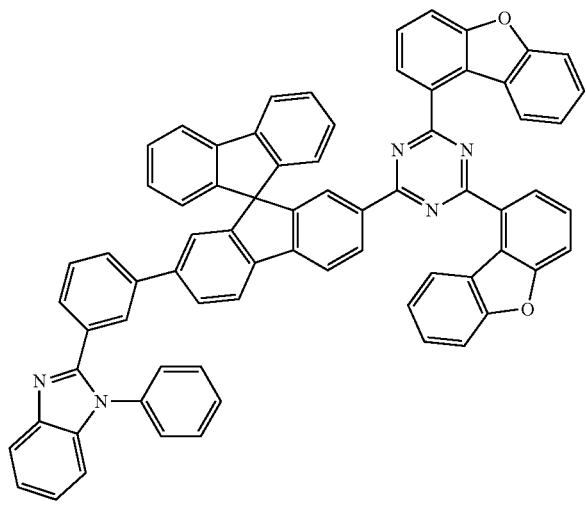
formula (E-16)
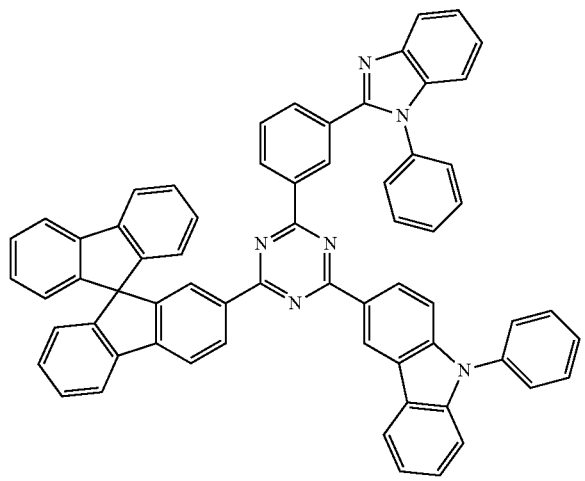
formula (E-17)
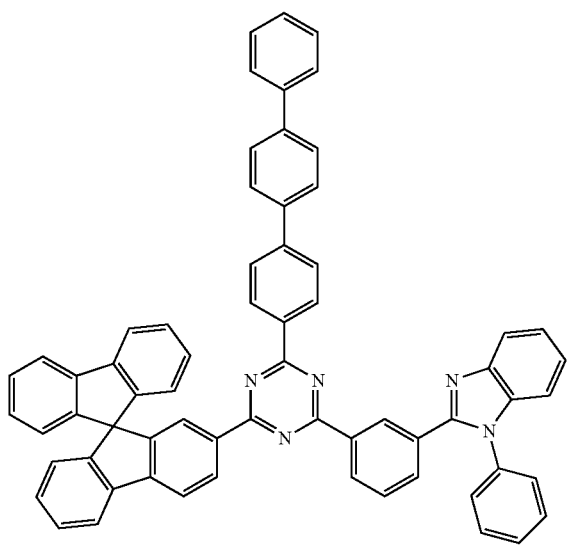
formula (E-18)
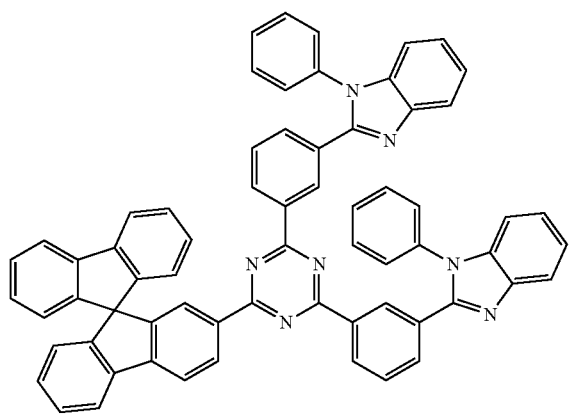

-continued
formula (E-19)
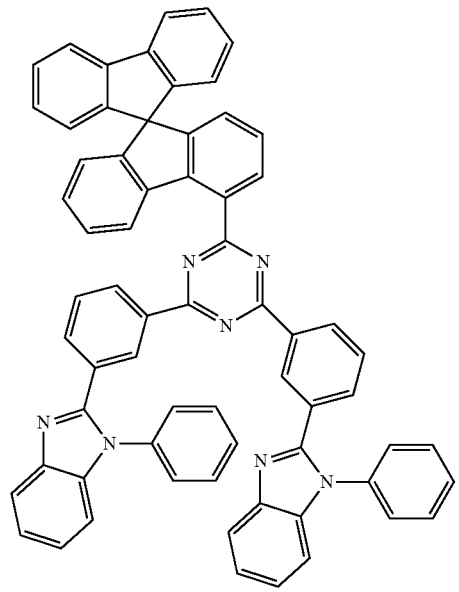
formula (E-20)
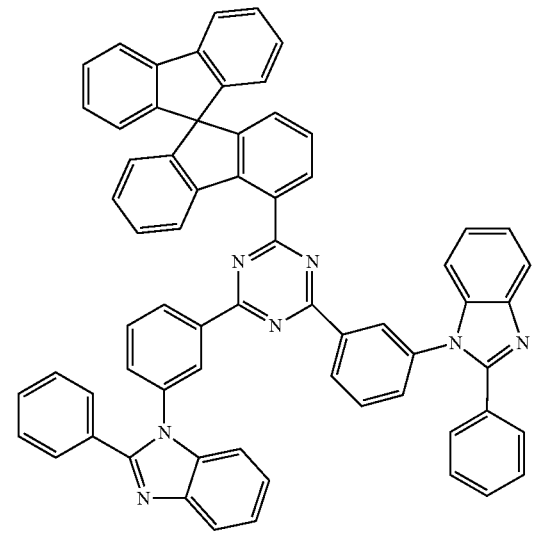
formula (E-21)
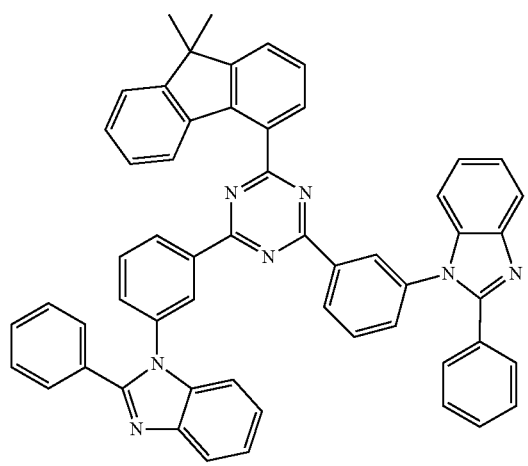
formula (E-22)
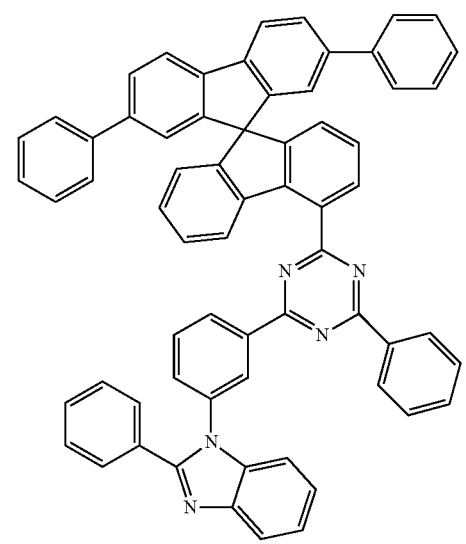

-continued
formula (E-23)
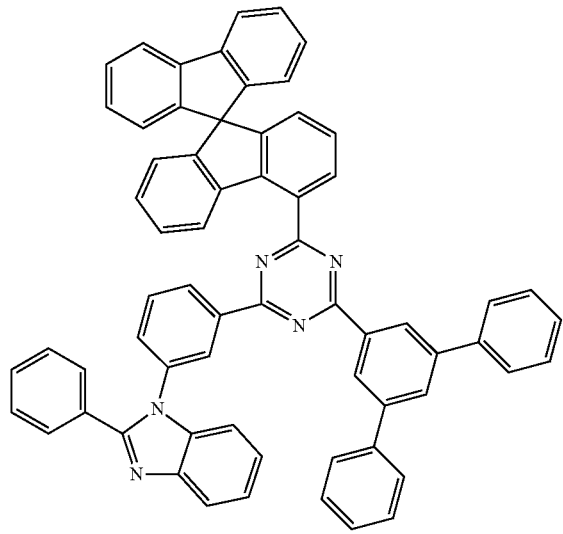
formula (E-24)
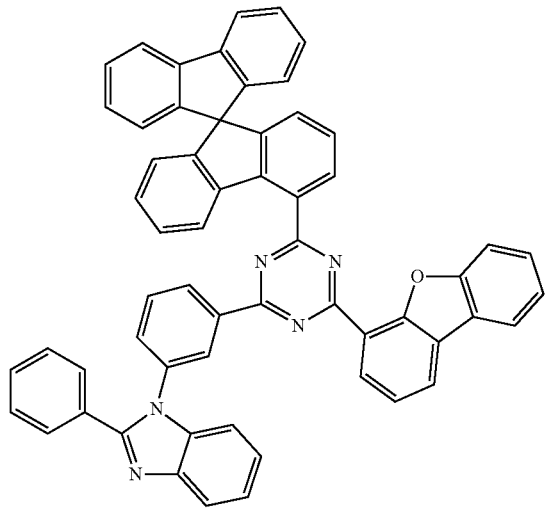
formula (E-25)
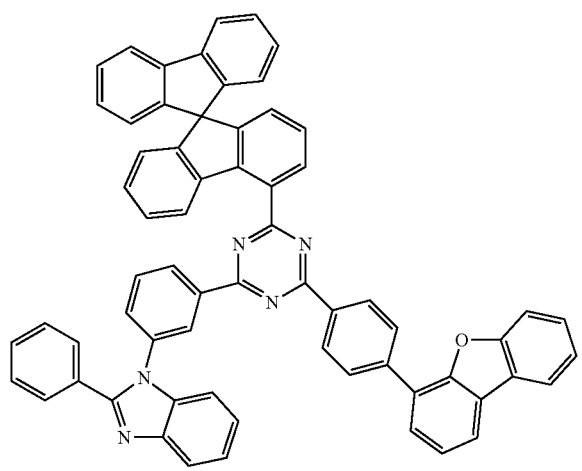
formula (E-26)
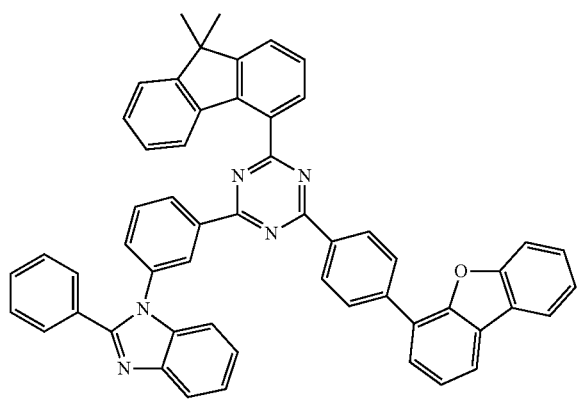
formula (E-27)
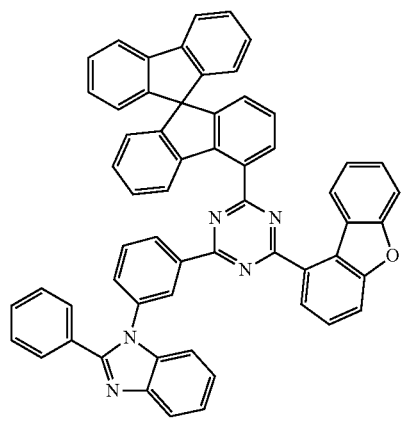
formula (E-28)
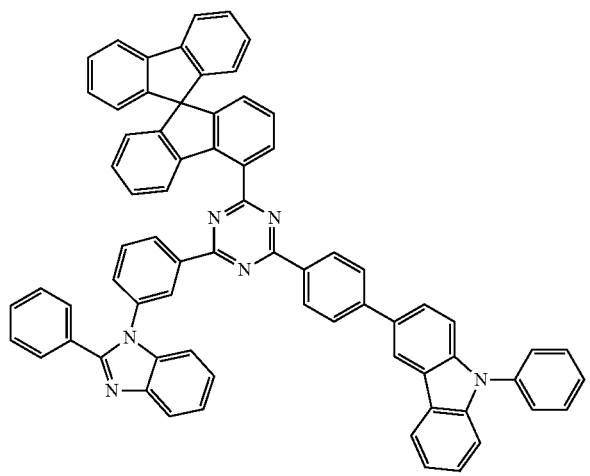

formula (E-29)
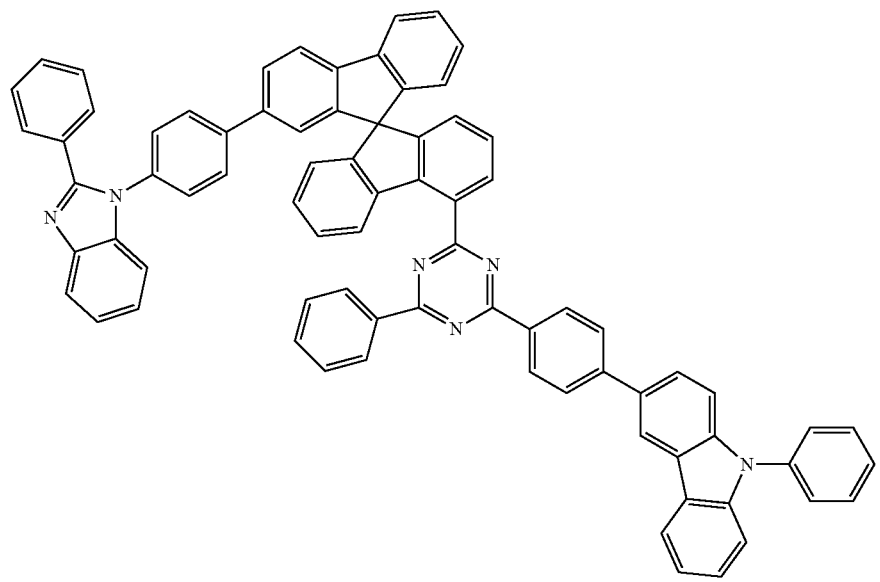
formula (E-30)
formula (E-31)
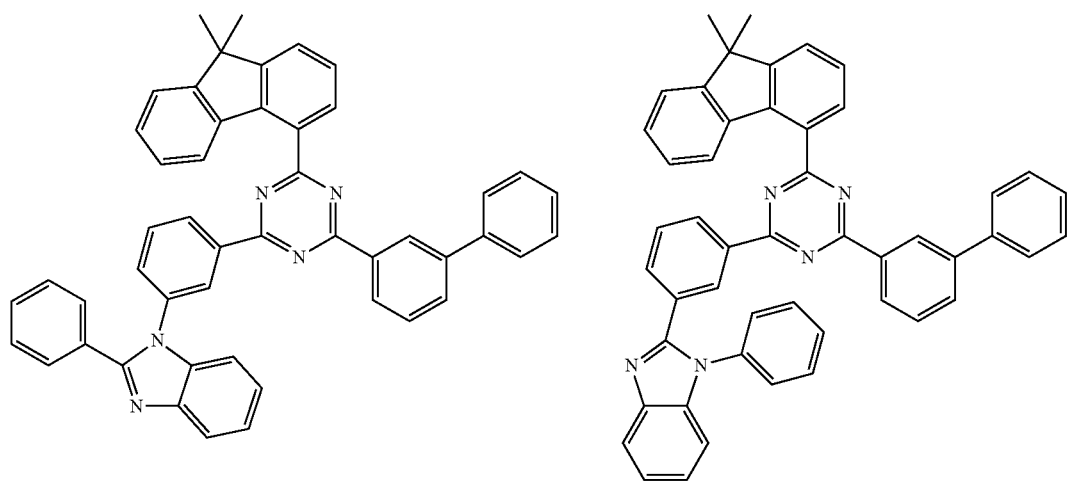
formula (E-32)
formula (E-33)
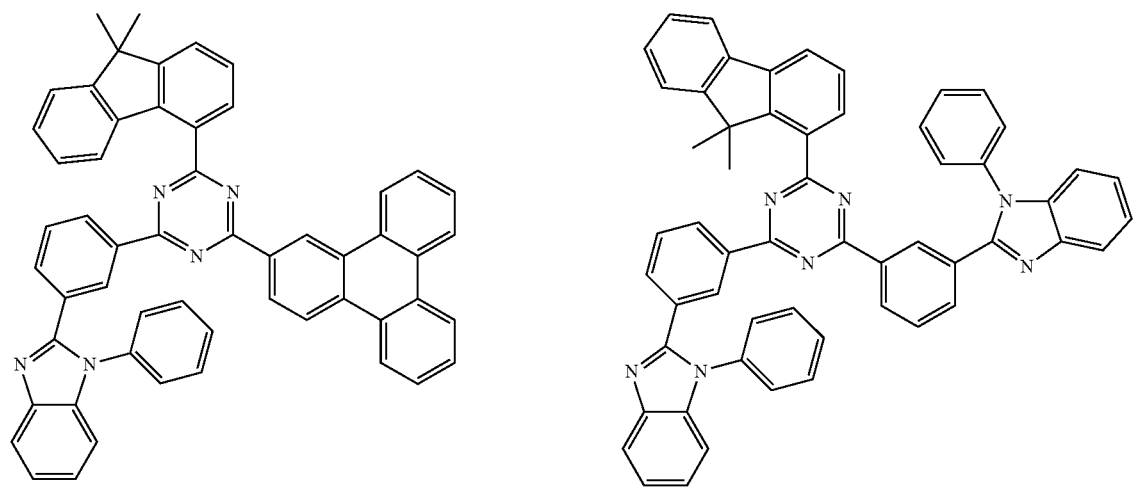

-continued
formula (E-34)
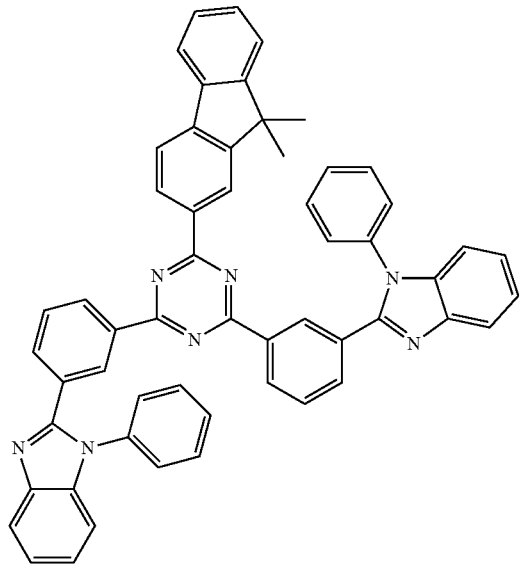
formula (E-35)
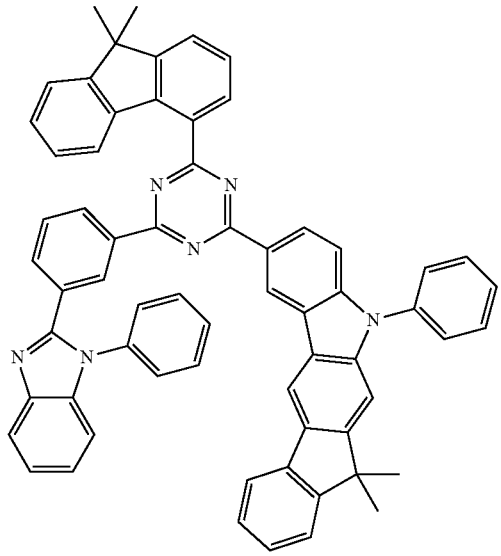
formula (E-36)
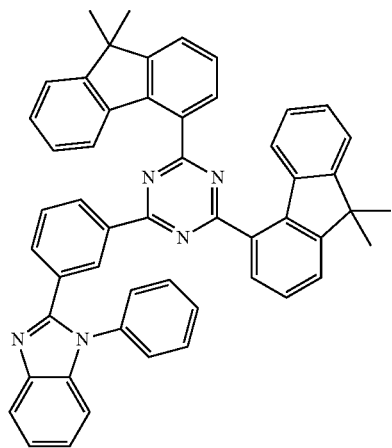
formula (E-37)
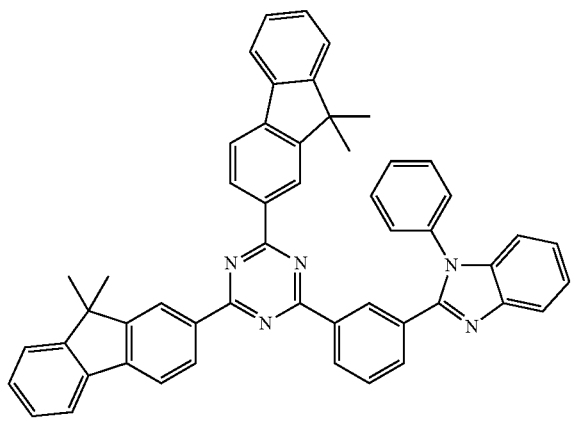
formula (E-38)
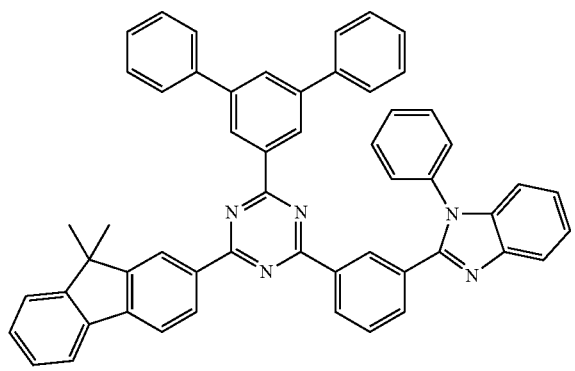
formula (E-39)
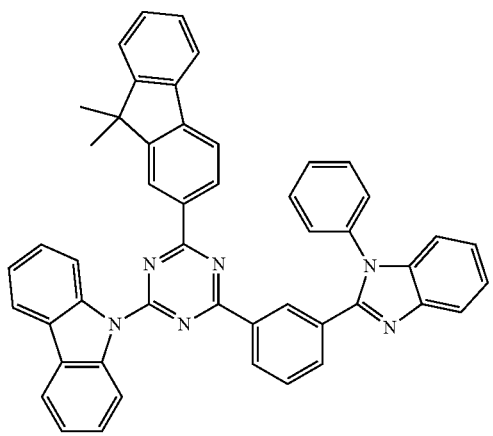

-continued
formula (E-40)
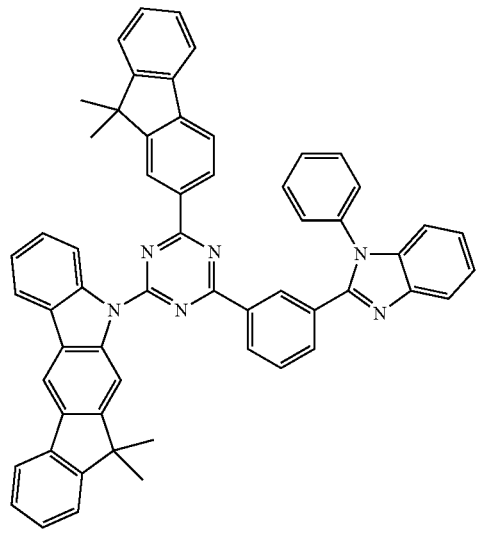
formula (E-41)
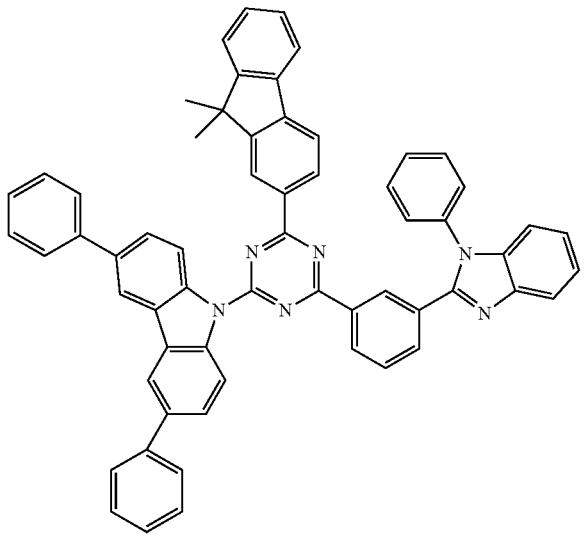
formula (E-42)
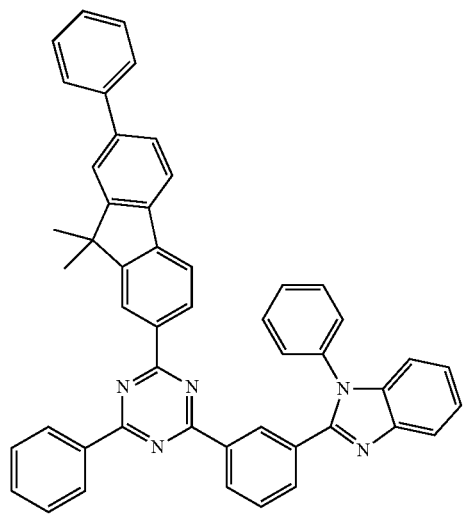
formula (E-43)
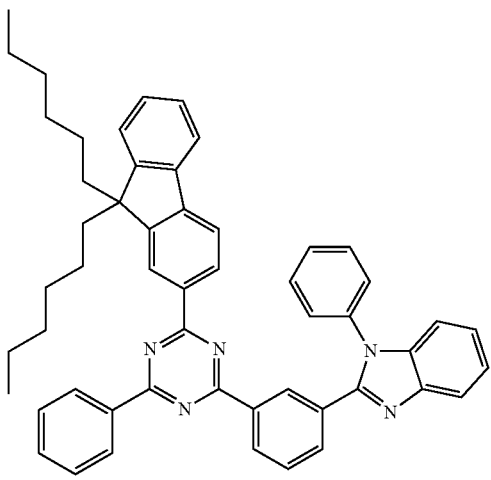
formula (E-44)
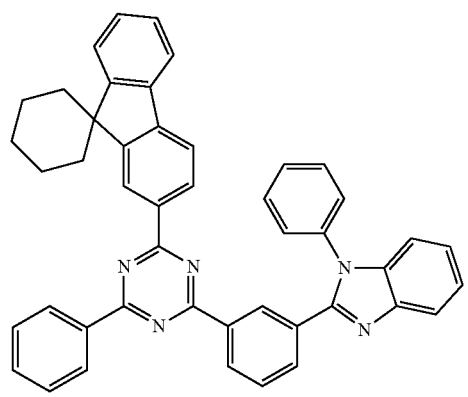
formula (E-45)
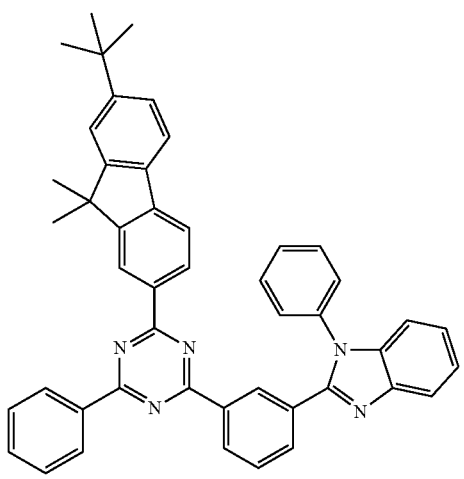

-continued
formula (E-46)
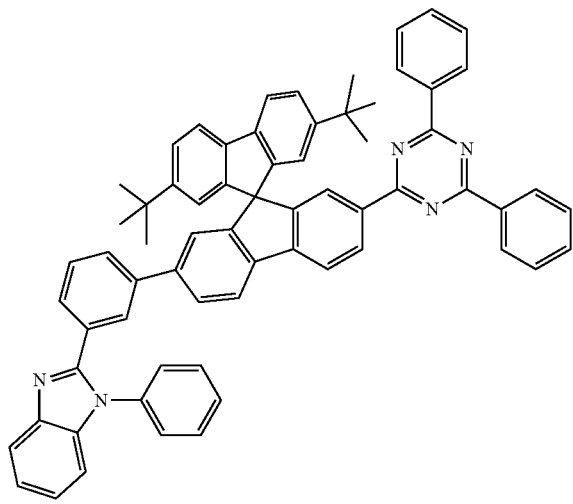
formula (E-47)
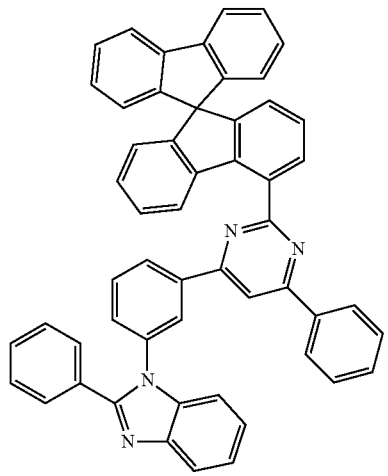
formula (E-48)
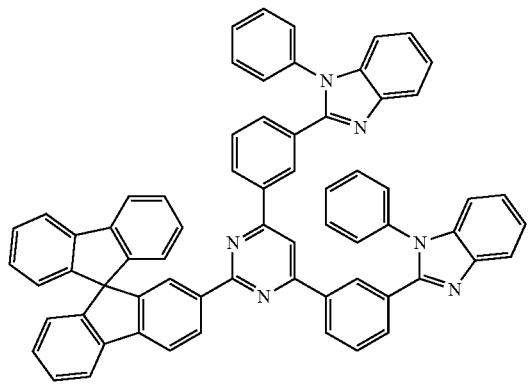
formula (E-49)
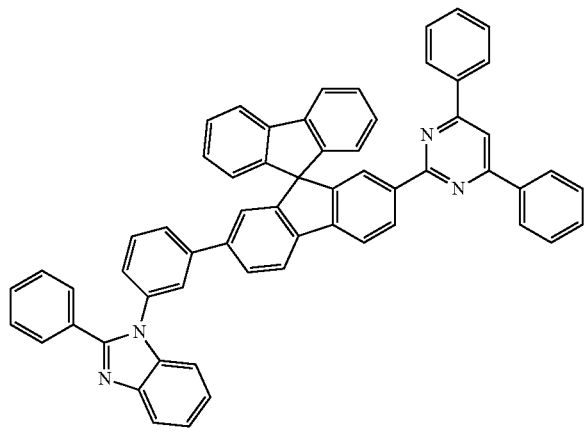
formula (E-50)
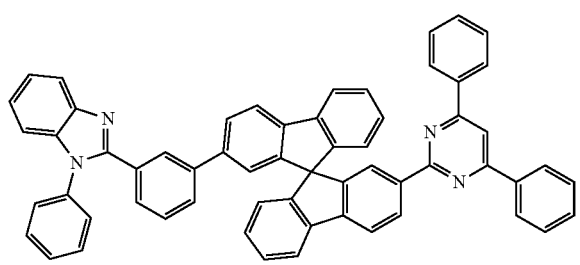
formula (E-51)
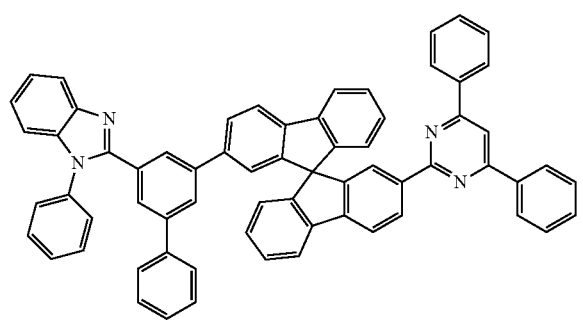
formula (E-52)
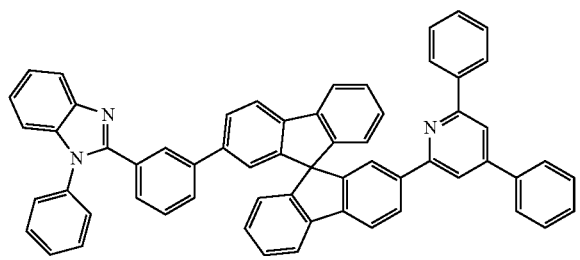
formula (E-53)
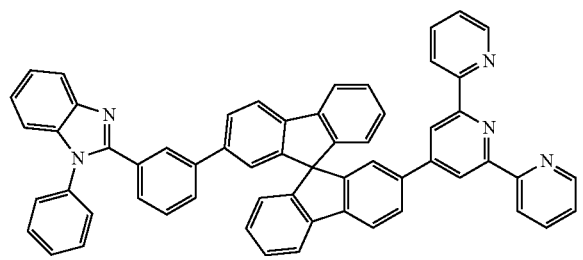

formula (E-54)
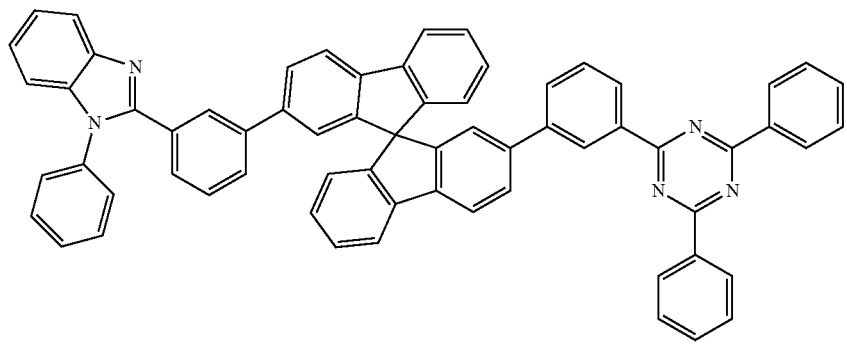
formula (E-55)
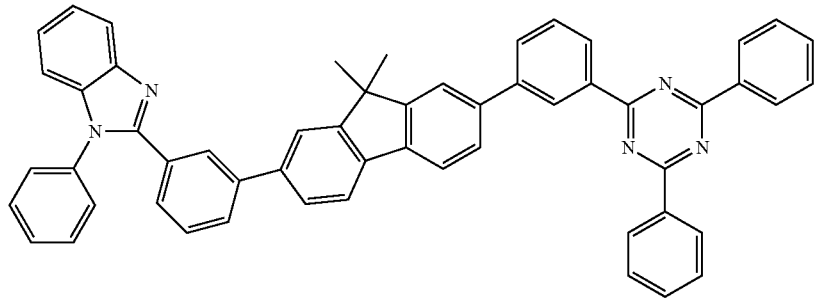
formula (E-56)
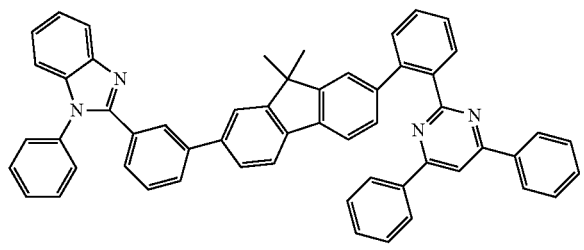
formula (E-57)
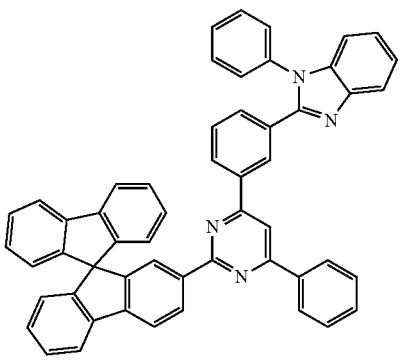
formula (E-58)
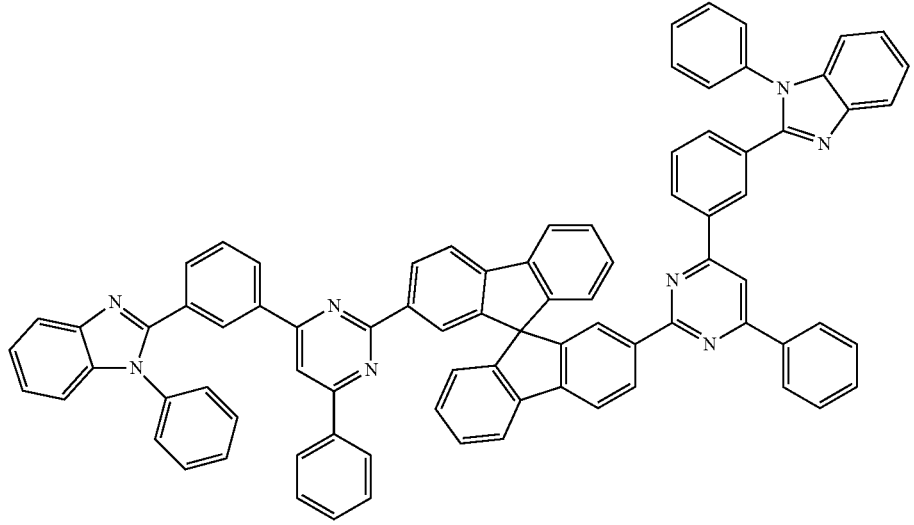

formula (E-59)
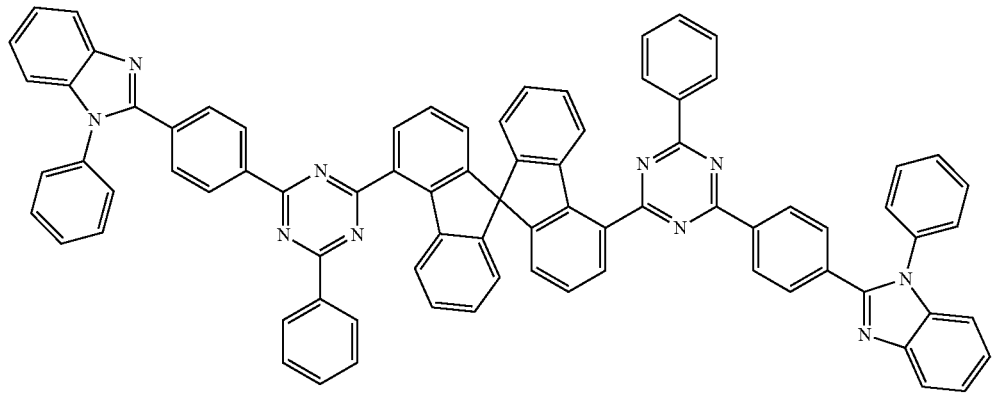
formula (E-60)
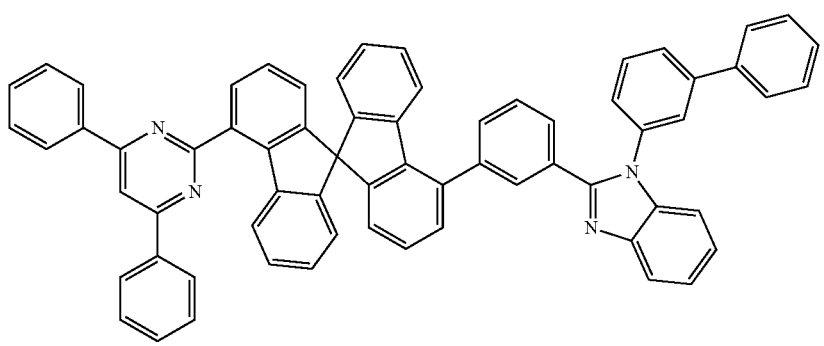
formula (E-61)
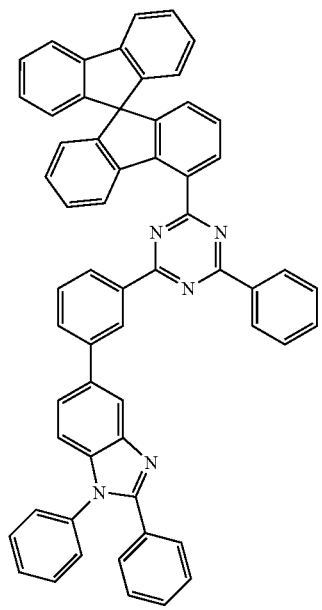
formula (E-62)
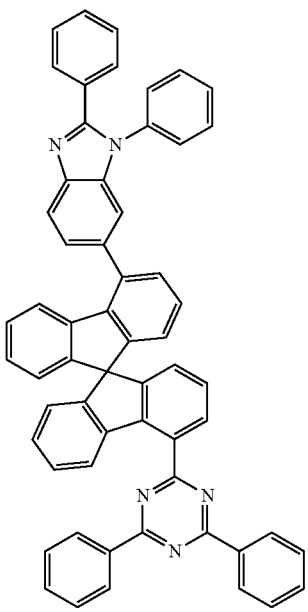

formula (E-63)
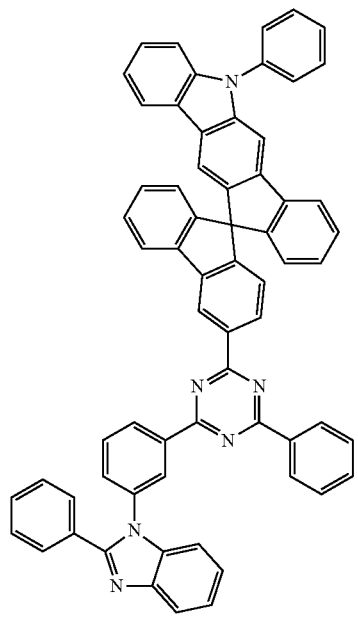
formula (E-64)
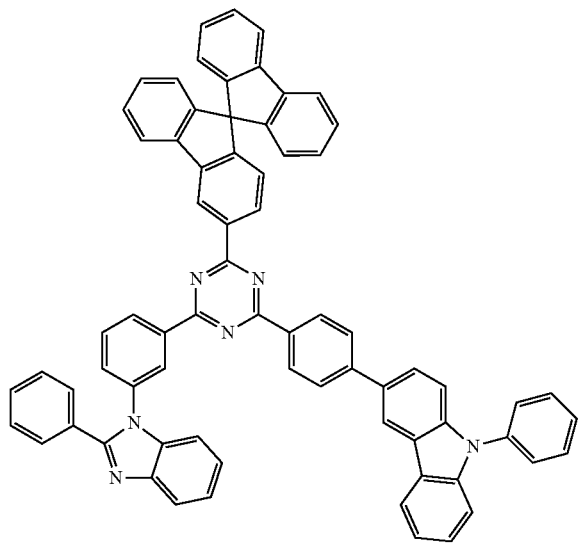
formula (E-65)
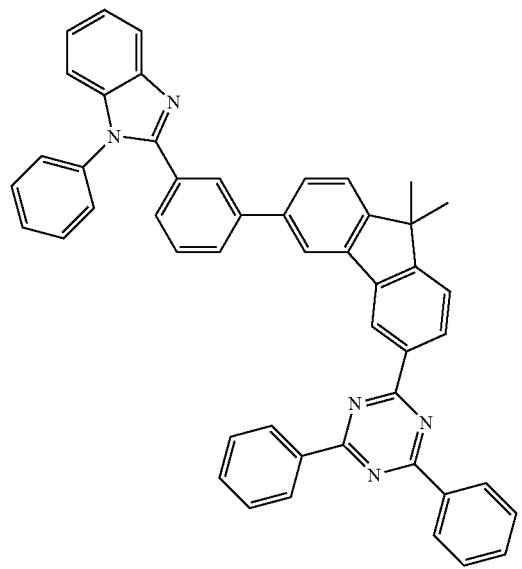
formula (E-66)
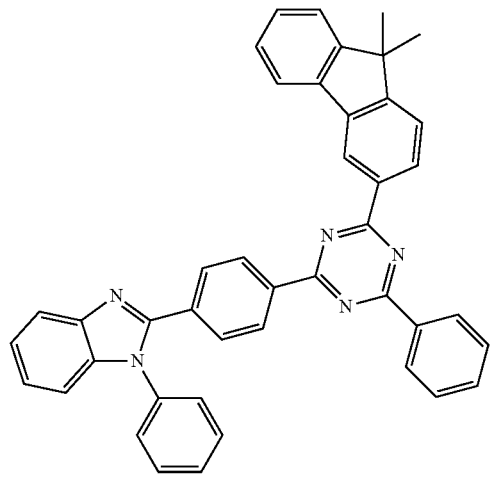

-continued
formula (E-67)
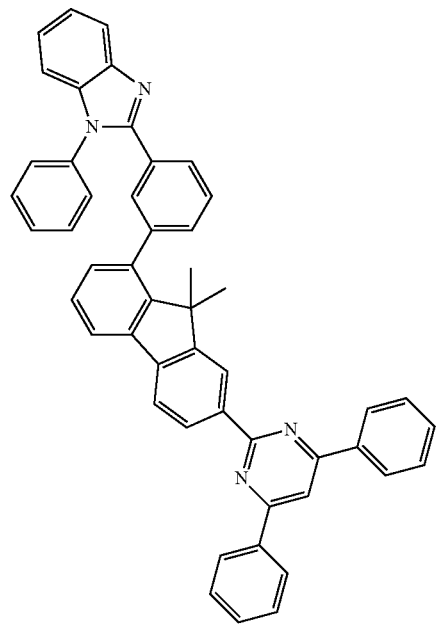
formula (E-68)
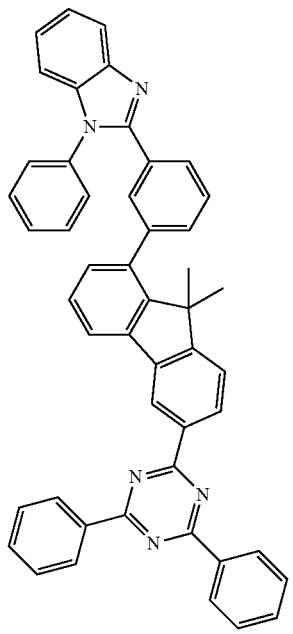
formula (E-69)
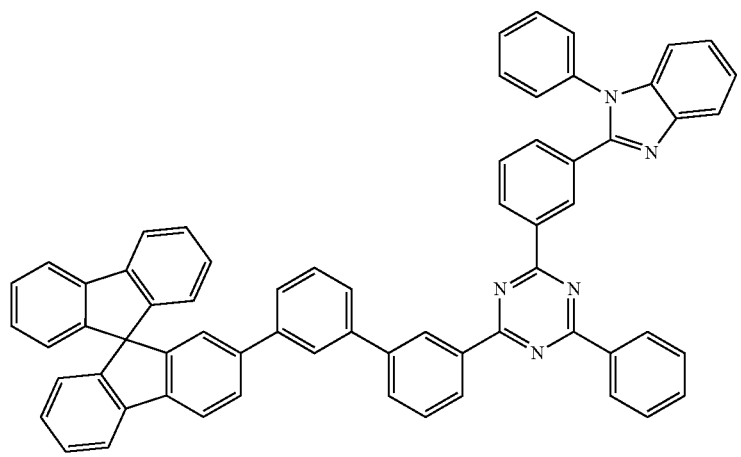
formula (E-70)
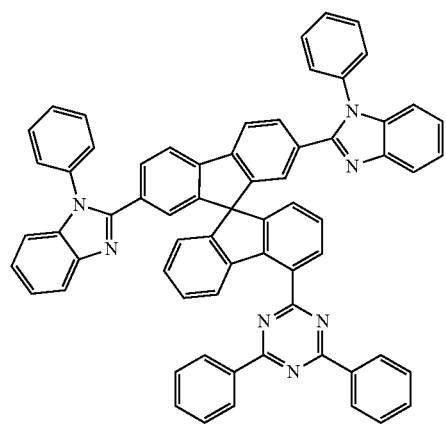
formula (E-71)
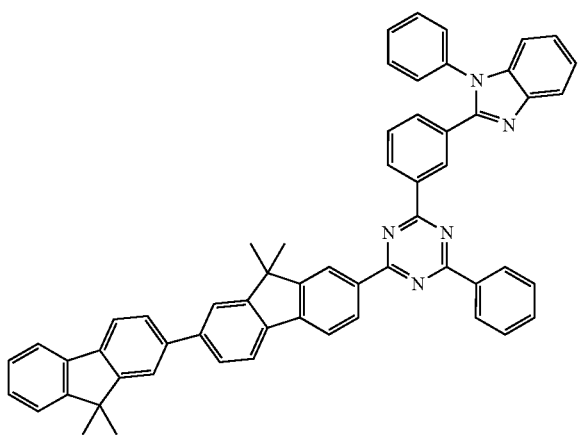

-continued
formula (E-72)
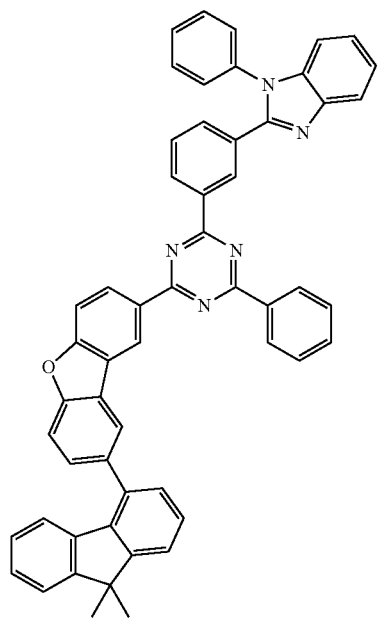
formula (E-73)
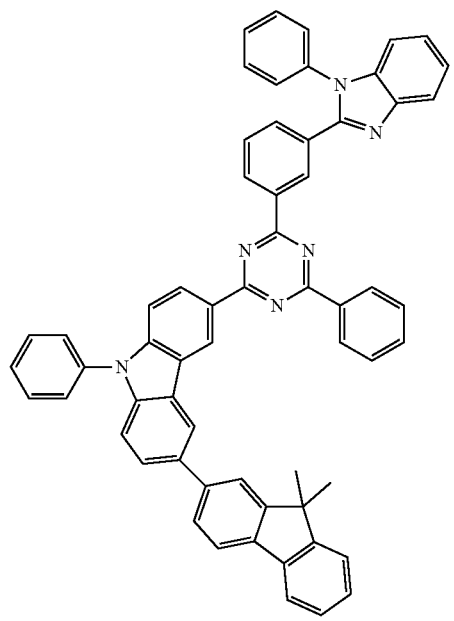
formula (E-74)
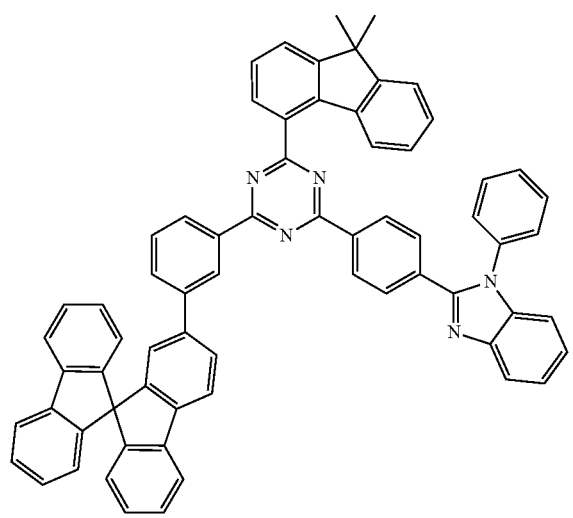
formula (E-75)
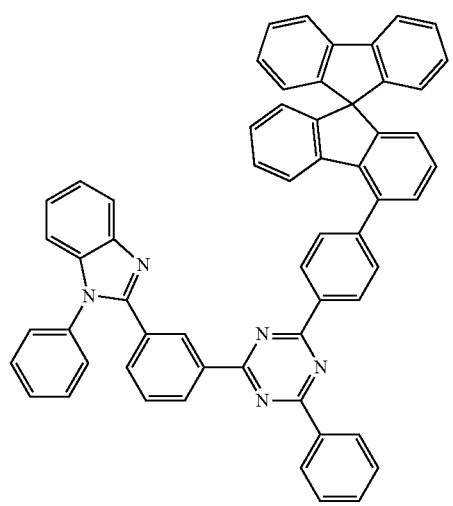
formula (E-76)
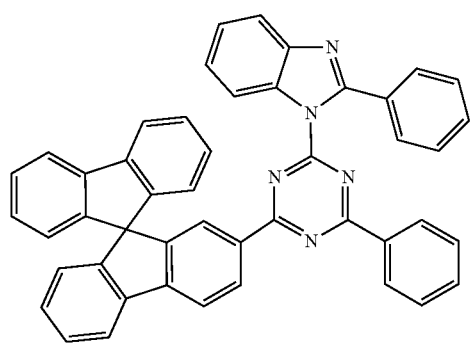
formula (E-77)
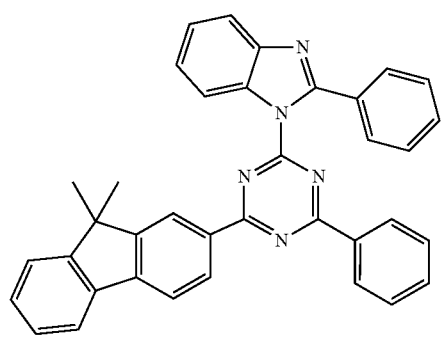

-continued
formula (E-78)
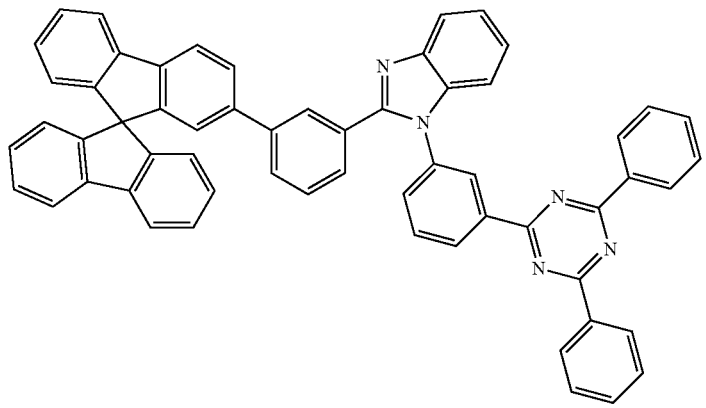
formula (E-79)
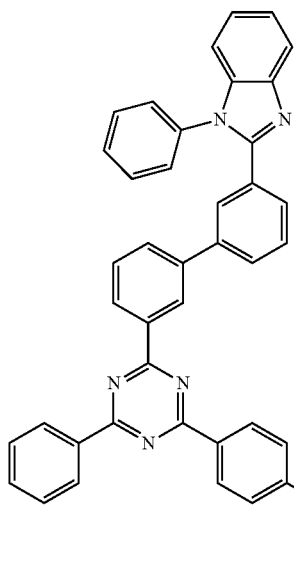
formula (E-80)
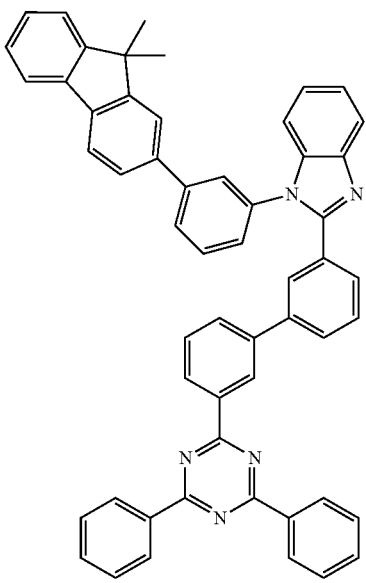
formula (E-81)
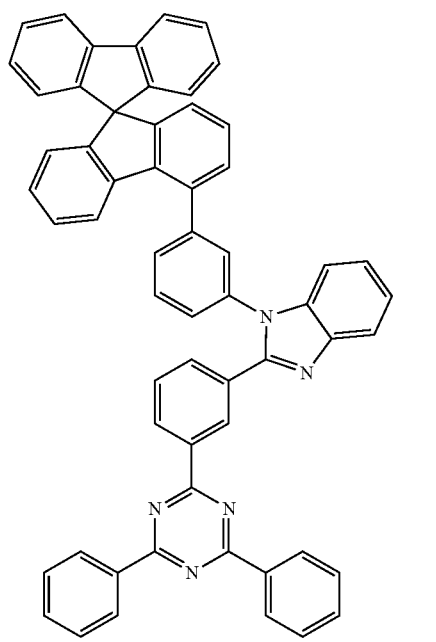
formula (E-82)
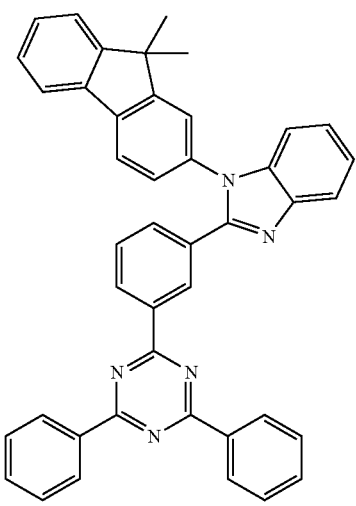

-continued
formula (E-83)
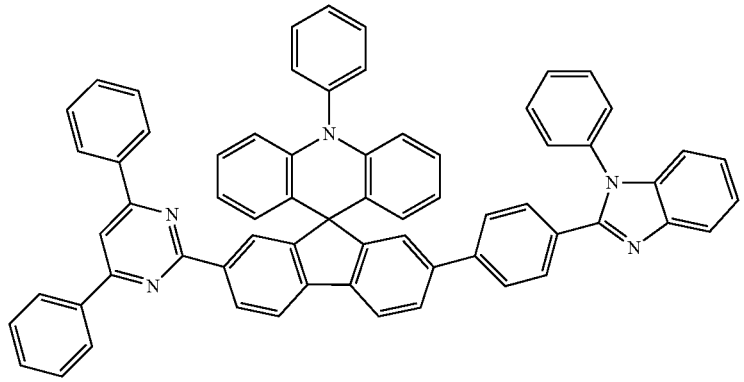
formula (E-84)
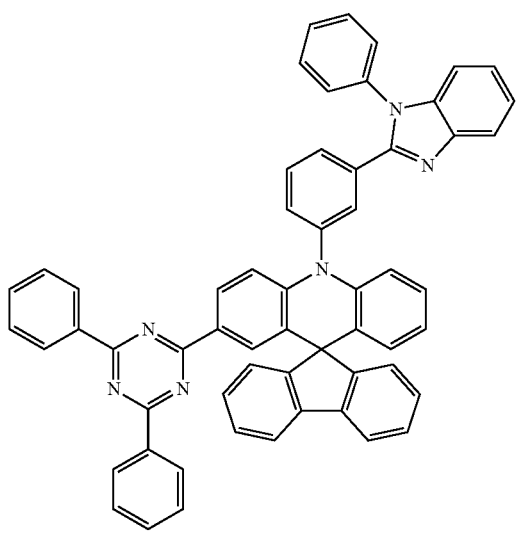
formula (E-85)
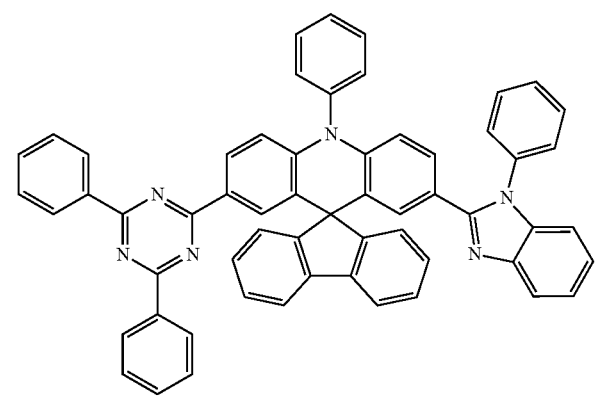
formula (E-86)
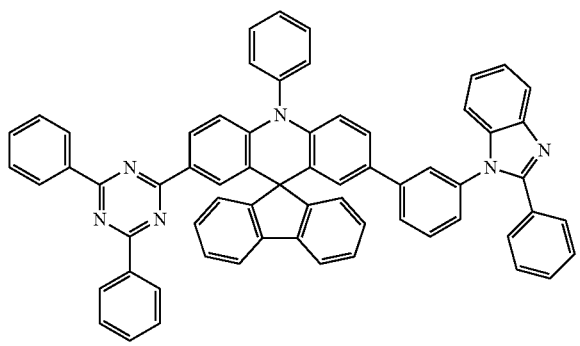
formula (E-87)
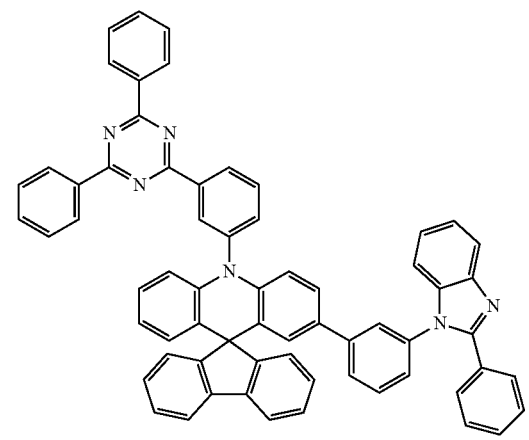

formula (E-88)

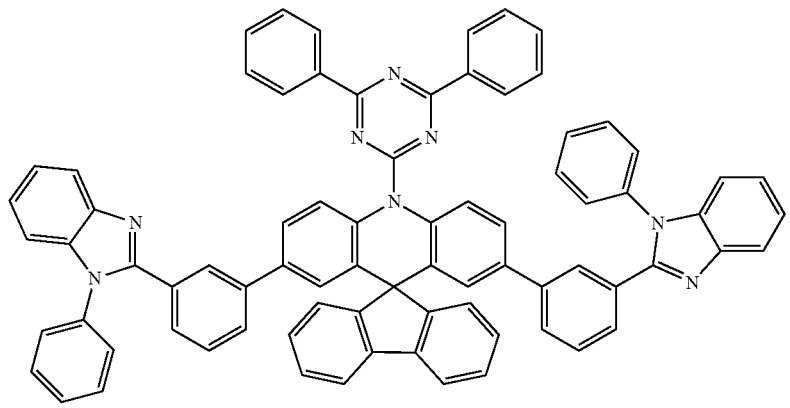

formula (E-89)  formula (E-90)

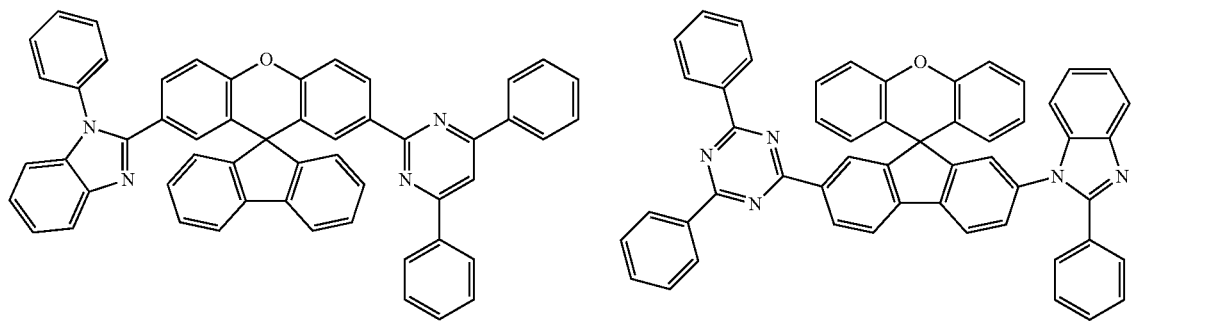

formula (E-91)

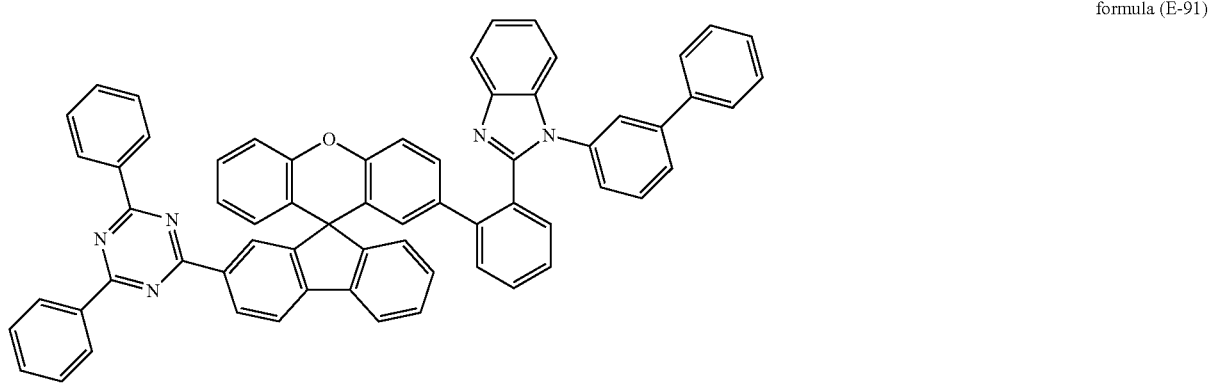 [SMILES: c1ccc(-c2cccc(-n3c(-c4ccccc4-c4ccc5c(c4)C4(c6ccccc6O5)c5ccccc5-c5ccc(-c6nc(-c7ccccc7)nc(-c7ccccc7)n6)cc54)nc4ccccc43)c2)cc1]

The compounds according to the invention can be used in organic electronic devices. The compounds according to the invention are employed in electron-injecting, electron-transporting and/or in emitting layers here.

The present invention therefore furthermore relates to the use of a compound according to the invention in an electronic device, preferably in an electron-injecting, electron-transporting and/or in an emitting layer.

The compounds according to the invention can be the only component of a layer here or used in combination with one or more other materials in a layer.

Further improvements of efficiency data of electronic devices comprising the compounds can be achieved here if the compounds according to the invention are employed in compositions with other materials.

The compounds according to the invention are preferably employed in compositions with materials which are typically employed in devices, in particular electronic devices, such as electroluminescent devices.

The present invention therefore also relates to a composition comprising one or more compounds according to the invention and at least one additional functional molecule selected from the group consisting of fluorescent emitters, phosphorescent emitters, matrix materials, electron-transport materials, electron-injection materials, hole-conductor materials, hole-injection materials, electron-blocking materials, hole-blocking materials and n-dopants.

In the literature, the term host material is frequently also used instead of the term matrix material. Some authors use the term host material for matrix materials for fluorescent emitters, whereas the term matrix material stands for materials which are used together with phosphorescent emitters in the emission layer. In the present case, the term matrix material (host material) is used independently of the emitter and denotes a material which can be employed in the emission layer with fluorescent or phosphorescent emitters.

The individual materials are well known to the person skilled in the art, and he is presented with absolutely no difficulties in selecting suitable compounds from a wide range.

In a preferred embodiment of the present invention, the organic electronic device comprises one or more of the compounds according to the invention in the electron-transport layer (ETL). The ETL here may be a pure layer consisting of the compound according to the invention or it may also comprise at least one electron-transport material. The person skilled in the art will be able to choose from a multiplicity of known electron-transport materials here. The combined use of the compound according to the invention with an electron-transport material in the ETL results in organic electronic devices having particularly good performance data.

The present invention therefore relates to a composition comprising at least one of the compounds according to the invention and at least one ETM. The ETM is preferably selected from the group of the non-metallic electron-transport materials.

Preferred electron-transport materials for the composition according to the invention are selected from the pyridines, pyrimidines, pyridazines, pyrazines, oxadiazoles, quinolines, quinoxalines, anthracenes, benzanthracenes, pyrenes, perylenes, benzimidazoles, triazines, ketones, lactams, oxazoles, phenanthrolines, phosphine oxides and phenazines. The triazines and lactams are very preferred here.

The layer thickness of the ETL is preferably 5 to 150 nm.

The concentration of the compound according to the invention in the ETL is preferably in the range from 10% by vol. to 90% by vol., very preferably in the range from 20% by vol. to 80% by vol., very particularly preferably in the range from 30% by vol. to 70% by vol. and especially preferably in the range from 40% by vol. to 60% by vol., based on the entire electron-transport layer.

In addition to the electron-transport layer, the device according to the invention may also have an electron-injection layer (EIL), which is located between the cathode and the electron-transport layer. Preferred materials which are employed as electron-injection material (EIM) in the EIL are selected from the group of the alkali metals, alkali-metal complexes, in particular the alkali-metal oxinates (in particular substituted or unsubstituted Li hydroxyquinolines), and the alkali-metal or alkaline-earth metal fluorides, and also oxides or carbonates thereof. Very preferred electron-injection materials are Li, LiF, $Li_2O$, $BaF_2$, MgO, NaF, Cs, CsF, $Cs_2CO_3$, Liq, where LiF and Liq are particularly preferred and LiF represents a very particularly preferred electron-injection material.

The layer thickness of the EIL is preferably 0.5 to 5 nm.

Furthermore preferred EIMs are substituted lithium 8-hydroxyquinolinates, in particular those which are disclosed in DE 102013013876.0 and very particularly those of the following formulae (C-1) to (C-34):

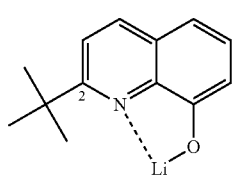

formula (C-1)

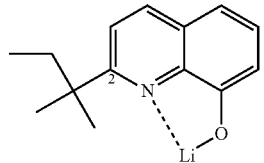

formula (C-2)

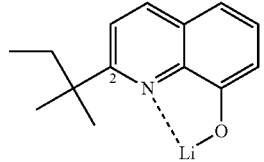

formula (C-3)

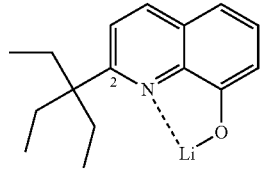

formula (C-4)

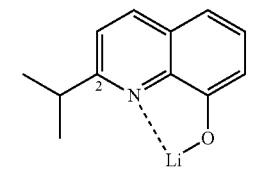

formula (C-5)

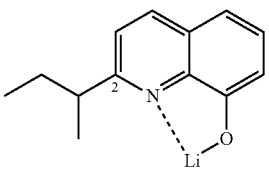

formula (C-6)

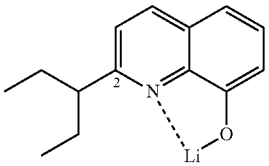

formula (C-7)

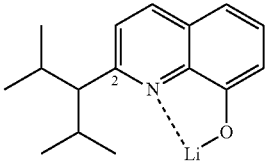

formula (C-8)

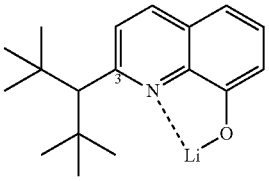

formula (C-9)

-continued
formula (C-10)
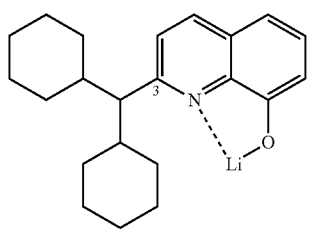
formula (C-11)
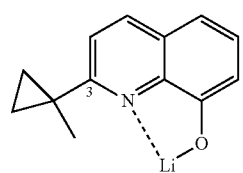
formula (C-12)
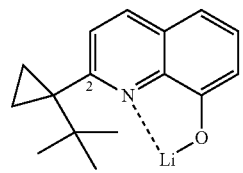
formula (C-13)
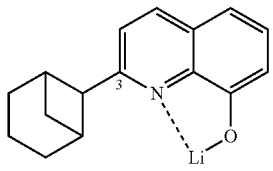
formula (C-14)
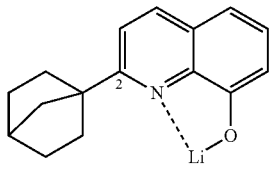
formula (C-15)
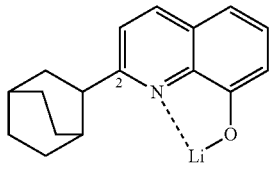
formula (C-16)
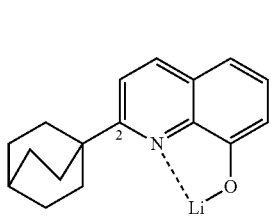
formula (C-17)
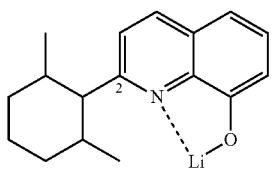
-continued
formula (C-18)
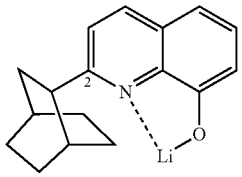
formula (C-19)
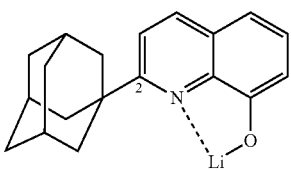
formula (C-20)
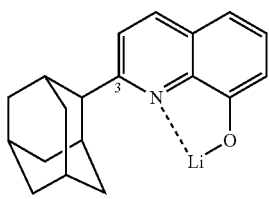
formula (C-21)
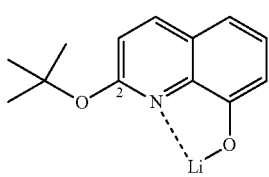
formula (C-22)
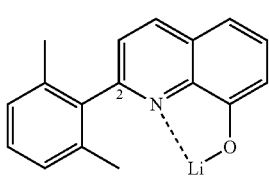
formula (C-23)
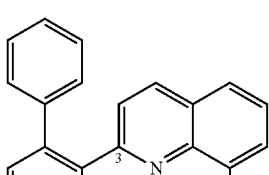
formula (C-24)
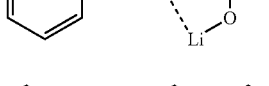
formula (C-25)
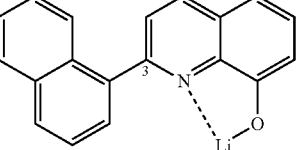

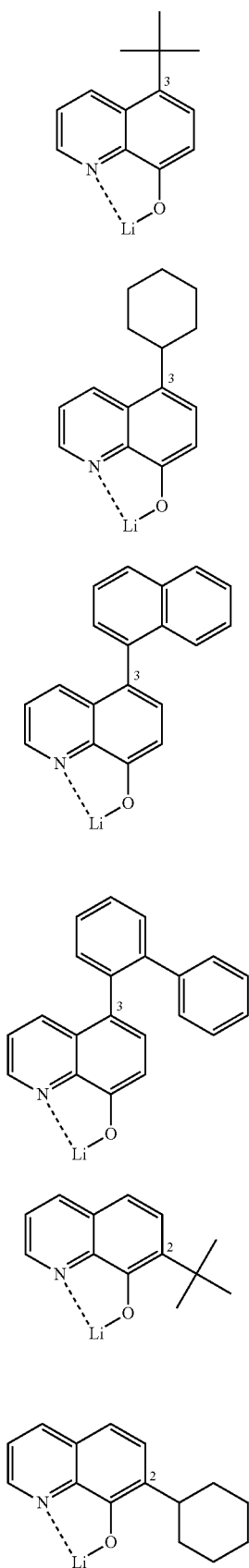

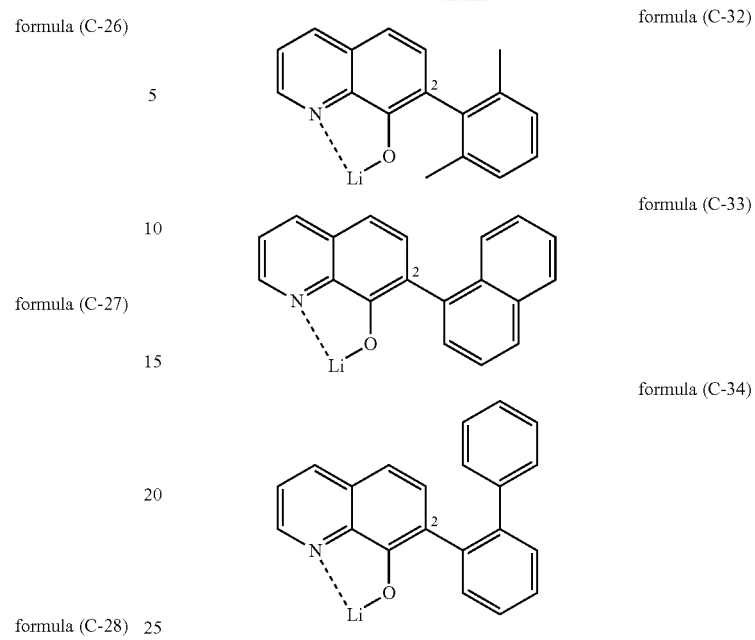

Further increases in performance of organic electronic devices can be achieved if the compound according to the invention is employed in an electron-transport layer in combination with an n-dopant. The n-dopant here can be both an inorganic and also an organic material.

An n-dopant in the present application is taken to mean an organic or inorganic compound which is capable of releasing electrons (electron donor), i.e. a compound which acts as reducing agent.

The compounds employed for the n-doping can be employed as precursor, where these precursor compounds liberate n-dopants by activation.

Preferred n-dopants are selected from electron-rich metal complexes; P=N compounds; N-heterocyclic compounds, particularly preferably naphthylenecarbodiimides, pyridines, acridines and phenazines; fluorenes and free-radical compounds.

Particularly preferred electron-rich metal complexes are described, inter alia, in WO 2005/86251 A2, where this specification is incorporated into the present application by way of reference for disclosure purposes. Neutral electron-rich metal complexes are preferred here.

Particularly preferred P=N compounds are disclosed, inter alia, in WO 2012/175535 A1, where this specification is incorporated into the present application by way of reference for disclosure purposes.

A further group of n-dopants is represented by N-heterocyclic compounds. N-heterocyclic compounds are cyclic compounds whose ring structure contains at least one nitrogen atom besides hydrogen and carbon. These compounds may be saturated, partially unsaturated or heteroaromatic.

N-heterocyclic compounds can preferably be employed as precursor, where precursor compounds are distinguished by the fact that their function as n-dopant only commences after activation. Preferred N-heterocyclic compounds which can be employed, in particular, as precursor are described, inter alia, in WO 2009/00237 A1, where this specification is incorporated into the present application by way of reference for disclosure purposes.

A further group of N-heterocyclic compounds which are suitable as n-dopant is represented by naphthylenecarbodiimides. Naphthylenecarbodiimides contain at least one carbodiimide group (N=C=N) and a naphthylene group.

Surprising advantages can be achieved by the naphthylenecarbodiimides described in WO 2012/168358 A1, where this specification is incorporated into the present application by way of reference for disclosure purposes.

The preferred N-heterocyclic compounds which can be employed as n-dopants furthermore include pyridine, acridine and phenazine derivatives. These compounds contain pyridine, acridine and phenazine structural elements and are known in the art. Preferred acridines and phenazines are described, inter alia, in US 2007/0145355 A1, where this specification is incorporated into the present application by way of reference for disclosure purposes.

Surprising advantages can be achieved by the pyridines described in EP 2 452 946 A1 and EP 2 463 927 A1, where these specifications are incorporated into the present application by way of reference for disclosure purposes.

According to a particular embodiment of the present invention, fluorenes can be employed as n-dopants. Preferred fluorenes are described, inter alia, in WO 2012/031735 A1, where this specification is incorporated into the present application by way of reference for disclosure purposes.

The preferred n-dopants include free-radical compounds which are known in the art. Preferred free-radical compounds contain heterocyclic groups. Particularly preferred free-radical compounds are disclosed, inter alia, in EP 1 837 926 A1 and WO 2007/107306 A1, where these specifications are incorporated into the present application by way of reference for disclosure purposes.

Of the said n-dopants, the electron-rich metal complexes described in WO 2005/86251 A2 are particularly preferred, where the metal complexes of the formula $W_2(hpp)_4$ in which hpp stands for the anion of 1,3,4,6,7,8-hexahydro-2H-pyrimido[1,2-a]pyrimidine are very particularly preferred. Neutral electron-rich metal complexes are particularly preferred here.

In the case of n-doping, an electron transfer takes place from the HOMO (highest occupied molecular orbital) level of the n-dopant to the LUMO (lowest unoccupied molecular orbital) level of the matrix material, where the electron is generally not strongly localised, but instead counts amongst the charge carriers.

A refinement of the invention proposes that the value of a difference between the HOMO of the n-dopant and the LUMO of the compound according to the invention is preferably less than about 1 eV, further preferably the value of the difference is less than about 0.5 eV.

The compounds according to the invention preferably have an LUMO level of about 1 eV or greater, very preferably 1.5 eV or greater.

Molecular orbitals, in particular also the highest occupied molecular orbital (HOMO) and the lowest unoccupied molecular orbital (LUMO), their energy levels and the energy of the lowest triplet state $T_1$ or the lowest excited singlet state $S_1$ of the materials are determined in the present application with the aid of quantum-chemical calculations. In order to calculate organic substances without metals, firstly a geometry optimisation is carried out using the "Ground State/Semi-empirical/Default Spin/AM1/Charge 0/Spin Singlet" method. An energy calculation is subsequently carried out on the basis of the optimised geometry. The "TD-SCF/DFT/Default Spin/B3PW91" method with the "6-31G(d)" base set is used here (charge 0, spin singlet). For metal-containing compounds, the geometry is optimised via the "Ground State/Hartree-Fock/Default Spin/LanL2MB/Charge 0/Spin Singlet" method. The energy calculation is carried out analogously to the method described above for the organic substances, with the difference that the "LanL2DZ" base set is used for the metal atom and the "6-31G(d)" base set is used for the ligands. The energy calculation gives the HOMO energy level HEh or LUMO energy level LEh in hartree units. The HOMO and LUMO energy levels in electron volts, calibrated with reference to cyclic voltammetry measurements, are determined therefrom as follows:

HOMO (eV)=((HE$h$*27.212)−0.9899)/1.1206

LUMO (eV)=((LE$h$*27.212)−2.0041)/1.385

For the purposes of this application, these values are to be regarded as HOMO and LUMO energy levels respectively of the materials.

The lowest triplet state $T_1$ is defined as the energy of the triplet state having the lowest energy which arises from the quantum-chemical calculation described.

The lowest excited singlet state $S_1$ is defined as the energy of the excited singlet state having the lowest energy which arises from the quantum-chemical calculation described.

The method described herein is independent of the software package used and always gives the same results. Examples of frequently used programs for this purpose are "Gaussian09W" (Gaussian Inc.) and Q-Chem 4.1 (Q-Chem, Inc.).

In still a further preferred embodiment of the present invention, the organic electronic device comprises one or more of the compounds according to the invention in the emission layer (EML). The compound according to the invention is employed here as matrix material in the EML together with one or more emitters. Possible emitters here are both fluorescent and phosphorescent emitters, where phosphorescent emitters are preferred.

The term phosphorescent emitter (also called phosphorescent dopant) typically encompasses compounds in which the light emission takes place predominantly through a spin-forbidden transition, for example a transition from a triplet state or a state having a higher spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present application.

The phosphorescent compounds are preferably those which emit light from a triplet state.

The term fluorescent emitter (also fluorescent dopant) encompasses compounds in which the light emission takes place predominantly through a transition from an excited singlet state.

Both fluorescent and also phosphorescent emitters are well known to the person skilled in the art from the prior art, and he is presented with absolutely no difficulties in selecting suitable emitters.

Examples of phosphorescent dopants are revealed by the applications WO 2000/70655, WO 2001/41512, WO 2002/

02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention.

Explicit examples of phosphorescent dopants are shown in the following table.

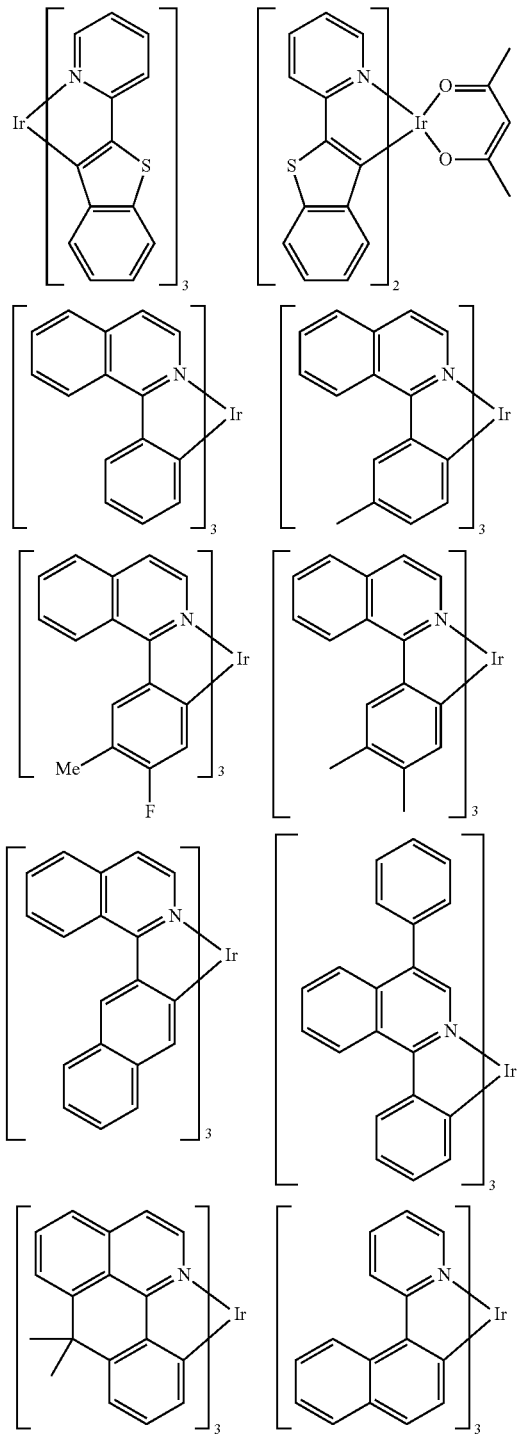
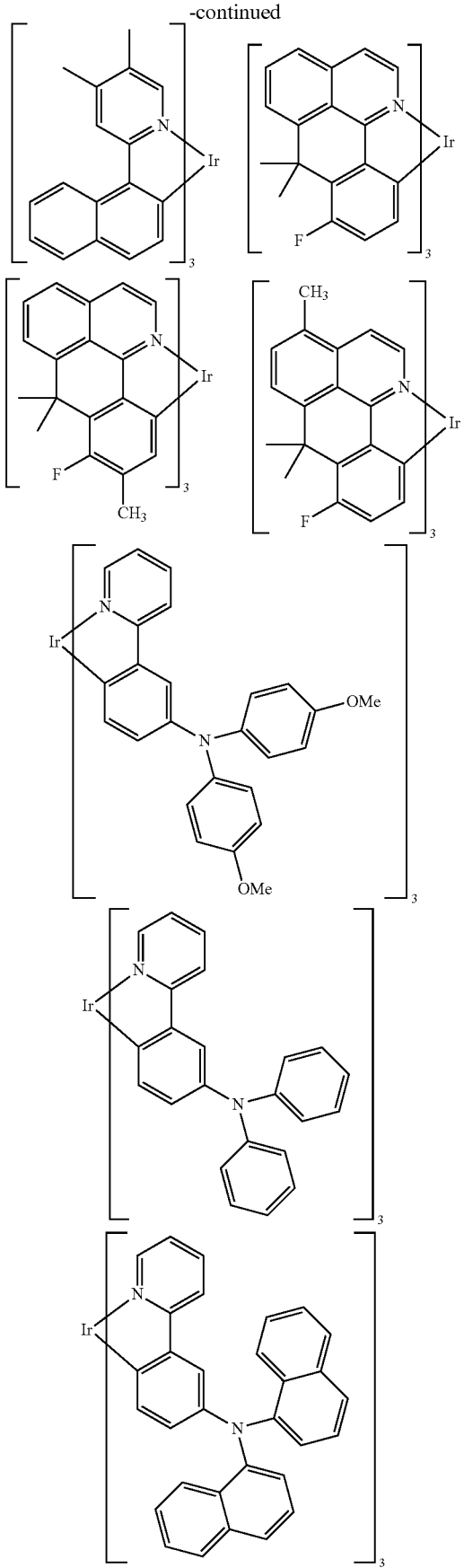

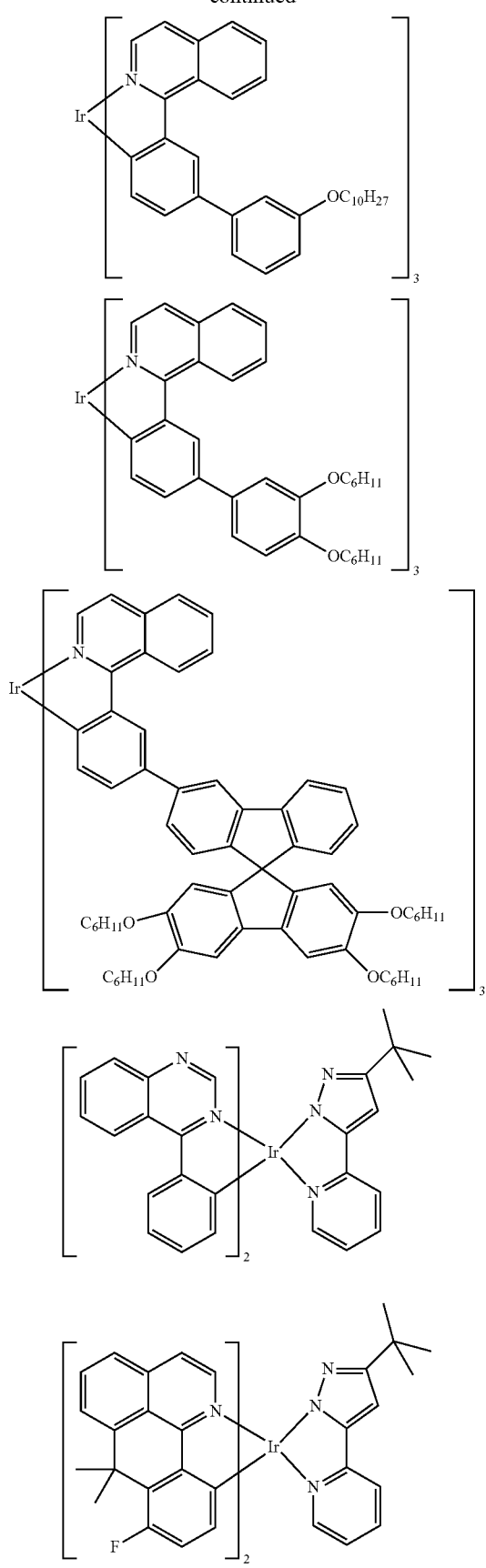
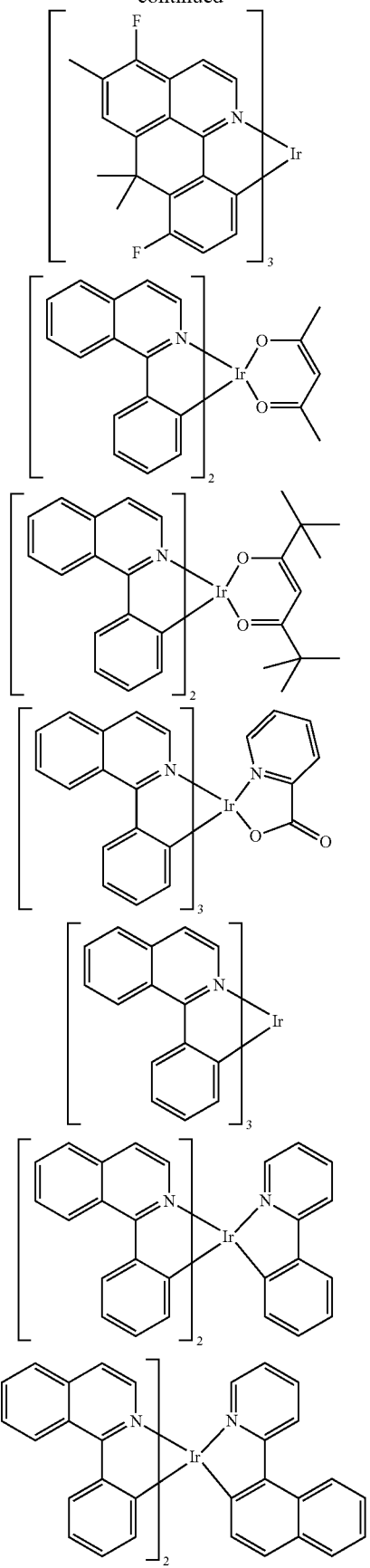

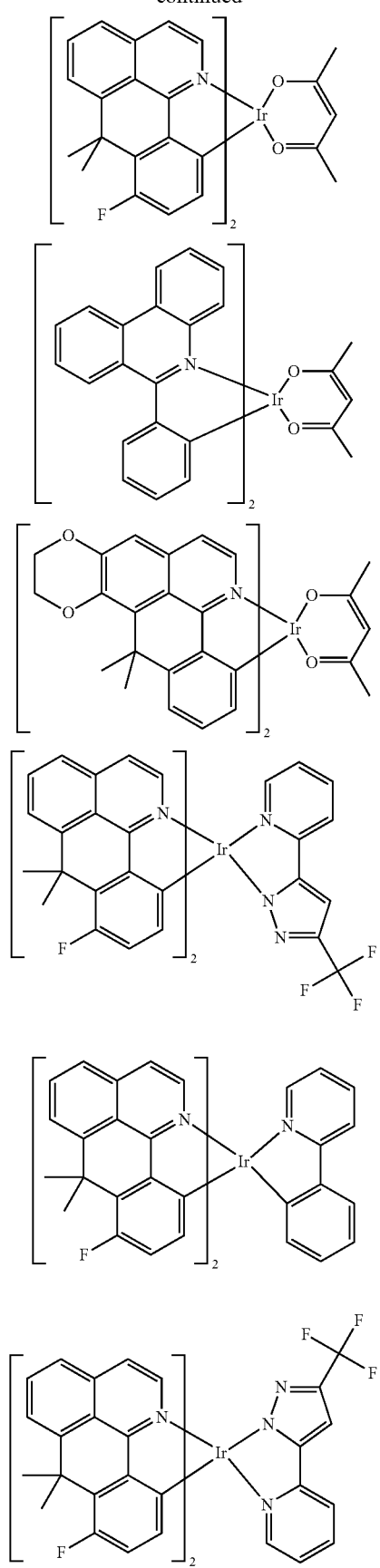
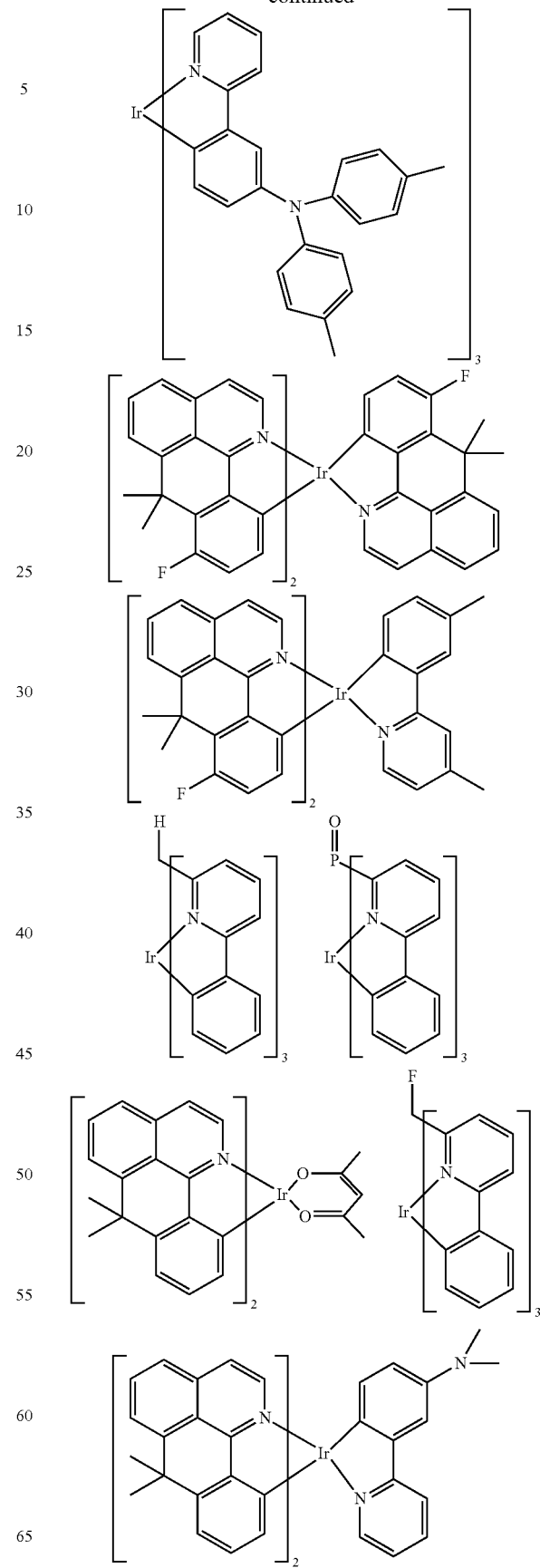

-continued
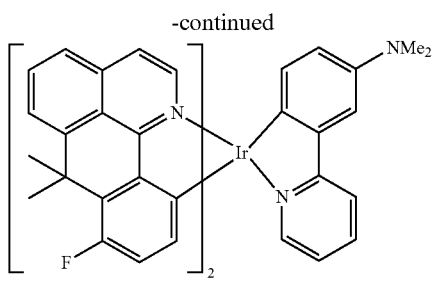
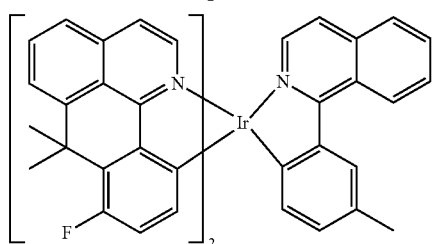
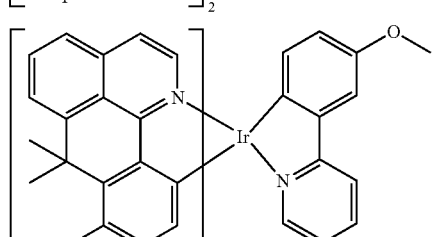
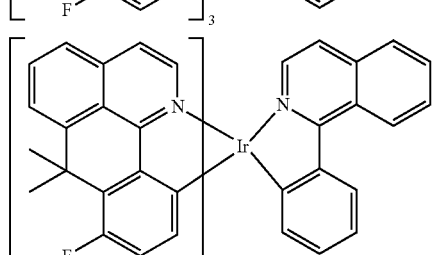
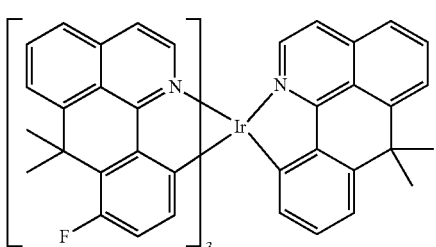
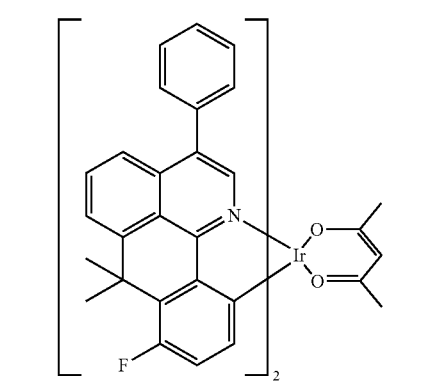
-continued
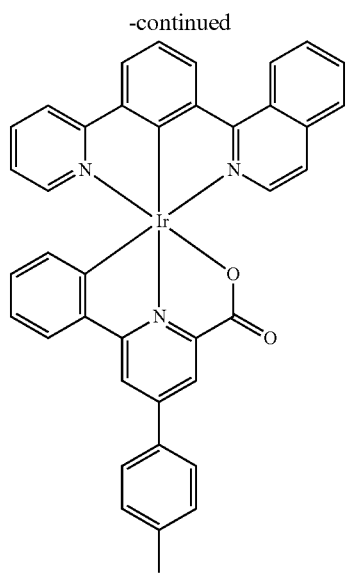
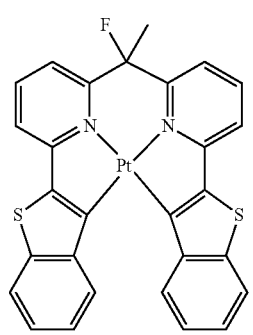
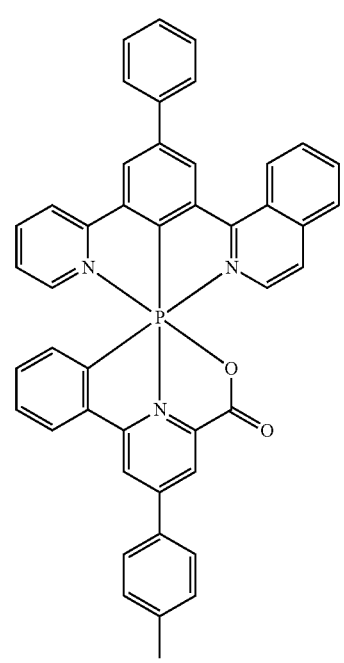

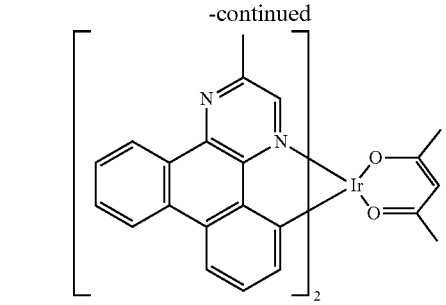
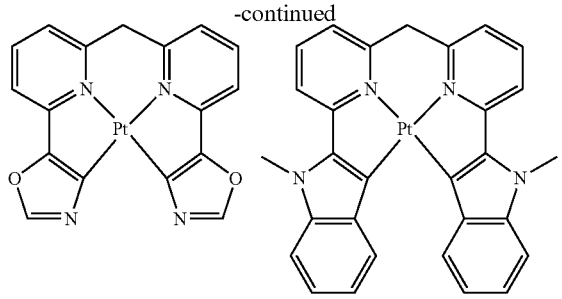
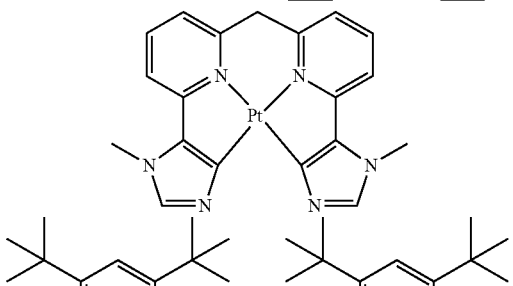
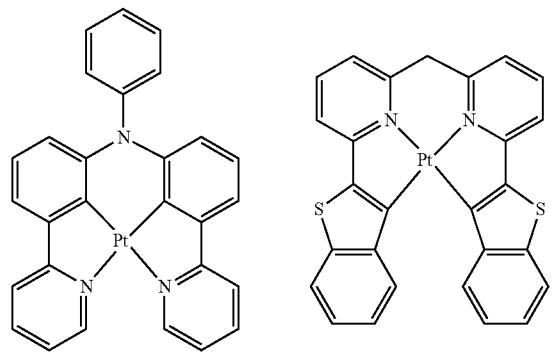
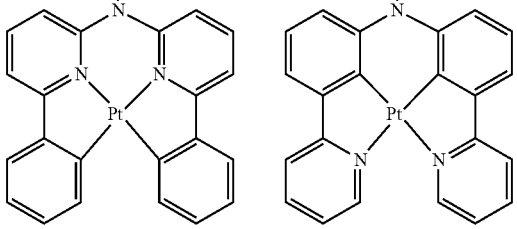
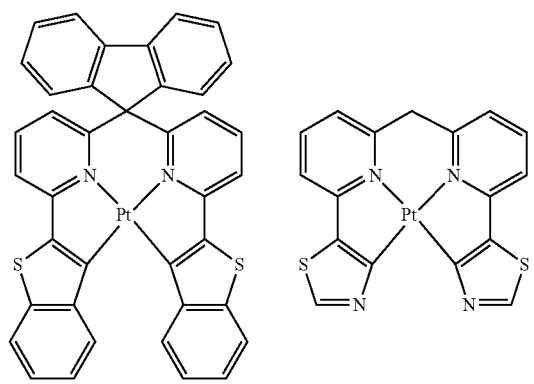
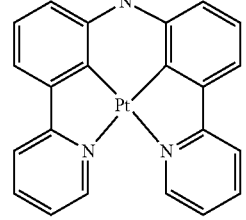
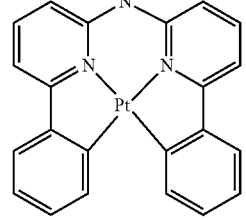
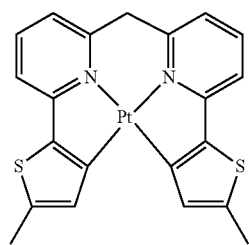
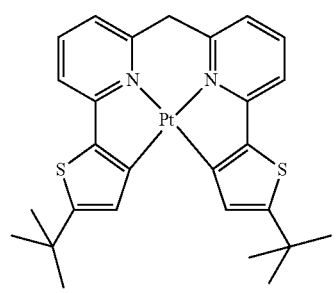
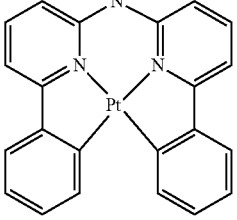

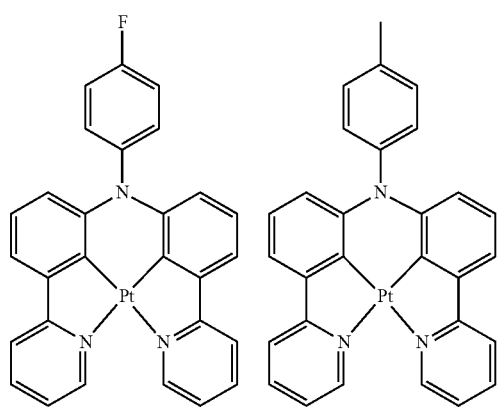
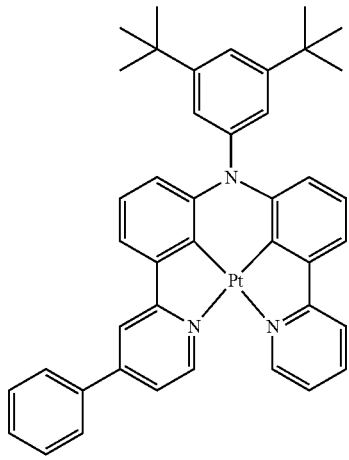
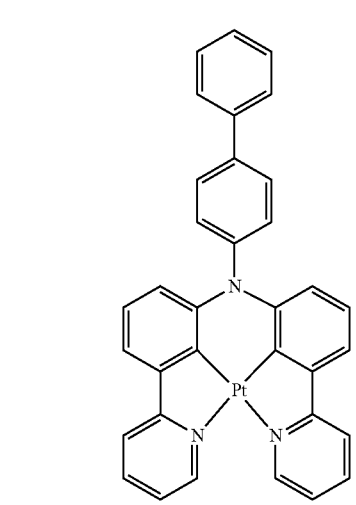
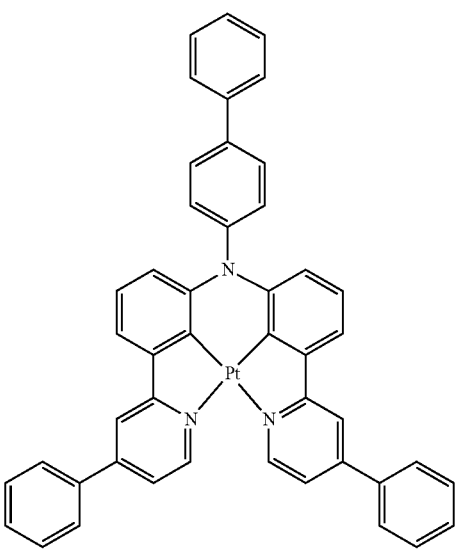
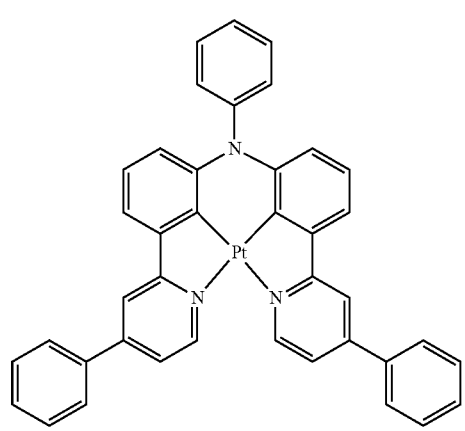
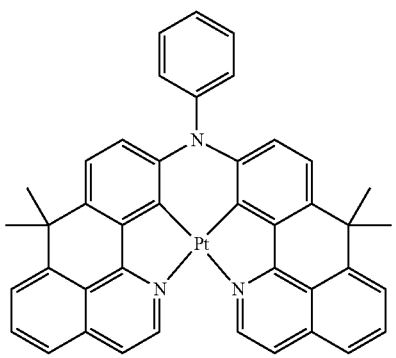

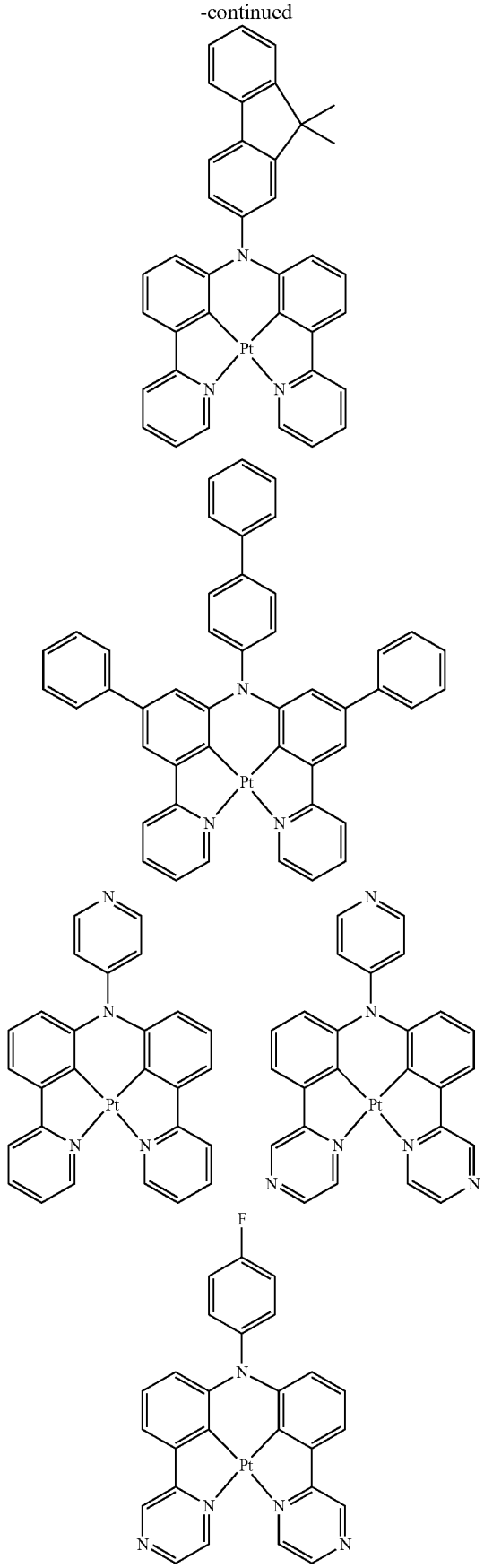
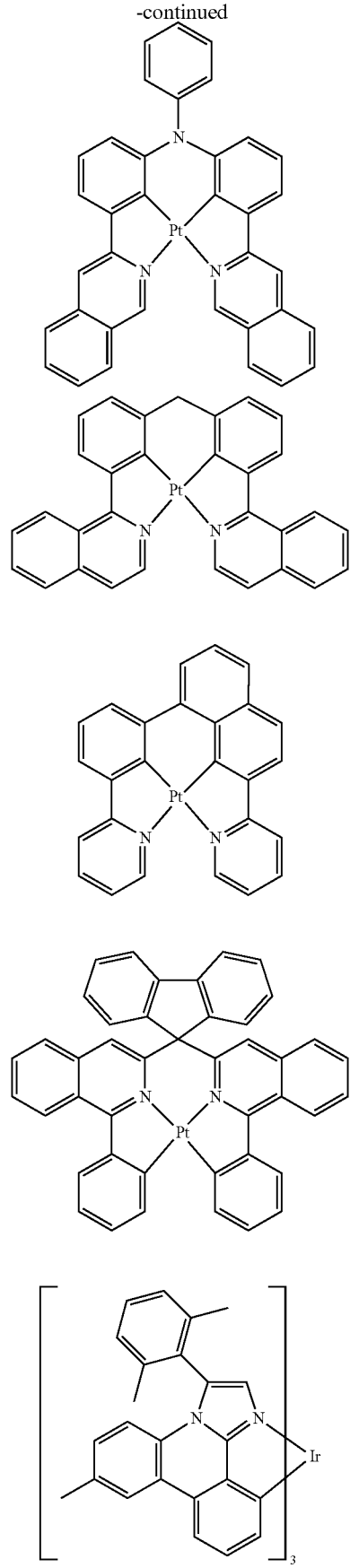

-continued
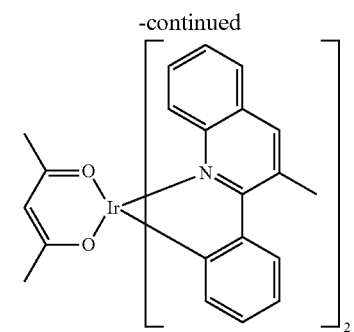
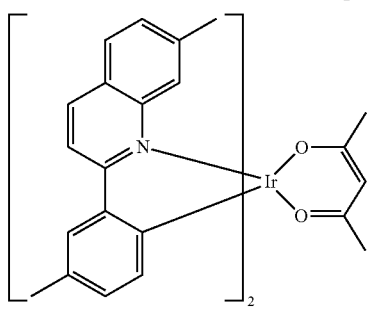
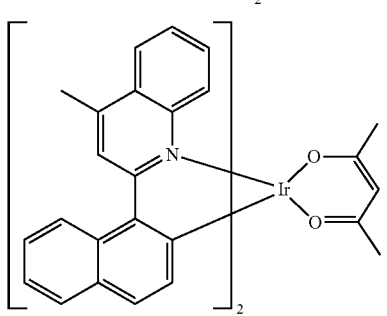
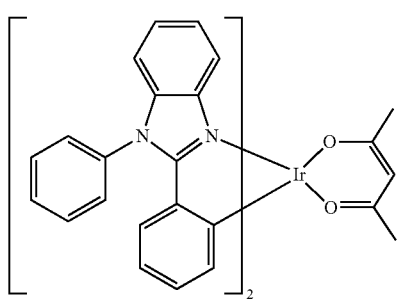
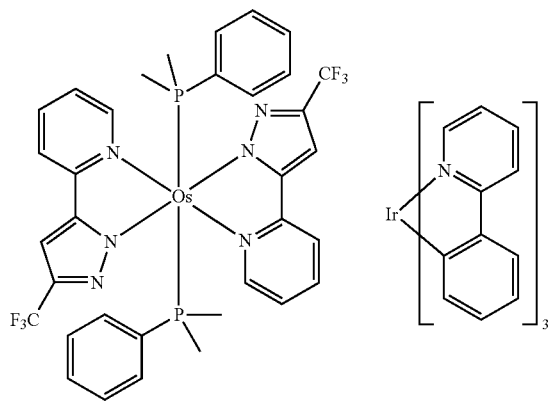
-continued
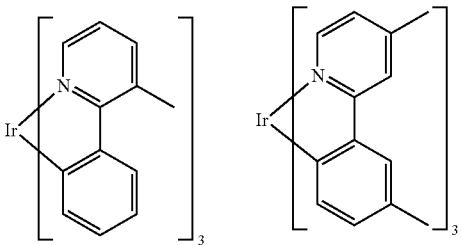
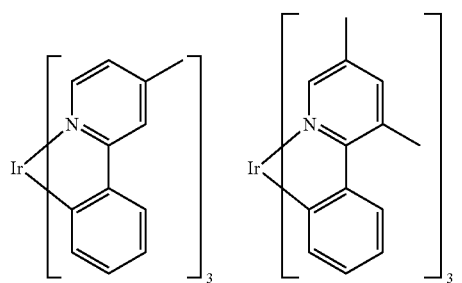
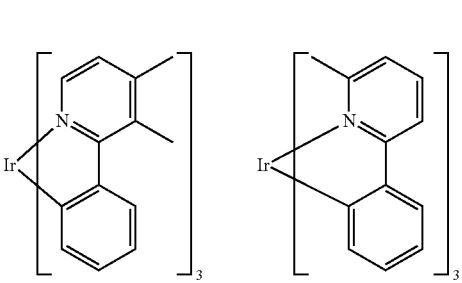
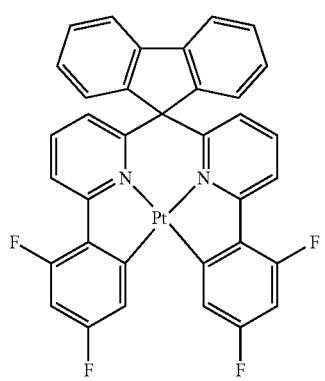
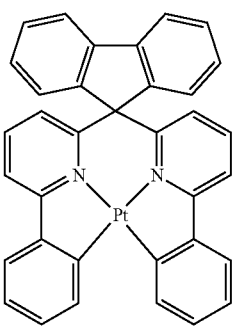

95
-continued
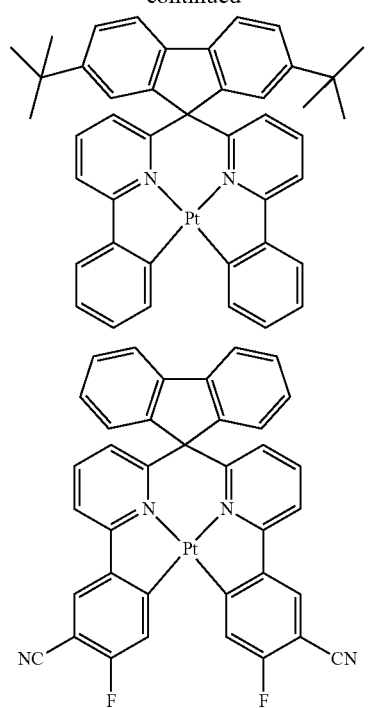
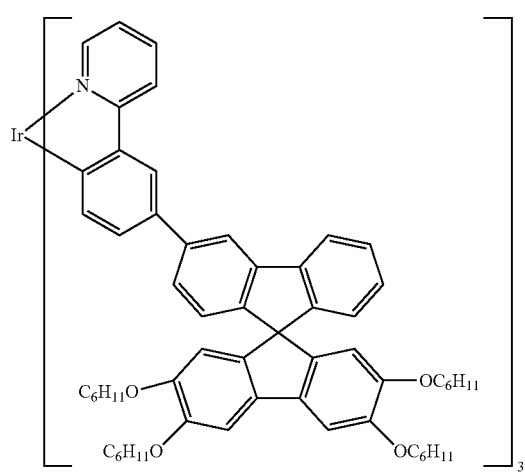
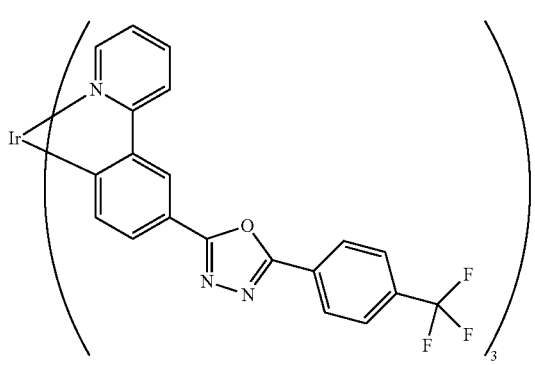
96
-continued
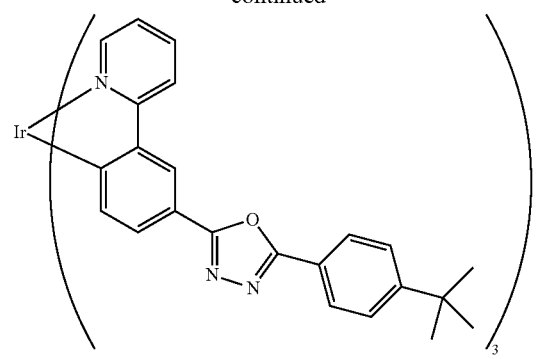
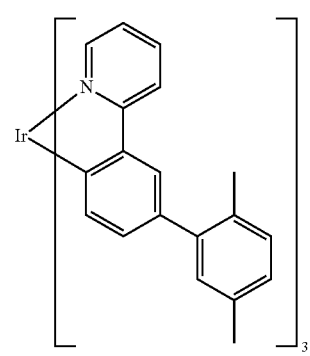
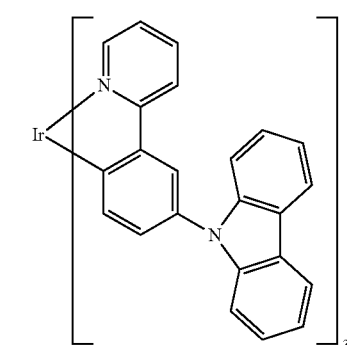
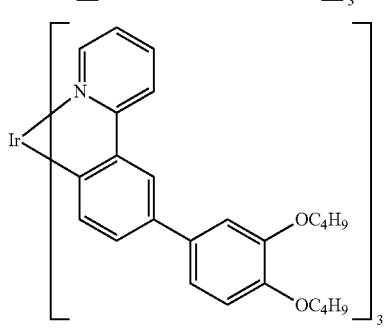
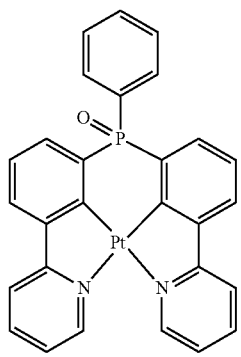

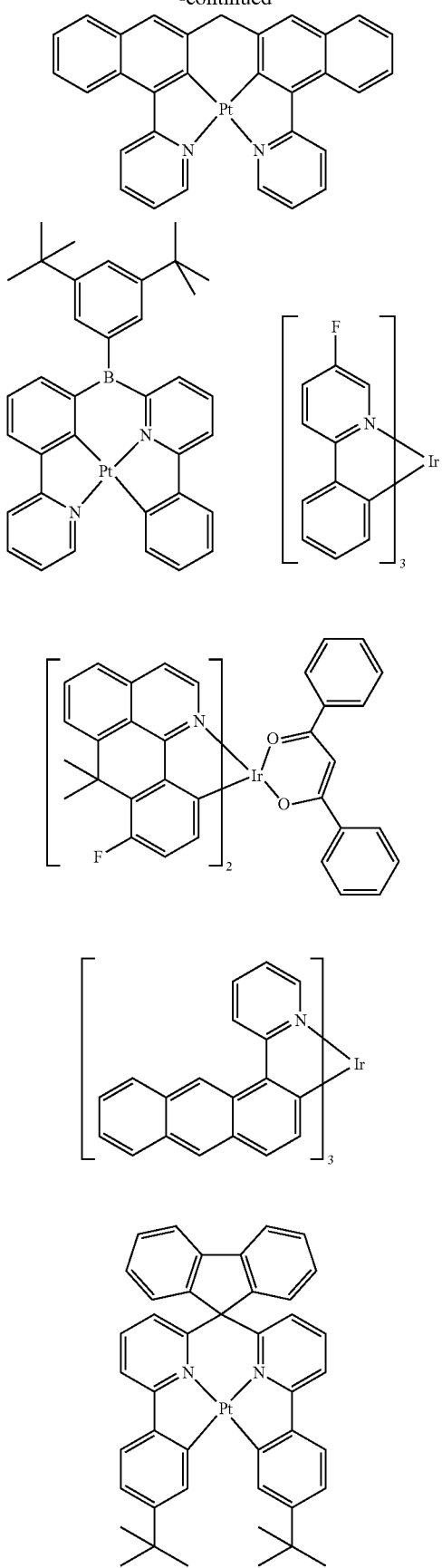

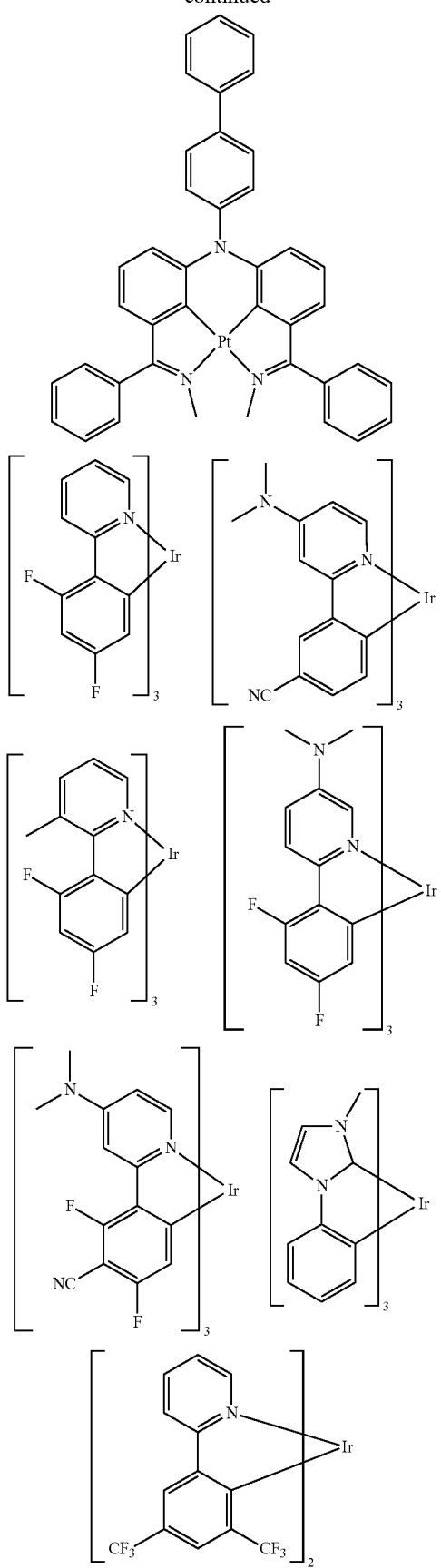
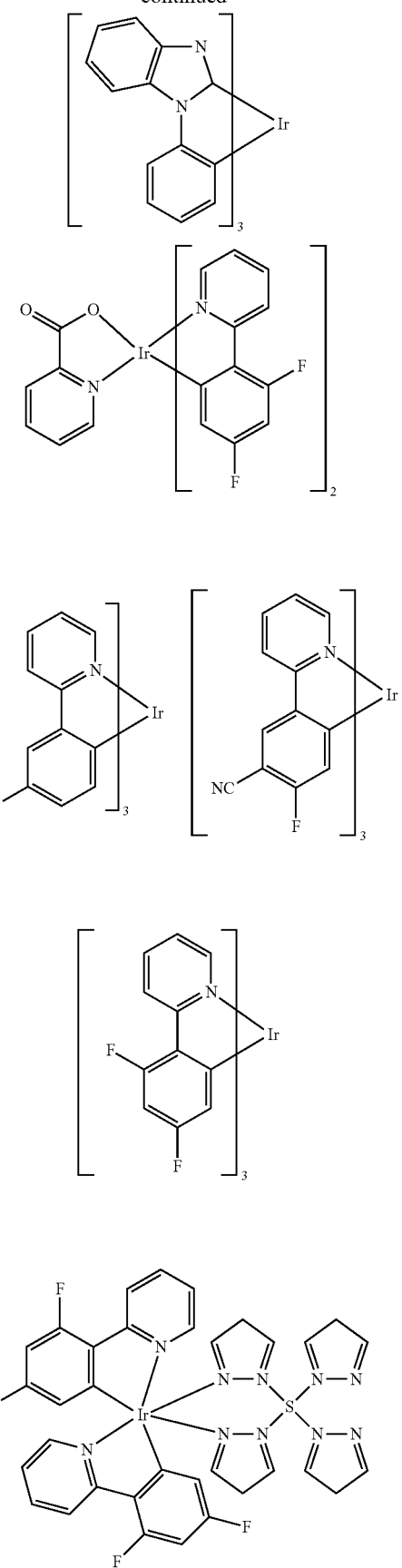

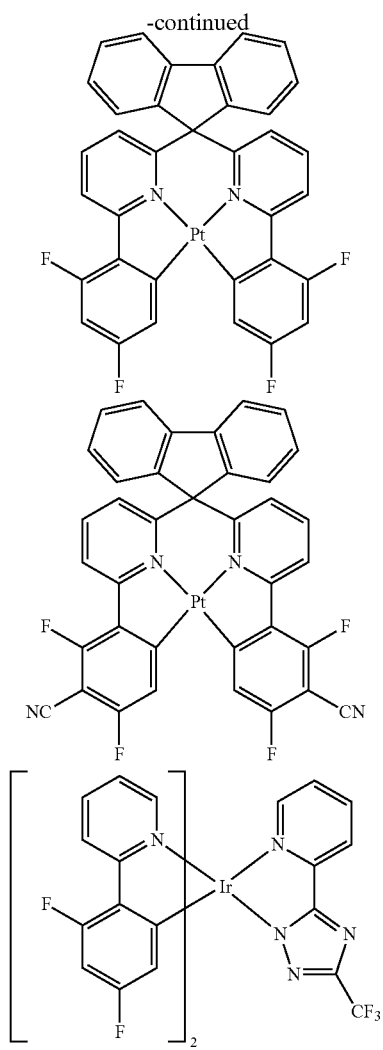
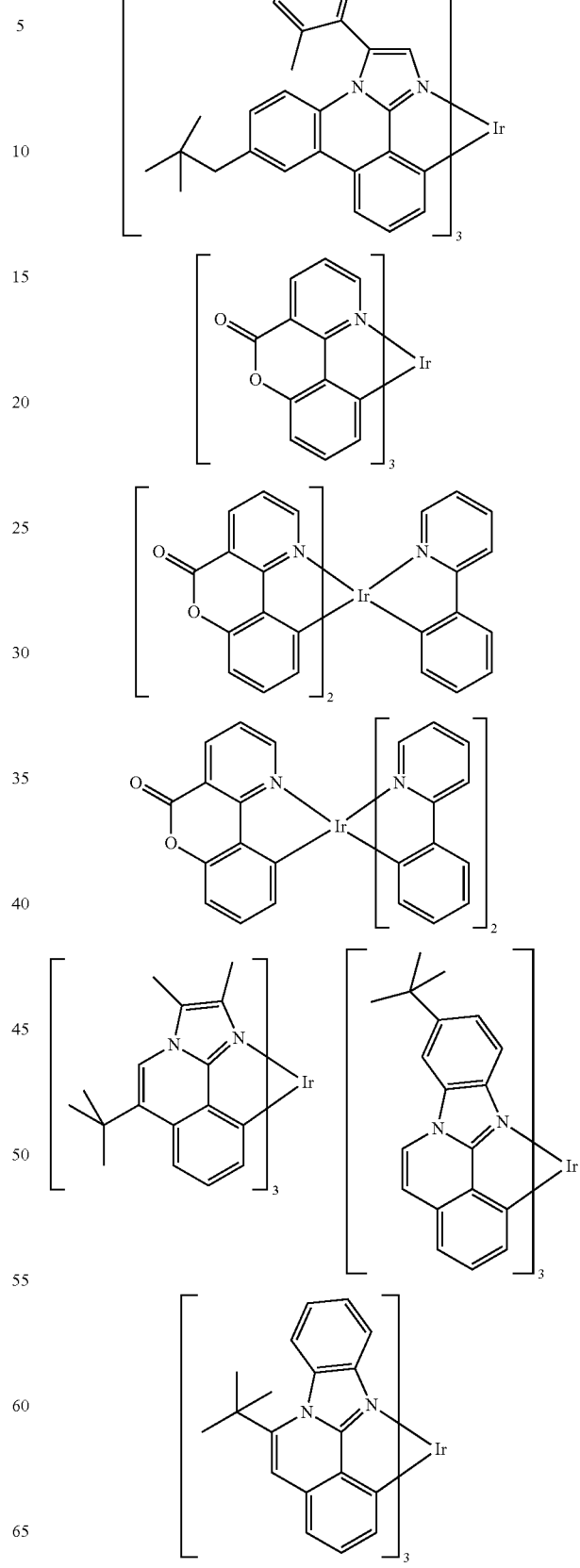

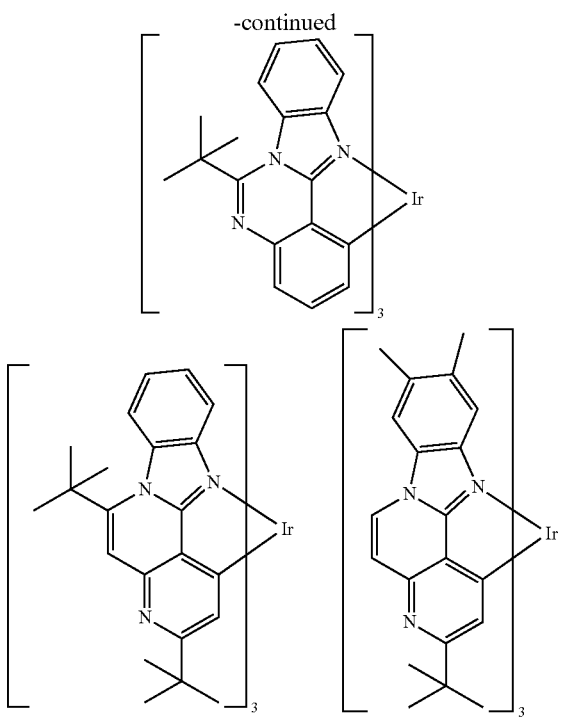

In a further preferred embodiment of the invention, the compounds are used as a matrix component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix component, where the further mixed-matrix component(s) fulfil(s) other functions. The two different matrix materials may be present here in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. Greater details on mixed-matrix systems are given, inter alia, in the application WO 2010/108579.

Particularly suitable matrix materials which can be used in combination with the compounds according to the invention as matrix components of a mixed-matrix system are selected from the preferred matrix materials indicated below for phosphorescent dopants or the preferred matrix materials for fluorescent dopants, depending on what type of dopant is employed in the mixed-matrix system.

Suitable matrix materials, preferably for fluorescent dopants, are materials from various classes of substance. Preferred matrix materials are selected from the classes of the lactams (for example WO 2011/116865, WO 2011/137951, WO 2013/064206, WO 2014/056567, EP 13003343.4, EP 14000729.5), oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopants are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAlQ.

The present invention therefore also relates to a composition comprising at least one compound according to the invention and at least one further matrix material.

The present invention furthermore also relates to a composition comprising at least one compound according to the invention and at least one further matrix material and furthermore at least one fluorescent or phosphorescent emitter, preferably a phosphorescent emitter.

The present invention also relates to a composition comprising at least one compound according to the invention and at least one wide band gap material, where wide band gap material is taken to mean a material in the sense of the disclosure content of U.S. Pat. No. 7,294,849. These systems exhibit particularly advantageous performance data in electroluminescent devices.

Systems comprising a plurality of matrix materials (mixed-matrix systems) are employed in light-emitting layers of organic electroluminescent devices. The light-emitting layer furthermore also comprises one or more dopants.

The compounds and compositions according to the invention can be employed in organic electronic devices. The present invention therefore also relates to an organic electronic device comprising one or more of the compounds or compositions according to the invention.

The organic electronic device according to the invention is preferably selected from the group consisting of the organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs, LECs or LEECs), organic laser diodes (O-lasers) and organic light-emitting diodes (OLEDs). Particular preference is given here to organic electroluminescent devices, very particularly preferably OLECs and OLEDs and especially preferably OLEDs.

OLEDs in the sense of the present invention are taken to mean both organic light-emitting diodes comprising small organic molecules (SMOLEDs) and also polymeric light-emitting diodes (PLEDs), where SMOLEDs represent preferred OLEDs.

As already mentioned above, the organic layer comprising the compound or composition according to the invention is preferably a layer of the device having an electron-transporting function. It is particularly preferably an electron-injection layer (EIL), electron-transport layer (ETL), hole-blocking layer (HBL) or emitting layer (EML).

A hole-transport layer (HTL) in accordance with the present application is a layer having a hole-transporting function which is located between the anode and the emitting layer (EML).

An electron-transport layer (ETL) in accordance with the present application is a layer having an electron-transporting function which is located between the cathode and the emitting layer (EML).

The structure of organic electronic devices, and in particular also of organic electroluminescent devices, is well known to the person skilled in the art from the prior art.

An electronic, in particular electroluminescent, organic device according to the invention comprises at least one organic layer which comprises at least one compound of the formula (1). An organic layer is distinguished by the fact that it comprises at least one organic or organometallic compound. An organic device need not necessarily comprise only layers built up from organic or organometallic materials.

The electronic device according to the invention comprises an anode, a cathode and at least one organic layer which comprises at least one compound according to the invention.

As already mentioned, particularly preferred organic electronic devices in the sense of the present invention are the organic electroluminescent devices, and here in particular the OLEDs.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, can also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali-metal or alkaline-earth metal fluorides, but also the corresponding oxides or carbonates (for example LiF, $Li_2O$, $BaF_2$, MgO, NaF, CsF, $Cs_2CO_3$, etc.). Likewise suitable for this purpose are organic alkali-metal complexes, for example Liq (lithium quinolinate) or substituted Li hydroxyquinolinates.

The anode preferably comprises materials having a high work function. The anode preferably has a work function greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to enable either irradiation of the organic material (O-SCs) or the coupling-out of light (OLEDs/PLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers. It is furthermore preferred for a p-doped hole-transport material to be applied to the anode as hole-injection layer, where metal oxides, for example $MoO_3$ or $WO_3$, or (per)fluorinated electron-deficient aromatic compounds are suitable as p-dopants. Further suitable p-dopants are HAT-CN (hexacyanohexaazatriphenylene) or the compound NPD9 from Novaled. A layer of this type simplifies hole injection in materials having a low HOMO, i.e. an HOMO having a large modulus.

According to a preferred embodiment, at least two organic layers may be arranged between the anode and the cathode.

In the further layers, it is generally possible to use all materials as are used in accordance with the prior art for the layers, and the person skilled in the art will be able to combine each of these materials with the materials according to the invention in an electronic device without inventive step. Typical ETMs, EIMs, emitters and matrix materials have already been disclosed above.

An organic electroluminescent device comprises a cathode, an anode and at least one emitting layer (EML). Apart from these layers, it may also comprise further layers, for example in each case one or more hole-injection layers (HIL), hole-transport layers (HTL), hole-blocking layers (HBL), electron-transport layers (ETL), electron-injection layers (EIL), exciton-blocking layers (ExBL), electron-blocking layers (EBL), charge-generation layers and/or organic or inorganic p/n junctions. A typical structure of an organic electroluminescent device is: anode/HIL/HTL/EML/ETL/EIL/cathode.

It is possible here for one or more hole-transport layers to be p-doped, for example with metal oxides, such as $MoO_3$ or $WO_3$, or with (per)fluorinated electron-deficient aromatic compounds, and/or for one or more electron-transport layers to be n-doped. Likewise, interlayers which have, for example, an exciton-blocking function and/or control the charge balance in the electroluminescent device may be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. A hybrid system is also possible, where one or more layers fluoresce and one or more other layers phosphoresce.

The device is correspondingly (depending on the application) structured, provided with contacts and finally hermetically sealed, since the lifetime of such devices is drastically shortened in the presence of water and/or air.

Preference is furthermore given to an electronic device, in particular an organic electroluminescent device, characterised in that one or more layers are applied by means of a sublimation process, in which the materials are applied by vapour deposition in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an electronic device, in particular an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

Preference is furthermore given to an electronic device, in particular an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, by suitable substitution.

The electronic device, in particular the organic electroluminescent device, can also be produced as a hybrid system by applying one or more layers from solution and applying one or more other layers by vapour deposition. Thus, it is, for example, possible to apply an emitting layer comprising at least one emitter and a matrix material from solution and to apply a hole-blocking layer and/or an electron-transport layer thereto by vacuum vapour deposition.

These processes are generally known to the person skilled in the art and can be applied by him without difficulties to electronic devices, in particular organic electroluminescent devices comprising a compound according to the invention.

For the production of organic electronic devices from solution, formulations comprising the compound according to the invention or the composition according to the invention are necessary.

The present invention therefore also relates to a formulation comprising at least one compound according to the invention or at least one composition according to the invention and at least one solvent.

This formulation can be, for example, a solution, dispersion or emulsion. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-di-isopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

Devices comprising the compounds according to the invention can be employed in a very versatile manner. Thus, for example, electroluminescent devices can be employed in displays for televisions, mobile telephones, computers and cameras. However, the devices can also be used in lighting applications. Furthermore, electroluminescent devices can be utilised in medicine or the cosmetics area for phototherapy. Thus, a multiplicity of diseases (psoriasis, atopic dermatitis, inflammation, acne, skin cancer, etc.) can be treated or skin wrinkling, skin reddening and skin ageing can be prevented or reduced. Furthermore, the light-emitting devices can be used to keep beverages, meals or foods fresh or to sterilise equipment (for example medical equipment).

The present invention therefore relates to an electronic device, preferably an organic electroluminescent device, very preferably an OLED or OLEC and very particularly preferably an OLED, comprising at least one compound according to the invention or at least one composition according to the invention for use for phototherapy in medicine.

The present invention furthermore preferably relates to an electronic device, preferably an organic electroluminescent device, very preferably an OLED or OLEC and very particularly preferably an OLED, comprising at least one compound according to the invention or at least one composition according to the invention for use for the phototherapeutic treatment of skin diseases.

The present invention furthermore very preferably relates to an electronic device, preferably an organic electroluminescent device, very preferably an OLED or OLEC and very particularly preferably an OLED, comprising at least one compound according to the invention or at least one composition according to the invention for use for the phototherapeutic treatment of psoriasis, atopic dermatitis, inflammatory diseases, vitiligo, wound healing, skin cancer and jaundice, in particular jaundice of the newborn.

The present invention furthermore relates to the use of the electronic device, preferably an organic electroluminescent device, very preferably an OLED or OLEC and very particularly preferably an OLED, comprising at least one compound according to the invention or at least one composition according to the invention in the cosmetics area, preferably for the treatment of acne, skin ageing, and of cellulite.

The electronic devices according to the invention, in particular the organic electroluminescent devices, are distinguished over the prior art by the following surprising advantages:

1. The organic electroluminescent devices according to the invention have very high efficiency.
2. The organic electroluminescent devices according to the invention simultaneously have an improved lifetime.
3. The organic electroluminescent devices according to the invention simultaneously have a reduced operating voltage.

4. The compounds according to the invention can be prepared very easily and inexpensively, can be processed well and can be evaporated very well, so that the compounds according to the invention are very highly suitable for the commercial mass production of organic electronic devices, in particular of organic electroluminescent devices.

The above-mentioned preferred embodiments can be combined with one another as desired. In a particularly preferred embodiment of the invention, the above-mentioned preferred embodiments apply simultaneously.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, are themselves inventive and should not merely be regarded as part of the embodiments of the present invention. For these features, independent protection may be sought in addition or as an alternative to each invention claimed at present.

The teaching on technical action disclosed with the present invention can be abstracted and combined with other examples.

The person skilled in the art will be able to use the descriptions to produce further electronic devices according to the invention without inventive step and thus carry out the invention throughout the range claimed.

EXAMPLES

Example 1

Synthesis of 2-[3-[7'-(4,6-diphenyl-1,3,5-triazin-2-yl)-9,9'-spirobi[fluoren]-2'-yl]phenyl]-1-phenylbenzimidazole 6a

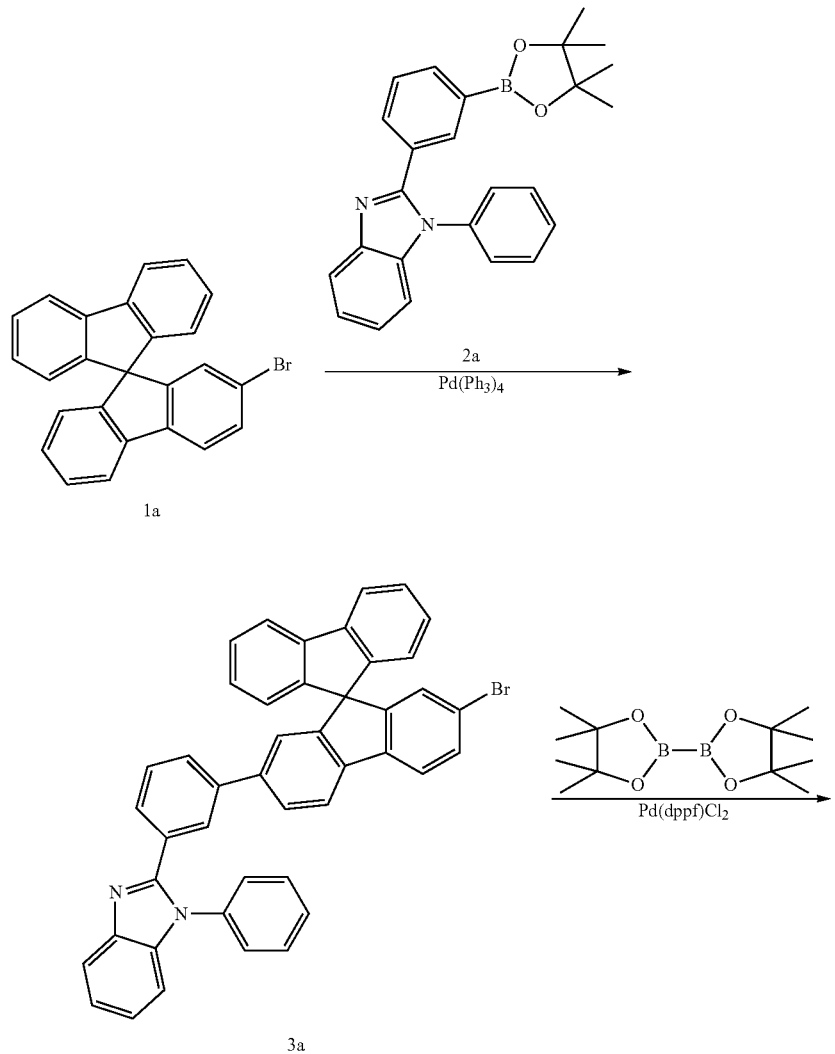

-continued

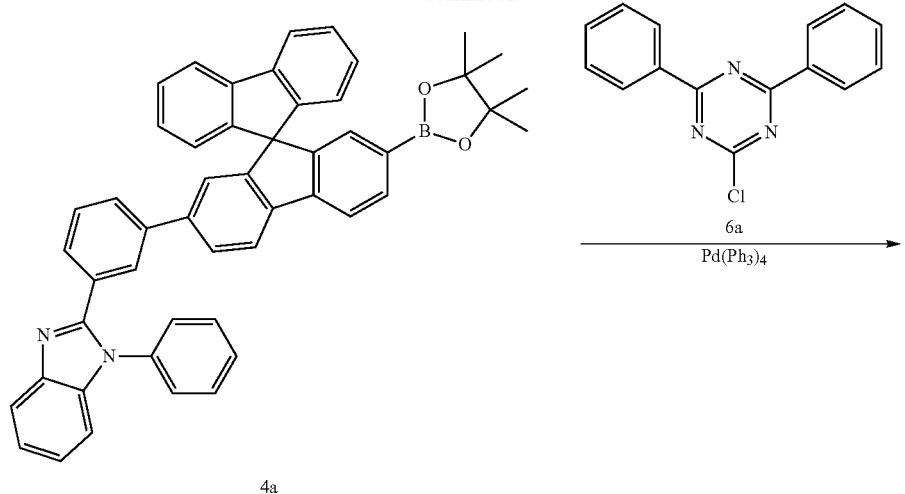

4a

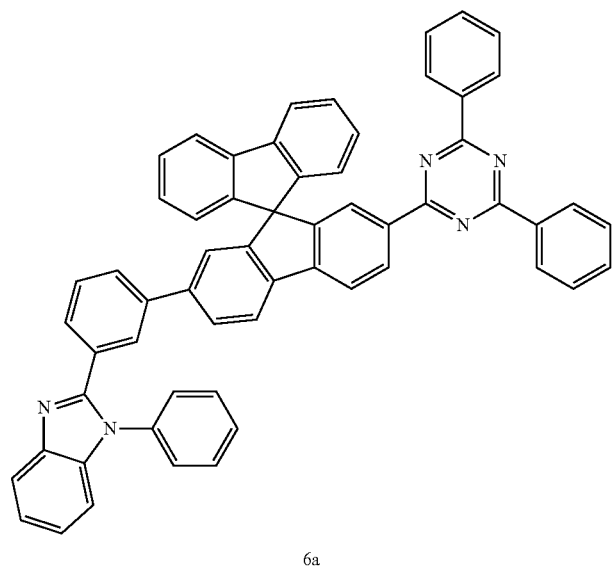 [SMILES: c1ccc(-c2nc(-c3ccccc3)nc(-c3ccc4c(c3)C3(c5ccccc5-c5ccccc53)c3cc(-c5cccc(-c6nc7ccccc7n6-c6ccccc6)c5)ccc3-4)n2)cc1]

6a

Synthesis of 2-[3-(7'-bromo-9,9'-spirobi[fluoren]-2'-yl)phenyl]-1-phenylbenzimidazole (3a)

Variant A 50.0 g (105 mmol, 1.00 eq.) of 2,7-dibromo-9,9'-spirobifluorene 1a, 41.7 g (105 mmol, 1.00 eq.) of 1-phenyl-2-[3-(4,4,5,5-tetramethyl-1,3,2-dioxaborolan-2-yl)phenyl]-1H-benzimidazole 2a and 36.4 g (263 mmol, 2.50 eq.) of potassium carbonate in 400 ml of toluene, 400 ml of 1,4-dioxane and 200 ml of DI water are initially introduced in a 2 l four-necked flask under protective gas and degassed. 1.22 g (1.05 mmol, 0.01 eq.) of tetrakis(triphenylphosphine) palladium(0) are subsequently added, and the mixture is heated under reflux overnight. When the reaction is complete, the batch is cooled, filtered through Celite and diluted with 1 l of toluene. The solution is washed 3× with 300 ml of semi-saturated sodium chloride solution in each case and, after drying over sodium sulfate, evaporated to about 200 ml in a rotary evaporator. The solid which has precipitated out is filtered off and dried in vacuo. The disubstituted by-product is separated off by means of sublimation, giving 22.0 g (33.1 mmol, 32%) of the desired product 3a.

Variant B

The procedure is carried out analogously to that of variant A, where tetrakis(triphenylphosphine)palladium(0) is replaced by 0.01 eq. of palladium(II) acetate and 0.01 eq. of dicyclohexyl-(2',6'-dimethoxybiphenyl-2-yl)phosphine (SPhos).

The following are reacted analogously:
| No. | Starting material 1 | Starting material 2 | Product 3 | Var. | Yield |
|---|---|---|---|---|---|
| 3b | 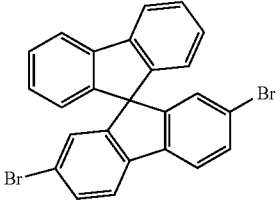 [171408-84-7] | 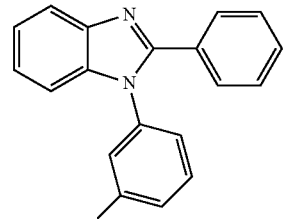 [1549686-33-0] | 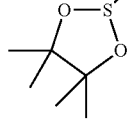 | A | 54% |
| 3c | 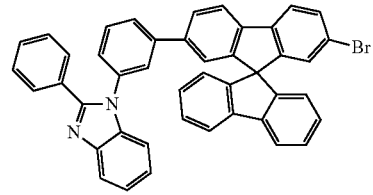 [SMILES: Brc1ccc2c(c1)C1(c3ccccc3-c3ccccc31)c1cc(-c3cccc(-n4c(-c5ccccc5)nc5ccccc54)c3)ccc1-2] [67665-47-8] | 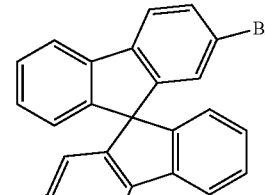 | 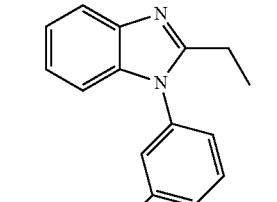 | A | 35% |
| 3d | 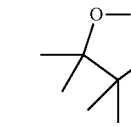 [1257321-41-7] | 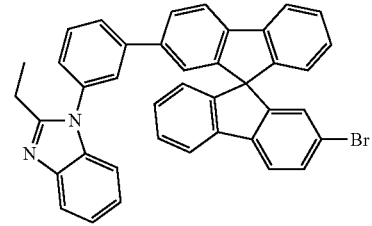 [SMILES: CCc1nc2ccccc2n1-c1cccc(-c2ccc3c(c2)C2(c4ccccc4-c4ccc(Br)cc42)c2ccccc2-3)c1] [1169709-19-6] | 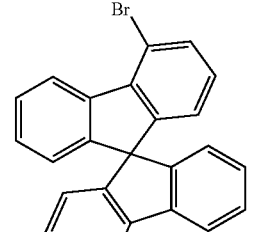 | B | 41% |

-continued

| No. | Starting material 1 | Starting material 2 | Product 3 | Var. | Yield |
|---|---|---|---|---|---|
| 3e | [67665-47-8] | [1169709-19-6] | | A | 59% |
| 3f | [67665-47-8] | [1146340-38-6] | | B | 32% |
| 3g | [1257321-41-7] | [1505512-90-2] | | B | 62% |

-continued
| No. | Starting material 1 | Starting material 2 | Product 3 | Var. | Yield |
|---|---|---|---|---|---|
| 3h | 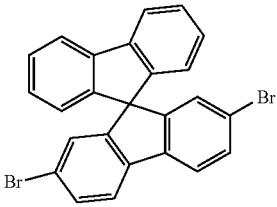 [171408-84-7] | 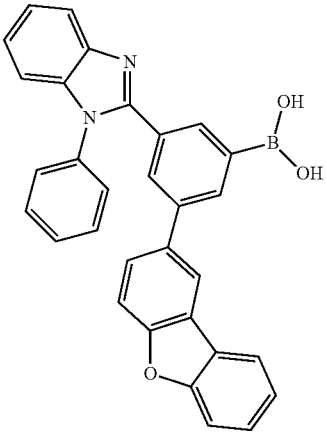 [1172134-18-7] | 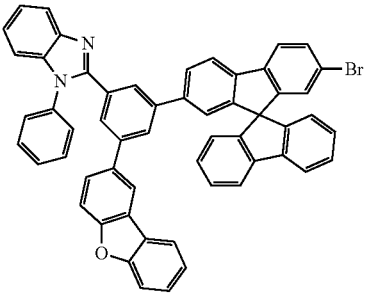 [SMILES: Brc1ccc2c(c1)C1(c3ccccc3-c3ccccc31)c1cc(-c3cc(-c4ccc5oc6ccccc6c5c4)cc(-c4nc5ccccc5n4-c4ccccc4)c3)ccc1-2] | B | 44% |
| 3i | 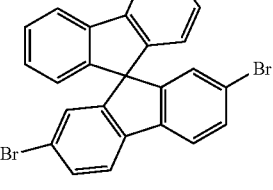 [171408-84-7] | 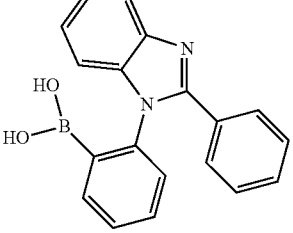 [1553408-82-4] | 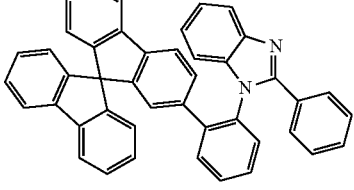 | A | 21% |
| 3j | 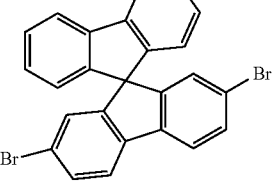 [171408-84-7] | 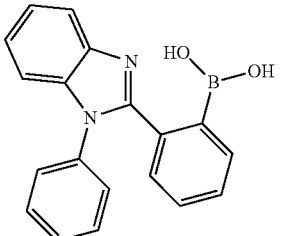 [58534-74-0] | 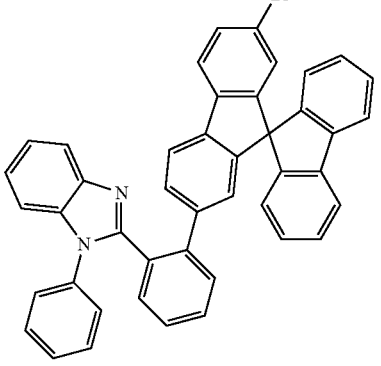 | B | 15% |
| 3k | 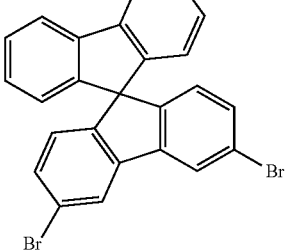 [1373114-50-1] | 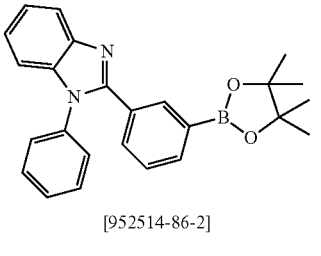 [SMILES: CC1(C)OB(c2cccc(-c3nc4ccccc4n3-c3ccccc3)c2)OC1(C)C] [952514-86-2] | 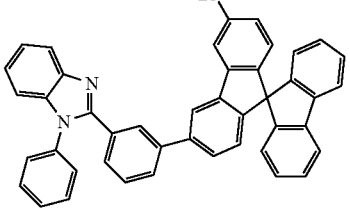 | A | 64% |

-continued
| No. | Starting material 1 | Starting material 2 | Product 3 | Var. | Yield |
|---|---|---|---|---|---|
| 3l | 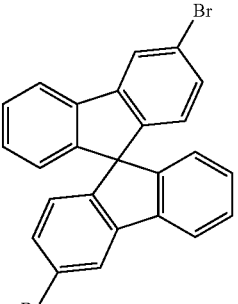 [1418299-83-8] | 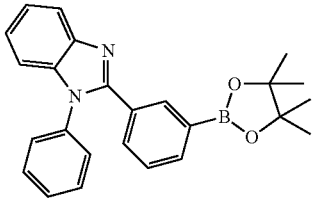 [952514-86-2] | 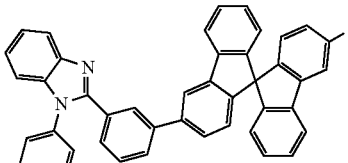 | A | 38% |
| 3m | 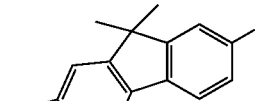 [28320-32-3] | 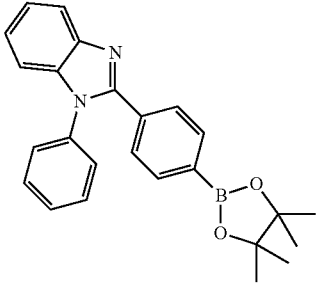 [1146340-38-6] | 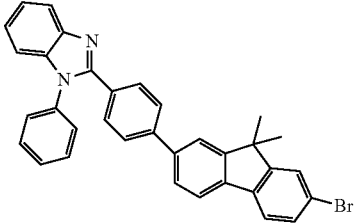 [SMILES: CC1(C)c2cc(Br)ccc2-c2ccc(-c3ccc(-c4nc5ccccc5n4-c4ccccc4)cc3)cc21] | B | 32% |
| 3n | 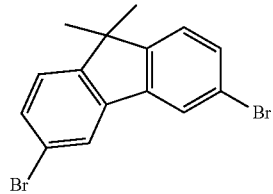 [865702-19-8] | 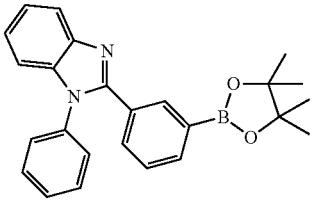 [952514-86-2] | 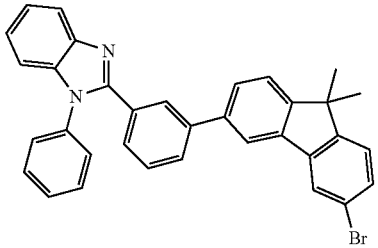 [SMILES: CC1(C)c2ccc(Br)cc2-c2cc(-c3cccc(-c4nc5ccccc5n4-c4ccccc4)c3)ccc21] | B | 53% |
| 3o | 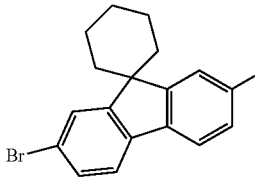 [736138-41-3] | 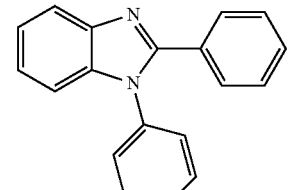 [1549686-33-0] | 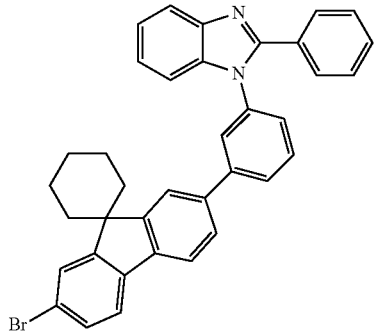 [SMILES: Brc1ccc2c(c1)C1(CCCCC1)c1cc(-c3cccc(-n4c(-c5ccccc5)nc5ccccc54)c3)ccc1-2] | A | 41% |

-continued

| No. | Starting material 1 | Starting material 2 | Product 3 | Var. | Yield |
|---|---|---|---|---|---|
| 3p | [880800-04-4] | [1384871-80-0] | | B | 58% |
| 3q | [198142-65-3] | [1219956-29-2] | | B | 17% |
| 3r | [1303969-26-7] | [1172134-16-5] | | A | 39% |
| 3s | [28320-32-3] | [1316275-47-4] | | B | 28% |

Var.—variant

Synthesis of 1-phenyl-2-[3-[7'-(4,4,5,5-tetramethyl-1,3,2-dioxaborolan-2-yl)-9,9'-spirobi[fluoren]-2'-yl]phenyl]benzimidazole 4a 22.0 g (33.1 mmol, 1.00 eq.) of 2-[3-(7'-bromo-9,9'-spirobi[fluoren]-2'-yl)phenyl]-1-phenylbenzimidazole 3a, 8.84 g (30.1 mmol, 0.91 eq.) of bis(pinacolato)diboron and 26.0 g (265 mmol, 8.00 eq.) of potassium acetate in 500 ml of dried 1,4-dioxane are initially introduced in a 1 l four-necked flask and degassed for 30 minutes. 812 mg (0.995 mmol, 0.0300 eq.) of 1,1-bis(diphenylphosphino)ferrocenepalladium(II) dichloride complex with DCM are subsequently added, and the mixture is heated to an internal temperature of 80° C. After stirring overnight, the batch is cooled, and the solid which has precipitated out is filtered off with suction. The filtrate is evaporated to about 50 ml in a rotary evaporator, and the solid which has precipitated out is likewise filtered off with suction. The solids are combined and dried, giving 21.0 g (29.5 mmol, 89%) of the boronic ester 4a.

The following are reacted analogously:

| No. | Starting material 3 | Product 4 | Yield |
|---|---|---|---|
| 4b | | | 95% |
| 4c | | | 87% |
| 4d | | | 97% |

-continued

| No. | Starting material 3 | Product 4 | Yield |
|---|---|---|---|
| 4e | | | 94% |
| 4f | | | 88% |
| 4g | | | 47% |
| 4h | | | 81% |

-continued

| No. | Starting material 3 | Product 4 | Yield |
|---|---|---|---|
| 4i | | | 79% |
| 4j | | | 74% |
| 4k | | | 55% |
| 4l | | | 47% |

-continued

| No. | Starting material 3 | Product 4 | Yield |
|---|---|---|---|
| 4m | | | 85% |
| 4n | | | 82% |
| 4o | | | 87% |
| 4p | | | 66% |

| No. | Starting material 3 | Product 4 | Yield |
|---|---|---|---|
| 4q | | | 58% |
| 4r | | | 84% |
| 4s | | | 77% |

Synthesis of 2-[3-[7'-(4,6-diphenyl-1,3,5-triazin-2-yl)-9,9'-spirobi[fluoren]-2'-yl]phenyl]-1-phenylbenzimidazole 6a Variant A 21.0 g (29.5 mmol, 1.00 eq.) of 1-phenyl-2-[3-[7'-(4,4,5,5-tetramethyl-1,3,2-dioxaborolan-2-yl)-9,9'-spirobi[fluoren]-2'-yl]phenyl]benzimidazole 4a and 7.90 g (29.5 mmol, 1.00 eq.) of 2-chloro-4,6-diphenyl-1,3,5-triazine 5a together with 3.75 g (35.4 mmol, 1.20 eq.) of sodium carbonate in 200 ml of toluene, 200 ml of 1,4-dioxane and 100 ml of DI water are initially introduced in a 1 l three-necked flask and degassed for 20 minutes. After addition of 1.02 g (0.885 mmol, 0.0300 eq.) of tetrakis(triphenylphosphine)palladium (0), the batch is heated under reflux for 2 days and cooled when the reaction is complete. The solid which has precipitated out is filtered off with suction, washed with water and a little toluene and subsequently recrystallised a number of times from toluene/heptane until an HPLC purity of >99.9% is achieved. Sublimation gives 11.5 g (14.0 mmol, 43%) of a colourless solid 6a.

Variant B

The procedure is carried out analogously to that of variant A, where tetrakis(triphenylphosphine)palladium(0) is replaced by 0.01 eq. of palladium(II) acetate and 0.04 eq. of tri(o-tolyl)phosphine.

Variant C

The procedure is carried out analogously to that of variant A, where tetrakis(triphenylphosphine)palladium(0) is replaced by 0.01 eq. of palladium(II) acetate and 0.01 eq. of dicyclohexyl-(2',6'-dimethoxy-biphenyl-2-yl)phosphine (SPhos).

The following are prepared analogously:

| No. | Starting material 4 | Starting material 5 |
|---|---|---|
| 6b | 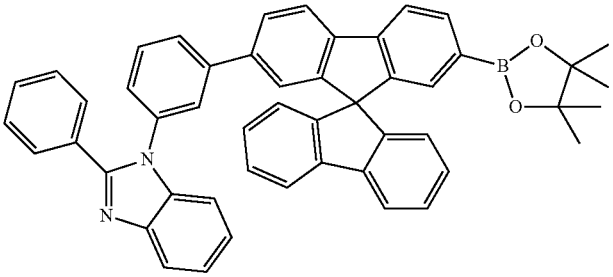 [SMILES: CC1(C)OB(c2ccc3c(c2)C2(c4ccccc4-c4ccccc42)c2cc(-c4cccc(-n5c(-c6ccccc6)nc6ccccc65)c4)ccc2-3)OC1(C)C] | 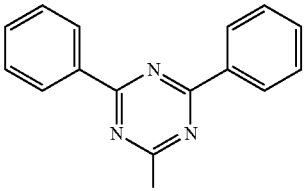   [3842-55-5] |
| 6c | 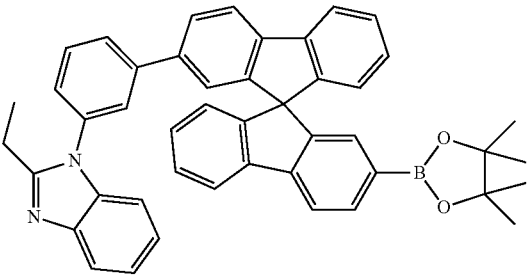 [SMILES: CCc1nc2ccccc2n1-c1cccc(-c2ccc3c(c2)C2(c4ccccc4-c4ccc(B5OC(C)(C)C(C)(C)O5)cc42)c2ccccc2-3)c1] | 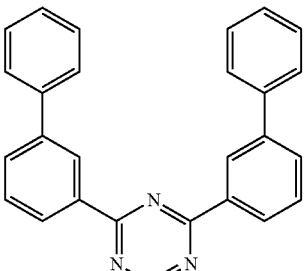   [1205748-61-3] |
| 6d | 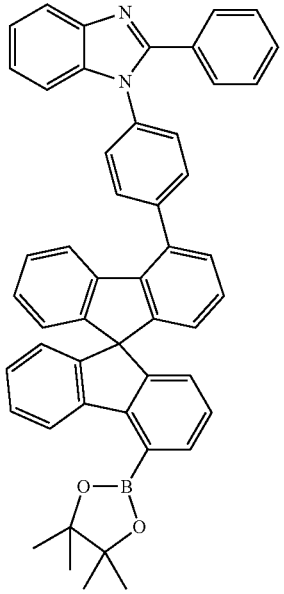 [SMILES: CC1(C)OB(c2cccc3c2-c2ccccc2C32c3ccccc3-c3c(-c4ccc(-n5c(-c6ccccc6)nc6ccccc65)cc4)cccc32)OC1(C)C] | 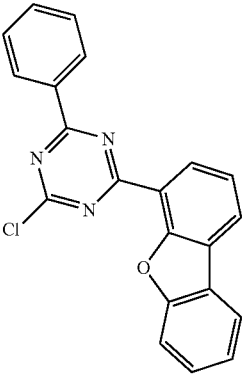   [1472729-25-1] |

-continued
6e 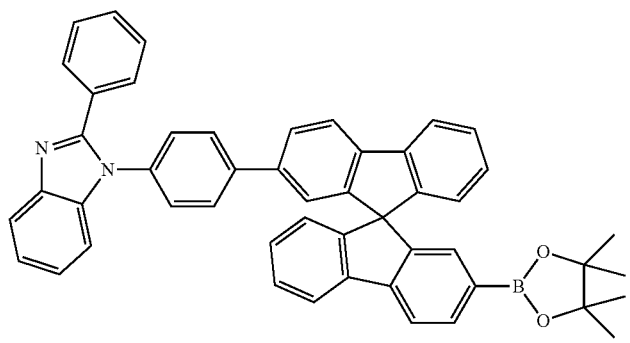 [SMILES: CC1(C)OB(c2ccc3c(c2)C2(c4ccccc4-3)c3ccccc3-c3ccc(-c4ccc(-n5c(-c6ccccc6)nc6ccccc65)cc4)cc32)OC1(C)C]
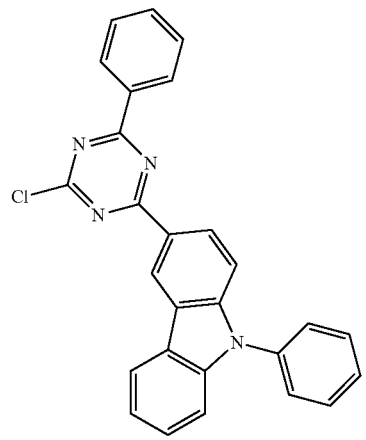
[1476785-42-8]
6f 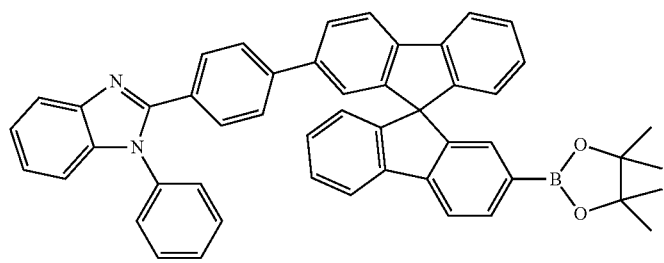 [SMILES: CC1(C)OB(c2ccc3c(c2)C2(c4ccccc4-3)c3ccccc3-c3ccc(-c4ccc(-c5nc6ccccc6n5-c5ccccc5)cc4)cc32)OC1(C)C]
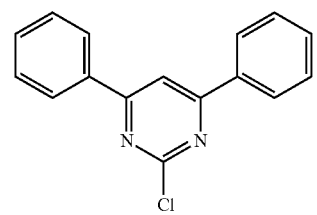
[2915-16-4]
6g 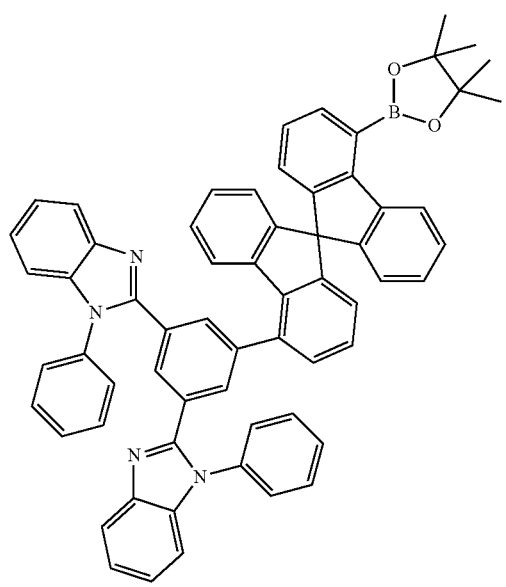 [SMILES: CC1(C)OB(c2cccc3c2-c2ccccc2C32c3ccccc3-c3c(-c4cc(-c5nc6ccccc6n5-c5ccccc5)cc(-c5nc6ccccc6n5-c5ccccc5)c4)cccc32)OC1(C)C]
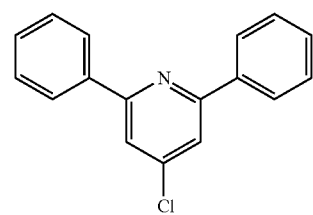
[133785-60-1]

| | | |
|---|---|---|
| 6h | 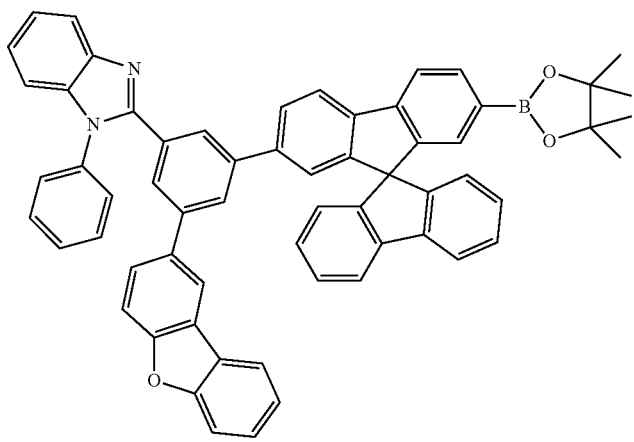 [SMILES: CC1(C)OB(c2ccc3c(c2)C2(c4ccccc4-c4ccccc42)c2cc(-c4cc(-c5ccc6oc7ccccc7c6c5)cc(-c5nc6ccccc6n5-c5ccccc5)c4)ccc2-3)OC1(C)C] | 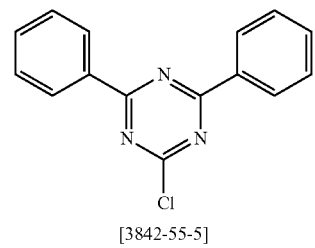 [SMILES: Clc1nc(-c2ccccc2)nc(-c2ccccc2)n1]
[3842-55-5] |
| 6i | 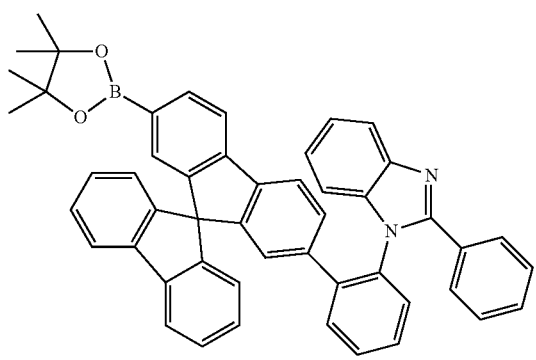 [SMILES: CC1(C)OB(c2ccc3c(c2)C2(c4ccccc4-c4ccccc42)c2cc(-c4ccccc4-n4c(-c5ccccc5)nc5ccccc54)ccc2-3)OC1(C)C] | 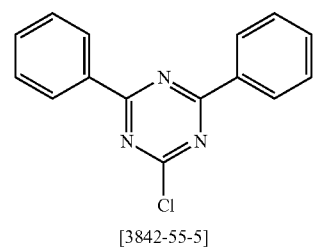 [SMILES: Clc1nc(-c2ccccc2)nc(-c2ccccc2)n1]
[3842-55-5] |
| 6j | 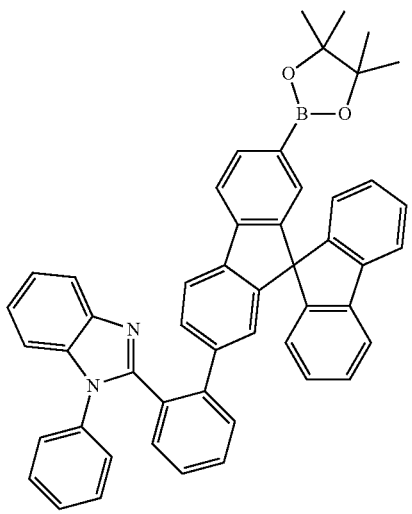 [SMILES: CC1(C)OB(c2ccc3c(c2)C2(c4ccccc4-c4ccccc42)c2cc(-c4ccccc4-c4nc5ccccc5n4-c4ccccc4)ccc2-3)OC1(C)C] | 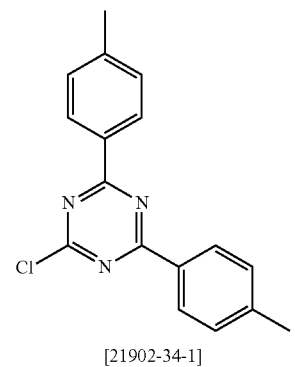 [SMILES: Cc1ccc(-c2nc(Cl)nc(-c3ccc(C)cc3)n2)cc1]
[21902-34-1] |

-continued
| | | | |
|---|---|---|---|
| 6k | 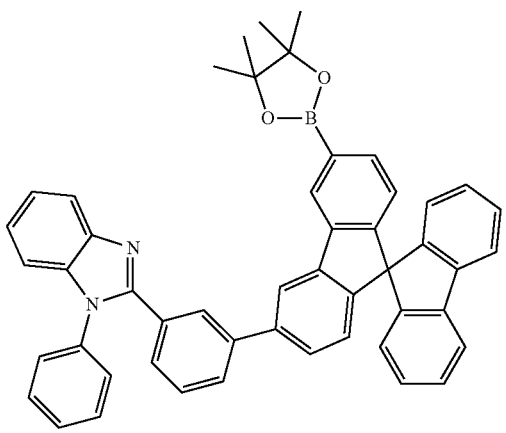 [SMILES: CC1(C)OB(c2ccc3c(c2)-c2cc(-c4cccc(-c5nc6ccccc6n5-c5ccccc5)c4)ccc2C32c3ccccc3-c3ccccc32)OC1(C)C] | 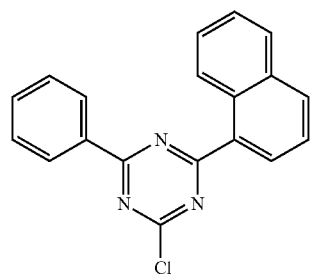
[1472062-95-5] | |
| 6l | 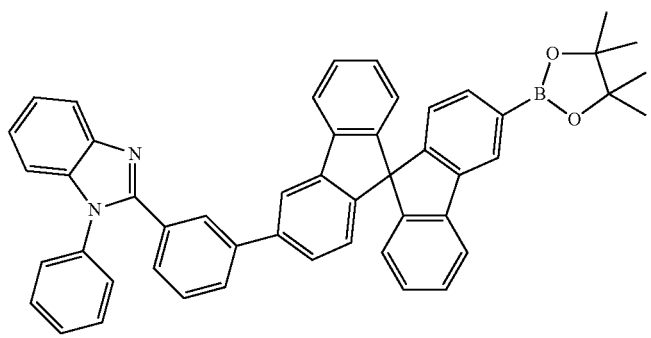 [SMILES: CC1(C)OB(c2ccc3c(c2)-c2ccccc2C32c3ccccc3-c3cc(-c4cccc(-c5nc6ccccc6n5-c5ccccc5)c4)ccc32)OC1(C)C] | 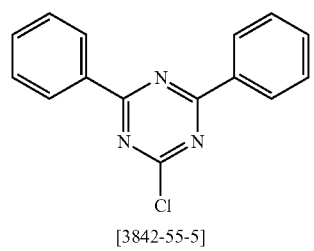 [SMILES: Clc1nc(-c2ccccc2)nc(-c2ccccc2)n1]
[3842-55-5] | |
| 6m | 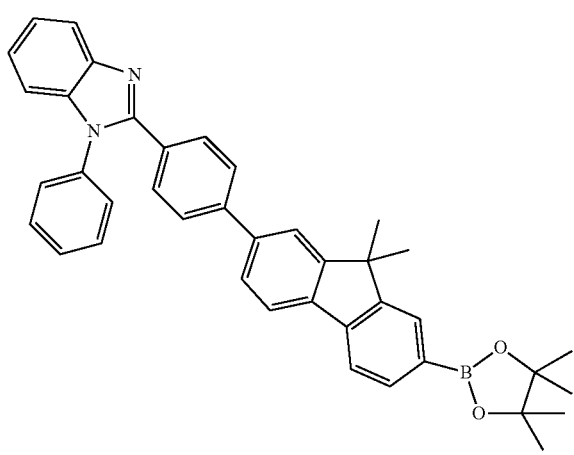 [SMILES: CC1(C)c2cc(B3OC(C)(C)C(C)(C)O3)ccc2-c2ccc(-c3ccc(-c4nc5ccccc5n4-c4ccccc4)cc3)cc21] | 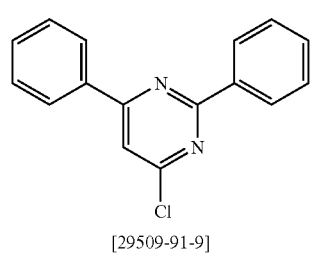 [SMILES: Clc1cc(-c2ccccc2)nc(-c2ccccc2)n1]
[29509-91-9] | |
| 6n | 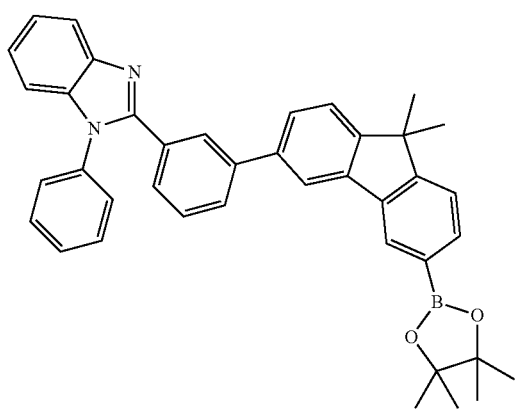 [SMILES: CC1(C)c2ccc(B3OC(C)(C)C(C)(C)O3)cc2-c2cc(-c3cccc(-c4nc5ccccc5n4-c4ccccc4)c3)ccc21] | 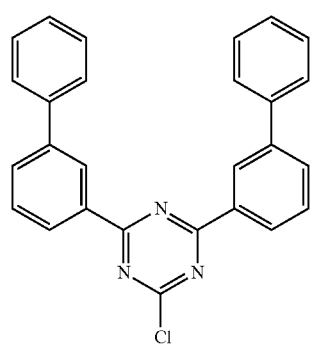
[1205748-61-3] | |

-continued
6o 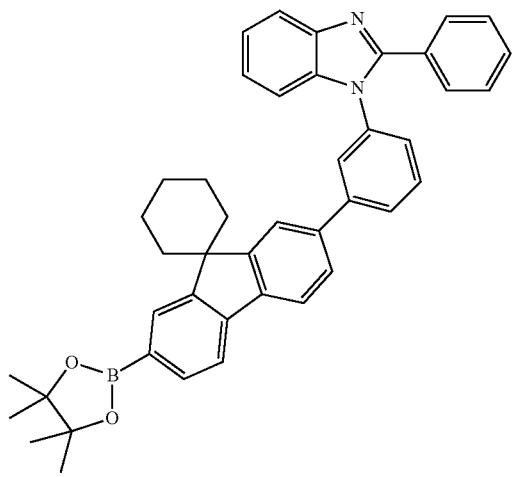 [SMILES: CC1(C)OB(c2ccc3c(c2)C2(CCCCC2)c2cc(-c4cccc(-n5c(-c6ccccc6)nc6ccccc65)c4)ccc2-3)OC1(C)C] 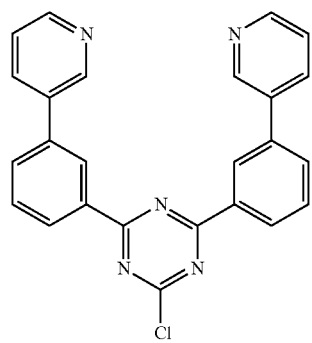
[1396311-93-5]
6p 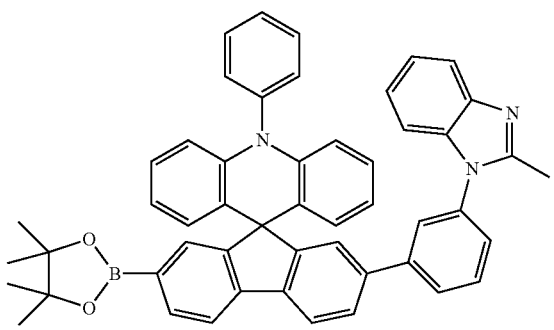 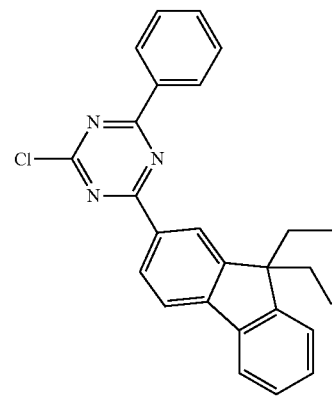
[1015814-06-8]
6q 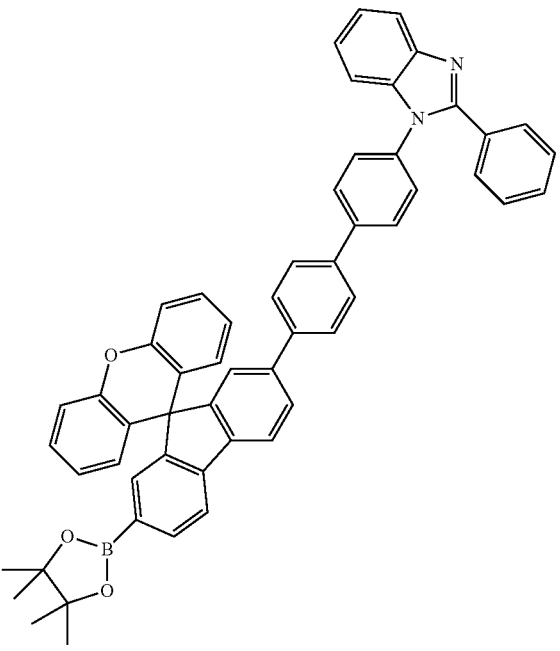 [SMILES: CC1(C)OB(c2ccc3c(c2)C2(c4ccccc4Oc4ccccc42)c2cc(-c4ccc(-c5ccc(-n6c(-c7ccccc7)nc7ccccc76)cc5)cc4)ccc2-3)OC1(C)C] 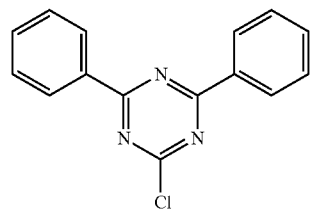
[3842-55-5]

-continued
| | | | | |
|---|---|---|---|---|
| 6r | 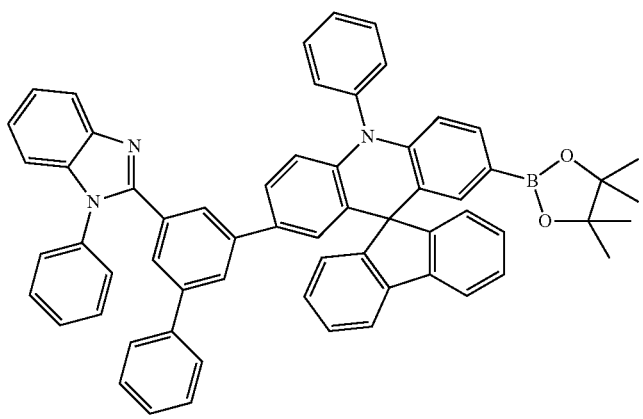 [SMILES: CC1(C)OB(c2ccc3c(c2)C2(c4ccccc4-c4ccccc42)c2cc(-c4cc(-c5ccccc5)cc(-c5nc6ccccc6n5-c5ccccc5)c4)ccc2N3c2ccccc2)OC1(C)C] | | 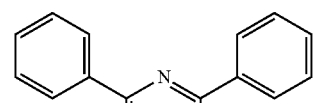[3842-55-5] | |
| | 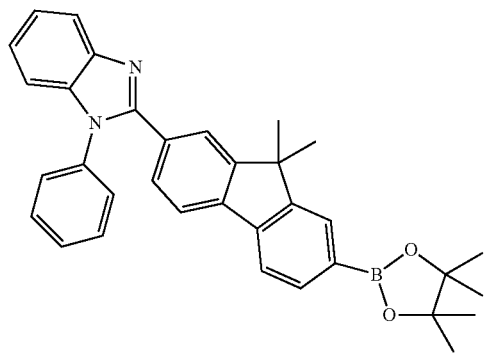 [SMILES: CC1(C)c2cc(B3OC(C)(C)C(C)(C)O3)ccc2-c2ccc(-c3nc4ccccc4n3-c3ccccc3)cc21] | | 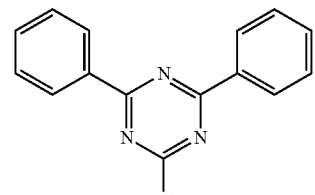[3842-55-5] | |
| No. | Product 6 | Var. | Yield |
|---|---|---|---|
| 6b | 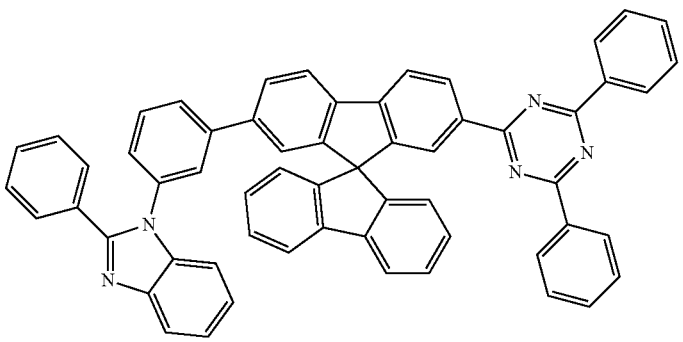 [SMILES: c1ccc(-c2nc(-c3ccccc3)nc(-c3ccc4c(c3)C3(c5ccccc5-c5ccccc53)c3cc(-c5cccc(-n6c(-c7ccccc7)nc7ccccc76)c5)ccc3-4)n2)cc1] | B | 57% |
| 6c | 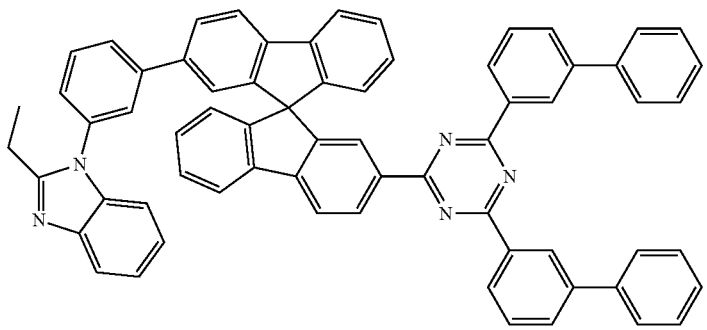 [SMILES: CCc1nc2ccccc2n1-c1cccc(-c2ccc3c(c2)C2(c4ccccc4-3)c3ccccc3-c3ccc(-c4nc(-c5cccc(-c6ccccc6)c5)nc(-c5cccc(-c6ccccc6)c5)n4)cc32)c1] | A | 38% |

| | | | |
|---|---|---|---|
| 6d | 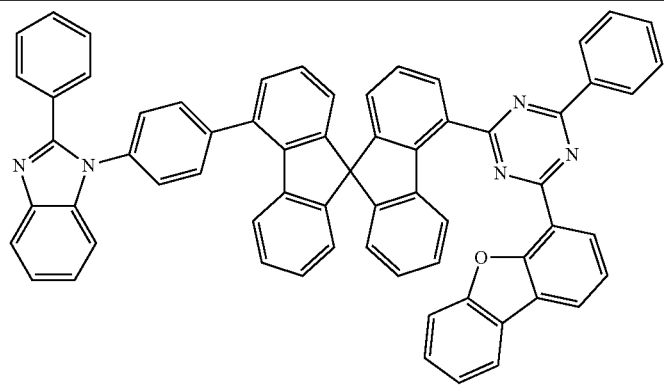 | A | 42% |
| 6e | 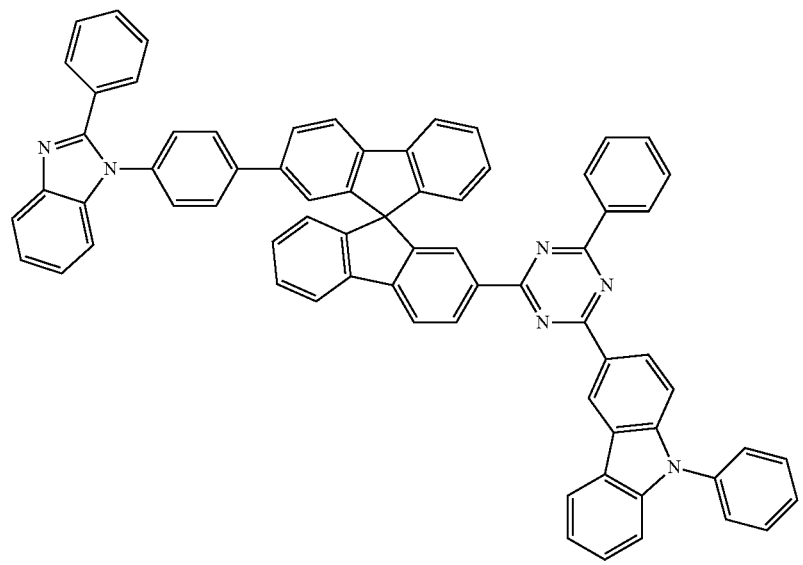 [SMILES: c1ccc(-c2nc(-c3ccc4c(c3)C3(c5ccccc5-c5ccc(-c6ccc(-n7c(-c8ccccc8)nc8ccccc87)cc6)cc53)c3ccccc3-4)nc(-c3ccc4c(c3)c3ccccc3n4-c3ccccc3)n2)cc1] | C | 61% |
| 6f | 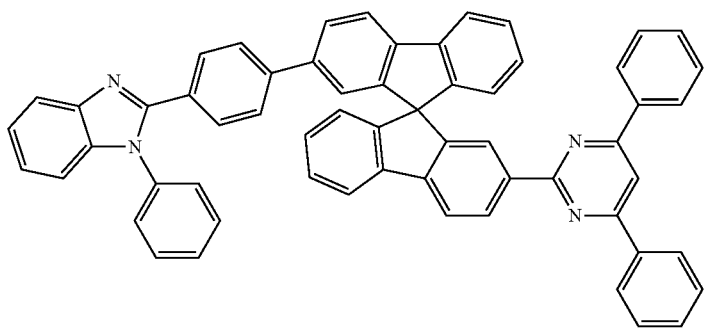 [SMILES: c1ccc(-c2cc(-c3ccccc3)nc(-c3ccc4c(c3)C3(c5ccccc5-c5ccc(-c6ccc(-c7nc8ccccc8n7-c7ccccc7)cc6)cc53)c3ccccc3-4)n2)cc1] | B | 37% |

| | | | |
|---|---|---|---|
| 6g | 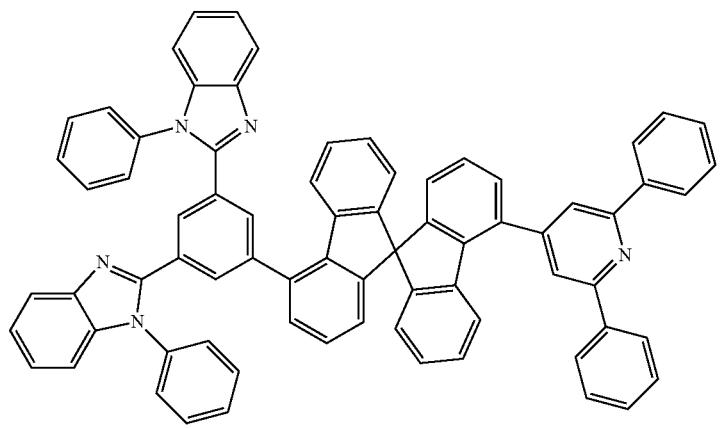 [SMILES: c1ccc(-c2cc(-c3cccc4c3-c3ccccc3C43c4ccccc4-c4c(-c5cc(-c6nc7ccccc7n6-c6ccccc6)cc(-c6nc7ccccc7n6-c6ccccc6)c5)cccc43)cc(-c3ccccc3)n2)cc1] | C | 39% |
| 6h | 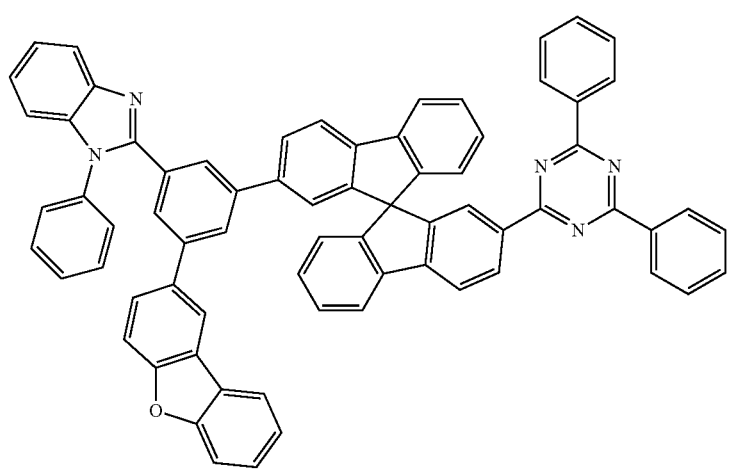 [SMILES: c1ccc(-c2nc(-c3ccccc3)nc(-c3ccc4c(c3)C3(c5ccccc5-c5ccc(-c6cc(-c7ccc8oc9ccccc9c8c7)cc(-c7nc8ccccc8n7-c7ccccc7)c6)cc53)c3ccccc3-4)n2)cc1] | C | 31% |
| 6i | 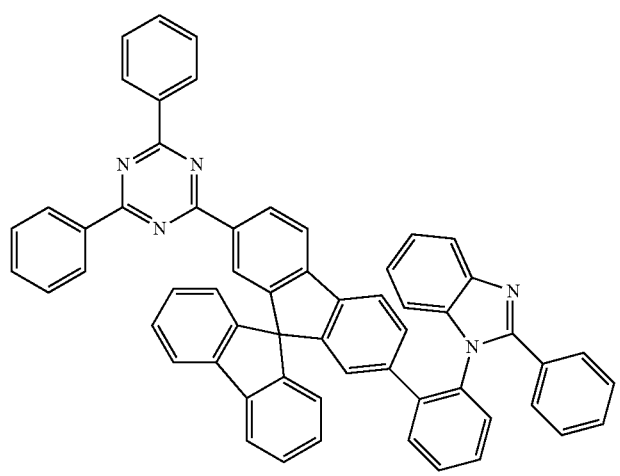 [SMILES: c1ccc(-c2nc(-c3ccccc3)nc(-c3ccc4c(c3)C3(c5ccccc5-c5ccccc53)c3cc(-c5ccccc5-n5c(-c6ccccc6)nc6ccccc65)ccc3-4)n2)cc1] | A | 48% |

| | | | |
|---|---|---|---|
| 6j | 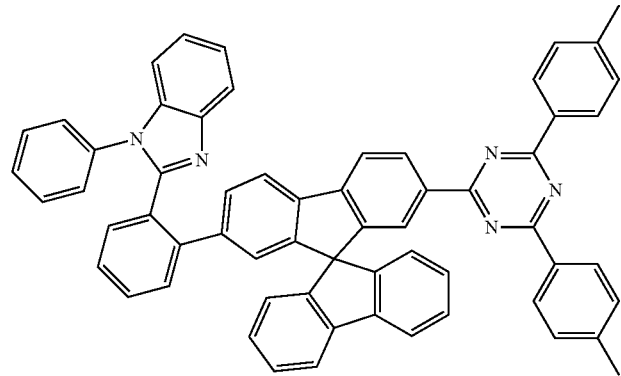 [SMILES: Cc1ccc(-c2nc(-c3ccc(C)cc3)nc(-c3ccc4c(c3)C3(c5ccccc5-c5ccccc53)c3cc(-c5ccccc5-c5nc6ccccc6n5-c5ccccc5)ccc3-4)n2)cc1] | A | 24% |
| 6k | 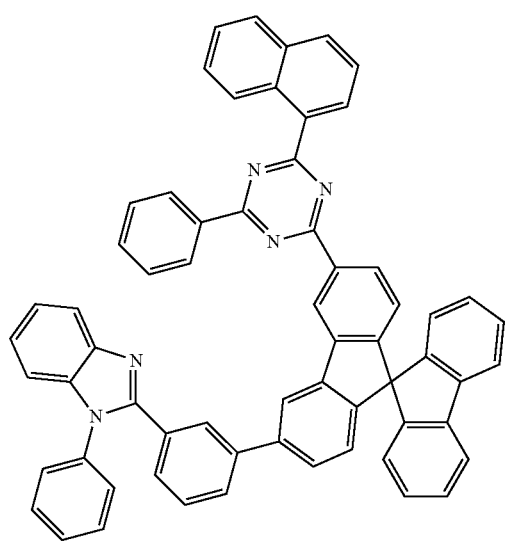 [SMILES: c1ccc(-c2nc(-c3ccc4c(c3)-c3cc(-c5cccc(-c6nc7ccccc7n6-c6ccccc6)c5)ccc3C43c4ccccc4-c4ccccc43)nc(-c3cccc4ccccc34)n2)cc1] | B | 51% |
| 6l | 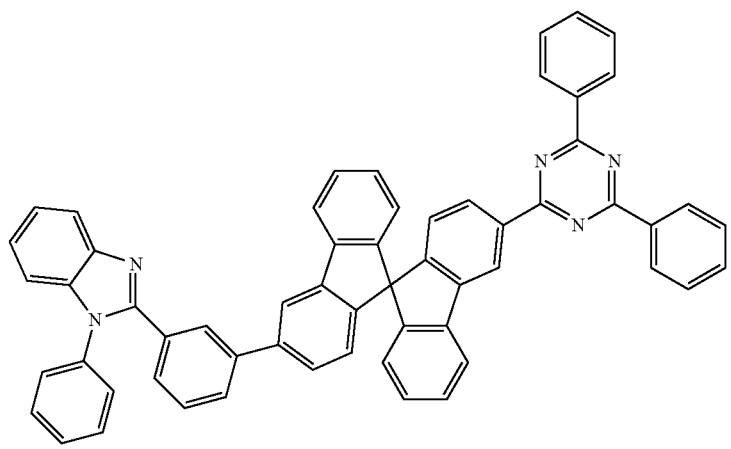 [SMILES: c1ccc(-c2nc(-c3ccccc3)nc(-c3ccc4c(c3)-c3ccccc3C43c4ccccc4-c4cc(-c5cccc(-c6nc7ccccc7n6-c6ccccc6)c5)ccc43)n2)cc1] | B | 38% |

| | | | |
|---|---|---|---|
| 6m | 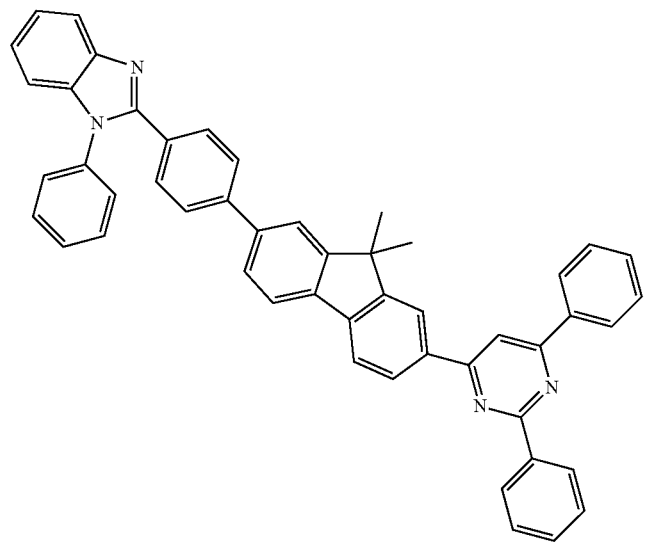 [SMILES: CC1(C)c2cc(-c3ccc(-c4nc5ccccc5n4-c4ccccc4)cc3)ccc2-c2ccc(-c3cc(-c4ccccc4)nc(-c4ccccc4)n3)cc21] | C | 34% |
| 6n | 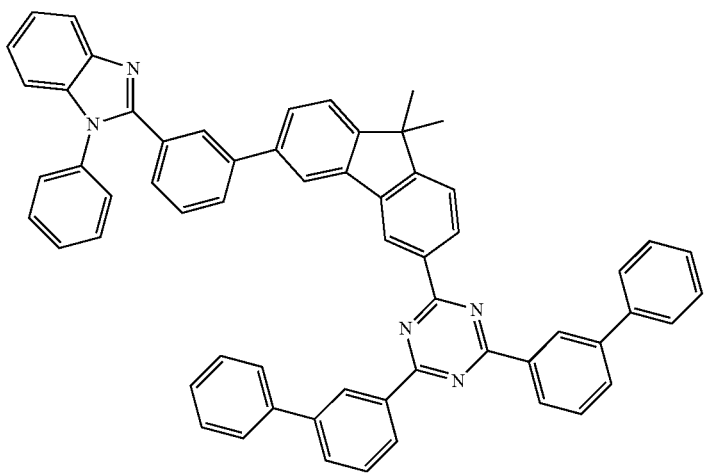 [SMILES: CC1(C)c2ccc(-c3cccc(-c4nc5ccccc5n4-c4ccccc4)c3)cc2-c2cc(-c3nc(-c4cccc(-c5ccccc5)c4)nc(-c4cccc(-c5ccccc5)c4)n3)ccc21] | C | 44% |
| 6o | 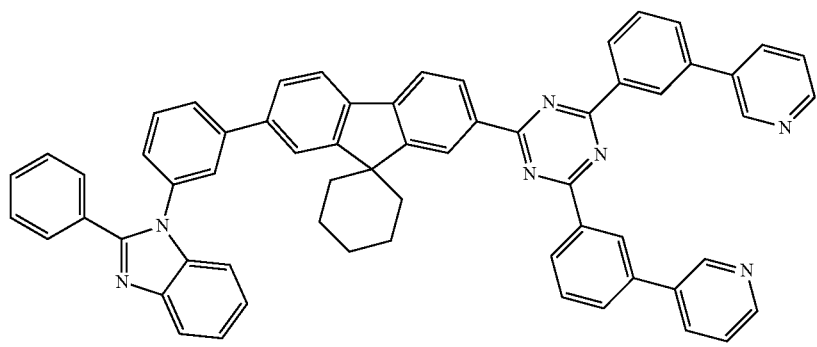 [SMILES: c1ccc(-c2nc3ccccc3n2-c2cccc(-c3ccc4c(c3)C3(CCCCC3)c3cc(-c5nc(-c6cccc(-c7cccnc7)c6)nc(-c6cccc(-c7cccnc7)c6)n5)ccc3-4)c2)cc1] | A | 53% |

-continued
| | | | |
|---|---|---|---|
| 6p | 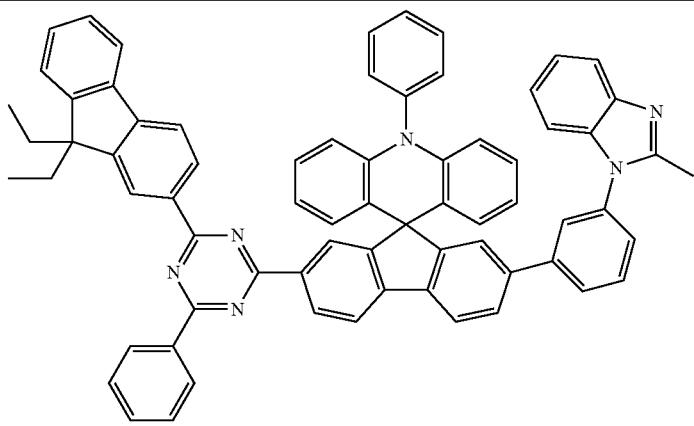 | C | 42% |
| 6q | 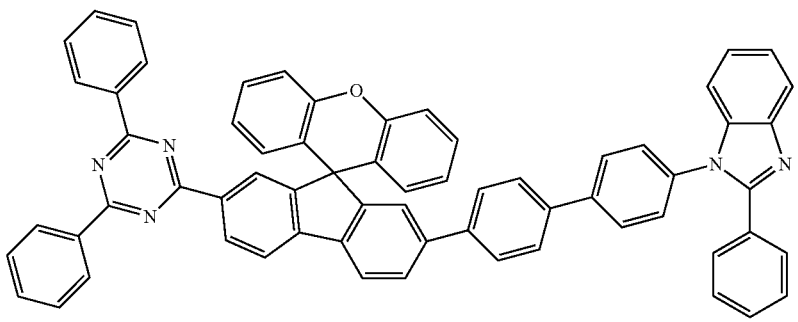 [SMILES: c1ccc(-c2nc(-c3ccccc3)nc(-c3ccc4c(c3)C3(c5ccccc5Oc5ccccc53)c3cc(-c5ccc(-c6ccc(-n7c(-c8ccccc8)nc8ccccc87)cc6)cc5)ccc3-4)n2)cc1] | B | 31% |
| 6r | 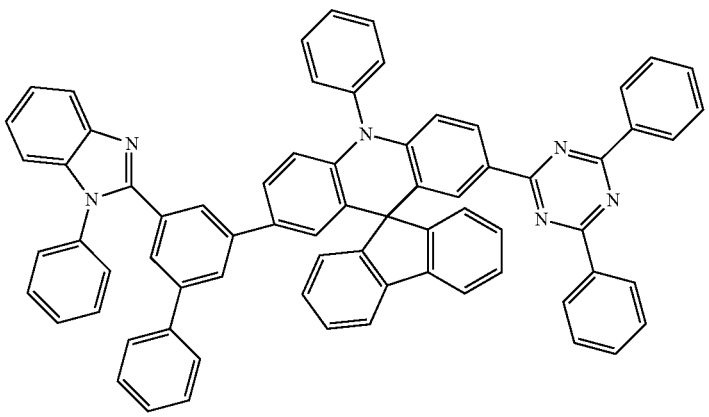 [SMILES: c1ccc(-c2cc(-c3ccc4c(c3)C3(c5ccccc5-c5ccccc53)c3cc(-c5nc(-c6ccccc6)nc(-c6ccccc6)n5)ccc3N4c3ccccc3)cc(-c3nc4ccccc4n3-c3ccccc3)c2)cc1] | B | 35% |
| | 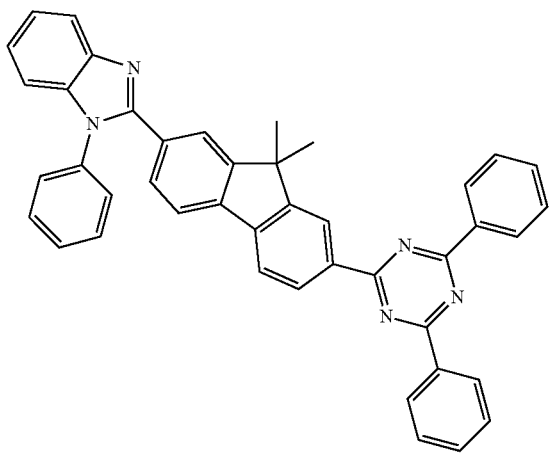 [SMILES: CC1(C)c2cc(-c3nc(-c4ccccc4)nc(-c4ccccc4)n3)ccc2-c2ccc(-c3nc4ccccc4n3-c3ccccc3)cc21] | B | 39% |
Var.—variant

Example 2

2-(3-[1-Phenyl-1H-benzimidazol-2-yl]phenyl)-4-phenyl-6-(9,9'-spirobi[9H-fluoren]-2-yl)-1,3,5-triazine 11a

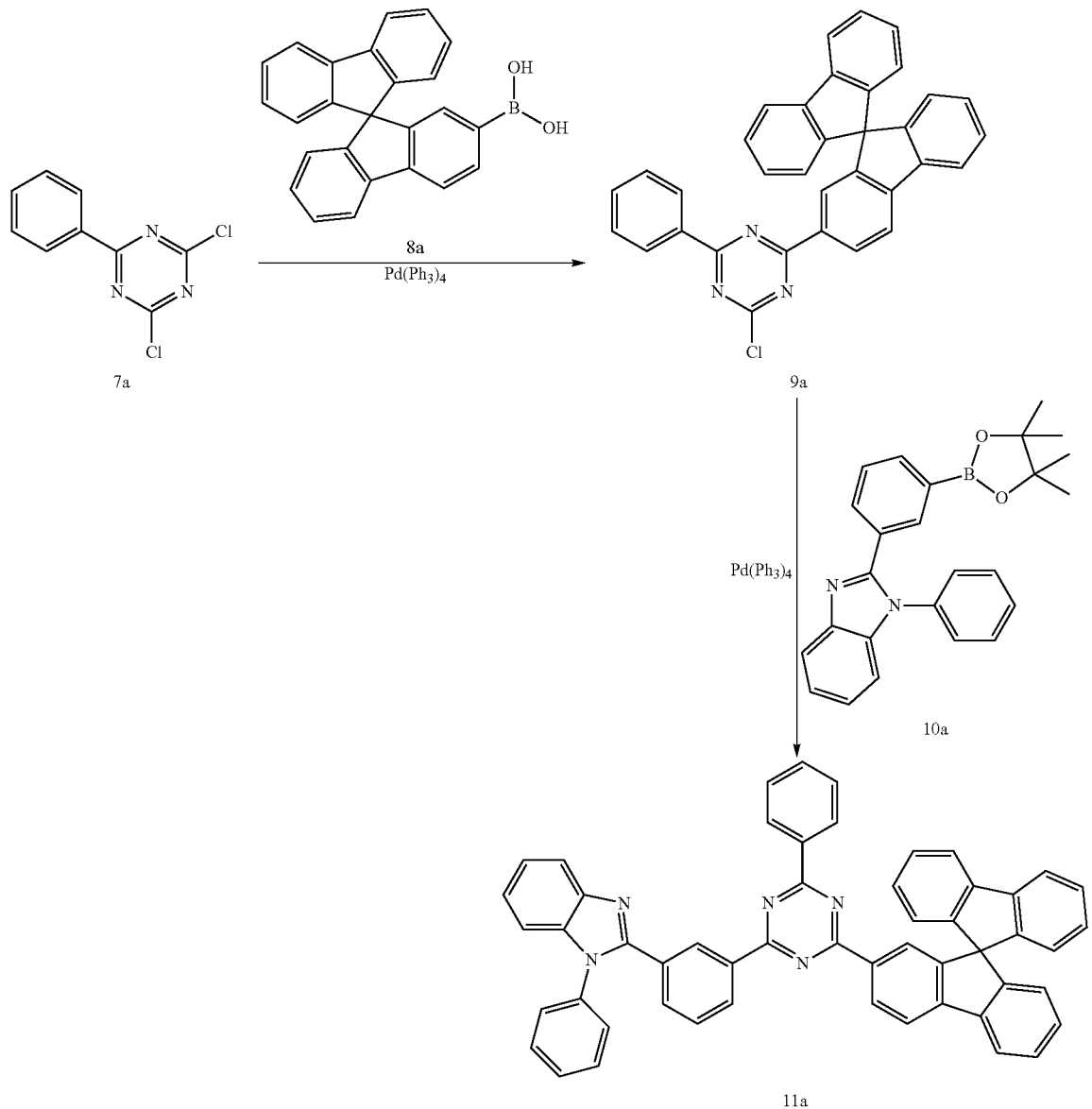

Synthesis of 2-chloro-4-phenyl-6-(9,9'-spirobi[9H-fluoren]-2-yl)-1,3,5-triazine 9a

Variant A

24.5 g (67.9 mmol, 1.00 eq.) of 9,9'-spirobifluoren-2'-ylbrononic acid 7a, 15.4 g (68.3 mmol, 1.01 eq.) of 2,4-dichloro-6-phenyl-1,3,5-triazine 8a and 9.04 g (85.3 mmol, 1.26 eq.) of sodium carbonate in 300 ml of toluene, 300 ml of 1,4-dioxane and 300 ml of DI water are initially introduced in a 2 l four-necked flask under protective gas and degassed. 0.850 g (0.736 mmol, 0.01 eq.) of tetrakis(triphenylphosphine)palladium(0) is subsequently added, and the mixture is heated under reflux for 24 hours. When the reaction is complete, the batch is cooled and diluted with 100 ml of ethyl acetate. The phases are separated in a separating funnel, the aqueous phase is extracted three times with ethyl acetate, and the combined organic phases are washed once more with water. The mixture is subsequently dried over sodium sulfate, and the solution is evaporated until a brownish solid precipitates out. The solid is filtered off, washed by stirring with hot ethanol and, after refiltration, dried in vacuo. The product is purified by means of column chromatography using heptane/dichloromethane 5:1 as eluent, giving 9.90 g (19.6 mmol, 29%) of a colourless solid.

Variant B

The procedure is carried out analogously to that of variant A, where tetrakis(triphenylphosphine)palladium(0) is replaced by 0.01 eq. of palladium(II) acetate and 0.04 eq. of tri(o-tolyl)phosphine.

Variant C

The procedure is carried out analogously to that of variant A, where tetrakis(triphenylphosphine)palladium(0) is replaced by 0.01 eq. of palladium(II) acetate and 0.01 eq. of dicyclohexyl-(2',6'-dimethoxybiphenyl-2-yl)phosphine (SPhos).

Variant D

The procedure is carried out analogously to that of variant A, where tetrakis(triphenylphosphine)palladium(0) is replaced by 0.02 eq. of 1,1-bis(diphenylphosphino)ferrocenepalladium(II) dichloride complex with DCM and dried toluene is used as solvent.

The following are prepared analogously:

| No. | Starting material 7 | Starting material 8 | Product 9 | Var. | Yield |
|---|---|---|---|---|---|
| 9b | [1402225-89-1] | [236389-21-2] | | A | 34% |
| 9c | [20354-40-9] | [236389-21-2] | | B | 29% |
| 9d | [1700-02-3] | [1361305-38-5] | | B | 41% |
| 9e | [51800-19-2] | [1241891-39-3] | | C | 17% |

-continued
| No. | Starting material 7 | Starting material 8 | Product 9 | Var. | Yield |
|---|---|---|---|---|---|
| 9f | 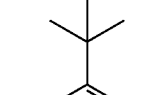 [1491751-92-8] | 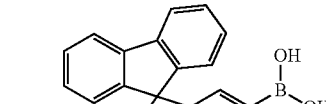 [1222537-26-9] | 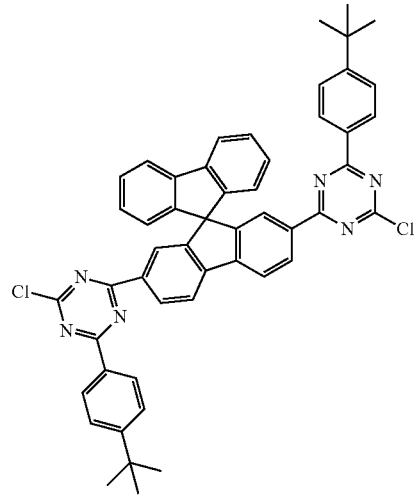 [SMILES: CC(C)(C)c1ccc(-c2nc(Cl)nc(-c3ccc4c(c3)C3(c5ccccc5-c5ccccc53)c3cc(-c5nc(Cl)nc(-c6ccc(C(C)(C)C)cc6)n5)ccc3-4)n2)cc1] | A | 26% |
| 9g | 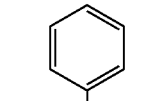 [1700-02-3] | 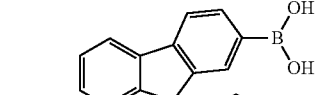 [1222007-94-4] | 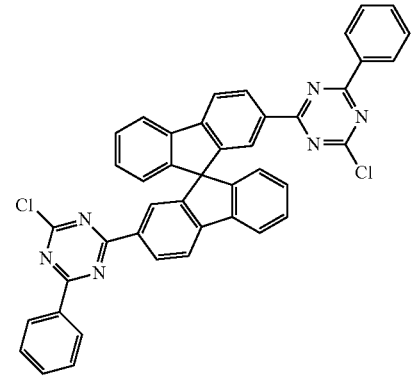 [SMILES: Clc1nc(-c2ccccc2)nc(-c2ccc3c(c2)C2(c4ccccc4-3)c3ccccc3-c3ccc(-c4nc(Cl)nc(-c5ccccc5)n4)cc32)n1] | A | 11% |
| 9h | 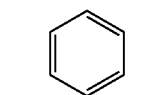 [10202-45-6] | 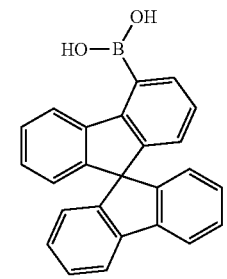 [1421789-05-0] | 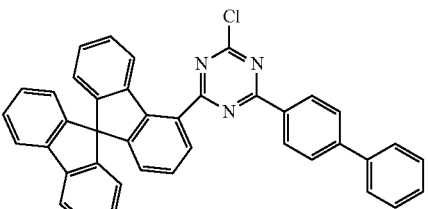 | B | 25% |

-continued
| No. | Starting material 7 | Starting material 8 | Product 9 | Var. | Yield |
|---|---|---|---|---|---|
| 9i | 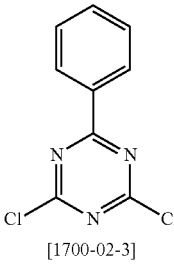 [1700-02-3] | 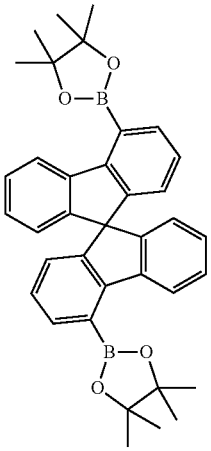 [1257321-47-3] |  | D | 18% |
| 9j | 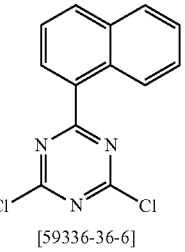 [59336-36-6] | 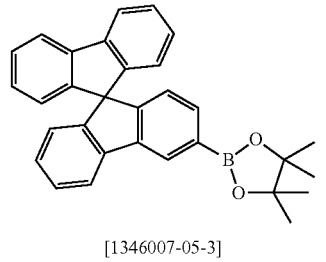 [SMILES: CC1(C)OB(c2ccc3c(c2)-c2ccccc2C32c3ccccc3-c3ccccc32)OC1(C)C] [1346007-05-3] | 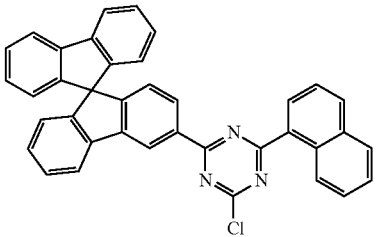 [SMILES: Clc1nc(-c2ccc3c(c2)-c2ccccc2C32c3ccccc3-c3ccccc32)nc(-c2cccc3ccccc23)n1] | B | 54% |
| 9k | 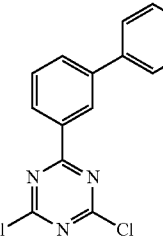 [1402225-89-1] | 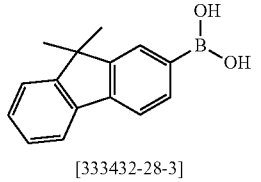 [SMILES: CC1(C)c2ccccc2-c2ccc(B(O)O)cc21] [333432-28-3] | 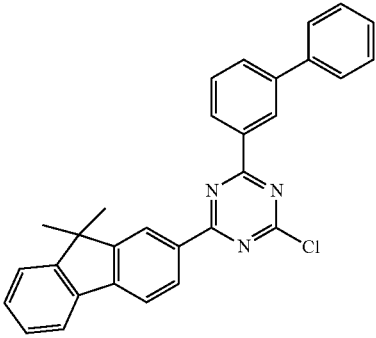 [SMILES: CC1(C)c2ccccc2-c2ccc(-c3nc(Cl)nc(-c4cccc(-c5ccccc5)c4)n3)cc21] | C | 41% |
| 9l | 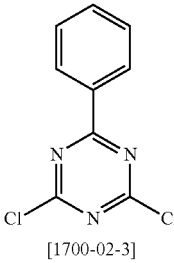 [1700-02-3] | 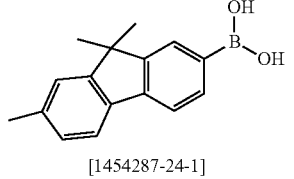 [SMILES: Cc1ccc2c(c1)C(C)(C)c1cc(B(O)O)ccc1-2] [1454287-24-1] | 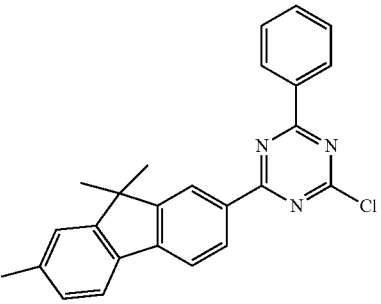 [SMILES: Cc1ccc2c(c1)C(C)(C)c1cc(-c3nc(Cl)nc(-c4ccccc4)n3)ccc1-2] | B | 31% |

-continued
| No. | Starting material 7 | Starting material 8 | Product 9 | Var. | Yield |
|---|---|---|---|---|---|
| 9m | 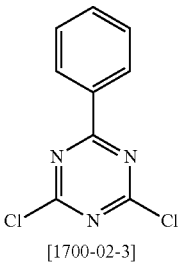 [SMILES: Clc1nc(Cl)nc(-c2ccccc2)n1] [1700-02-3] | 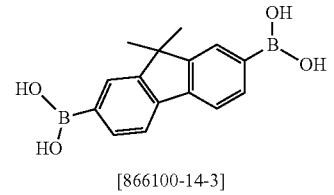 [SMILES: CC1(C)c2cc(B(O)O)ccc2-c2ccc(B(O)O)cc21] [866100-14-3] | 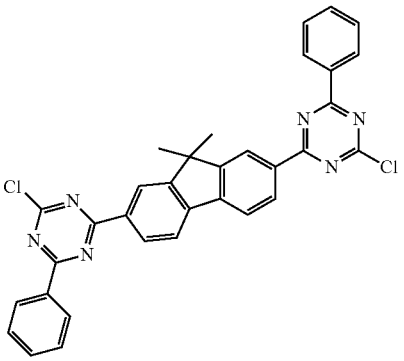 [SMILES: CC1(C)c2cc(-c3nc(Cl)nc(-c4ccccc4)n3)ccc2-c2ccc(-c3nc(Cl)nc(-c4ccccc4)n3)cc21] | A | 19% |
| 9n | 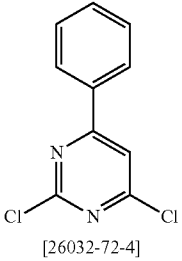 [SMILES: Clc1cc(-c2ccccc2)nc(Cl)n1] [26032-72-4] | 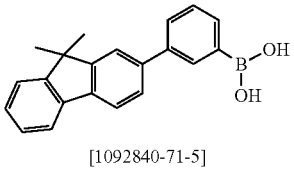 [SMILES: CC1(C)c2ccccc2-c2ccc(-c3cccc(B(O)O)c3)cc21] [1092840-71-5] | 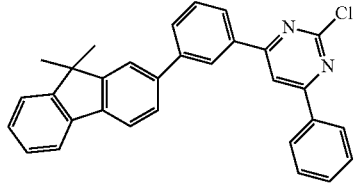 [SMILES: CC1(C)c2ccccc2-c2ccc(-c3cccc(-c4cc(-c5ccccc5)nc(Cl)n4)c3)cc21] | B | 38% |
| 9o | 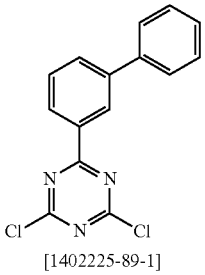 [SMILES: Clc1nc(Cl)nc(-c2cccc(-c3ccccc3)c2)n1] [1402225-89-1] | 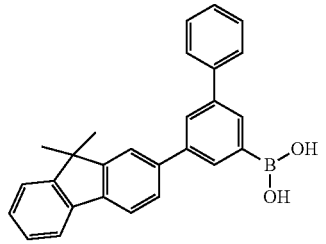 [881-11-75-7] | 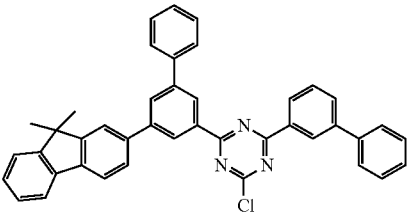 [SMILES: CC1(C)c2ccccc2-c2ccc(-c3cc(-c4ccccc4)cc(-c4nc(Cl)nc(-c5cccc(-c6ccccc6)c5)n4)c3)cc21] | C | 42% |
| 9p | 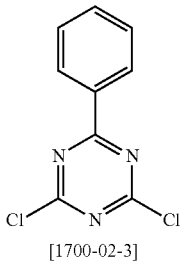 [SMILES: Clc1nc(Cl)nc(-c2ccccc2)n1] [1700-02-3] | 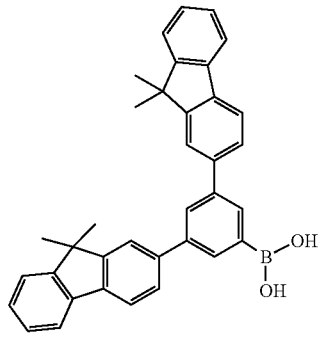 [881913-13-9] | 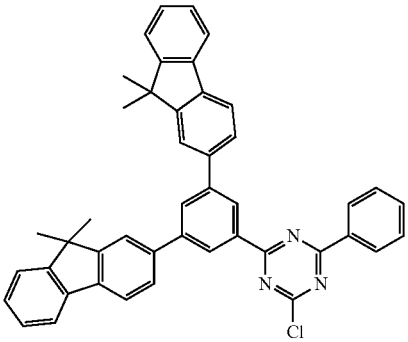 [SMILES: CC1(C)c2ccccc2-c2ccc(-c3cc(-c4ccc5c(c4)C(C)(C)c4ccccc4-5)cc(-c4nc(Cl)nc(-c5ccccc5)n4)c3)cc21] | A | 51% |

-continued
| No. | Starting material 7 | Starting material 8 | Product 9 | Var. | Yield |
|---|---|---|---|---|---|
| 9q | 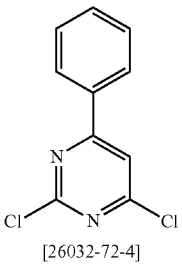 [SMILES: Clc1cc(-c2ccccc2)nc(Cl)n1] [26032-72-4] | 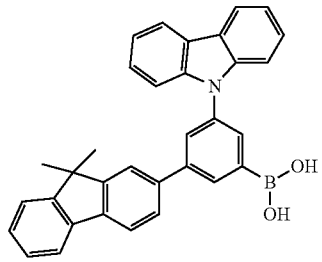 [1292291-83-8] | 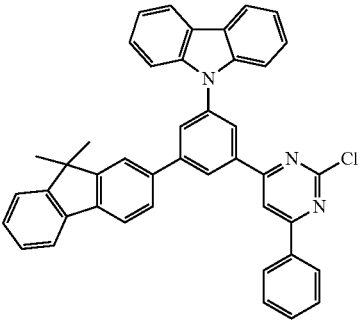 [SMILES: CC1(C)c2ccccc2-c2ccc(-c3cc(-c4cc(-c5ccccc5)nc(Cl)n4)cc(-n4c5ccccc5c5ccccc54)c3)cc21] | A | 24% |
| 9r | 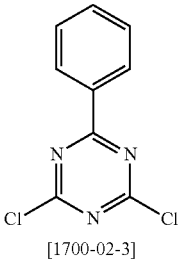 [SMILES: Clc1nc(Cl)nc(-c2ccccc2)n1] [1700-02-3] | 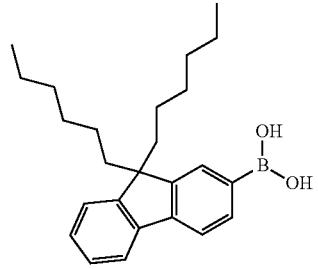 [400607-32-1] | 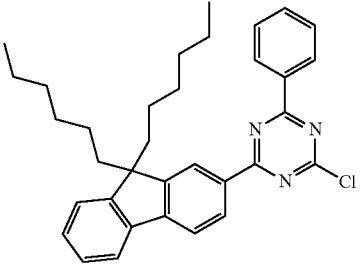 [SMILES: CCCCCCC1(CCCCCC)c2ccccc2-c2ccc(-c3nc(Cl)nc(-c4ccccc4)n3)cc21] | D | 18% |
| 9s | 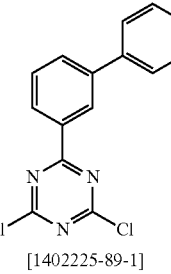 [1402225-89-1] | 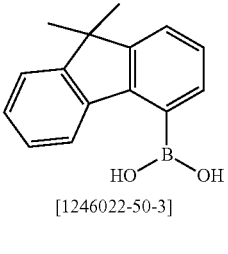 [SMILES: CC1(C)c2ccccc2-c2c(B(O)O)cccc21] [1246022-50-3] | 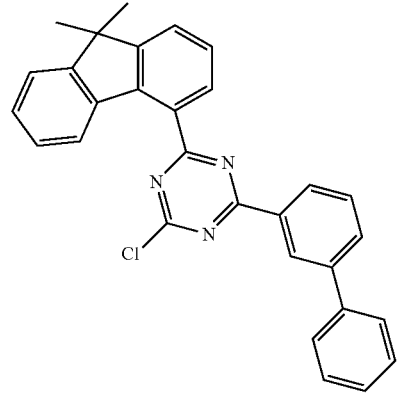 [SMILES: CC1(C)c2ccccc2-c2c(-c3nc(Cl)nc(-c4cccc(-c5ccccc5)c4)n3)cccc21] | A | 36% |
| 9t | 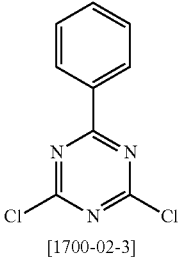 [SMILES: Clc1nc(Cl)nc(-c2ccccc2)n1] [1700-02-3] | 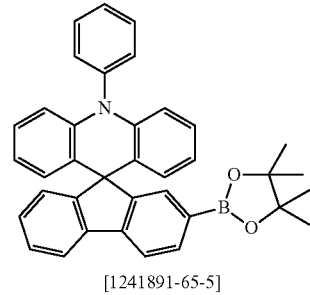 [SMILES: CC1(C)OB(c2ccc3c(c2)C2(c4ccccc4-3)c3ccccc3N(c3ccccc3)c3ccccc32)OC1(C)C] [1241891-65-5] | 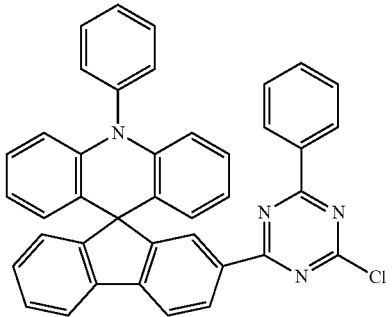 [SMILES: Clc1nc(-c2ccccc2)nc(-c2ccc3c(c2)C2(c4ccccc4-3)c3ccccc3N(c3ccccc3)c3ccccc32)n1] | B | 47% |

| No. | Starting material 7 | Starting material 8 | Product 9 | Var. | Yield |
|---|---|---|---|---|---|
| 9u | 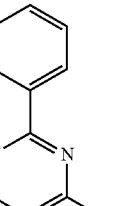 [1700-02-3] | 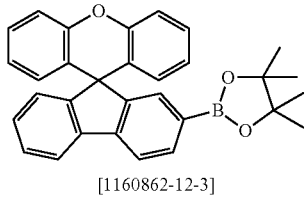 [SMILES: CC1(C)OB(c2ccc3c(c2)C2(c4ccccc4Oc4ccccc42)c2ccccc2-3)OC1(C)C] [1160862-12-3] | 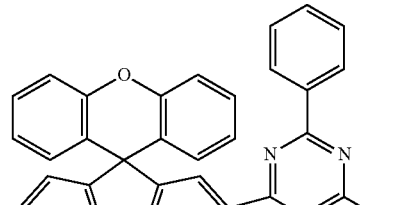 | B | 27% |
| 9v | 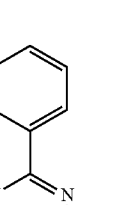 [1700-02-3] | 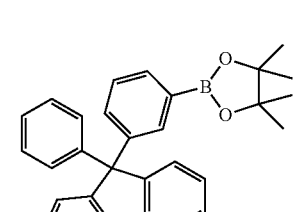 [1260032-45-8] | 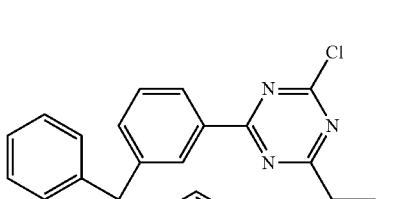 | D | 42% |

Var.—variant

Synthesis of 2-(3-[1-phenyl-1H-benzimidazol-2-yl]phenyl)-4-phenyl-6-(9,9'-spirobi[9H-fluoren]-2-yl)-1,3,5-triazine 11a Variant A 9.90 g (19.6 mmol, 1.00 eq.) of 2-chloro-4-phenyl-6-(9,9'-spirobi[9H-fluoren]-2-yl)-1,3,5-triazine 9a, 8.53 g (21.5 mmol, 1.10 eq.) of 1-phenyl-2-[3-(4,4,5,5-tetramethyl-1,3,2-dioxaborolan-2-yl)phenyl]-1H-benzimidazole 10a and 4.57 g (43.1 mmol, 2.20 eq.) of sodium carbonate in 35 ml of toluene, 35 ml of 1,4-dioxane and 35 ml of DI water are initially introduced in a 250 ml three-necked flask under protective gas and degassed. 1.13 g (0.980 mmol, 0.05 eq.) of tetrakis(triphenylphosphine)palladium(0) are subsequently added, and the mixture is heated under reflux for 48 hours. When the reaction is complete, the batch is cooled, and the solid which has precipitated out is filtered off with suction. The crude product obtained is purified by means of extraction, triple recrystallisation from heptane/toluene and sublimation, giving 4.83 g (6.54 mmol, 33%) of a solid having an HPLC purity >99.9%.

Variant B

The procedure is carried out analogously to that of variant A, where tetrakis(triphenylphosphine)palladium(0) is replaced by 0.02 eq. of 1,1-bis(diphenylphosphino)ferrocenepalladium(II) dichloride complex with DCM and dried toluene is used as solvent.

Variant C 4.15 ml (24.4 mmol, 1.10 eq.) of diisopropylethylamine (Hünig base) are added to a solution of 10.2 g (22.2 mmol, 1.00 eq.) of 2-biphenyl-3-yl-4-chloro-6-(9,9-dimethyl-9H-fluoren-2-yl)-1,3,5-triazine 9k and 4.31 g (22.2 mmol, 1.00 eq.) of 2-phenyl-1H-benzimidazole 10k in 150 ml of THF at room temperature. The reaction mixture is stirred overnight, and, when the reaction is complete, the solvent is removed in vacuo. After addition of 200 ml of dichloromethane, the solution is extracted three times with water, dried over sodium sulfate, and the solvent is removed in a rotary evaporator. The purification is carried out analogously to variant A, giving 5.57 g (9.02 mmol, 41%) of the desired product 11k.

The following are prepared analogously:
| No. | Starting material 9 | Starting material 10 |
|---|---|---|
| 11b | 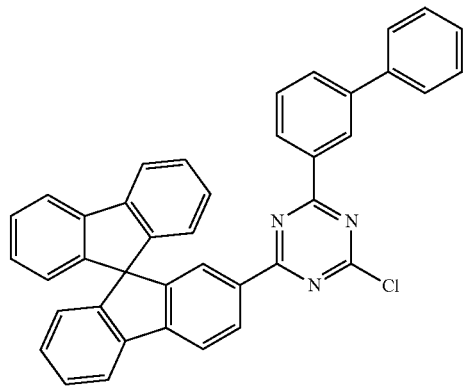 [SMILES: Clc1nc(-c2cccc(-c3ccccc3)c2)nc(-c2ccc3c(c2)C2(c4ccccc4-c4ccccc42)c2ccccc2-3)n1] | 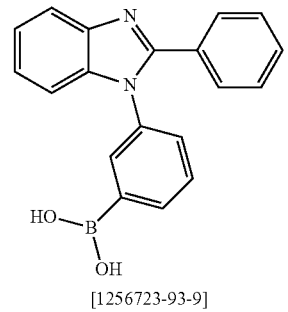 [SMILES: OB(O)c1cccc(-n2c(-c3ccccc3)nc3ccccc32)c1]
[1256723-93-9] |
| 11c | 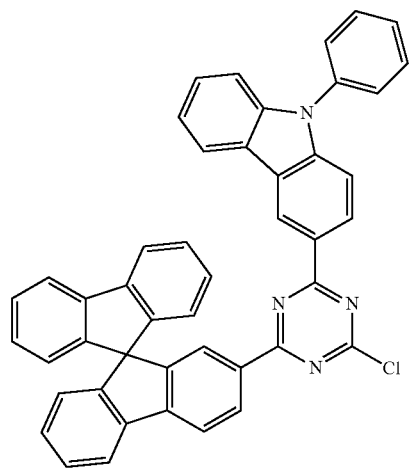 [SMILES: Clc1nc(-c2ccc3c(c2)C2(c4ccccc4-c4ccccc42)c2ccccc2-3)nc(-c2ccc3c(c2)c2ccccc2n3-c2ccccc2)n1] | 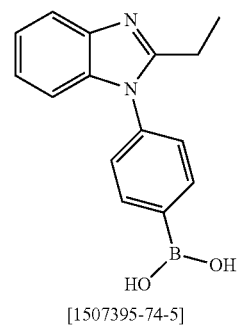 [SMILES: CCc1nc2ccccc2n1-c1ccc(B(O)O)cc1]
[1507395-74-5] |
| 11d | 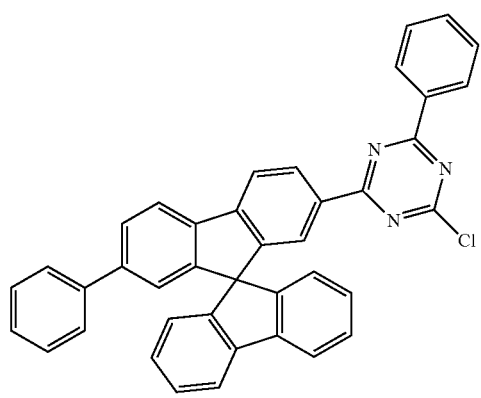 [SMILES: Clc1nc(-c2ccccc2)nc(-c2ccc3c(c2)C2(c4ccccc4-c4ccccc42)c2cc(-c4ccccc4)ccc2-3)n1] | 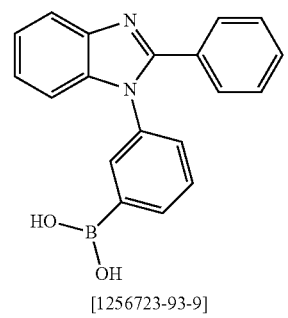 [SMILES: OB(O)c1cccc(-n2c(-c3ccccc3)nc3ccccc32)c1]
[1256723-93-9] |

-continued
11e 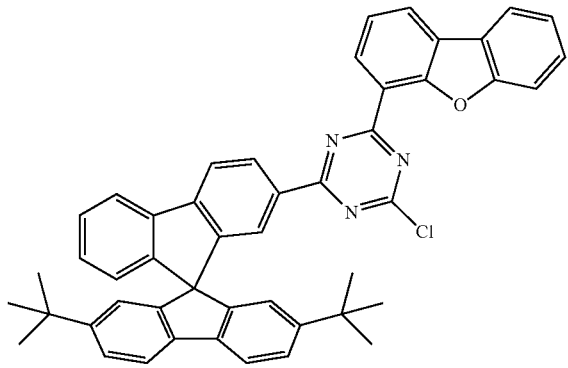 [SMILES: CC(C)(C)c1ccc2c(c1)C1(c3ccccc3-c3ccc(-c4nc(Cl)nc(-c5cccc6c5oc5ccccc56)n4)cc31)c1cc(C(C)(C)C)ccc1-2] 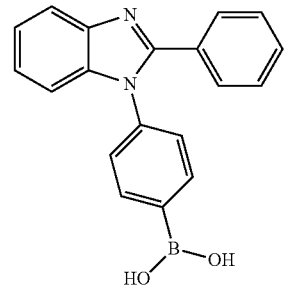
[867044-33-5]
11f 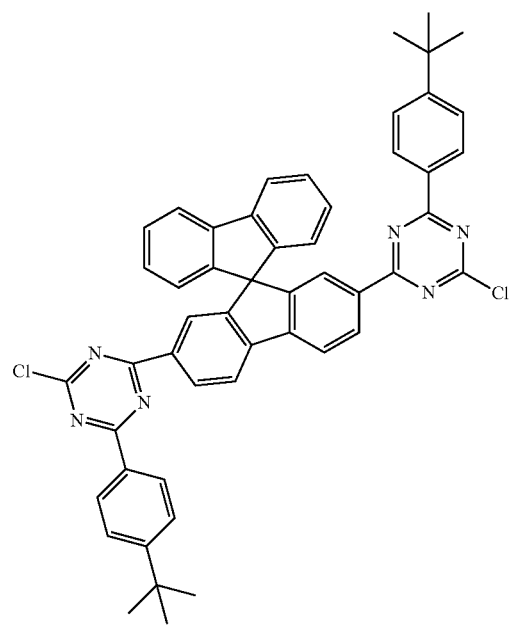 [SMILES: CC(C)(C)c1ccc(-c2nc(Cl)nc(-c3ccc4c(c3)C3(c5ccccc5-c5ccccc53)c3cc(-c5nc(Cl)nc(-c6ccc(C(C)(C)C)cc6)n5)ccc3-4)n2)cc1] 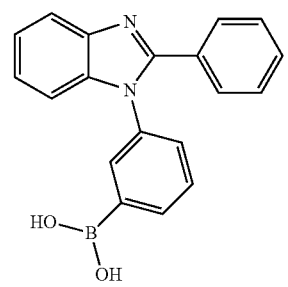
[1256723-93-9]
11g 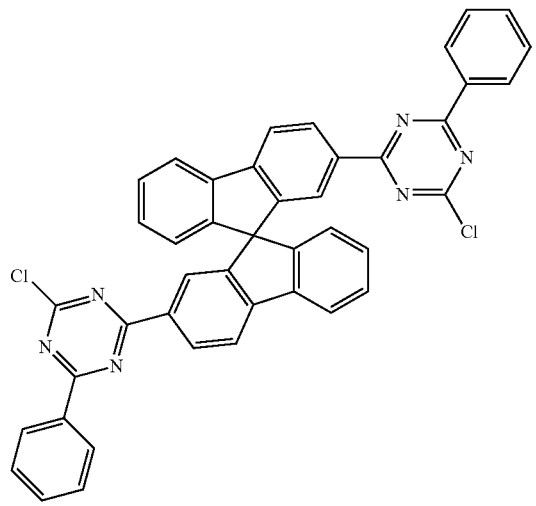 [SMILES: Clc1nc(-c2ccccc2)nc(-c2ccc3c(c2)C2(c4ccccc4-3)c3ccccc3-c3ccc(-c4nc(Cl)nc(-c5ccccc5)n4)cc32)n1] 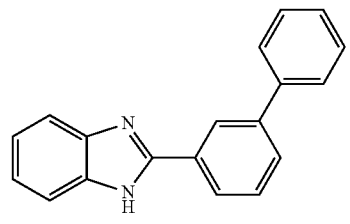
[897445-67-9]

| | | |
|---|---|---|
| 11h | 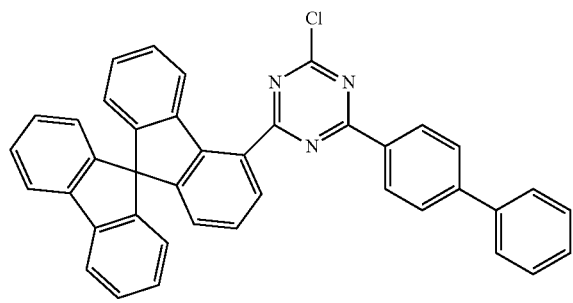 [SMILES: Clc1nc(-c2ccc(-c3ccccc3)cc2)nc(-c2cccc3c2-c2ccccc2C32c3ccccc3-c3ccccc32)n1] | 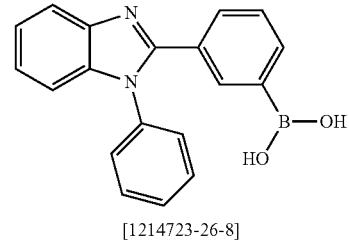 [SMILES: OB(O)c1cccc(-c2nc3ccccc3n2-c2ccccc2)c1]
[1214723-26-8] |
| 11i | 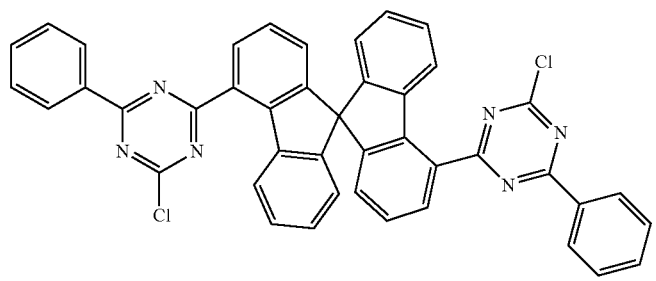 [SMILES: Clc1nc(-c2ccccc2)nc(-c2cccc3c2-c2ccccc2C32c3ccccc3-c3c(-c4nc(Cl)nc(-c5ccccc5)n4)cccc32)n1] | 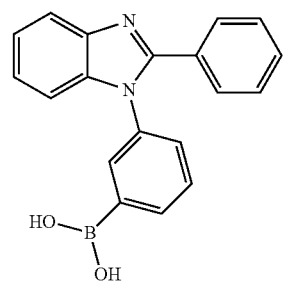
[1256723-93-9] |
| 11j | 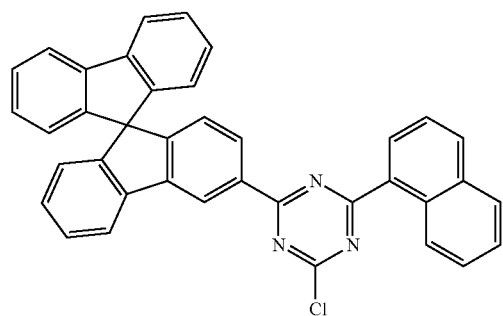 [SMILES: Clc1nc(-c2ccc3c(c2)-c2ccccc2C32c3ccccc3-c3ccccc32)nc(-c2cccc3ccccc23)n1] | 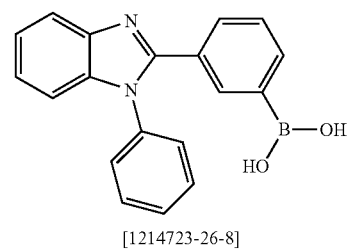 [SMILES: OB(O)c1cccc(-c2nc3ccccc3n2-c2ccccc2)c1]
[1214723-26-8] |
| 11k | 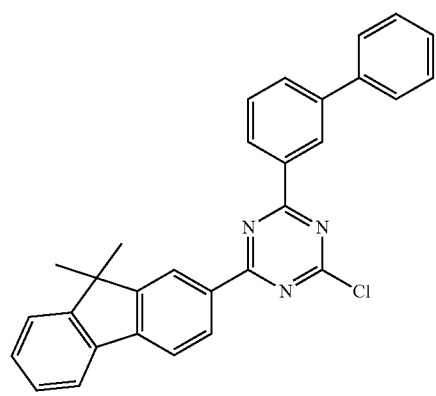 [SMILES: CC1(C)c2ccccc2-c2ccc(-c3nc(Cl)nc(-c4cccc(-c5ccccc5)c4)n3)cc21] | 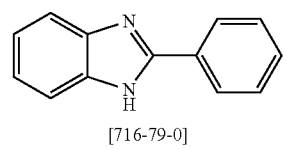 [SMILES: c1ccc(-c2nc3ccccc3[nH]2)cc1]
[716-79-0] |

-continued
| | | |
|---|---|---|
| 11l | 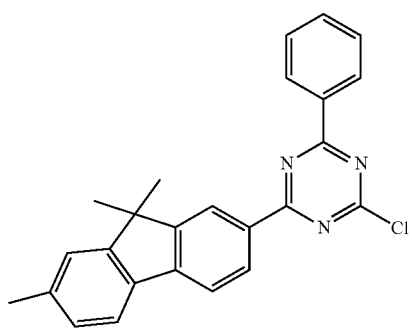 [SMILES: Cc1ccc2c(c1)C(C)(C)c1cc(-c3nc(Cl)nc(-c4ccccc4)n3)ccc1-2] | 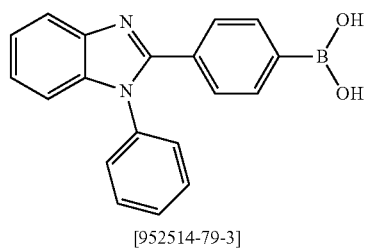 [SMILES: OB(O)c1ccc(-c2nc3ccccc3n2-c2ccccc2)cc1]
[952514-79-3] |
| 11m | 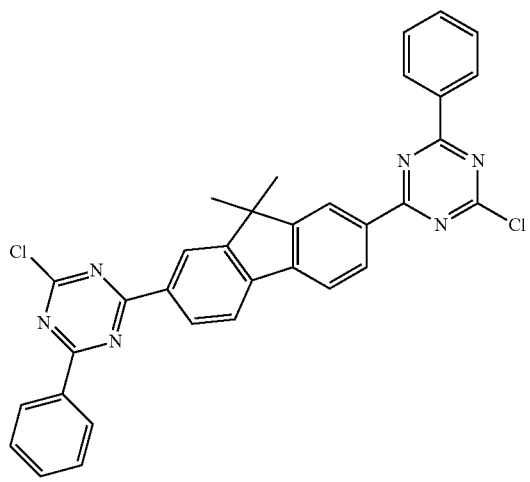 [SMILES: CC1(C)c2cc(-c3nc(Cl)nc(-c4ccccc4)n3)ccc2-c2ccc(-c3nc(Cl)nc(-c4ccccc4)n3)cc21] | 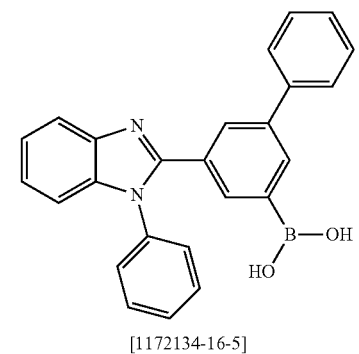 [SMILES: OB(O)c1cc(-c2ccccc2)cc(-c2nc3ccccc3n2-c2ccccc2)c1]
[1172134-16-5] |
| 11n | 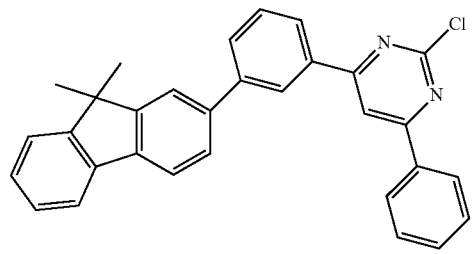 [SMILES: CC1(C)c2ccccc2-c2ccc(-c3cccc(-c4cc(-c5ccccc5)nc(Cl)n4)c3)cc21] | 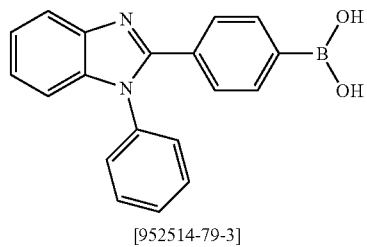 [SMILES: OB(O)c1ccc(-c2nc3ccccc3n2-c2ccccc2)cc1]
[952514-79-3] |
| 11o | 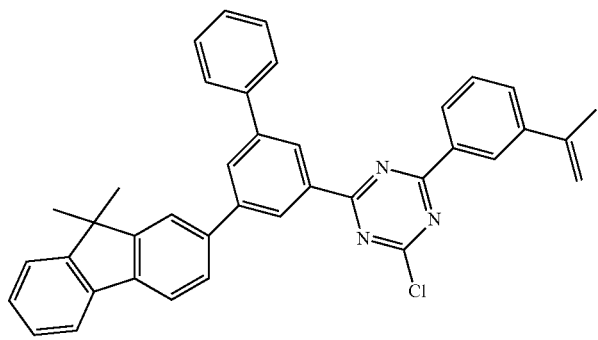 [SMILES: C=C(C)c1cccc(-c2nc(Cl)nc(-c3cc(-c4ccccc4)cc(-c4ccc5c(c4)C(C)(C)c4ccccc4-5)c3)n2)c1] | 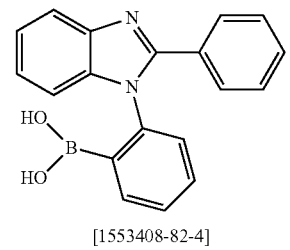 [SMILES: OB(O)c1ccccc1-n1c(-c2ccccc2)nc2ccccc21]
[1553408-82-4] |

-continued
11p 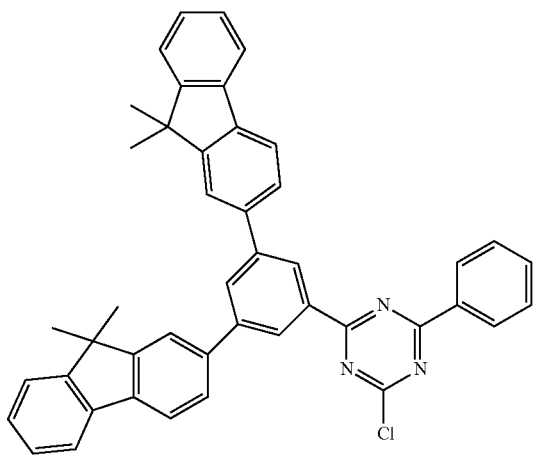 [SMILES: CC1(C)c2ccccc2-c2ccc(-c3cc(-c4ccc5c(c4)C(C)(C)c4ccccc4-5)cc(-c4nc(Cl)nc(-c5ccccc5)n4)c3)cc21] 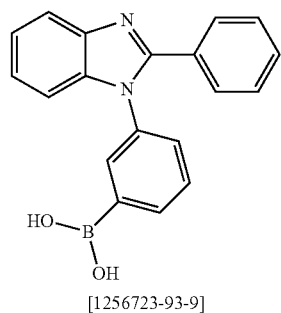 [SMILES: OB(O)c1cccc(-n2c(-c3ccccc3)nc3ccccc32)c1]
[1256723-93-9]
11q 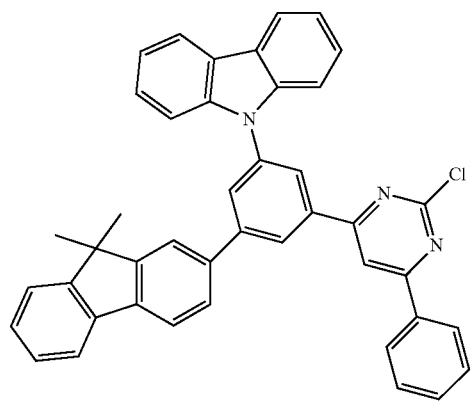 [SMILES: CC1(C)c2ccccc2-c2ccc(-c3cc(-c4cc(-c5ccccc5)nc(Cl)n4)cc(-n4c5ccccc5c5ccccc54)c3)cc21] 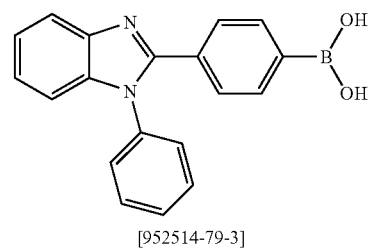 [SMILES: OB(O)c1ccc(-c2nc3ccccc3n2-c2ccccc2)cc1]
[952514-79-3]
11r 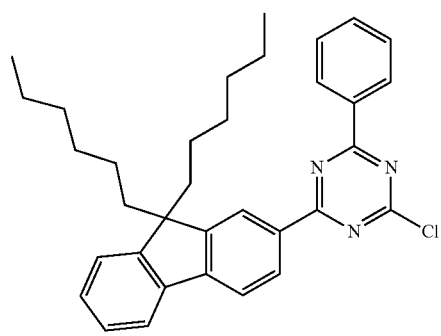 [SMILES: CCCCCCC1(CCCCCC)c2ccccc2-c2ccc(-c3nc(Cl)nc(-c4ccccc4)n3)cc21] 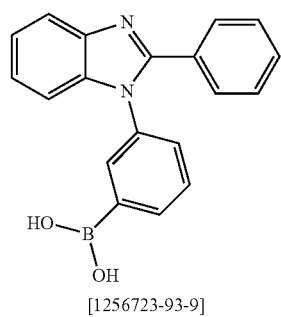 [SMILES: OB(O)c1cccc(-n2c(-c3ccccc3)nc3ccccc32)c1]
[1256723-93-9]
11s 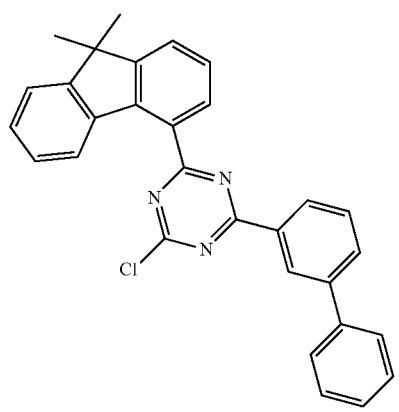 [SMILES: CC1(C)c2ccccc2-c2c(-c3nc(Cl)nc(-c4cccc(-c5ccccc5)c4)n3)cccc21] 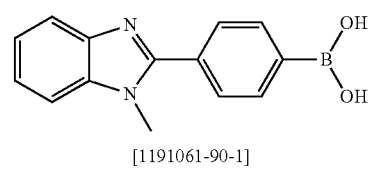 [SMILES: Cn1c(-c2ccc(B(O)O)cc2)nc2ccccc21]
[1191061-90-1]

| | | |
|---|---|---|
| 11t | 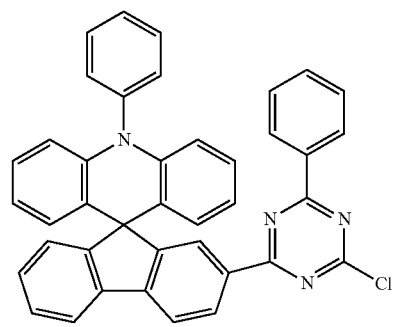 [SMILES: Clc1nc(-c2ccccc2)nc(-c2ccc3c(c2)C2(c4ccccc4-3)c3ccccc3N(c3ccccc3)c3ccccc32)n1] | 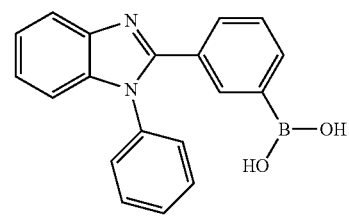[1214723-26-8] |
| 11u | 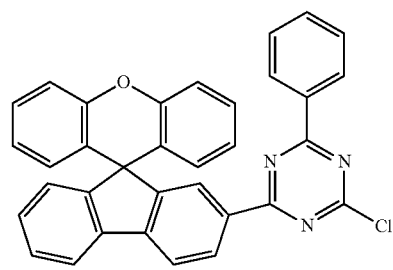 [SMILES: Clc1nc(-c2ccccc2)nc(-c2ccc3c(c2)C2(c4ccccc4Oc4ccccc42)c2ccccc2-3)n1] | 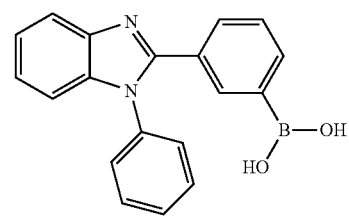[1214723-26-8] |
| 11v | 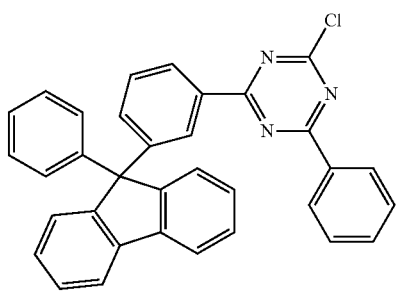 [SMILES: Clc1nc(-c2ccccc2)nc(-c2cccc(C3(c4ccccc4)c4ccccc4-c4ccccc43)c2)n1] | 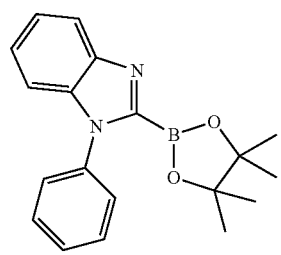[1316275-47-4] |
| No. | Product 11 | Var. | Yield |
|---|---|---|---|
| 11b | 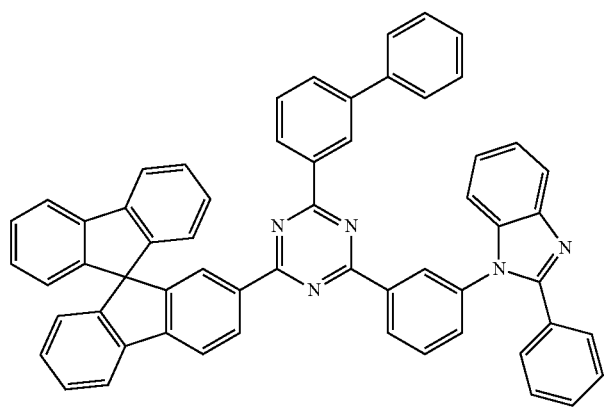 [SMILES: c1ccc(-c2cccc(-c3nc(-c4cccc(-n5c(-c6ccccc6)nc6ccccc65)c4)nc(-c4ccc5c(c4)C4(c6ccccc6-c6ccccc64)c4ccccc4-5)n3)c2)cc1] | B | 71% |

| | | | |
|---|---|---|---|
| 11c | 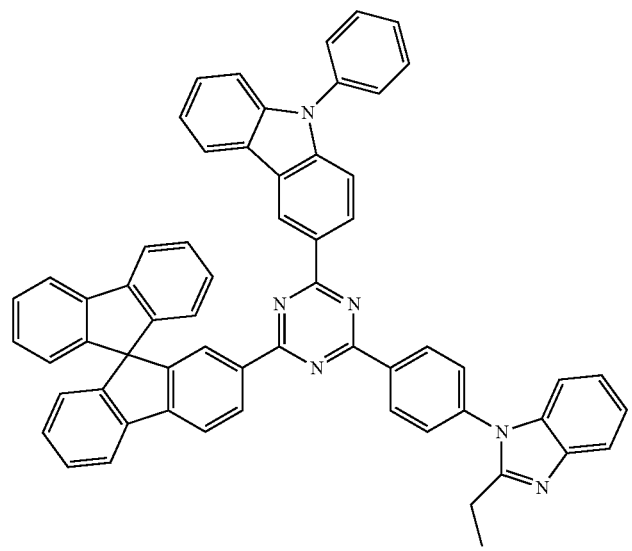 [SMILES: CCc1nc2ccccc2n1-c1ccc(-c2nc(-c3ccc4c(c3)C3(c5ccccc5-c5ccccc53)c3ccccc3-4)nc(-c3ccc4c(c3)c3ccccc3n4-c3ccccc3)n2)cc1] | B | 43% |
| 11d | 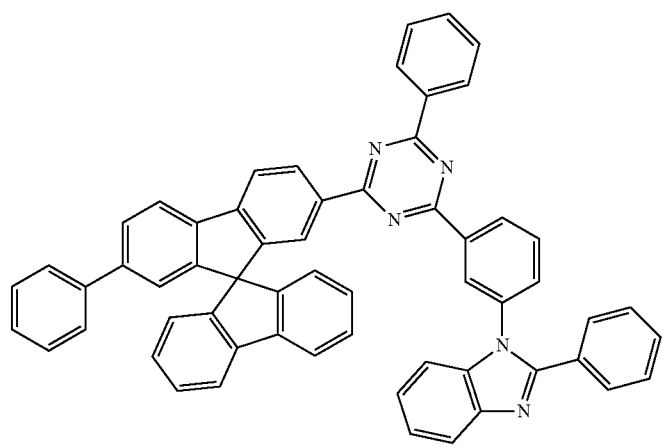 [SMILES: c1ccc(-c2ccc3c(c2)C2(c4ccccc4-c4ccccc42)c2cc(-c4nc(-c5ccccc5)nc(-c5cccc(-n6c(-c7ccccc7)nc7ccccc76)c5)n4)ccc2-3)cc1] | B | 55% |
| 11e | 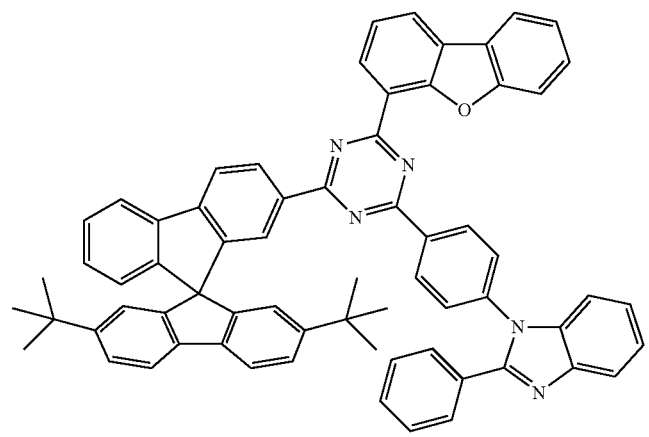 [SMILES: CC(C)(C)c1ccc2c(c1)C1(c3ccccc3-c3ccc(-c4nc(-c5ccc(-n6c(-c7ccccc7)nc7ccccc76)cc5)nc(-c5cccc6c5oc5ccccc56)n4)cc31)c1cc(C(C)(C)C)ccc1-2] | A | 29% |

| | | | |
|---|---|---|---|
| 11f | 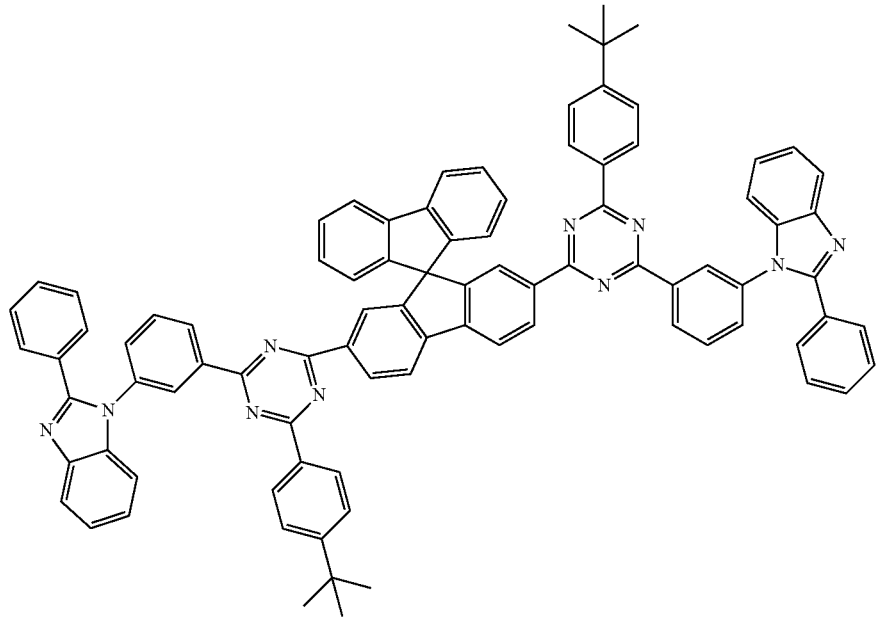 [SMILES: CC(C)(C)c1ccc(-c2nc(-c3cccc(-n4c(-c5ccccc5)nc5ccccc54)c3)nc(-c3ccc4c(c3)C3(c5ccccc5-c5ccccc53)c3cc(-c5nc(-c6ccc(C(C)(C)C)cc6)nc(-c6cccc(-n7c(-c8ccccc8)nc8ccccc87)c6)n5)ccc3-4)n2)cc1] | B | 47% |
| 11g | 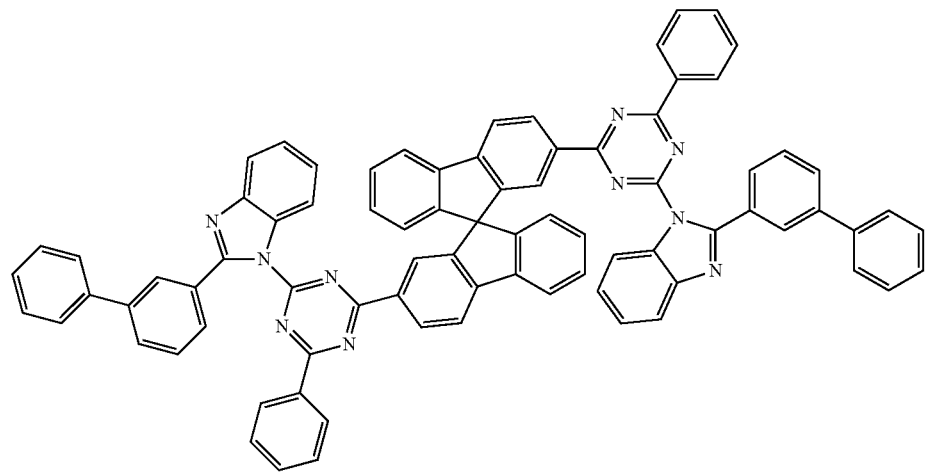 [SMILES: c1ccc(-c2cccc(-c3nc4ccccc4n3-c3nc(-c4ccccc4)nc(-c4ccc5c(c4)C4(c6ccccc6-5)c5ccccc5-c5ccc(-c6nc(-c7ccccc7)nc(-n7c(-c8cccc(-c9ccccc9)c8)nc8ccccc87)n6)cc54)n3)c2)cc1] | C | 63% |
| 11h | 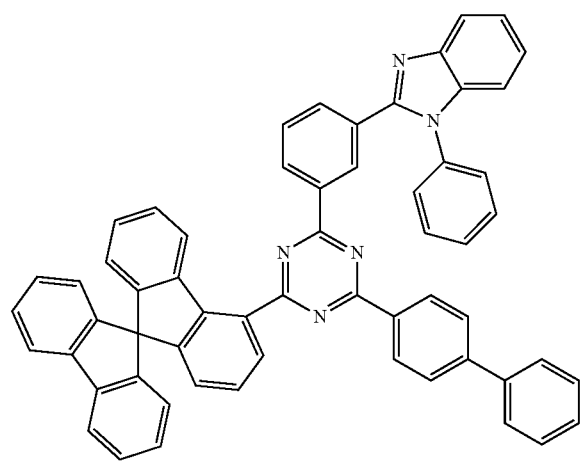 [SMILES: c1ccc(-c2ccc(-c3nc(-c4cccc(-c5nc6ccccc6n5-c5ccccc5)c4)nc(-c4cccc5c4-c4ccccc4C54c5ccccc5-c5ccccc54)n3)cc2)cc1] | A | 47% |

-continued
| | | | |
|---|---|---|---|
| 11i | 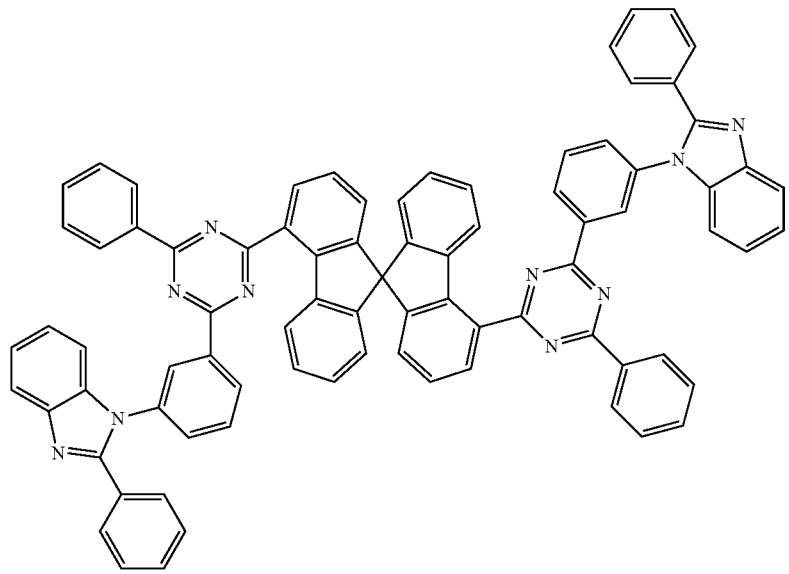 [SMILES: c1ccc(-c2nc(-c3cccc(-n4c(-c5ccccc5)nc5ccccc54)c3)nc(-c3cccc4c3-c3ccccc3C43c4ccccc4-c4c(-c5nc(-c6ccccc6)nc(-c6cccc(-n7c(-c8ccccc8)nc8ccccc87)c6)n5)cccc43)n2)cc1] | A | 31% |
| 11j | 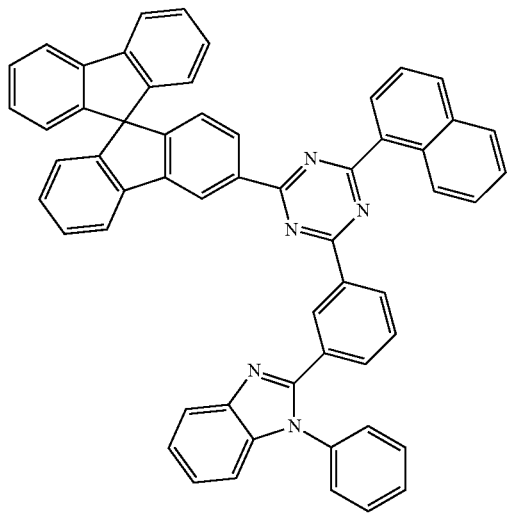 [SMILES: c1ccc(-n2c(-c3cccc(-c4nc(-c5ccc6c(c5)-c5ccccc5C65c6ccccc6-c6ccccc65)nc(-c5cccc6ccccc56)n4)c3)nc3ccccc32)cc1] | B | 36% |
| 11k | 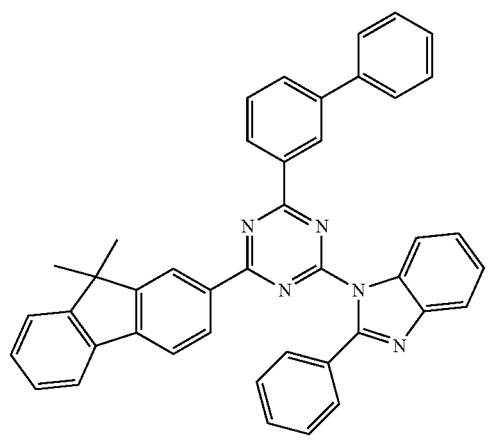 [SMILES: CC1(C)c2ccccc2-c2ccc(-c3nc(-c4cccc(-c5ccccc5)c4)nc(-n4c(-c5ccccc5)nc5ccccc54)n3)cc21] | B | 41% |

| 11l | 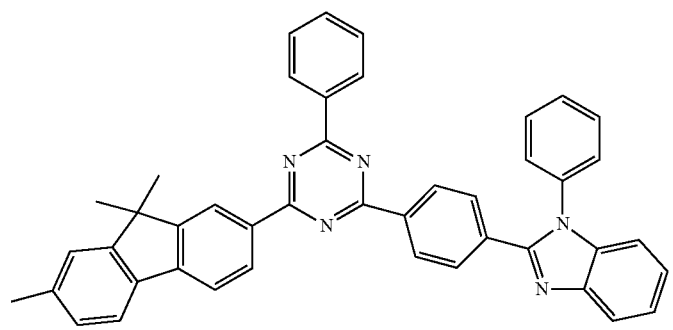 [SMILES: Cc1ccc2c(c1)C(C)(C)c1cc(-c3nc(-c4ccccc4)nc(-c4ccc(-c5nc6ccccc6n5-c5ccccc5)cc4)n3)ccc1-2] | A | 58% |
| 11m | 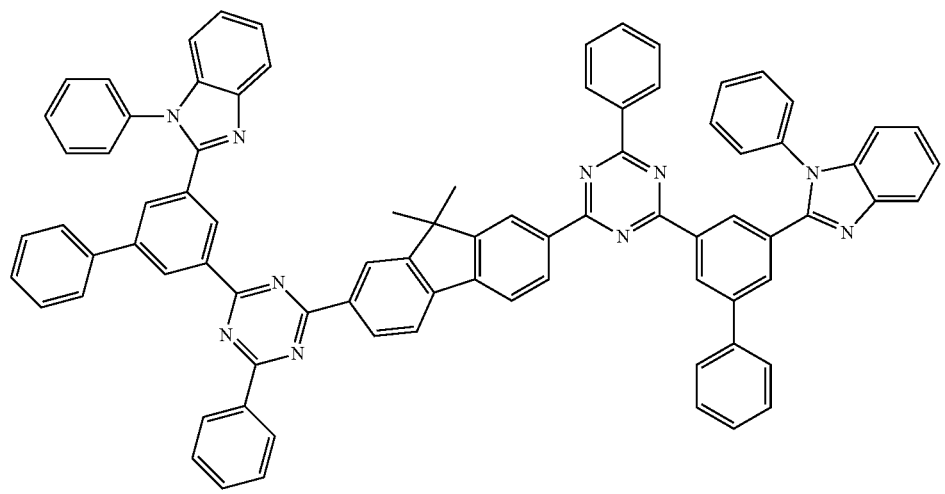 [SMILES: CC1(C)c2cc(-c3nc(-c4ccccc4)nc(-c4cc(-c5ccccc5)cc(-c5nc6ccccc6n5-c5ccccc5)c4)n3)ccc2-c2ccc(-c3nc(-c4ccccc4)nc(-c4cc(-c5ccccc5)cc(-c5nc6ccccc6n5-c5ccccc5)c4)n3)cc21] | A | 26% |
| 11n | 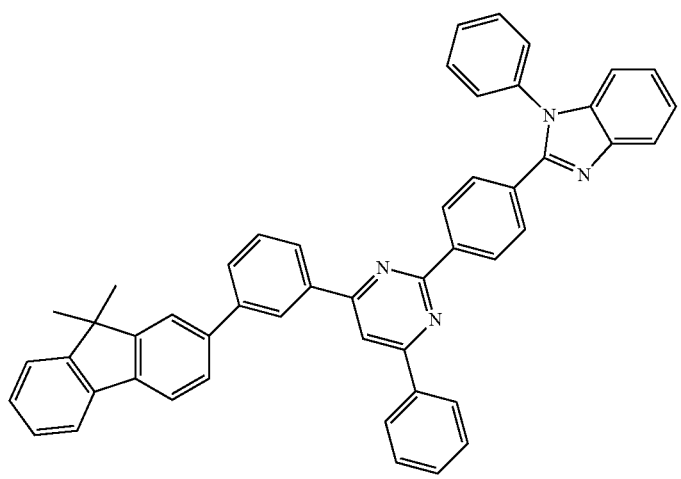 [SMILES: CC1(C)c2ccccc2-c2ccc(-c3cccc(-c4cc(-c5ccccc5)nc(-c5ccc(-c6nc7ccccc7n6-c6ccccc6)cc5)n4)c3)cc21] | B | 74% |

| | | | |
|---|---|---|---|
| 11o | 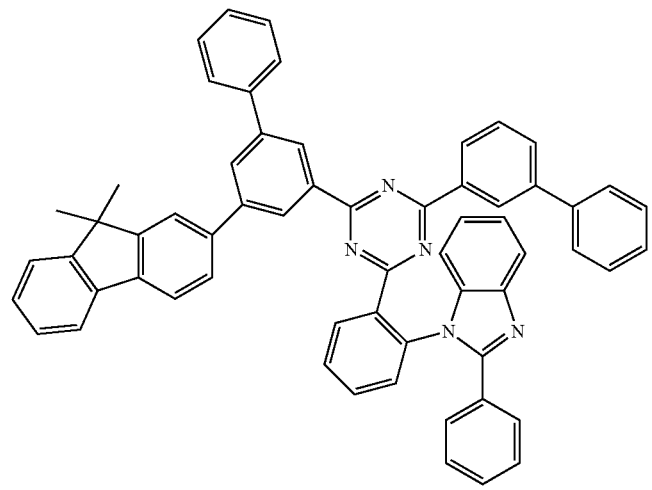 [SMILES: CC1(C)c2ccccc2-c2ccc(-c3cc(-c4ccccc4)cc(-c4nc(-c5cccc(-c6ccccc6)c5)nc(-c5ccccc5-n5c(-c6ccccc6)nc6ccccc65)n4)c3)cc21] | A | 42% |
| 11p | 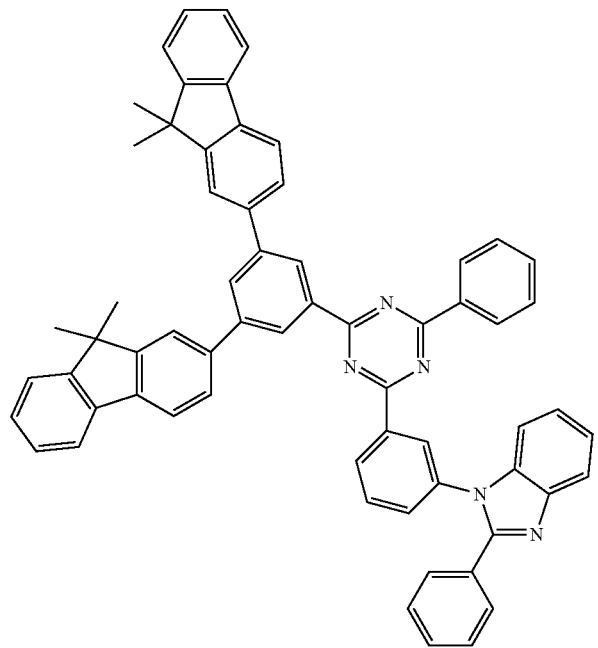 [SMILES: CC1(C)c2ccccc2-c2ccc(-c3cc(-c4ccc5c(c4)C(C)(C)c4ccccc4-5)cc(-c4nc(-c5ccccc5)nc(-c5cccc(-n6c(-c7ccccc7)nc7ccccc76)c5)n4)c3)cc21] | A | 37% |
| 11q | 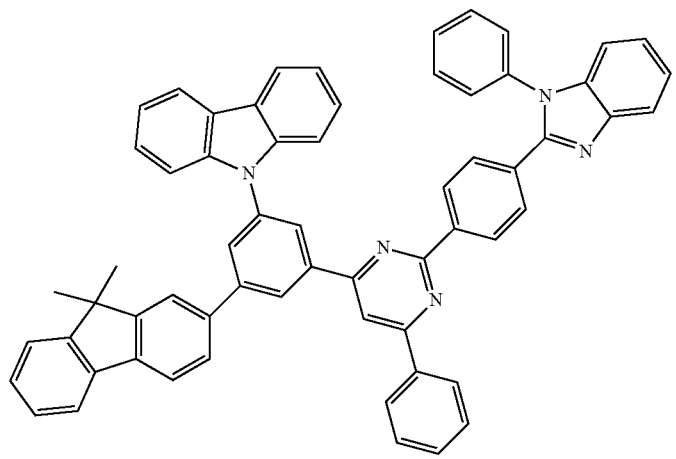 [SMILES: CC1(C)c2ccccc2-c2ccc(-c3cc(-c4cc(-c5ccccc5)nc(-c5ccc(-c6nc7ccccc7n6-c6ccccc6)cc5)n4)cc(-n4c5ccccc5c5ccccc54)c3)cc21] | B | 32% |

-continued
| | | | |
|---|---|---|---|
| 11r | 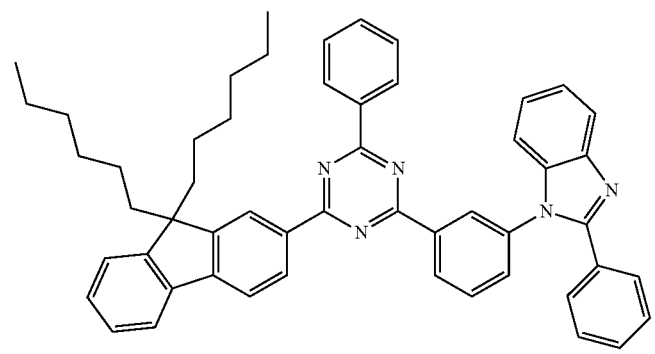 [SMILES: CCCCCCC1(CCCCCC)c2ccccc2-c2ccc(-c3nc(-c4ccccc4)nc(-c4cccc(-n5c(-c6ccccc6)nc6ccccc65)c4)n3)cc21] | A | 21% |
| 11s | 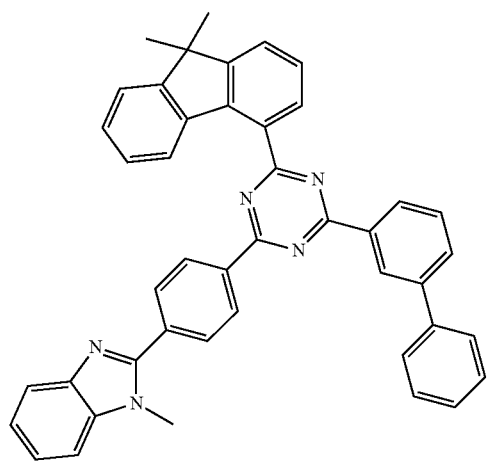 [SMILES: Cn1c(-c2ccc(-c3nc(-c4cccc(-c5ccccc5)c4)nc(-c4cccc5c4-c4ccccc4C5(C)C)n3)cc2)nc2ccccc21] | A | 62% |
| 11t | 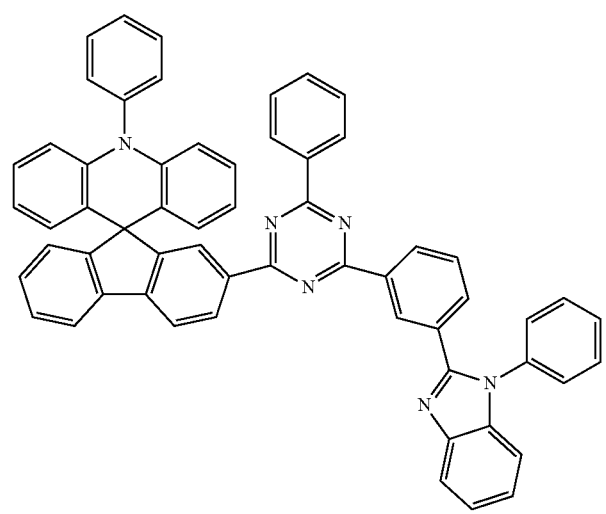 [SMILES: c1ccc(-c2nc(-c3cccc(-c4nc5ccccc5n4-c4ccccc4)c3)nc(-c3ccc4c(c3)C3(c5ccccc5-4)c4ccccc4N(c4ccccc4)c4ccccc43)n2)cc1] | B | 33% |

| | | | |
|---|---|---|---|
| 11u | 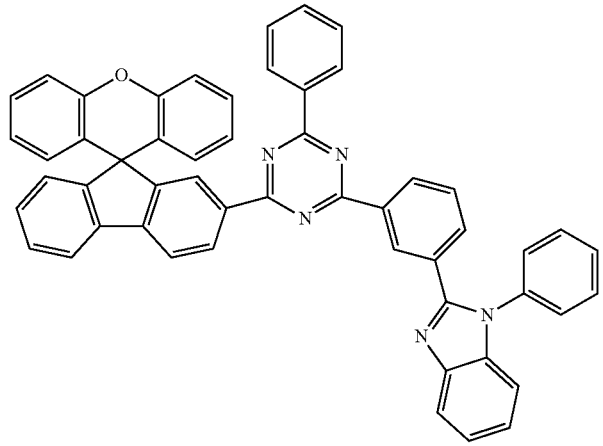 [SMILES: c1ccc(-c2nc(-c3cccc(-c4nc5ccccc5n4-c4ccccc4)c3)nc(-c3ccc4c(c3)C3(c5ccccc5Oc5ccccc53)c3ccccc3-4)n2)cc1] | A | 29% |
| 11v | 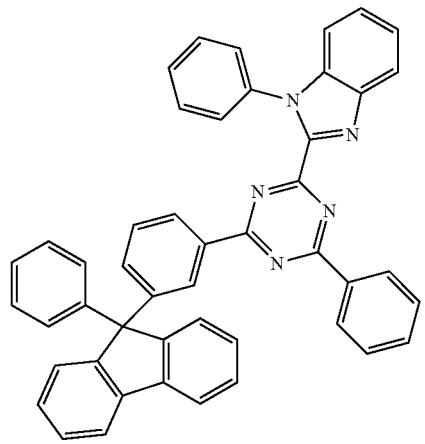 [SMILES: c1ccc(-c2nc(-c3cccc(C4(c5ccccc5)c5ccccc5-c5ccccc54)c3)nc(-c3nc4ccccc4n3-c3ccccc3)n2)cc1] | A | 58% |

Example 3

Production and Characterisation of the OLEDs

The data of various OLEDs are presented in the following Examples V1 to E16 (see Tables 1 and 2).

Pre-treatment for Examples V1-E16: Glass plates coated with structured ITO (indium tin oxide) in a thickness of 50 nm are coated with 20 nm of PEDOT:PSS (poly(3,4-ethylenedioxythiophene) poly(styrenesulfonate), purchased as CLEVIOS™ P VP AI 4083 from Heraeus Precious Metals GmbH, Germany, applied by spin coating from aqueous solution) for improved processing. These coated glass plates form the substrates to which the OLEDs are applied.

The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as IC1:IC3: TEG1 (55%:35%:10%) here means that material IC1 is present in the layer in a proportion by volume of 55%, IC3 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The term U1000 in Table 2 denotes the voltage required for a luminous density of 1000 cd/m$^2$. CE1000 and PE1000 denote the current and power efficiency respectively which are achieved at 1000 cd/m$^2$. Finally, EQE1000 denotes the external quantum efficiency at an operating luminous density of 1000 cd/m$^2$. The lifetime LT is defined as the time after which the luminous density drops from the initial luminous density to a certain proportion L1 on operation at constant current. An expression of L0;j0=4000 cd/m$^2$ and L1=70% in Table 2 means that the lifetime indicated in column LT corresponds to the time after which the initial luminous density drops from 4000 cd/m² to 2800 cd/m². Analogously, L0;j0=20 mA/cm², L1=80% means that the luminous density drops to 80% of its initial value after time LT on operation at 20 mA/cm².

The data of the various OLEDs are summarised in Table 2. Examples V1-V3 are comparative examples in accordance with the prior art, Examples E1-E16 show data of OLEDs according to the invention.

Some of the examples are explained in greater detail below in order to illustrate the advantages of the OLEDs according to the invention.

Use of Mixtures According to the Invention in the Electron-Transport Layer (ETL or EIL) of OLEDs On use in the electron-injection and electron-transport layer in OLEDs, the materials according to the invention give rise to significant improvements over the prior art with respect to the lifetime of the components and/or the efficiency. The use of compound EG1 according to the invention enables an increase in the lifetime of between 20% and 40% to be observed compared with the prior art (comparison of Examples V1 and V2 with E1, and comparison of V3 with E2). A further technical advantage of the compounds according to the invention is an increased efficiency by about 10% compared with the prior art (comparison of experiment V1 with E1).

TABLE 1

Structure of the OLEDs
HTL/IL (HATCN: 5 nm)/EBL/EML/HBL/ETL/EIL

| Ex. | HTL Thickness | EBL Thickness | EML Thickness | HBL Thickness | ETL Thickness | EIL Thickness |
|---|---|---|---|---|---|---|
| V1 | SpA1 70 nm | SpMA1 90 nm | IC1:IC3:TEG1 (40%:40%:20%) 30 nm | — | SdT1:LiQ (50%:50%) 40 nm | — |
| V2 | SpA1 70 nm | SpMA1 90 nm | IC1:IC3:TEG1 (40%:40%:20%) 30 nm | — | SdT2:LiQ (50%:50%) 40 nm | — |
| V3 | SpA1 70 nm | SpMA1 90 nm | IC1:TEG1 (90%:10%) 30 nm | — | SdT3:LiQ 40 nm | LiF 1 nm |
| E1 | SpA1 70 nm | SpMA1 90 nm | IC1:IC3:TEG1 (40%:40%:20%) 30 nm | — | EG1:LiQ (50%:50%) 40 nm | — |
| E2 | SpA1 70 nm | SpMA1 90 nm | IC1:TEG1 (90%:10%) 30 nm | — | EG2 40 nm | LiF 1 nm |
| E3 | SpA1 70 nm | SpMA1 90 nm | IC1:TEG1 (90%:10%) 30 nm | IC1 10 nm | EG3:LiQ (50%:50%) 30 nm | — |
| E4 | SpA1 70 nm | SpMA1 90 nm | IC1:TEG1 (90%:10%) 30 nm | IC1 10 nm | EG4 30 nm | LiF 1 nm |
| E5 | SpA1 70 nm | SpMA1 90 nm | IC1:TEG1 (90%:10%) 30 nm | EG5 10 nm | EG5:LiQ (50%:50%) 30 nm | — |
| E6 | SpA1 70 nm | SpMA1 90 nm | IC1:TEG1 (90%:10%) 30 nm | IC1 10 nm | EG6 30 nm | LiQ 3 nm |
| E7 | SpA1 70 nm | SpMA1 90 nm | IC1:IC3:TEG1 (60%:30%:10%) 30 nm | IC1 10 nm | EG7:LiQ (50%:50%) 30 nm | LiQ 1 nm |
| E8 | SpA1 140 nm | SpMA1 20 nm | H1:SEB (95%:5%) 20 nm | — | EG9 (50%:50%) 30 nm | — |
| E9 | SpA1 140 nm | SpMA1 20 nm | H1:SEB (95%:5%) 20 nm | — | EG9 (50%:50%) 30 nm | LiQ 3 nm |
| E10 | SpA1 140 nm | SpMA1 20 nm | H1:SEB (95%:5%) 20 nm | — | EG10:LiQ (50%:50%) 30 nm | — |
| E141 | SpA1 140 nm | SpMA1 20 nm | H1:SEB (95%:5%) 20 nm | — | EG11:LiQ (50%:50%) 30 nm | — |
| E12 | SpA1 140 nm | SpMA1 20 nm | H1:SEB (95%:5%) 20 nm | — | EG12:LiQ (50%:50%) 30 nm | — |
| E13 | SpA1 70 nm | SpMA1 90 nm | EG13:IC3:TEG1 (45%:45%:10%) 30 nm | — | ST2:LiQ (50%:50%) 40 nm | — |
| E14 | SpA1 90 nm | SpMA1 130 nm | IC5:TER3 (92%:8%) 40 nm | — | EG14:LiQ (50%:50%) 40 nm | — |
| E15 | SpA1 90 nm | SpMA1 130 nm | IC5:TER3 (92%:8%) 40 nm | — | EG15:LiQ (50%:50%) 40 nm | — |
| E16 | SpA1 90 nm | SpMA1 130 nm | IC5:TER3 (92%:8%) 40 nm | — | EG16:LiQ (50%:50%) 40 nm | — |

TABLE 2

Data of the OLEDs

| Ex. | U1000 (V) | CE1000 (cd/A) | PE1000 (lm/W) | EQE 1000 | CIE x/y at 1000 cd/m² | $L_0; j_0$ | L1 % | LT (h) |
|---|---|---|---|---|---|---|---|---|
| V1 | 3.4 | 55 | 51 | 15.1% | 0.33/0.63 | 20 mA/cm² | 80 | 180 |
| V2 | 3.3 | 60 | 57 | 16.5% | 0.33/0.62 | 20 mA/cm² | 80 | 160 |
| V3 | 3.2 | 61 | 60 | 16.8% | 0.34/0.62 | 20 mA/cm² | 80 | 125 |
| E1 | 3.3 | 59 | 56 | 16.4% | 0.33/0.62 | 20 mA/cm² | 80 | 220 |
| E2 | 3.2 | 62 | 61 | 16.7% | 0.33/0.63 | 20 mA/cm² | 80 | 155 |
| E3 | 3.4 | 57 | 53 | 16.2% | 0.34/0.62 | 20 mA/cm² | 80 | 135 |
| E4 | 3.5 | 60 | 54 | 16.5% | 032/0.64 | 20 mA/cm² | 80 | 130 |

TABLE 2-continued
Data of the OLEDs
| Ex. | U1000 (V) | CE1000 (cd/A) | PE1000 (lm/W) | EQE 1000 | CIE x/y at 1000 cd/m$^2$ | $L_0$; $j_0$ | L1 % | LT (h) |
|---|---|---|---|---|---|---|---|---|
| E5 | 3.6 | 59 | 51 | 16.0% | 0.33/0.63 | 20 mA/cm$^2$ | 80 | 120 |
| E6 | 3.2 | 60 | 59 | 16.1% | 0.31/0.64 | 20 mA/cm$^2$ | 80 | 105 |
| E7 | 3.6 | 61 | 53 | 16.6% | 0.33/0.63 | 20 mA/cm$^2$ | 80 | 235 |
| E8 | 4.6 | 8.1 | 5.5 | 7.2% | 0.13/014 | 6000 cd/m$^2$ | 80 | 50 |
| E9 | 4.5 | 7.8 | 5.2 | 6.7% | 0.14/015 | 6000 cd/m$^2$ | 80 | 25 |
| E13 | 4.9 | 7.4 | 4.7 | 6.9% | 0.14/0.13 | 6000 cd/m$^2$ | 80 | 45 |
| E11 | 4.7 | 8.3 | 5.5 | 7.5% | 0.14/013 | 6000 cd/m$^2$ | 80 | 40 |
| E12 | 5.2 | 8.5 | 5.1 | 7.7% | 0.14/013 | 6000 cd/m$^2$ | 80 | 35 |
| E13 | 3.4 | 58 | 54 | 15.4% | 0.32/0.63 | 20 mA/cm$^2$ | 80 | 105 |
| E14 | 4.9 | 11.3 | 7.2 | 12.1% | 0.67/0.33 | 4000 cd/m$^2$ | 80 | 390 |
| E15 | 4.3 | 11.3 | 8.3 | 12.3% | 0.66/0.34 | 4000 cd/m$^2$ | 80 | 360 |
| E16 | 4.5 | 12.2 | 8.5 | 12.8% | 0.67/0.33 | 4000 cd/m$^2$ | 80 | 410 |
TABLE 3
Structural formulae of the materials for the OLEDs
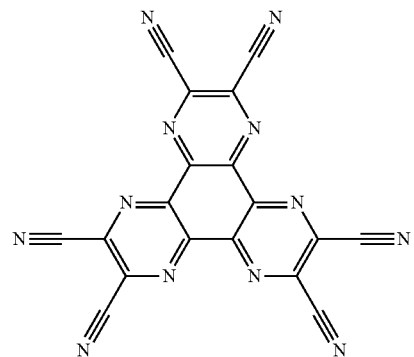 [SMILES: N#Cc1nc2c3nc(C#N)c(C#N)nc3c3nc(C#N)c(C#N)nc3c2nc1C#N]
HATCN
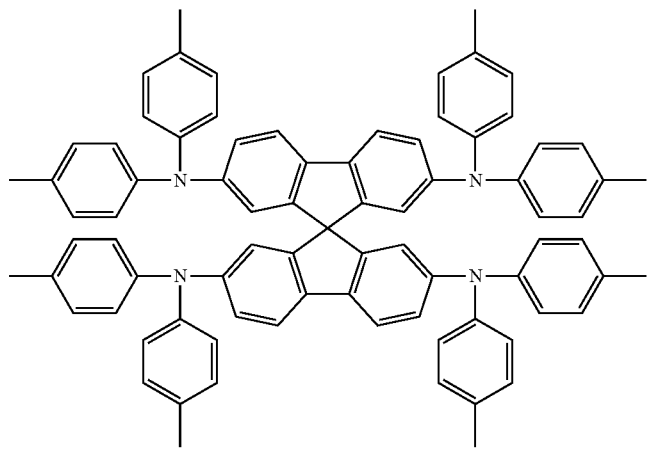
SpA1

TABLE 3-continued
Structural formulae of the materials for the OLEDs
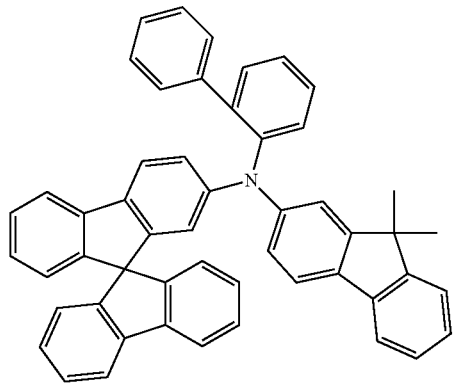 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
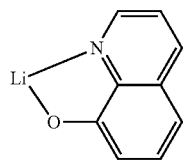
LiQ
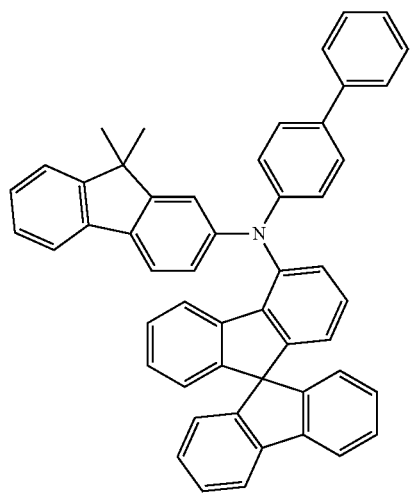 [SMILES: CC1(C)c2ccccc2-c2ccc(N(c3ccc(-c4ccccc4)cc3)c3cccc4c3-c3ccccc3C43c4ccccc4-c4ccccc43)cc21]
SpMA2
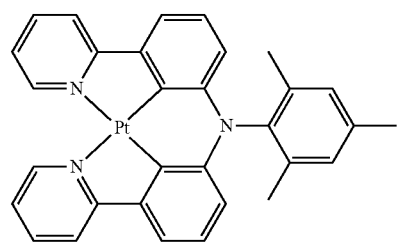
TER1

TABLE 3-continued
Structural formulae of the materials for the OLEDs
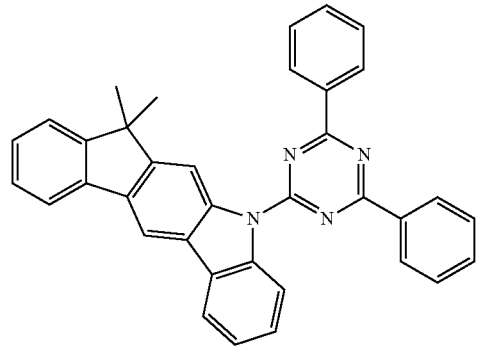 [SMILES: CC1(C)c2ccccc2-c2cc3c4ccccc4n(-c4nc(-c5ccccc5)nc(-c5ccccc5)n4)c3cc21]
IC1
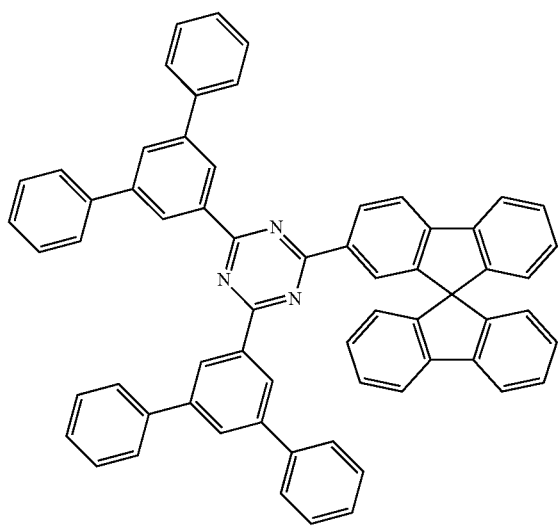 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
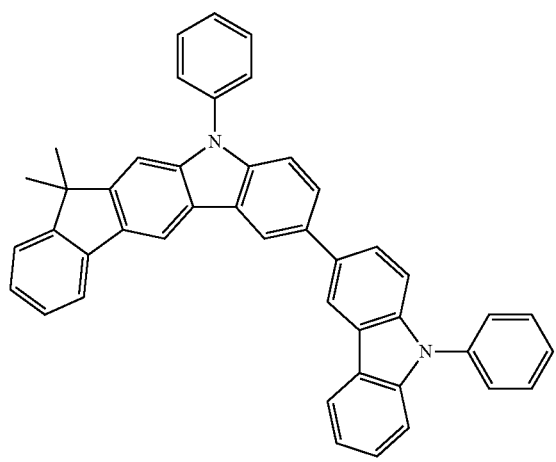 [SMILES: CC1(C)c2ccccc2-c2cc3c4cc(-c5ccc6c(c5)c5ccccc5n6-c5ccccc5)ccc4n(-c4ccccc4)c3cc21]
IC3

TABLE 3-continued
Structural formulae of the materials for the OLEDs
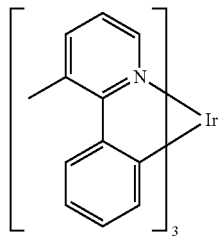
TEG1
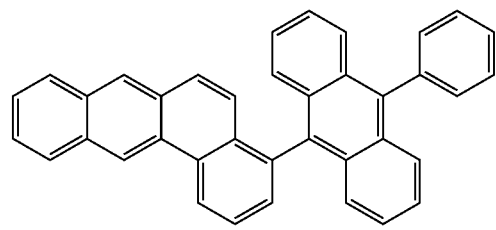 [SMILES: c1ccc(-c2c3ccccc3c(-c3cccc4c3ccc3cc5ccccc5cc34)c3ccccc23)cc1]
H1
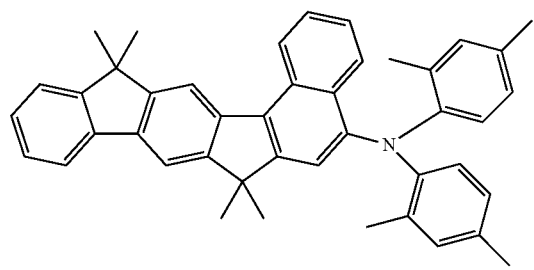 [SMILES: Cc1ccc(N(c2ccc(C)cc2C)c2cc3c(c4ccccc24)-c2cc4c(cc2C3(C)C)-c2ccccc2C4(C)C)c(C)c1]
SEB
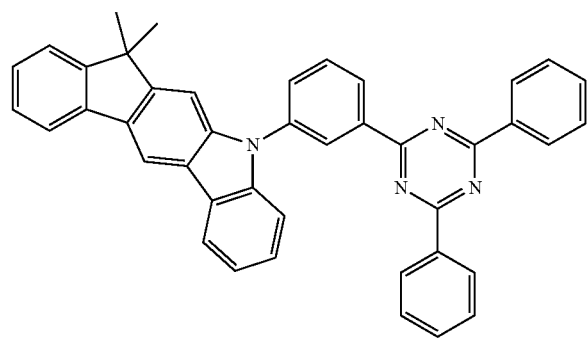 [SMILES: CC1(C)c2ccccc2-c2cc3c4ccccc4n(-c4cccc(-c5nc(-c6ccccc6)nc(-c6ccccc6)n5)c4)c3cc21]
IC5

TABLE 3-continued
Structural formulae of the materials for the OLEDs
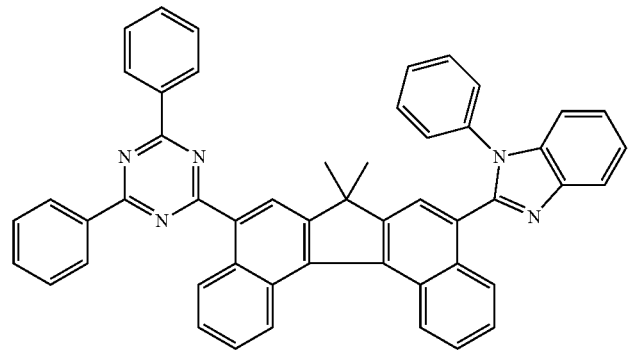 [SMILES: CC1(C)c2cc(-c3nc(-c4ccccc4)nc(-c4ccccc4)n3)c3ccccc3c2-c2c1cc(-c1nc3ccccc3n1-c1ccccc1)c1ccccc21]
SdT1
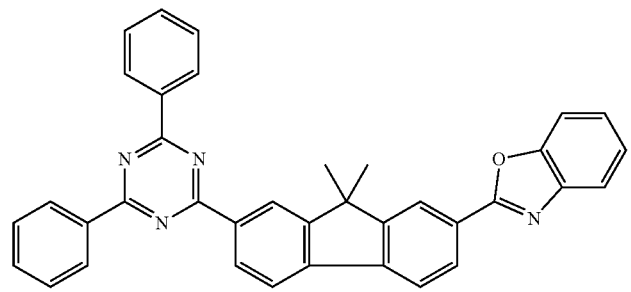 [SMILES: CC1(C)c2cc(-c3nc(-c4ccccc4)nc(-c4ccccc4)n3)ccc2-c2ccc(-c3nc4ccccc4o3)cc21]
SdT2
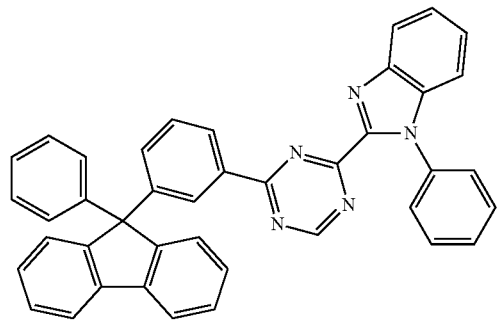 [SMILES: c1ccc(-n2c(-c3ncnc(-c4cccc(C5(c6ccccc6)c6ccccc6-c6ccccc65)c4)n3)nc3ccccc32)cc1]
SdT3
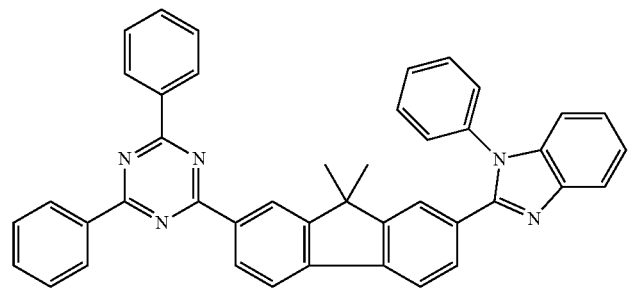 [SMILES: CC1(C)c2cc(-c3nc(-c4ccccc4)nc(-c4ccccc4)n3)ccc2-c2ccc(-c3nc4ccccc4n3-c3ccccc3)cc21]
EG1

TABLE 3-continued
Structural formulae of the materials for the OLEDs
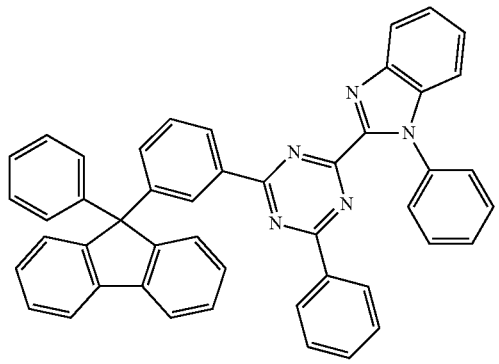 [SMILES: c1ccc(-c2nc(-c3cccc(C4(c5ccccc5)c5ccccc5-c5ccccc54)c3)nc(-c3nc4ccccc4n3-c3ccccc3)n2)cc1]
EG2
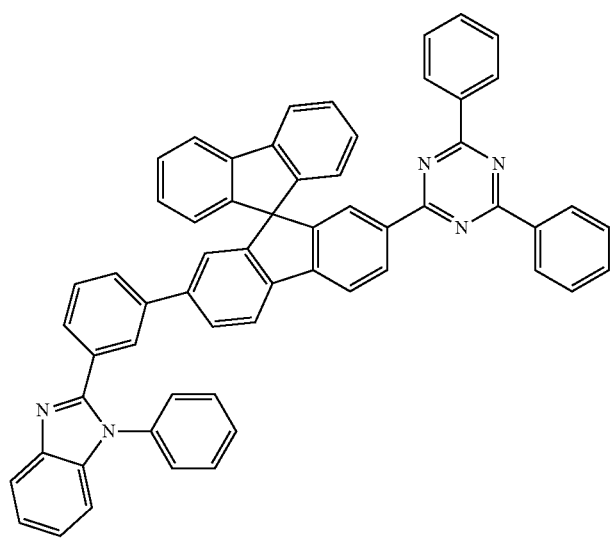 [SMILES: c1ccc(-c2nc(-c3ccccc3)nc(-c3ccc4c(c3)C3(c5ccccc5-c5ccccc53)c3cc(-c5cccc(-c6nc7ccccc7n6-c6ccccc6)c5)ccc3-4)n2)cc1]
EG3
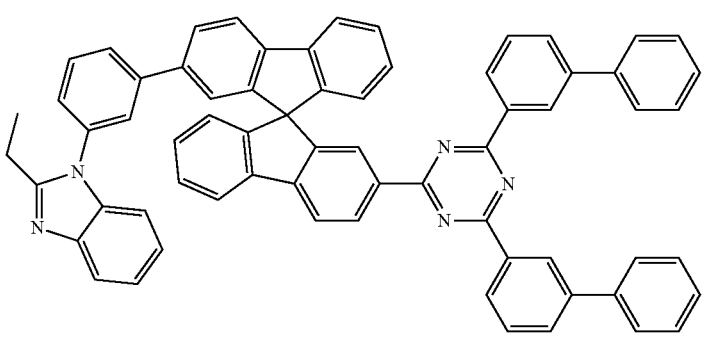 [SMILES: CCc1nc2ccccc2n1-c1cccc(-c2ccc3c(c2)C2(c4ccccc4-3)c3ccccc3-c3ccc(-c4nc(-c5cccc(-c6ccccc6)c5)nc(-c5cccc(-c6ccccc6)c5)n4)cc32)c1]
EG4

TABLE 3-continued
Structural formulae of the materials for the OLEDs
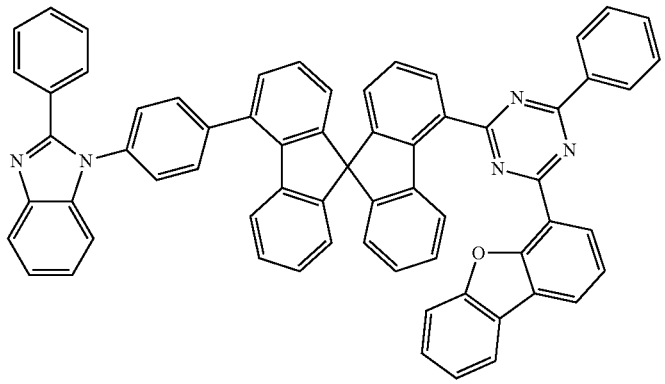 [SMILES: c1ccc(-c2nc(-c3cccc4c3-c3ccccc3C43c4ccccc4-c4c(-c5ccc(-n6c(-c7ccccc7)nc7ccccc76)cc5)cccc43)nc(-c3cccc4c3oc3ccccc34)n2)cc1]
EG5
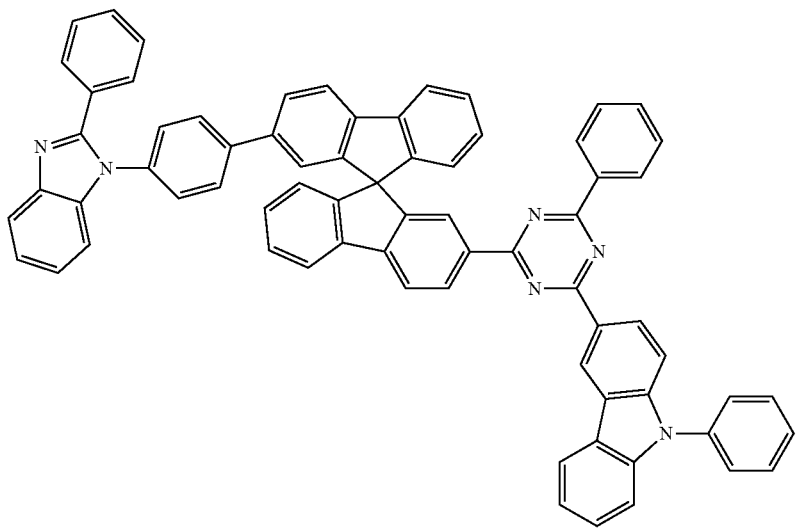 [SMILES: c1ccc(-c2nc(-c3ccc4c(c3)C3(c5ccccc5-c5ccc(-c6ccc(-n7c(-c8ccccc8)nc8ccccc87)cc6)cc53)c3ccccc3-4)nc(-c3ccc4c(c3)c3ccccc3n4-c3ccccc3)n2)cc1]
EG6
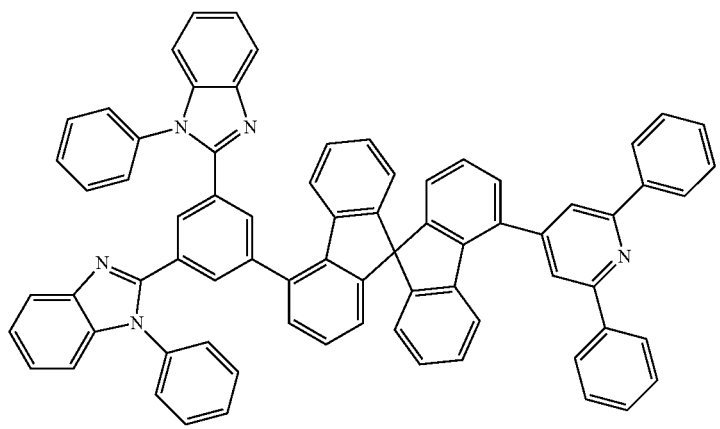 [SMILES: c1ccc(-c2cc(-c3cccc4c3-c3ccccc3C43c4ccccc4-c4c(-c5cc(-c6nc7ccccc7n6-c6ccccc6)cc(-c6nc7ccccc7n6-c6ccccc6)c5)cccc43)cc(-c3ccccc3)n2)cc1]
EG7

TABLE 3-continued
Structural formulae of the materials for the OLEDs
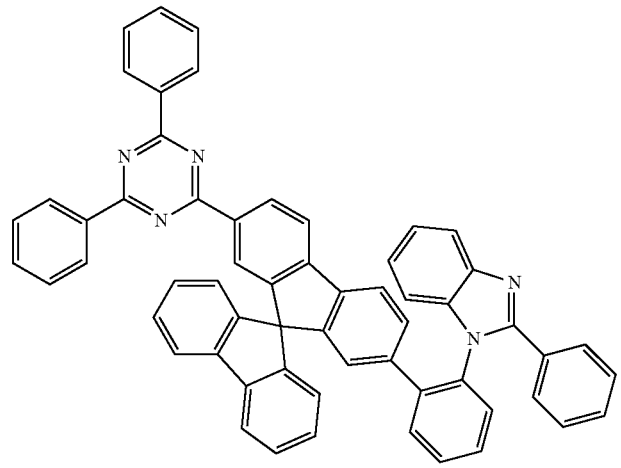 [SMILES: c1ccc(-c2nc(-c3ccccc3)nc(-c3ccc4c(c3)C3(c5ccccc5-c5ccccc53)c3cc(-c5ccccc5-n5c(-c6ccccc6)nc6ccccc65)ccc3-4)n2)cc1]
EG8
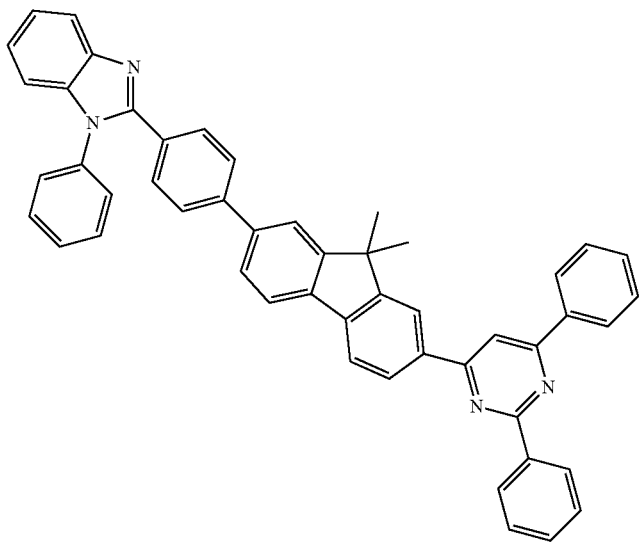 [SMILES: CC1(C)c2cc(-c3ccc(-c4nc5ccccc5n4-c4ccccc4)cc3)ccc2-c2ccc(-c3cc(-c4ccccc4)nc(-c4ccccc4)n3)cc21]
EG9
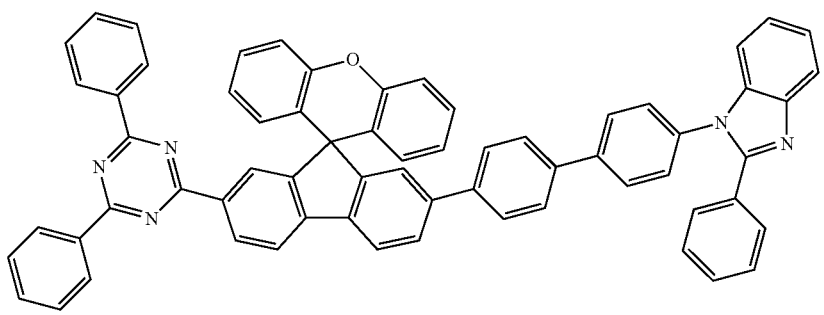 [SMILES: c1ccc(-c2nc(-c3ccccc3)nc(-c3ccc4c(c3)C3(c5ccccc5Oc5ccccc53)c3cc(-c5ccc(-c6ccc(-n7c(-c8ccccc8)nc8ccccc87)cc6)cc5)ccc3-4)n2)cc1]
EG10

TABLE 3-continued
Structural formulae of the materials for the OLEDs
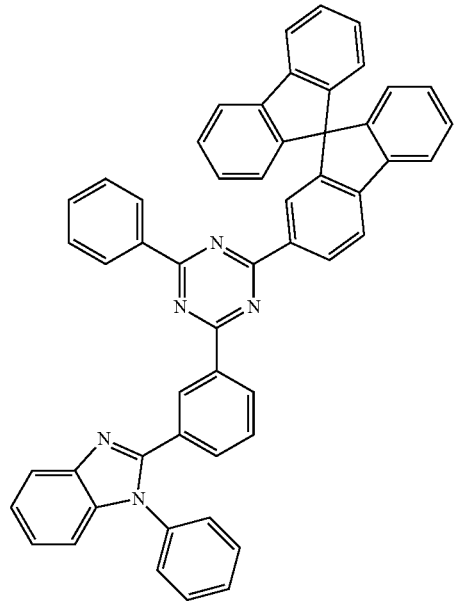 [SMILES: c1ccc(-c2nc(-c3cccc(-c4nc5ccccc5n4-c4ccccc4)c3)nc(-c3ccc4c(c3)C3(c5ccccc5-c5ccccc53)c3ccccc3-4)n2)cc1]
EG11
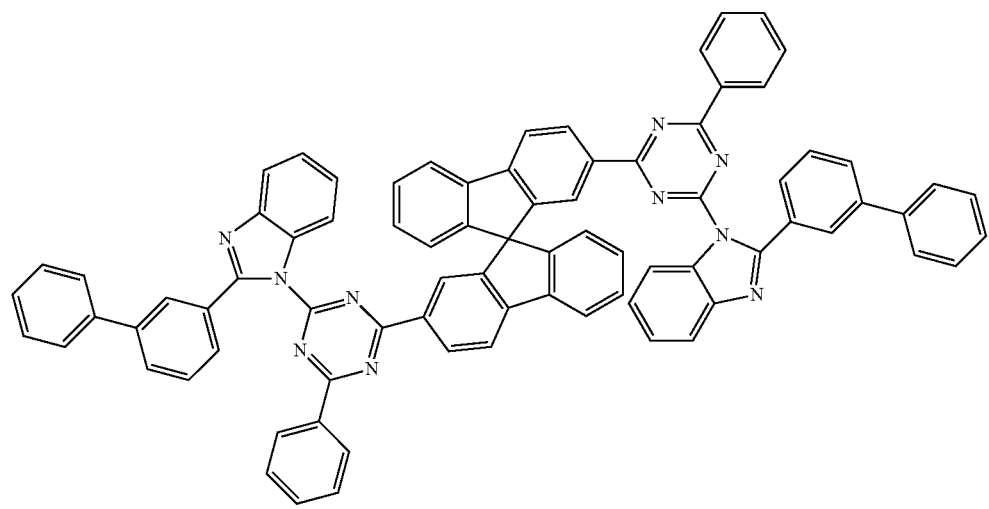 [SMILES: c1ccc(-c2cccc(-c3nc4ccccc4n3-c3nc(-c4ccccc4)nc(-c4ccc5c(c4)C4(c6ccccc6-5)c5ccccc5-c5ccc(-c6nc(-c7ccccc7)nc(-n7c(-c8cccc(-c9ccccc9)c8)nc8ccccc87)n6)cc54)n3)c2)cc1]
EG12

TABLE 3-continued
Structural formulae of the materials for the OLEDs
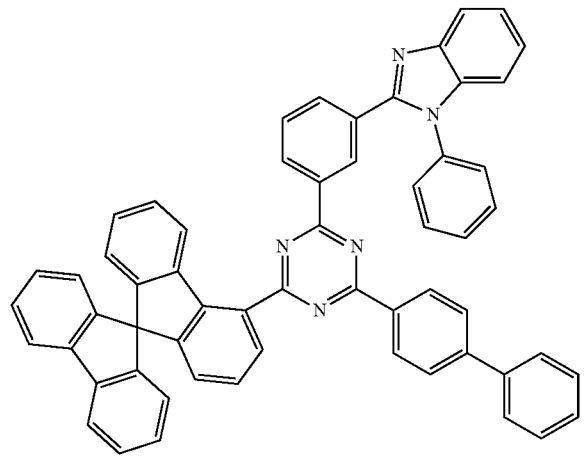 [SMILES: c1ccc(-c2ccc(-c3nc(-c4cccc(-c5nc6ccccc6n5-c5ccccc5)c4)nc(-c4cccc5c4-c4ccccc4C54c5ccccc5-c5ccccc54)n3)cc2)cc1]
EG13
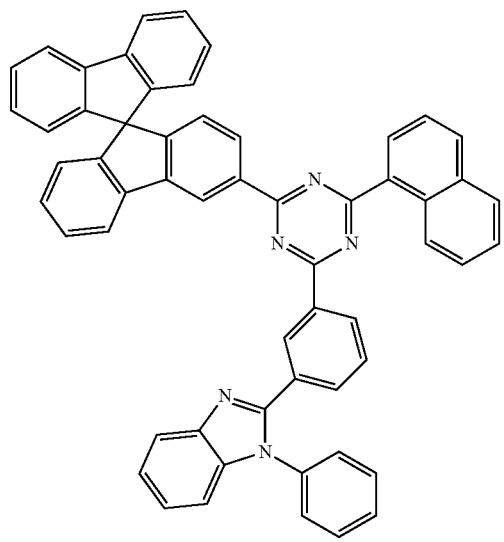 [SMILES: c1ccc(-n2c(-c3cccc(-c4nc(-c5ccc6c(c5)-c5ccccc5C65c6ccccc6-c6ccccc65)nc(-c5cccc6ccccc56)n4)c3)nc3ccccc32)cc1]
EG14
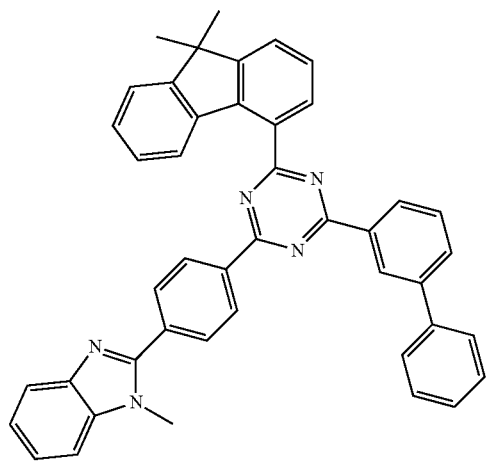 [SMILES: Cn1c(-c2ccc(-c3nc(-c4cccc(-c5ccccc5)c4)nc(-c4cccc5c4-c4ccccc4C5(C)C)n3)cc2)nc2ccccc21]
EG15

TABLE 3-continued

Structural formulae of the materials for the OLEDs

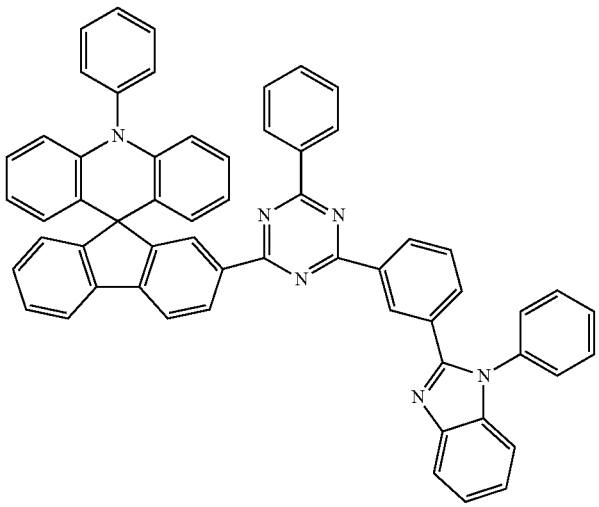 [SMILES: c1ccc(-c2nc(-c3cccc(-c4nc5ccccc5n4-c4ccccc4)c3)nc(-c3ccc4c(c3)C3(c5ccccc5-4)c4ccccc4N(c4ccccc4)c4ccccc43)n2)cc1]

EG16

The invention claimed is:

1. A compound comprising a compound fo the formula (33)

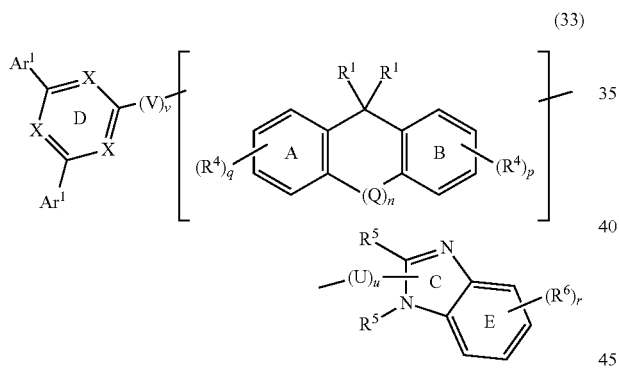

(33)

wherein $R^1$ is on each occurrence, identically or differently, H, D, F, Cl, Br, I, CHO, $N(Ar^1)_2$, $C(=O)Ar^1$, $P(=O)(Ar^1)_2$, $S(=O)Ar^1$, $S(=O)_2Ar^1$, $CR_2=CR_2Ar^1$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy, or thioalkoxy group having 1 to 40 C atoms or a straight-chain alkenyl, or alkynyl group having 2 to 40 C atoms or a branched or cyclic alkyl, alkenyl, alkynyl, alkoxy, or thioalkoxy group having 3 to 40 C atoms, each of which is optionally substituted by one or more radicals $R^2$, wherein one or more $CH_2$ groups are optionally replaced by $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S, or $CONR^2$ and wherein one or more H atoms is optionally replaced by D, F, Cl, Br, I, CN, or $NO_2$, an aromatic or heteroaromatic ring system having 5 to 60 aromatic ring atoms, which in each case is optionally substituted by one or more radicals $R^2$, an aryloxy or hetero-aryloxy group having 5 to 60 aromatic ring atoms, which is optionally substituted by one or more radicals $R^2$, or a combination of these systems; and wherein two or more adjacent substituents $R^1$ optionally define a mono- or polycyclic, aliphatic or aromatic ring system with one another;

$R^2$ is, identically or differently on each occurrence, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy, or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy, or thioalkoxy group having 3 to 40 C atoms, each of which is optionally substituted by one or more radicals $R^3$, wherein one or more non-adjacent $CH_2$ groups are optionally replaced by $R^3C=CR^3$, $C\equiv C$, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S, or $CONR^3$ and wherein one or more H atoms may be replaced by D, F, Cl, Br, I, CN, or $NO_2$, or aromatic or heteroaromatic ring system having 5 to 60 aromatic ring atoms, which in each case is optionally substituted by one or more radicals $R^3$, an aryloxy, arylalkoxy, or heteroaryloxy group having 5 to 60 aromatic ring atoms, which is optionally substituted by one or more radicals $R^3$, a diarylamino group, diheteroarylamino group, or arylheteroarylamino group having 10 to 40 aromatic ring atoms, which is optionally substituted by one or more radicals $R^3$, or a combination of two or more of these groups; and wherein two or more adjacent radicals $R^2$ optionally define a mono- or polycyclic, aliphatic or aromatic ring system with one another;

$R^3$ is, identically or differently on each occurrence, H, D, F or an aliphatic, aromatic, and/or heteroaromatic hydrocarbon radical having 1 to 20 C atoms, wherein one or more H atoms is optionally replaced by F; and wherein two or more substituents $R^3$ optionally define a mono- or polycyclic, aliphatic or aromatic ring system with one another;

$R^5$ is on each occurrence, identically or differently, a substituent selected from the group consisting of F, Cl, Br, I, CHO, $N(Ar^1)_2$, $C(=O)Ar^1$, $P(=O)(Ar^1)_2$, $S(=O)Ar^1$, $S(=O)_2Ar^1$, $CR_2=CR^2Ar^1$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy, or thioalkoxy group having 1 to 40 C atoms or a straight-chain alkenyl or alkynyl group having 2 to 40 C atoms or a branched or cyclic alkyl, alkenyl, alkynyl, alkoxy, or thioalkoxy group having 3 to 40 C atoms, each of which is optionally substituted by one or more radicals $R^2$, wherein one or more $CH_2$ groups are optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and wherein one or more H atoms is optionally replaced by D, F, Cl, Br, I, CN, or $NO_2$, an aromatic or heteroaromatic ring system having 5 to 60 aromatic ring atoms, which in each case is optionally substituted by one or more radicals $R^2$, an aryloxy or heteroaryloxy group having 5 to 60 aromatic ring atoms, which is optionally substituted by one or more radicals $R^2$, and a combination of these systems; and wherein two or more adjacent substituents $R^5$ cannot form a mono- or polycyclic, aliphatic or aromatic ring system with one another;

$R^4$ and $R^6$ are on each occurrence, identically or differently, H, D, F, Cl, Br, I, CHO, $N(Ar^1)_2$, $C(=O)Ar^1$, $P(=O)(Ar^1)_2$, $S(=O)Ar^1$, $S(=O)_2Ar^1$, $CR_2=CR^2Ar^1$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy, or thioalkoxy group having 1 to 40 C atoms or a straight-chain alkenyl or alkynyl group having 2 to 40 C atoms or a branched or cyclic alkyl, alkenyl, alkynyl, alkoxy, or thioalkoxy group having 3 to 40 C atoms, each of which is optionally substituted by one or more radicals $R^2$, wherein one or more $CH_2$ groups is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $CONR^2$ and wherein one or more H atoms is optionally replaced by D, F, Cl, Br, I, CN, or $NO_2$, an aromatic or heteroaromatic ring system having 5 to 60 aromatic ring atoms, which in each case is optionally substituted by one or more radicals $R^2$, an aryloxy or heteroaryloxy group having 5 to 60 aromatic ring atoms, which is optionally substituted by one or more radicals $R^2$, or a combination of these systems; and wherein two or more adjacent substituents $R^4$ cannot form a mono- or polycyclic, aliphatic or aromatic ring system with one another; and wherein two or more adjacent substituents $R^6$ optionally define a mono- or polycyclic, aliphatic or aromatic ring system with one another;

Q is $C=O$, $C=S$, S, $C(R^2)_2$, $NR_2$, or O;

n is 0 or 1, wherein n=0 means that the two aromatic rings A and B are not linked to one another via the group Q, but instead by a single bond;

p is 0, 1, 2, 3, or 4;

q is 0, 1, 2, 3, or 4;

r is 0, 1, 2, 3, or 4;

X is, identically or differently on each occurrence, selected from the group consisting of N and $CR^1$, wherein at least one X is equal to N;

$Ar^1$ is on each occurrence, identically or differently, an aromatic or heteroaromatic ring system having 5 to 30 aromatic ring atoms, which is optionally substituted by one or more radicals $R^2$; wherein two of the radicals $Ar^1$ are optionally linked to one another by a single bond or a bridge selected from the group consisting of $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$ and $P(=O)R^2$, V is a divalent group;

U is a divalent group;

v is 0 or 1, wherein v=0 means that the ring D is connected directly to the remainder of the compound via a single covalent bond;

u is 0 or 1, wherein u=0 means that the ring C is connected directly to the remainder of the compound via a single covalent bond.

2. The compound according to claim 1, wherein the compound is a small molecule having a molecular weight of at most 3000 g/mol.

3. The compound according to claim 1, wherein the compound of the formula (33) has the formula (1):

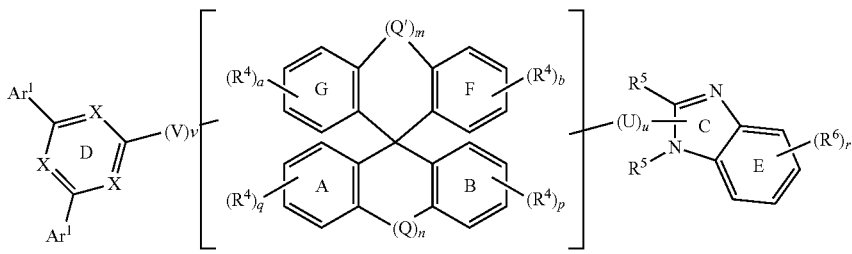

(1)

wherein

Q' is, identically to or differently from one another, $C=O$, $C=S$, S, $C(R^2)_2$, $NR^2$, or O;

A is 0, 1, 2, 3, or 4;

B is 0, 1, 2, 3, or 4;

a+b is always less than or equal to 7;

m is 0 or 1, wherein m=0 means that the two aromatic rings are not linked to one another via the group Q', but instead by a single bond;

V is a divalent group;

U is a divalent group;

V is 0 or 1, where v=0 means that the ring D is connected directly to the remainder of the compound via a single covalent bond;

U is 0 or 1, where u=0 means that the ring C is connected directly to the remainder of the compound via a single covalent bond.

4. The compound according to claim 1, wherein the compound of the formula (33) has the formula (4):

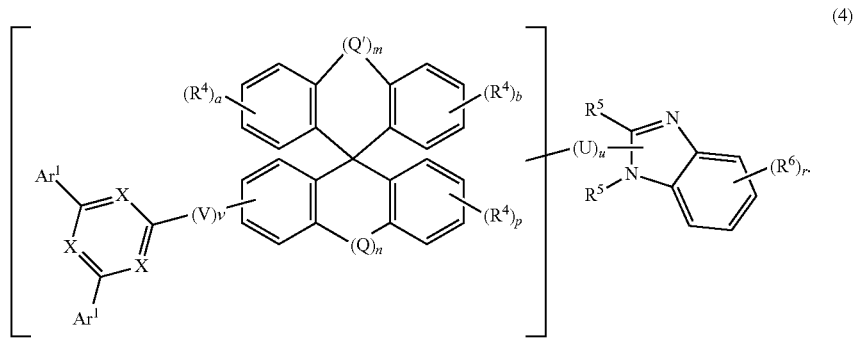

(4)

5. The compound according to claim 1, wherein the compound of the formula (33) has the formula (5):

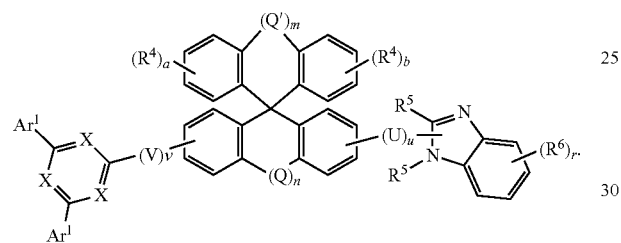

(5)

6. The compound according to claim 1, wherein the compound of the formula (33) has the formula (14):

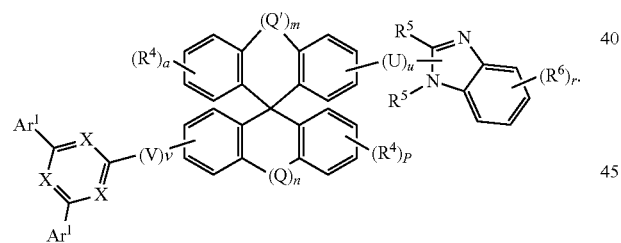

(14)

7. The compound according to claim 1, wherein two or more adjacent substituents $R^1$ do not form a mono- or polycyclic, aliphatic or aromatic ring system with one another.

8. The compound according to claim 1, wherein the compound of the formula (33) has the formula (34):

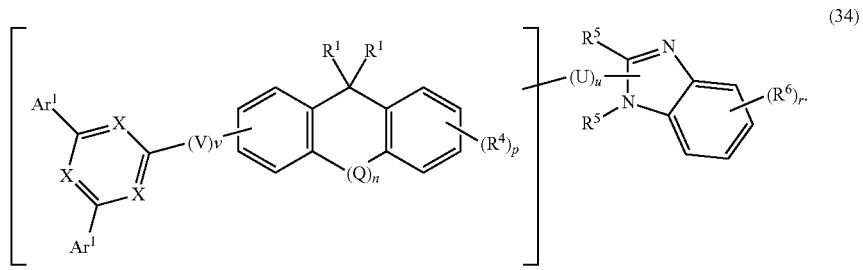

(34)

9. The compound according to claim 1, wherein the compound of the formula (33) has the formula (35):

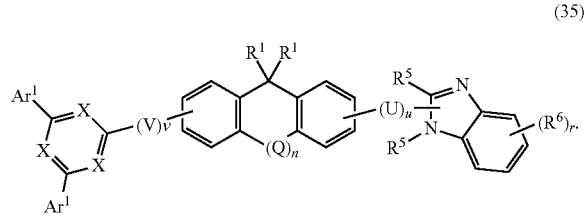

(35)

10. A composition comprising at least one compound of claim 1 and at least one further compound selected from the group consisting of fluorescent emitters, phosphorescent emitters, matrix materials, electron-transport materials, electron-injection materials, hole-conductor materials, hole-injection materials, electron-blocking materials, hole-blocking materials, wide band gap materials, and n-dopants.

11. The composition of claim 10, wherein the additional compound is an electron-transport material or matrix material.

12. A formulation comprising at least one compound of claim 1 and at least one solvent.

13. A formulation comprising at least one composition of claim 10 at least one solvent.

14. An electronic device comprising at least one compound of claim 1.

15. An electronic device comprising at least one composition of claim 10.

16. The electronic device of claim 14, wherein the device is selected from the group consisting of organic integrated circuits, organic field-effect transistors, organic thin-film transistors, organic electroluminescent devices, organic solar cells, organic optical detectors, and organic photoreceptors.

17. The electronic device of claim 14, wherein the device is selected from the group consisting of organic light-emitting transistors, organic field-quench devices, organic light-emitting electrochemical cells, organic laser diodes, and organic light-emitting diodes.

18. The electronic device of claim 15, wherein the device is selected from the group consisting of organic light-emitting transistors, organic field-quench devices, organic light-emitting electrochemical cells, organic laser diodes, and organic light-emitting diodes.

19. A process for producing an electronic device according to claim 14, comprising applying at least one organic layer by gas-phase deposition or from solution.

20. A process for producing an electronic device according to claim 15, comprising applying at least one organic layer by gas-phase deposition or from solution.

* * * * *